US009962435B2

(12) United States Patent
Hennessy et al.

(10) Patent No.: US 9,962,435 B2
(45) **Date of Patent: *May 8, 2018**

(54) WEST NILE VIRUS VACCINE

(71) Applicant: Boehringer Ingelheim Vetmedica, Inc., St. Joseph, MO (US)

(72) Inventors: Kristina J. Hennessy, Leawood, KS (US); Phillip Wayne Hayes, Maurice, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/346,198

(22) Filed: Nov. 8, 2016

(65) Prior Publication Data

US 2017/0049877 A1 Feb. 23, 2017

Related U.S. Application Data

(60) Continuation of application No. 14/250,436, filed on Apr. 11, 2014, now Pat. No. 9,517,259, which is a division of application No. 12/937,504, filed as application No. PCT/US2009/055564 on Aug. 31, 2009, now Pat. No. 8,821,889.

(60) Provisional application No. 61/093,081, filed on Aug. 29, 2008, provisional application No. 61/117,086, filed on Nov. 21, 2008.

(51) Int. Cl.

| | |
|---|---|
| *A61K 39/12* | (2006.01) |
| *A61K 39/08* | (2006.01) |
| *A61K 39/145* | (2006.01) |
| *A61K 39/193* | (2006.01) |
| *A61K 39/245* | (2006.01) |
| *C07K 14/005* | (2006.01) |
| *C12N 7/00* | (2006.01) |
| *A61K 39/00* | (2006.01) |

(52) U.S. Cl.

CPC .............. *A61K 39/12* (2013.01); *A61K 39/08* (2013.01); *A61K 39/145* (2013.01); *A61K 39/193* (2013.01); *A61K 39/245* (2013.01); *C07K 14/005* (2013.01); *C12N 7/00* (2013.01); *A61K 2039/521* (2013.01); *A61K 2039/5252* (2013.01); *A61K 2039/543* (2013.01); *A61K 2039/545* (2013.01); *A61K 2039/552* (2013.01); *A61K 2039/55566* (2013.01); *A61K 2039/70* (2013.01); *C12N 2710/16034* (2013.01); *C12N 2710/16071* (2013.01); *C12N 2710/16734* (2013.01); *C12N 2760/16134* (2013.01); *C12N 2760/16171* (2013.01); *C12N 2770/24122* (2013.01); *C12N 2770/24134* (2013.01); *C12N 2770/24171* (2013.01); *C12N 2770/36134* (2013.01); *C12N 2770/36171* (2013.01)

(58) Field of Classification Search
None
See application file for complete search history.

(56) References Cited

U.S. PATENT DOCUMENTS

| | | | | |
|---|---|---|---|---|
| 6,235,282 | B1 | 5/2001 | Riviere et al. | |
| 6,812,219 | B2 | 11/2004 | LaColla et al. | |
| 6,878,372 | B2 | 4/2005 | Monath et al. | |
| 7,101,861 | B2 | 9/2006 | Sommadossi et al. | |
| 7,105,493 | B2 | 9/2006 | Sommadossi et al. | |
| 7,148,206 | B2 | 12/2006 | Sommadossi et al. | |
| 7,153,513 | B2 * | 12/2006 | Chu .................... | A61K 9/1075 424/218.1 |
| 7,163,929 | B2 | 1/2007 | Sommadossi et al. | |
| 7,227,011 | B2 | 6/2007 | Chang | |
| 7,244,430 | B2 | 7/2007 | Throsby et al. | |
| 7,425,437 | B2 | 9/2008 | UytdeHaag et al. | |
| 7,445,787 | B2 | 11/2008 | Chu | |
| 7,455,842 | B2 | 11/2008 | Yamshchikov | |
| 7,459,163 | B2 | 12/2008 | Yamshchikov | |
| 7,482,017 | B2 | 1/2009 | Barrett et al. | |
| 7,507,415 | B2 | 3/2009 | Arroyo et al. | |
| 7,556,812 | B2 | 7/2009 | Tangy et al. | |
| 7,585,621 | B2 | 9/2009 | Beall et al. | |
| 8,133,712 | B2 * | 3/2012 | Sterner ................ | C07K 14/005 424/202.1 |
| 8,821,889 | B2 * | 9/2014 | Hennessy ............. | A61K 39/08 424/201.1 |
| 9,517,259 | B2 * | 12/2016 | Hennessy ............. | A61K 39/08 |
| 2003/0091595 | A1 | 5/2003 | Chu | |
| 2003/0104008 | A1 | 6/2003 | Loosmore et al. | |

(Continued)

FOREIGN PATENT DOCUMENTS

| | | | |
|---|---|---|---|
| WO | 2003061555 | A2 | 7/2003 |
| WO | 2007051763 | A1 | 5/2007 |
| WO | 2010025469 | A1 | 3/2010 |

OTHER PUBLICATIONS

"West Nile Innovator + EWT"., Ft. Dodge Material Safety Data Sheet, Fort Dodge Animal Health—A Division of Wyeth Corporation, Jan. 23, 2004, pp. 1-5.
"West Nile Innovator + VEWT"., Fort Dodge Material Safety Data Sheet, Fort Dodge Animal Health, Apr. 10, 2007, pp. 1-6.
Anderson et al., "Isolation of West Nile Virus from Mosquitoes, Crows and a Cooper's Hawk in Connecticut". Science, vol. 286, Dec. 1999, pp. 2331-2333.
Arroyo et al., "ChimerVax-West Nile Virus Live-Attenuated Vaccine: Preclinical Evaluation of Safety, Immogenicity, and Efficacy". Journal of Virology, vol. 78, No. 22, Nov. 2004, pp. 12497-12507.
Blood-Horse Staff, "Fort Dodge Releases West Nile DNA Vaccine"., BloodHorse.com, Jul. 19, 2005, 1 page. [Accessed at http://www.bloodhorse.com/horse-racing/articles/29112/fort-dodge-releases-west-nile- . . . on Apr. 9, 2013.].

(Continued)

*Primary Examiner* — Shanon A. Foley
(74) *Attorney, Agent, or Firm* — Marc Began; Judy Jarecki-Black

(57) ABSTRACT

The invention provides for immunogenic compositions against West Nile Virus. The immunogenic compositions, in alternate embodiments, also include other equine pathogens. The West Nile Virus composition of the present invention advantageously provides for protection against North American Dominant West Nile Virus strains or isolates.

21 Claims, 120 Drawing Sheets

(56) References Cited

U.S. PATENT DOCUMENTS

| | | | | |
|---|---|---|---|---|
| 2003/0148261 | A1 | 8/2003 | Fikrig et al. | |
| 2008/0279891 | A1 | 11/2008 | Johnston et al. | |
| 2009/0130146 | A1 | 5/2009 | Broeker | |
| 2011/0159033 | A1 | 6/2011 | Hennessy et al. | |
| 2014/0328877 | A1 | 11/2014 | Hennessy et al. | |
| 2017/0049877 | A1* | 2/2017 | Hennessy | A61K 39/08 |

OTHER PUBLICATIONS

Dauphin et al., "West Nile Virus: Recent Trends in Diagnosis and Vaccine Development". Vaccine, vol. 25, 2007, pp. 5563-5576.
Davis et al., "Phylogenetic analysis of North American West Nile virus isolates, 2001-2004: Evidence for the emergence of a dominant genotype". 2005, Virology, vol. 342, pp. 252-265.
Hall et al., "West Nile Virus Vaccines". Expert Opinion on Biological Therapy, vol. 4, No. 8, 2004, pp. 1295-1305.
Imam et al., "Challenge of Hamsters With Japanese B, St. Louis and Murray Valley Encephalitis Viruses After Immunization by West Nile Infection Plus Specific Vaccine". 1957, The Journal of Immunology, vol. 79, pp. 243-252.
International Search Report for PCT/US2009/055564 dated Dec. 3, 2009.
Kramer et al., "West Nile virus"., The Lancet Neurology, vol. 6, 2007, pp. 171-181.
Lanciotti et al., "Origin of the West Nile Virus Responsible for the Outbreak of Encephalitis in the Northeastern United States". Science, vol. 286, No. 17, Dec. 1999, pp. 2333-2337. [Accessed at www.sciencemag.org on Dec. 20, 2010].
Lustig et al., "A Live Attenuated West Nile Virus Strain as a Potential Veterinary Vaccine". Viral Immunology, vol. 13, No. 4, 2000, pp. 401-410.
Malkinson et al., "Use of Live and Inactivated Vaccines in the Control of West Nile Fever in Domestic Geese". Annals of the New York Academy of Sciences, 2001, pp. 255-261.
Minke et al., "Equine viral vaccines: the past, the present and future". Veterinary Research, vol. 35, 2004, pp. 425-443.
Monath et al., "West Nile Virus Vaccine". Current Drug Targets-Infectious Disorders, vol. 1, No. 1, 2001, pp. 37-50.
Moudy et al., "A Newly Emergent Genotype of West Nile Virus is transmitted Earlier and More Efficiently by Culex Mosquitoes". The American Journal of Tropical Medicine and Hygiene, vol. 77, No. 2, 2007, pp. 365-370.
Snapinn et al., "Declining Growth Rate of West Nile Virus in North America". Mar. 2007, Journal of Virology, vol. 81, No. 5, pp. 2531-2534.
Steele et al., "Pathology of Fatal West Nile Virus Infections in Native and Exotic Birds during the 1999 Outbreak in New York City, New York". 2000, Veterinary Pathology, vol. 37, pp. 208-224.
Wang et al., "Immunization of Mice Again West Nile Virus with Recombinant Envelope Protein".The Journal of Immunology, vol. 167, 2001, pp. 5273-5277.
Written Opinion of the International Searching Authority for PCT/US2009/055564 dated Dec. 3, 2009.

* cited by examiner

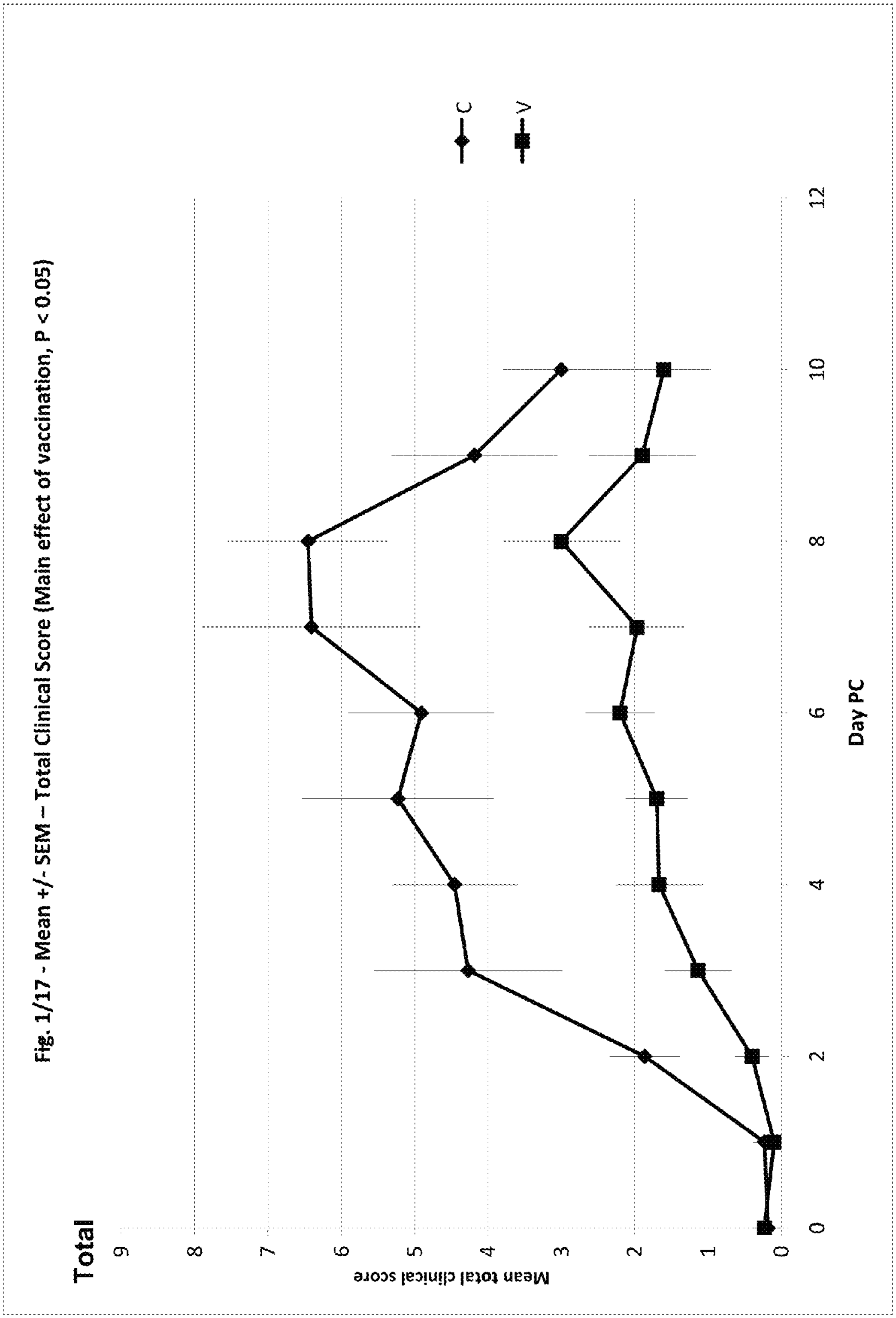
Fig. 1/17 - Mean +/- SEM – Total Clinical Score (Main effect of vaccination, P < 0.05)
Total
Mean total clinical score
0
1
2
3
4
5
6
7
8
9
Day PC
0
2
4
6
8
10
12
C
V

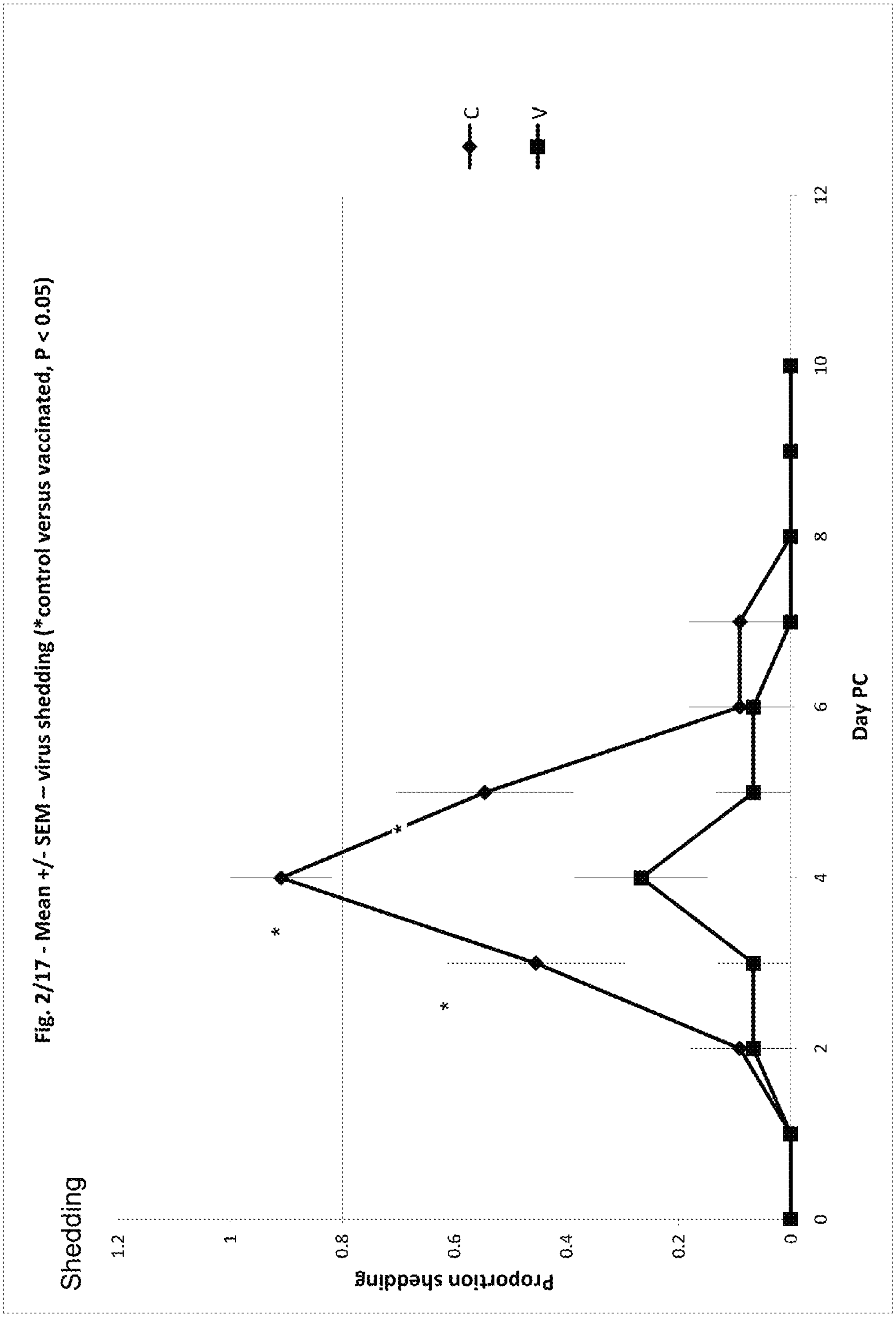
Fig. 2/17 - Mean +/- SEM – virus shedding (*control versus vaccinated, P < 0.05)
Shedding
Proportion shedding
1.2
1
0.8
0.6
0.4
0.2
0
Day PC
0
2
4
6
8
10
12
*
*
*
C
V

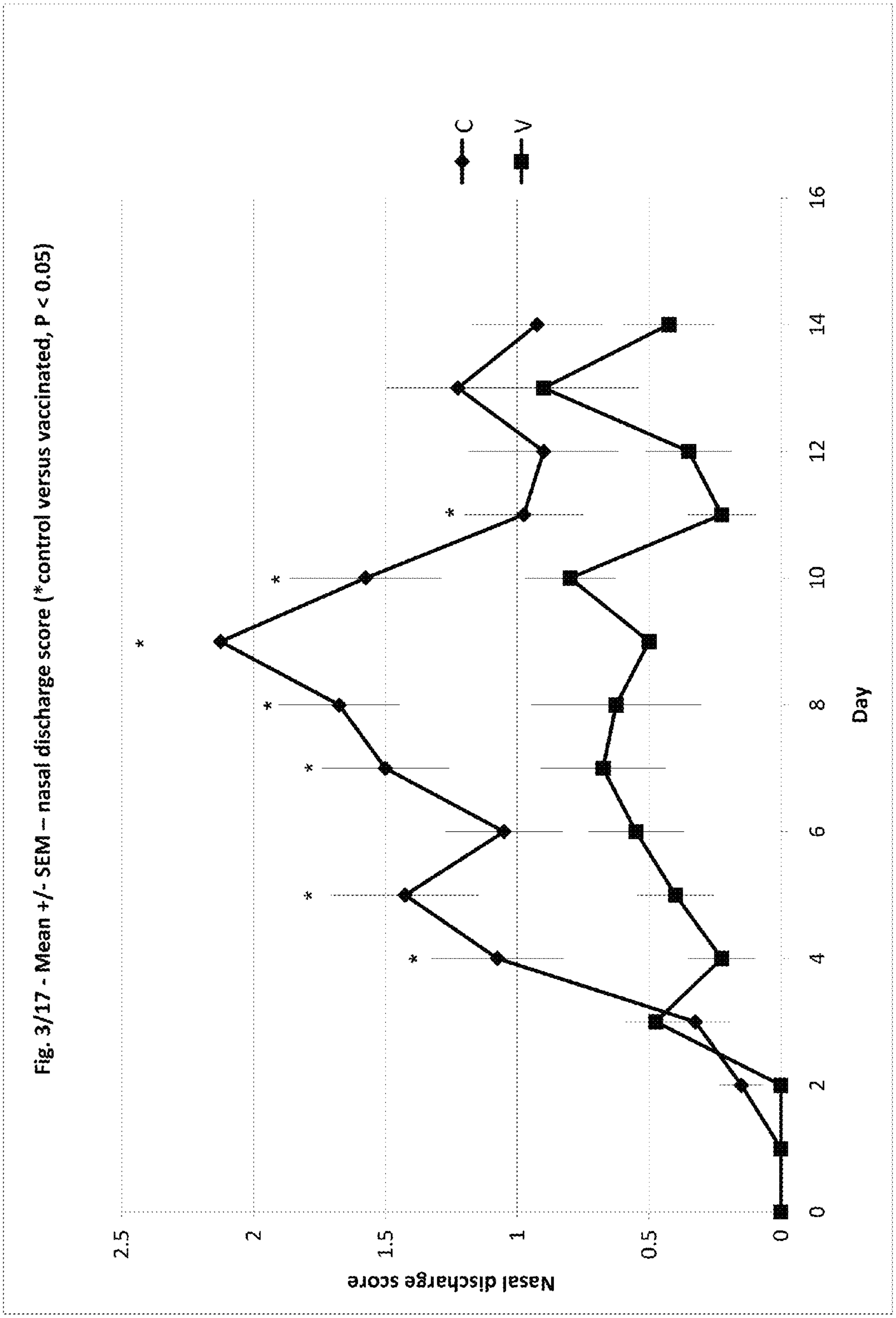
Fig. 3/17 - Mean +/- SEM – nasal discharge score (*control versus vaccinated, P < 0.05)

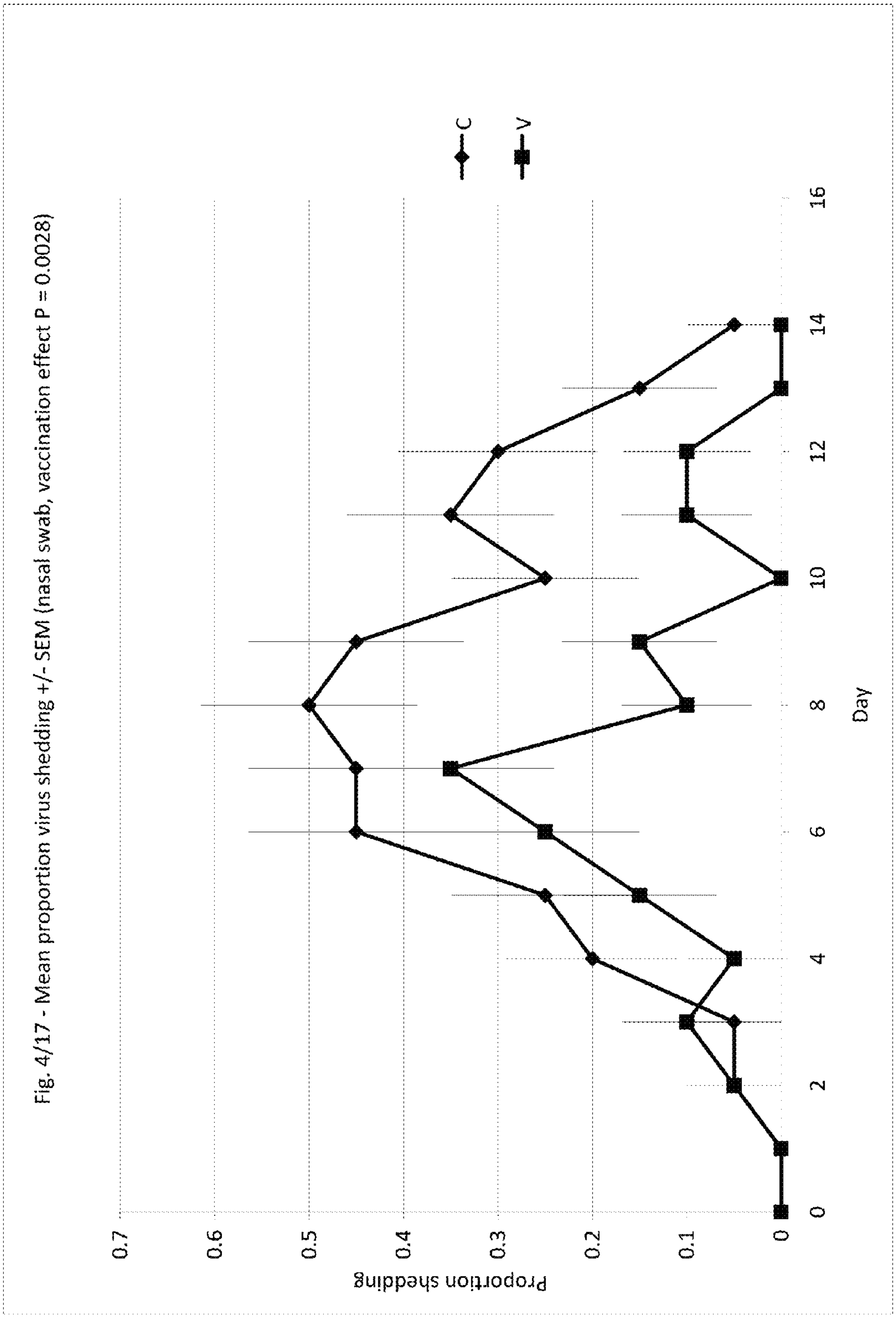
Fig. 4/17 - Mean proportion virus shedding +/- SEM (nasal swab, vaccination effect P = 0.0028)

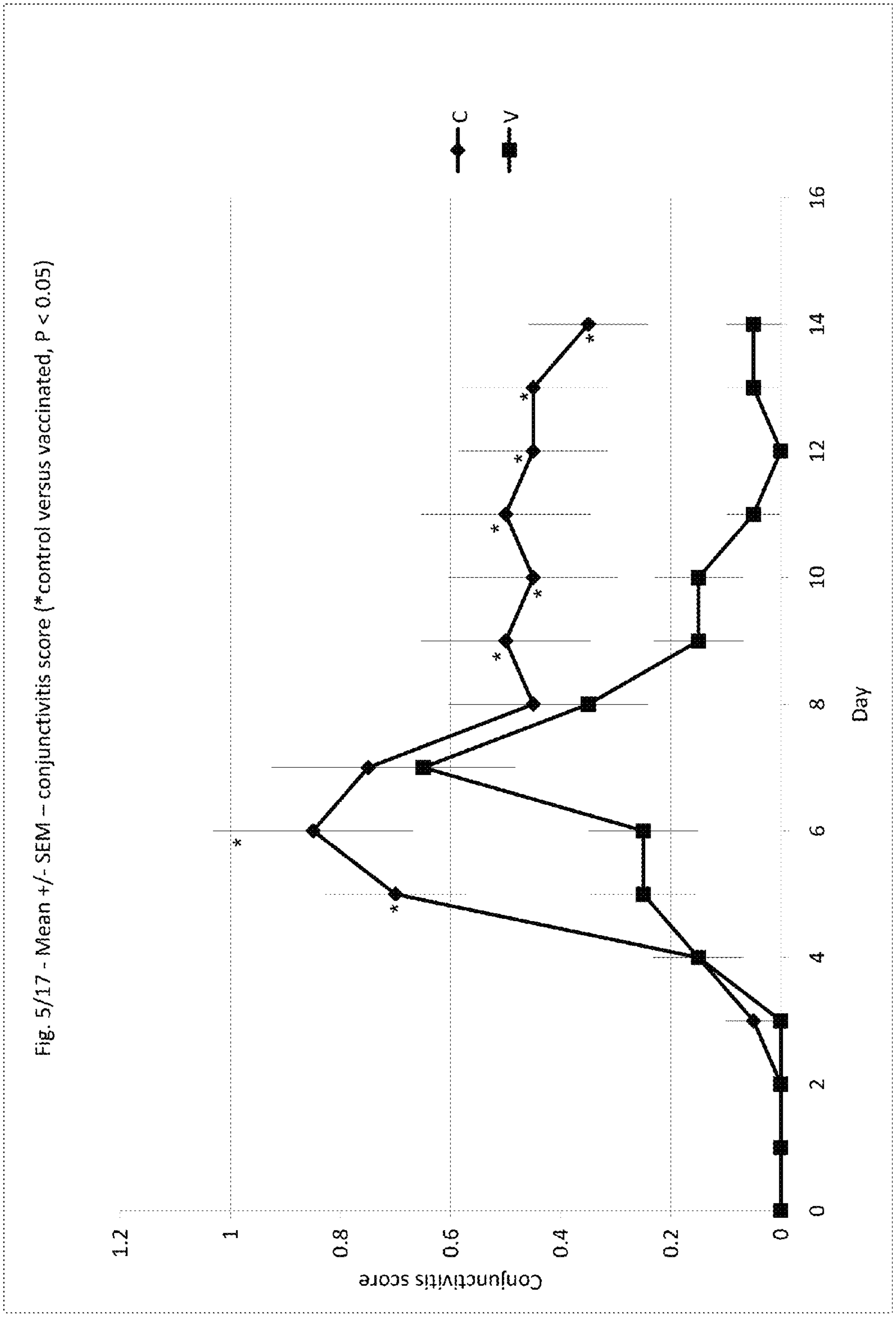
Fig. 5/17 - Mean +/- SEM – conjunctivitis score (*control versus vaccinated, P < 0.05)
Conjunctivitis score
1.2
1
0.8
0.6
0.4
0.2
0
0
2
4
6
8
10
12
14
16
Day
C
V
*

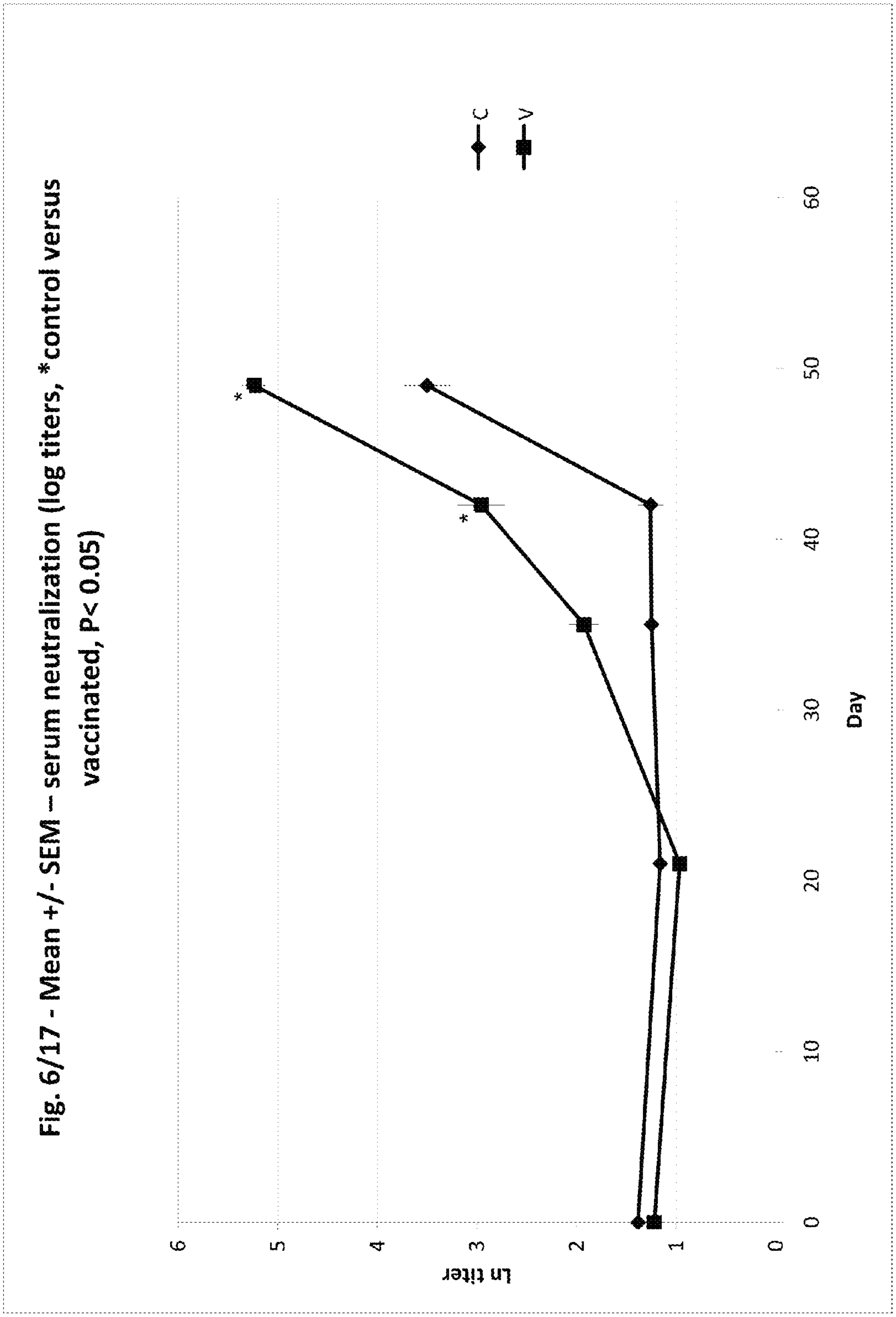
Fig. 6/17 - Mean +/- SEM – serum neutralization (log titers, *control versus vaccinated, P< 0.05)
Ln titer
0
1
2
3
4
5
6
Day
0
10
20
30
40
50
60
C
V
*
*

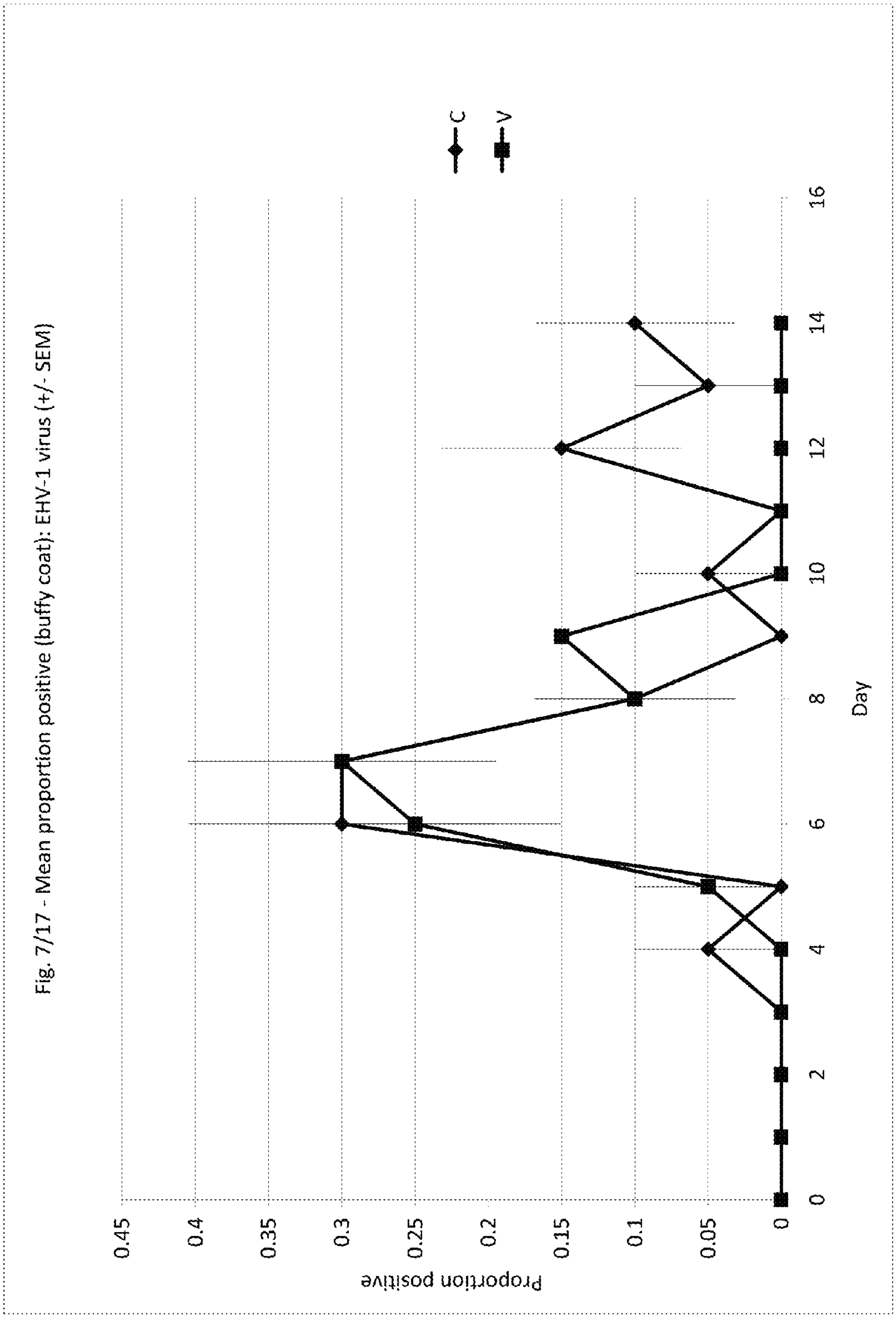
Fig. 7/17 - Mean proportion positive (buffy coat): EHV-1 virus (+/- SEM)
Proportion positive
0
0.05
0.1
0.15
0.2
0.25
0.3
0.35
0.4
0.45
Day
0
2
4
6
8
10
12
14
16
C
V

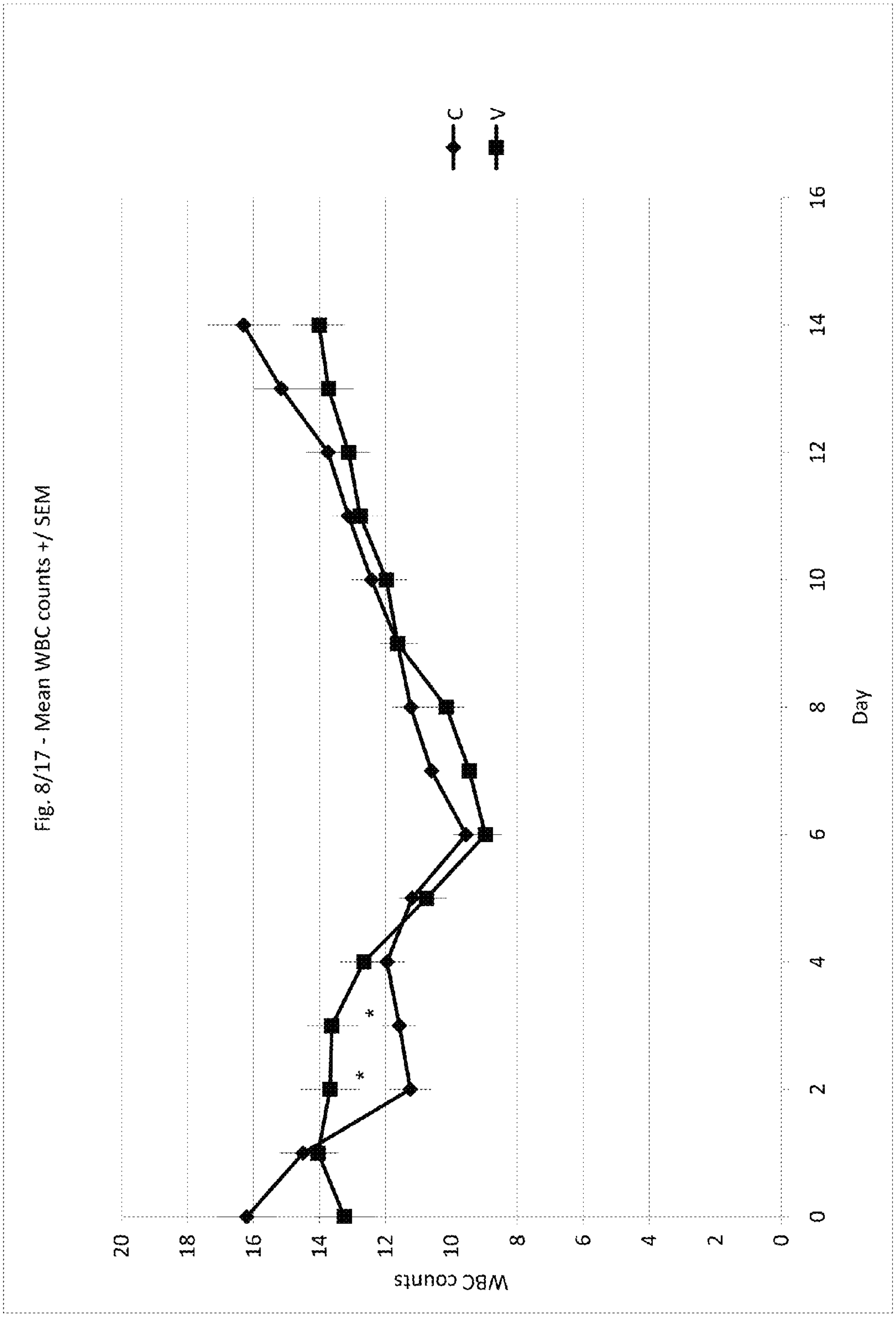
Fig. 8/17 - Mean WBC counts +/ SEM

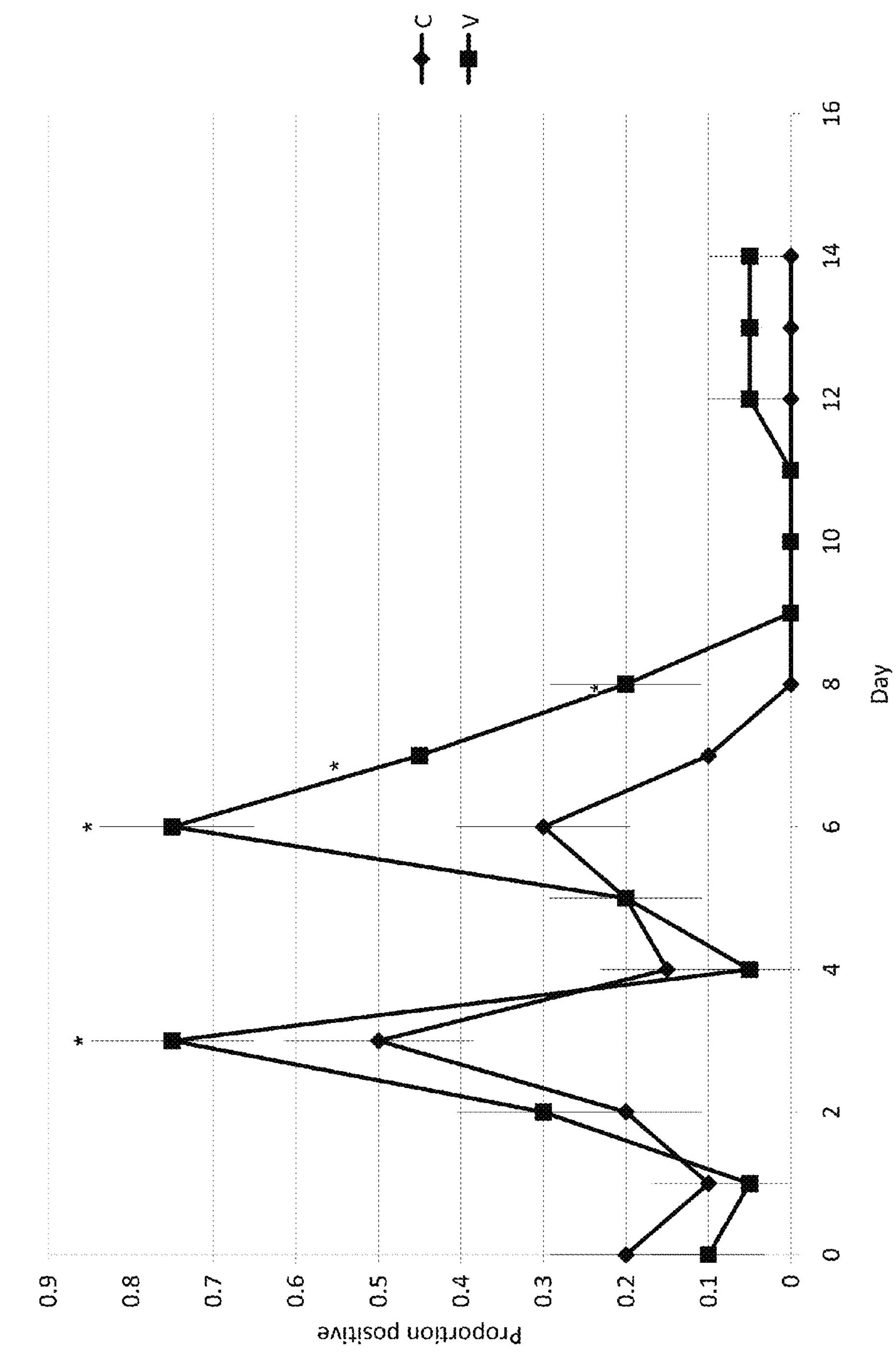
Fig. 9/17 - Mean proportion pyrexic +/- SEM (*control versus vaccinated, P < 0.05)

```
    NY99 E  TTCAACTGCC  TTGGAATGAG  CAACAGAGAC  30
    WN02 E  TTCAACTGCC  TTGGAATGAG  CAACAGAGAC  30
      HEF1  ----------  ----------  ----------  -
      HEF3  ----------  ----------  ----------  -
  HER3 rev  ----------  ----------  ----------  -
  HER4 rev  ----------  ----------  ----------  -
 Consensus  ----------  ----------  ----------
      100%
Conservation
        0%

    NY99 E  TTCTTGGAAG  GAGTGTCTGG  AGCAACATGG  60
    WN02 E  TTCTTGGAAG  GAGTGTCTGG  AGCAACATGG  60
      HEF1  ----------  ----------  ----------  -
      HEF3  ----------  ----------  ----------  -
  HER3 rev  ----------  ----------  ----------  -
  HER4 rev  ----------  ----------  ----------  -
 Consensus  ----------  ----------  ----------
      100%
Conservation
        0%

    NY99 E  GTGGATTTGG  TTCTCGAAGG  CGACAGCTGC  90
    WN02 E  GTGGATTTGG  TTCTCGAAGG  CGACAGCTGC  90
      HEF1  ----------  ----------  ----------  -
      HEF3  ----------  ----------  ----------  -
  HER3 rev  ----------  ----------  ----------  -
  HER4 rev  ----------  ----------  ----------  -
 Consensus  ----------  ----------  ----------
      100%
Conservation
        0%

    NY99 E  GTGACTATCA  TGTCTAAGGA  CAAGCCTACC  120
    WN02 E  GTGACTATCA  TGTCTAAGGA  CAAGCCTACC  120
      HEF1  ----------  ----------  ----------  -
      HEF3  ----------  ----------  ----------  -
  HER3 rev  ----------  ----------  ----------  -
  HER4 rev  ----------  ----------  ----------  -
 Consensus  ----------  ----------  ----------
      100%
Conservation
        0%
```

Fig. 10A/17

```
NY99 E     ATCGATGTGA AGATGATGAA TATGGAGGCG 150
WN02 E     ATCGATGTGA AGATGATGAA TATGGAGGCG 150
HEF1       --CGATGTGN -GANGANGAA TATGGAGGCG 27
HEF3       ---------- ---------- ---------- -
HER3 rev   ---------- ---------- ---------- -
HER4 rev   ---------- ---------- ---------- -
Consensus  --CGATGTG- -GA-GA-GAA TATGGAGGCG
100%
Conservation
0%
NY99 E     GCCAACCTGG CAGAGGTCCG CAGTTATTGC 180
WN02 E     GCCAACCTGG CAGAGGTCCG CAGTTATTGC 180
HEF1       GCCAACCTGG CAGAGGTCCG CAGTTATTGC 57
HEF3       ---------- ---------- ---------- -
HER3 rev   ---------- ---------- ---------- -
HER4 rev   ---------- ---------- ---------- -
Consensus  GCCAACCTGG CAGAGGTCCG CAGTTATTGC
100%
Conservation
0%
NY99 E     TATTTGGCTA CCGTCAGCGA TCTCTCCACC 210
WN02 E     TATTTGGCTA CCGTCAGCGA TCTCTCCACC 210
HEF1       TATTTGGCTA CCGTCAGCGA TCTCTCCACC 87
HEF3       ---------- ---------- ---------- -
HER3 rev   ---------- ---------- ---------- -
HER4 rev   ---------- ---------- ---------- -
Consensus  TATTTGGCTA CCGTCAGCGA TCTCTCCACC
100%
Conservation
0%
NY99 E     AAAGCTGCGT GCCCGACCAT GGGAGAAGCT 240
WN02 E     AAAGCTGCGT GCCCGACCAT GGGAGAAGCT 240
HEF1       AAAGCTGCGT GCCCGACCAT GGGAGAAGCT 117
HEF3       ---------- ---------- ---------- -
HER3 rev   ---------- ---------- ---------- -
HER4 rev   ---------- ---------- ---------- -
Consensus  AAAGCTGCGT GCCCGACCAT GGGAGAAGCT
100%
Conservation
0%
```

Fig. 10B/17

```
     NY99 E  CACAATGACA AACGTGCTGA CCCAGCTTTT 270
     WN02 E  CACAATGACA AACGTGCTGA CCCAGCTTTT 270
       HEF1  CACAATGACA AACGTGCTGA CCCAGCTTTT 147
       HEF3  ---------- ---------- ---------- -
   HER3 rev  ---------- ---------- ---------- -
   HER4 rev  ---------- ---------- ---------- -
  Consensus  CACAATGACA AACGTGCTGA CCCAGCTTTT
       100%
Conservation
         0%
     NY99 E  GTGTGCAGAC AAGGAGTGGT GGACAGGGGC 300
     WN02 E  GTGTGCAGAC AAGGAGTGGT GGACAGGGGC 300
       HEF1  GTGTGCAGAC AAGGAGTGGT GGACAGGGGC 177
       HEF3  ---------- ---------- ---------- -
   HER3 rev  ---------- ---------- ---------- -
   HER4 rev  ---------- ---------- ---------- -
  Consensus  GTGTGCAGAC AAGGAGTGGT GGACAGGGGC
       100%
Conservation
         0%
     NY99 E  TGGGGCAACG GCTGCGGACT ATTTGGCAAA 330
     WN02 E  TGGGGCAACG GCTGCGGACT ATTTGGCAAA 330
       HEF1  TGGGGCAACG GCTGCGGACT ATTTGGCAAA 207
       HEF3  ---------- ---------- ---------- -
   HER3 rev  ---------- ---------- ---------- -
   HER4 rev  ---------- ---------- ---------- -
  Consensus  TGGGGCAACG GCTGCGGACT ATTTGGCAAA
       100%
Conservation
         0%
     NY99 E  GGAAGCATTG ACACATGCGC CAAATTTGCC 360
     WN02 E  GGAAGCATTG ACACATGCGC CAAATTTGCC 360
       HEF1  GGAAGCATTG ACACATGCGC CAAATTTGCC 237
       HEF3  ---------- ---------- ---------- -
   HER3 rev  ---------- ---------- ---------- -
   HER4 rev  ---------- ---------- ---------- -
  Consensus  GGAAGCATTG ACACATGCGC CAAATTTGCC
       100%
Conservation
         0%
```

Fig. 10C/17

| | | | | |
|---|---|---|---|---|
| NY99 E | TGCTCTACCA | AGGCAATAGG | AAGAACCATC | 390 |
| WN02 E | TGCTCTACCA | AGGCAATAGG | AAGAACCATC | 390 |
| HEF1 | TGCTCTACCA | AGGCAATAGG | AAGAACCATC | 267 |
| HEF3 | ---------- | ---------- | ---------- | - |
| HER3 rev | ---------- | ---------- | ---------- | - |
| HER4 rev | ---------- | ---------- | ---------- | - |
| **Consensus** | **TGCTCTACCA** | **AGGCAATAGG** | **AAGAACCATC** | |

100%
Conservation
0%
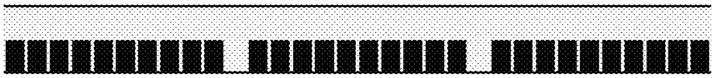

| | | | | |
|---|---|---|---|---|
| NY99 E | TTGAAAGAGA | ATATCAAGTA | CGAAGTGGCC | 420 |
| WN02 E | TTGAAAGAGA | ATATCAAGTA | CGAAGTGGCC | 420 |
| HEF1 | TTGAAAGAGA | ATATCAAGTA | CGAAGTGGCC | 297 |
| HEF3 | ---------- | ----CAAGTA | CGAAGTGGCC | 16 |
| HER3 rev | ---------- | ---------- | ---------- | - |
| HER4 rev | ---------- | ---------- | ---------- | - |
| **Consensus** | **TTGAAAGAGA** | **ATATCAAGTA** | **CGAAGTGGCC** | |

100%
Conservation
0%
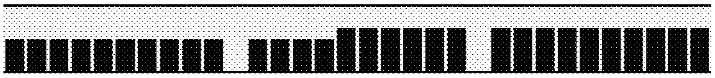

| | | | | |
|---|---|---|---|---|
| NY99 E | ATTTTTGTCC | ATGGACCAAC | TACTGTGGAG | 450 |
| WN02 E | ATTTTTGTCC | ATGGACCAAC | TACTGTGGAG | 450 |
| HEF1 | ATTTTTGTCC | ATGGACCAAC | TACTGTGGAG | 327 |
| HEF3 | ATTTTTGTCC | ATGGACCAAC | TACTGTGGAG | 46 |
| HER3 rev | ---------- | ---------- | ---------- | - |
| HER4 rev | ---------- | ---------- | ---------- | - |
| **Consensus** | **ATTTTTGTCC** | **ATGGACCAAC** | **TACTGTGGAG** | |

100%
Conservation
0%
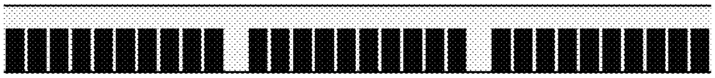

| | | | | |
|---|---|---|---|---|
| NY99 E | TCGCACGGAA | ACTACTCCAC | ACAGGTTGGA | 480 |
| WN02 E | TCGCACGGAA | ACTATTCCAC | ACAGGCTGGA | 480 |
| HEF1 | TCGCACGGAA | ACTACTCCAC | ACAGGTTGGA | 357 |
| HEF3 | TCGCACGGAA | ACTACTCCAC | ACAGGTTGGA | 76 |
| HER3 rev | ---------- | ---------- | ---------- | - |
| HER4 rev | ---------- | ---------- | ---------- | - |
| **Consensus** | **TCGCACGGAA** | **ACTACTCCAC** | **ACAGGTTGGA** | |

100%
Conservation
0%
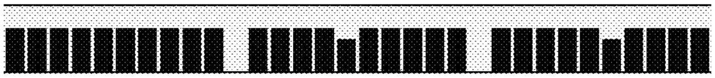

Fig. 10D/17

| | | | | |
|---|---|---|---|---|
| NY99 E | GCCACTCAGG | CAGGGAGATT | CAGCATCACT | 510 |
| WN02 E | GCCACTCAGG | CAGGGAGATT | CAGCATCACT | 510 |
| HEF1 | GCCACTCAGG | CAGGGAGATT | CAGCATCACT | 387 |
| HEF3 | GCCACTCAGG | CAGGGAGATT | CAGCATCACT | 106 |
| HER3 rev | ---------- | ---------- | ---------- | - |
| HER4 rev | ---------- | ---------- | ---------- | - |
| **Consensus** | **GCCACTCAGG** | **CAGGGAGATT** | **CAGCATCACT** | |

100%
Conservation
0%

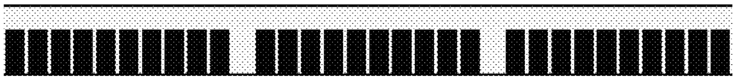

| | | | | |
|---|---|---|---|---|
| NY99 E | CCTGCGGCGC | CTTCACACAC | ACTAAAGCTT | 540 |
| WN02 E | CCTGCGGCGC | CTTCATACAC | ACTAAAGCTT | 540 |
| HEF1 | CCTGCGGCGC | CTTCATACAC | ACTAAAGCTT | 417 |
| HEF3 | CCTGCGGCGC | CTTCATACAC | ACTAAAGCTT | 136 |
| HER3 rev | ---------- | ---------- | ---------- | - |
| HER4 rev | ---------- | ---------- | ---------- | - |
| **Consensus** | **CCTGCGGCGC** | **CTTCATACAC** | **ACTAAAGCTT** | |

100%
Conservation
0%

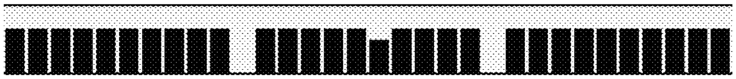

| | | | | |
|---|---|---|---|---|
| NY99 E | GGAGAATATG | GAGAGGTGAC | AGTGGACTGT | 570 |
| WN02 E | GGAGAATATG | GAGAGGTGAC | AGTGGACTGT | 570 |
| HEF1 | GGAGAATATG | GAGAGGTGAC | AGTGGACTGT | 447 |
| HEF3 | GGAGAATATG | GAGAGGTGAC | AGTGGACTGT | 166 |
| HER3 rev | ---------- | ---------- | ---------- | - |
| HER4 rev | ---------- | ---------- | ---------- | - |
| **Consensus** | **GGAGAATATG** | **GAGAGGTGAC** | **AGTGGACTGT** | |

100%
Conservation
0%

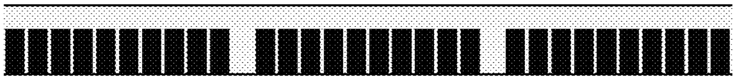

| | | | | |
|---|---|---|---|---|
| NY99 E | GAACCACGGT | CAGGGATTGA | CACCAATGCA | 600 |
| WN02 E | GAACCACGGT | CAGGGATTGA | CACCAATGCA | 600 |
| HEF1 | GAACCACGGT | CAGGGATTGA | CACCAATGCA | 477 |
| HEF3 | GAACCACGGT | CAGGGATTGA | CACCAATGCA | 196 |
| HER3 rev | ---------- | ---------- | ---------- | - |
| HER4 rev | ---------- | ---------- | ---------- | - |
| **Consensus** | **GAACCACGGT** | **CAGGGATTGA** | **CACCAATGCA** | |

100%
Conservation
0%

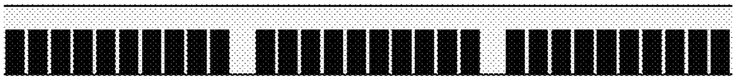

Fig. 10E/17

```
NY99 E     TACTACGTGA TGACTGTTGG AACAAAGACG 630
WN02 E     TACTACGTGA TGACTGTTGG AACAAAGACG 630
HEF1       TACTATGTGA TGACTGTTGG AACAAAGACG 507
HEF3       TACTATGTGA TGACTGTTGG AACAAAGACG 226
HER3 rev   -----TNTGA TGACTGTNGG AACAAAGACG 25
HER4 rev   ---------- ---------- ---------- -
Consensus  TACTATGTGA TGACTGTTGG AACAAAGACG
```

100%
Conservation
0%

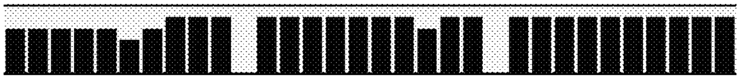

```
NY99 E     TTCTTGGTCC ATCGTGAGTG GTTCATGGAC 660
WN02 E     TTCTTGGTCC ATCGTGAGTG GTTCATGGAC 660
HEF1       TTCTTGGTCC ATCGTGAGTG GTTCATGGAC 537
HEF3       TTCTTGGTCC ATCGTGAGTG GTTCATGGAC 256
HER3 rev   TTCTNNNTCC ATCGTGAGTN NTTCATGGAC 55
HER4 rev   ---------- ---------- ---------- -
Consensus  TTCTTGGTCC ATCGTGAGTG GTTCATGGAC
```

100%
Conservation
0%

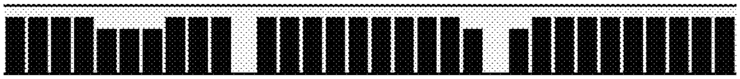

```
NY99 E     CTCAACCTCC CTTGGAGCAG TGCTGG-AAG 689
WN02 E     CTCAACCTCC CTTGGAGCAG TGCTGG-AAG 689
HEF1       CTCAACCTCC CTTGGAGCAG TGCTGG-AAG 566
HEF3       CTCAACCTCC CTTGGAGCAG TGCTGG-AAG 285
HER3 rev   CTCAACCTCC CTTGGAGCAG TGCTGG-AAG 84
HER4 rev   ---------- ----NAGCAG TGCTGGNANG 16
Consensus  CTCAACCTCC CTTGGAGCAG TGCTGG-AAG
```

100%
Conservation
0%

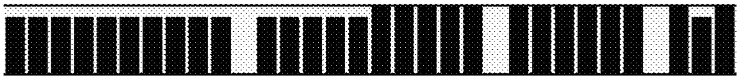

```
NY99 E     TACTGTGTGG AGGAACAGAG AGACGTTAAT 719
WN02 E     TACTGTGTGG AGGAACAGAG AGACGTTAAT 719
HEF1       TACTGTGTGG AGGAACAGAG AGACGTTAAT 596
HEF3       TACTGTGTGG AGGAACAGAG AGACGTTAAT 315
HER3 rev   TACTGTGTGG AGGAACAGAG AGACGTTAAT 114
HER4 rev   TACTGTGTGG AGGAACAGAG AGACGTTAAT 46
Consensus  TACTGTGTGG AGGAACAGAG AGACGTTAAT
```

100%
Conservation
0%

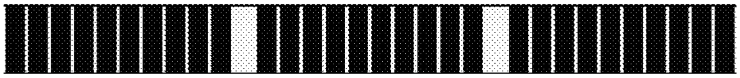

Fig. 10F/17

| | | | | |
|---|---|---|---|---|
| NY99 E | GGAGTTTGAG | GAACCACACG | CCACGAAGCA | 749 |
| WN02 E | GGAGTTTGAG | GAACCACACG | CCACGAAGCA | 749 |
| HEF1 | GGAGTTTGAG | GAACCACACG | CCACGAAGCA | 626 |
| HEF3 | GGAGTTTGAG | GAACCACACG | CCACGAAGCA | 345 |
| HER3 rev | GGAGTTTGAG | GAACCNCACG | CCACGAAGCA | 144 |
| HER4 rev | GGAGTTTGAG | GANCCACACG | CCACGAAGCA | 76 |
| Consensus | **GGAGTTTGAG** | **GAACCACACG** | **CCACGAAGCA** | |

100%
Conservation
0%

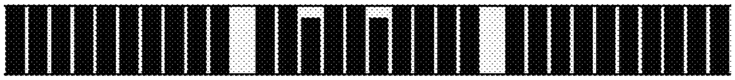

| | | | | |
|---|---|---|---|---|
| NY99 E | GTCTGTGATA | GCATTGGGCT | CACAAGAGGG | 779 |
| WN02 E | GTCTGTGATA | GCATTGGGCT | CACAAGAGGG | 779 |
| HEF1 | GTCTGTGATA | GCATTGGGCT | CACAAGAGGG | 656 |
| HEF3 | GTCTGTGATA | GCATTGGGCT | CACAAGAGGG | 375 |
| HER3 rev | GTCTGTGATA | GCATTGGGCT | CACAAGAGGG | 174 |
| HER4 rev | GTCTGTGATA | GCATTGGGCT | CACAAGAGGG | 106 |
| Consensus | **GTCTGTGATA** | **GCATTGGGCT** | **CACAAGAGGG** | |

100%
Conservation
0%

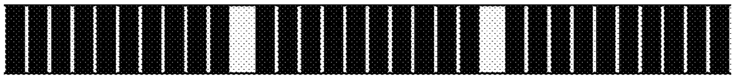

| | | | | |
|---|---|---|---|---|
| NY99 E | AGCTCTGCAG | CAAGCTTTGG | CTGGAGCCAT | 809 |
| WN02 E | AGCTCTGCAT | CAAGCTTTGG | CTGGAGCCAT | 809 |
| HEF1 | AGCTCTGCAT | CAAGCTTTGG | CTGGAGCCAT | 686 |
| HEF3 | AGCTCTGCAT | CAAGCTTTGG | CTGGAGCCAT | 405 |
| HER3 rev | AGCTCTGCAT | CAAGCTTTGG | CTGGAGCCAT | 204 |
| HER4 rev | AGCTCTGCAT | CAAGCTTTGG | CTGGAGCCAT | 136 |
| Consensus | **AGCTCTGCAT** | **CAAGCTTTGG** | **CTGGAGCCAT** | |

100%
Conservation
0%

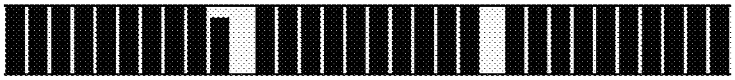

| | | | | |
|---|---|---|---|---|
| NY99 E | TCCTGTGGAA | TTTTCAAGCA | ACACTGTCAA | 839 |
| WN02 E | TCCTGTGGAA | TTTTCAAGCA | ACACTGTCAA | 839 |
| HEF1 | TCCTGTGGAA | TTTTCAAGCA | ACACTGTCAA | 716 |
| HEF3 | TCCTGTGGAA | TTTTCAAGCA | ACACTGTCAA | 435 |
| HER3 rev | TCCTGTGGAA | TTTTCAAGCA | ACACTGTCAA | 234 |
| HER4 rev | TCCTGTGGAA | TTTTCAAGCA | ACACTGTCAA | 166 |
| Consensus | **TCCTGTGGAA** | **TTTTCAAGCA** | **ACACTGTCAA** | |

100%
Conservation
0%

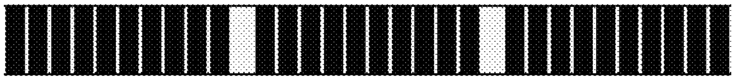

Fig. 10G/17

```
    NY99 E  GTTGACGTCG GGTCATTTGA AGTGTAGAGT 869
    WN02 E  GTTGACGTCG GGTCATTTGA AGTGTAGAGT 869
      HEF1  GTTGACGTCN GGTCATTTGA AGTGTAGAGT 746
      HEF3  GTTGACGTCG GGTCATTTGA AGTGTAGAGT 465
  HER3 rev  GTTGACGTCG GGTCATTTGA AGTGTAGAGT 264
  HER4 rev  GTTGACGTCG GGTCATTTGA AGTGTAGAGT 196
 Consensus  GTTGACGTCG GGTCATTTGA AGTGTAGAGT
```

100%
Conservation
0%

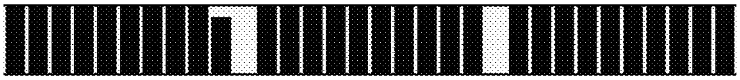

```
    NY99 E  GAAGATGGAA AAATTGCAGT TGAAGGGAAC 899
    WN02 E  GAAGATGGAA AAATTGCAGT TGAAGGGAAC 899
      HEF1  GAAGATGGAA AAATTGCAGT TGAAGGGAAC 776
      HEF3  GAAGATGGAA AAATTGCAGT TGAAGGGAAC 495
  HER3 rev  GAAGATGGAA AAATTGCAGT TGAAGGGAAC 294
  HER4 rev  GAAGATGGAA AAATTGCAGT TGAAGGGAAC 226
 Consensus  GAAGATGGAA AAATTGCAGT TGAAGGGAAC
```

100%
Conservation
0%

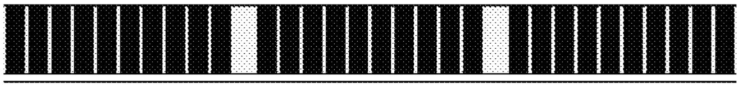

```
    NY99 E  AACCTATGGC GTCTGTTCAA AGGCTTTCAA 929
    WN02 E  AACCTATGGC GTCTGTTCAA AGGCTTTCAA 929
      HEF1  AACCTATGGC GTCTGTTCAA AGGCTTTCAA 806
      HEF3  AACCTATGGC GTCTGTTCAA AGGCTTTCAA 525
  HER3 rev  AACCTATGGC GTCTGTTCAA AGGCTTTCAA 324
  HER4 rev  AACCTATGGC GTCTGTTCAA AGGCTTTCAA 256
 Consensus  AACCTATGGC GTCTGTTCAA AGGCTTTCAA
```

100%
Conservation
0%

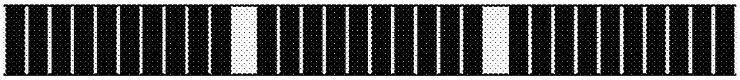

```
    NY99 E  GTTTCTTGGG ACTCCCGCAG ACACAGGTCA 959
    WN02 E  GTTTCTTGGG ACTCCCGCAG ACACAGGTCA 959
      HEF1  GTTTCTTGGG ACTCCCGCAG ACACNNNTCA 836
      HEF3  GTTTCTTGGG ACTCCCGCAG ACACAGGTCA 555
  HER3 rev  GTTTCTTGGG ACTCCCGCAG ACACAGGTCA 354
  HER4 rev  GTTTCTTGGG ACTCCCGCAG ACACAGGTCA 286
 Consensus  GTTTCTTGGG ACTCCCGCAG ACACAGGTCA
```

100%
Conservation
0%

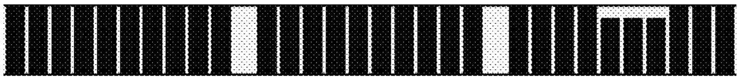

Fig. 10H/17

```
NY99 E     CGGCACTGTG GTGTTGGAAT TGCAGTACAC 989
WN02 E     CGGCACTGTG GTGTTGGAAT TGCAGTACAC 989
HEF1       CNGCACTGTG GTGTTGGNAT TGCAGTACAC 866
HEF3       CGGCACTGTG GTGTTGGAAT TGCAGTACAC 585
HER3 rev   CGGCACTGTG GTGTTGGAAT TGCAGTACAC 384
HER4 rev   CGGCACTGTG GTGTTGGAAT TGCAGTACAC 316
Consensus  CGGCACTGTG GTGTTGGAAT TGCAGTACAC
```

100%
Conservation
0%

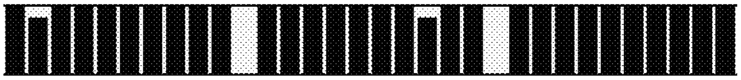

```
NY99 E     TGG-CACGGA TGGACCTTGC AAAGTTCCTA 1018
WN02 E     TGG-CACGGA TGGACCTTGC AAAGTTCCTA 1018
HEF1       TGGGCACGGA TGGACCTTGC AAAGTTNCTA 896
HEF3       TGG-CACGGA TGGACCTTGC AAAGTTCCTA 614
HER3 rev   TGG-CACGGA TGGACCTTGC AAAGTTCCTA 413
HER4 rev   TGG-CACGGA TGGACCTTGC AAAGTTCCTA 345
Consensus  TGG-CACGGA TGGACCTTGC AAAGTTCCTA
```

100%
Conservation
0%

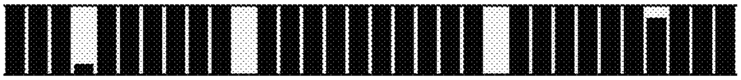

```
NY99 E     TCTCGTCAGT GGCTTCATTG AACGACCTAA 1048
WN02 E     TCTCGTCAGT GGCTTCATTG AACGACCTAA 1048
HEF1       TCTCGTCAGT NGCTTCATTG NACGANCTAA 926
HEF3       TCTCGTCAGT GGCTTCATTG AACGACCTAA 644
HER3 rev   TCTCGTCAGT GGCTTCATTG AACGACCTAA 443
HER4 rev   TCTCGTCAGT GGCTTCATTG AACGACCTAA 375
Consensus  TCTCGTCAGT GGCTTCATTG AACGACCTAA
```

100%
Conservation
0%

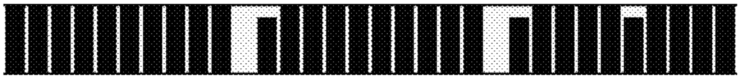

```
NY99 E     CGCCAGTGGG CAGATTGGTC ACTGTCAACC 1078
WN02 E     CGCCAGTGGG CAGATTGGTC ACTGTCAACC 1078
HEF1       CNNCNGTGGG NAGANNNGN- ---------- 945
HEF3       CGCCNGTGGG CAGATTGGTC ACTGTCAACC 674
HER3 rev   CGCCAGTGGG CAGATTGGTC ACTGTCAACC 473
HER4 rev   CGCCAGTGGG CAGATTGGTC ACTGTCAACC 405
Consensus  CGCCAGTGGG CAGATTGGTC ACTGTCAACC
```

100%
Conservation
0%

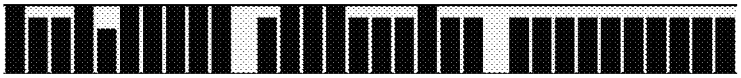

Fig. 10I/17

| | | | | |
|---|---|---|---|---|
| NY99 E | CTTTTGTTTC | AGTGGCCACG | GCCAACGCTA | 1108 |
| WN02 E | CTTTTGTTTC | AGTGGCCACG | GCCAACGCTA | 1108 |
| HEF1 | ---------- | ---------- | ---------- | 945 |
| HEF3 | CTTTTGTTTC | AGTGGCCACG | GCCAACGCTN | 704 |
| HER3 rev | CTTTTGTTTC | AGTGGCCACG | GCCAACGCTA | 503 |
| HER4 rev | CTTTTGTTTC | AGTGGCCACG | GCCAACGCTA | 435 |
| **Consensus** | **CTTTTGTTTC** | **AGTGGCCACG** | **GCCAACGCTA** | |

100%
Conservation
0%

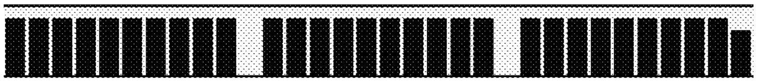

| | | | | |
|---|---|---|---|---|
| NY99 E | AGGTCCTGAT | TGAATTGGAA | CCACCCTTTG | 1138 |
| WN02 E | AGGTCCTGAT | TGAATTGGAA | CCACCCTTTG | 1138 |
| HEF1 | ---------- | ---------- | ---------- | 945 |
| HEF3 | AGGTCCTGAT | TGAATTGGAA | CCACCCTTTG | 734 |
| HER3 rev | AGGTCCTGAT | TGAATTGGAA | CCACCCTTTG | 533 |
| HER4 rev | AGGTCCTGAT | TGAATTGGAA | CCACCCTTTG | 465 |
| **Consensus** | **AGGTCCTGAT** | **TGAATTGGAA** | **CCACCCTTTG** | |

100%
Conservation
0%

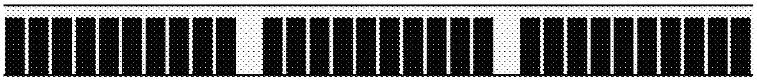

| | | | | |
|---|---|---|---|---|
| NY99 E | GAGACTCATA | CATAGTGGTG | GGCAGAGGAG | 1168 |
| WN02 E | GAGACTCATA | CATAGTGGTG | GGCAGAGGAG | 1168 |
| HEF1 | ---------- | ---------- | ---------- | 945 |
| HEF3 | GAGACTCATA | CATAGTGGTG | GGCAGANGAG | 764 |
| HER3 rev | GAGACTCATA | CATAGTGGTG | GGCAGAGGAG | 563 |
| HER4 rev | GAGACTCATA | CATAGTGGTG | GGCAGAGGAG | 495 |
| **Consensus** | **GAGACTCATA** | **CATAGTGGTG** | **GGCAGAGGAG** | |

100%
Conservation
0%

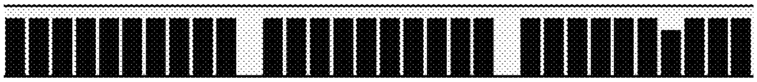

| | | | | |
|---|---|---|---|---|
| NY99 E | AACAACAGAT | CAATCACCAT | TGGCACAAGT | 1198 |
| WN02 E | AACAACAGAT | CAATCACCAT | TGGCACAAGT | 1198 |
| HEF1 | ---------- | ---------- | ---------- | 945 |
| HEF3 | AACAACAGAT | CAATCACCAT | TGGCACNAGT | 794 |
| HER3 rev | AACAACAGAT | CAATCACCAT | TGGCACAAGT | 593 |
| HER4 rev | AACAACAGAT | CAATCACCAT | TGGCACAAGT | 525 |
| **Consensus** | **AACAACAGAT** | **CAATCACCAT** | **TGGCACAAGT** | |

100%
Conservation
0%

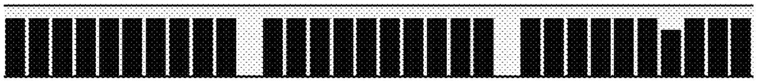

Fig. 10J/17

| | | | | |
|---|---|---|---|---|
| NY99 E | CTGGAAGCAG | CATTGGCAAA | GCCTTTACAA | 1228 |
| WN02 E | CTGGAAGTAG | CATTGGCAAA | GCCTTTACAA | 1228 |
| HEF1 | ---------- | ---------- | ---------- | 945 |
| HEF3 | CTGGAAGCAG | CATTGGCAAA | GCCTTTACNA | 824 |
| HER3 rev | CTGGAAGCAG | CATTGGCAAA | GCCTTTACAA | 623 |
| HER4 rev | CTGGAAGCAG | CATTGGCAAA | GCCTTTACAA | 555 |
| Consensus | **CTGGAAGCAG** | **CATTGGCAAA** | **GCCTTTACAA** | |

100%
Conservation
0%
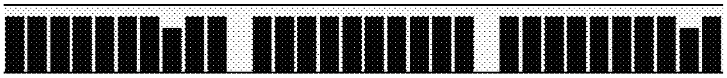

| | | | | |
|---|---|---|---|---|
| NY99 E | CCACCCTCAA | AGGAGCGCAG | AGACTAGCCG | 1258 |
| WN02 E | CCACCCTCAA | AGGAGCGCAG | AGACTAGCCG | 1258 |
| HEF1 | ---------- | ---------- | ---------- | 945 |
| HEF3 | CCACCCTCAA | AGGANCGCAN | ANACTAGCCG | 854 |
| HER3 rev | CCACCCTCAA | AGGAGCGCAG | AGACTAGCCG | 653 |
| HER4 rev | CCACCCTCAA | AGGAGCGCAG | AGACTAGCCG | 585 |
| Consensus | **CCACCCTCAA** | **AGGAGCGCAG** | **AGACTAGCCG** | |

100%
Conservation
0%
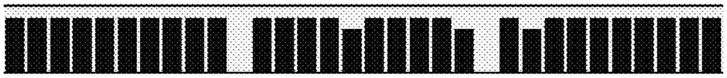

| | | | | |
|---|---|---|---|---|
| NY99 E | CTCTAGGAGA | CACAGCTTGG | GACTTTGGAT | 1288 |
| WN02 E | CTCTAGGAGA | CACAGCTTGG | GACTTTGGAT | 1288 |
| HEF1 | ---------- | ---------- | ---------- | 945 |
| HEF3 | C--------- | ---------- | ---------- | 855 |
| HER3 rev | CTCTAGGAGA | CACAGCTTGG | GACTTTGGAT | 683 |
| HER4 rev | CTCTAGGAGA | CACAGCTTGG | GACTTTGGAT | 615 |
| Consensus | **CTCTAGGAGA** | **CACAGCTTGG** | **GACTTTGGAT** | |

100%
Conservation
0%
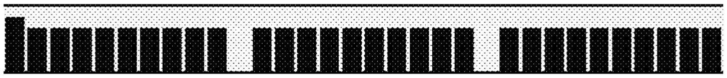

| | | | | |
|---|---|---|---|---|
| NY99 E | CAGTTGGAGG | GGTGTTCACC | TCAGTTGGGA | 1318 |
| WN02 E | CAGTTGGAGG | GGTGTTCACC | TCAGTTGGGA | 1318 |
| HEF1 | ---------- | ---------- | ---------- | 945 |
| HEF3 | ---------- | ---------- | ---------- | 855 |
| HER3 rev | CAGTTGGAGG | GGTGTTCACC | TCAGTTGGGA | 713 |
| HER4 rev | CAGTTGGAGG | GGTGTTCACC | TCAGTTGGGA | 645 |
| Consensus | **CAGTTGGAGG** | **GGTGTTCACC** | **TCAGTTGGGA** | |

100%
Conservation
0%
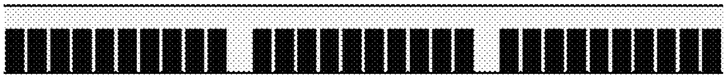

Fig. 10K/17

NY99 E AGGCTGTCCA TCAAGTGTTC GGAGGAGCAT 1348
WN02 E AGGCTGTCCA TCAAGTGTTC GGAGGAGCAT 1348
HEF1 ---------- ---------- ---------- 945
HEF3 ---------- ---------- ---------- 855
HER3 rev AGGCTGTCCA TCAAGTGTTC GGAGGAGCAT 743
HER4 rev AGGCTGTCCA TCAAGTGTTC GGAGGAGCAT 675
Consensus AGGCTGTCCA TCAAGTGTTC GGAGGAGCAT
100%
Conservation
0%

NY99 E TCCGCTCACT GTTCGGAGGC ATGTCCTGGA 1378
WN02 E TCCGCTCACT GTTCGGAGGC ATGTCCTGGA 1378
HEF1 ---------- ---------- ---------- 945
HEF3 ---------- ---------- ---------- 855
HER3 rev TCCGCTCACT GTTCGGAGGC ATGTCCTGGA 773
HER4 rev TCCGCTCACT GTTCGGAGGC ATGTCCTGGA 705
Consensus TCCGCTCACT GTTCGGAGGC ATGTCCTGGA
100%
Conservation
0%

NY99 E TAACGCAAGG ATTGCTGGGG GCTCTCCTGT 1408
WN02 E TAACGCAAGG ATTGCTGGGG GCTCTCCTGT 1408
HEF1 ---------- ---------- ---------- 945
HEF3 ---------- ---------- ---------- 855
HER3 rev TAACGCAAGG ATTGCTGGGG GCTCTCCTGT 803
HER4 rev TAACGCAAGG ATTGCTGGGG GCTCTCCTGT 735
Consensus TAACGCAAGG ATTGCTGGGG GCTCTCCTGT
100%
Conservation
0%

NY99 E TGTGGATGGG CATCAATGCT CGTGATAGGT 1438
WN02 E TGTGGATGGG CATCAATGCT CGTGATAGGT 1438
HEF1 ---------- ---------- ---------- 945
HEF3 ---------- ---------- ---------- 855
HER3 rev TGTGGATGGG CATCAATGCT CGTGATAGGT 833
HER4 rev TGTGGATGGG CATCAATGCT CGTGATAGGT 765
Consensus TGTGGATGGG CATCAATGCT CGTGATAGGT
100%
Conservation
0%

Fig. 10L/17

| | | | | |
|---|---|---|---|---|
| NY99 E | CCATAGCTCT | CACGTTTCTC | GCAGTTGGAG | 1468 |
| WN02 E | CCATAGCTCT | CACGTTTCTC | GCAGTTGGAG | 1468 |
| HEF1 | ---------- | ---------- | ---------- | 945 |
| HEF3 | ---------- | ---------- | ---------- | 855 |
| HER3 rev | CCATAGCTCT | CACGTTTCTC | GCAGTTGGAG | 863 |
| HER4 rev | CCATAGCTCT | CACGTTTCTC | GCAGTTGGAG | 795 |
| Consensus | **CCATAGCTCT** | **CACGTTTCTC** | **GCAGTTGGAG** | |

100%
Conservation
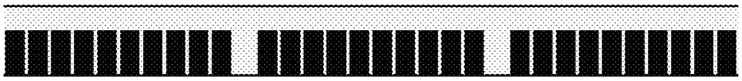
0%

| | | | | |
|---|---|---|---|---|
| NY99 E | GAGTTCTGCT | CTTCCTCTCC | GTGAACGTGC | 1498 |
| WN02 E | GAGTTCTGCT | CTTCCTCTCC | GTGAACGTGC | 1498 |
| HEF1 | ---------- | ---------- | ---------- | 945 |
| HEF3 | ---------- | ---------- | ---------- | 855 |
| HER3 rev | GAGTTCTGCT | CTTCCTTTCC | GTGAACGTGC | 893 |
| HER4 rev | GAGTTCTGCT | CTTCCTTTCC | GTGAACGTGC | 825 |
| Consensus | **GAGTTCTGCT** | **CTTCCTNTCC** | **GTGAACGTGC** | |

100%
Conservation
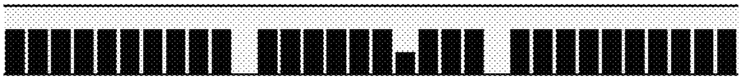
0%

| | | | | |
|---|---|---|---|---|
| NY99 E | ACGCT----- | ---------- | ---------- | 1503 |
| WN02 E | ATGCT----- | ---------- | ---------- | 1503 |
| HEF1 | ---------- | ---------- | ---------- | 945 |
| HEF3 | ---------- | ---------- | ---------- | 855 |
| HER3 rev | ACGCTGACAC | TGGGTGTGCC | ATAGACATCA | 923 |
| HER4 rev | ACGCTGACAC | TGGGTGTGCC | ATAGACATCA | 855 |
| Consensus | **ACGCT**----- | ---------- | ---------- | |

100%
Conservation
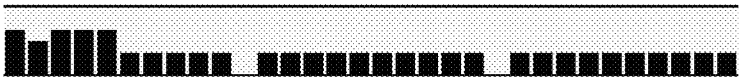
0%

| | | | | |
|---|---|---|---|---|
| NY99 E | ---------- | ---------- | ---------- | 1503 |
| WN02 E | ---------- | ---------- | ---------- | 1503 |
| HEF1 | ---------- | ---------- | ---------- | 945 |
| HEF3 | ---------- | ---------- | ---------- | 855 |
| HER3 rev | GCCGGCAAGA | GCTGAGA--- | ---------- | 940 |
| HER4 rev | GCCGGCAAGA | GCTGAGATGT | GGAAGTGGAG | 885 |
| Consensus | ---------- | ---------- | ---------- | |

100%
Conservation
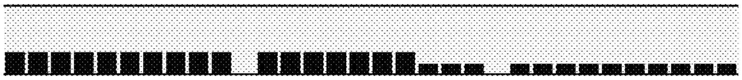
0%

Fig. 10M/17

```
NY99 E       ----------  ----------  ----------  1503
WN02 E       ----------  ----------  ----------  1503
HEF1         ----------  ----------  ----------  945
HEF3         ----------  ----------  ----------  855
HER3 rev     ----------  ----------  ----------  940
HER4 rev     TGTTCATACA  CAATGATGTG  GAGGCTTGGA  915

Consensus    ----------  ----------  ----------
100%
Conservation
0%

NY99 E       ----------  ----------  ----------  1503
WN02 E       ----------  ----------  ----------  1503
HEF1         ----------  ----------  ----------  945
HEF3         ----------  ----------  ----------  855
HER3 rev     ----------  ----------  ----------  940
HER4 rev     TGGACCGGTA  CAAGTATTAC  CCTGAAACGC  945

Consensus    ----------  ----------  ----------
100%
Conservation
0%

NY99 E       ----------  ----------  ----------  1503
WN02 E       ----------  ----------  ----------  1503
HEF1         ----------  ----------  ----------  945
HEF3         ----------  ----------  ----------  855
HER3 rev     ----------  ----------  ----------  940
HER4 rev     CACAAGGCCT  AGCCAAGATC  ATTCAGAAAG  975

Consensus    ----------  ----------  ----------
100%
Conservation
0%

NY99 E       ----------  ----------  ----------  1503
WN02 E       ----------  ----------  ----------  1503
HEF1         ----------  ----------  ----------  945
HEF3         ----------  ----------  ----------  855
HER3 rev     ----------  ----------  ----------  940
HER4 rev     CTCATAAGGA  AGGAGTGTGC  GNTCTACGAT  1005

Consensus    ----------  ----------  ----------
100%
Conservation
0%
```

Fig. 10N/17

```
NY99 E       TTCAACTGCC TTGGAATGAG CAACAGAGAC 30
WN02 E       TTCAACTGCC TTGGAATGAG CAACAGAGAC 30
DEF1         ---------- ---------- ---------- -
DEF3         ---------- ---------- ---------- -
DER3 rev     ---------- ---------- ---------- -
DER4 rev     ---------- ---------- ---------- -
Consensus    ---------- ---------- ----------
100%
Conservation
0%
NY99 E       TTCTTGGAAG GAGTGTCTGG AGCAACATGG 60
WN02 E       TTCTTGGAAG GAGTGTCTGG AGCAACATGG 60
DEF1         ---------- ---------- ---------- -
DEF3         ---------- ---------- ---------- -
DER3 rev     ---------- ---------- ---------- -
DER4 rev     ---------- ---------- ---------- -
Consensus    ---------- ---------- ----------
100%
Conservation
0%
NY99 E       GTGGATTTGG TTCTCGAAGG CGACAGCTGC 90
WN02 E       GTGGATTTGG TTCTCGAAGG CGACAGCTGC 90
DEF1         ---------- ---------- ---------- -
DEF3         ---------- ---------- ---------- -
DER3 rev     ---------- ---------- ---------- -
DER4 rev     ---------- ---------- ---------- -
Consensus    ---------- ---------- ----------
100%
Conservation
0%
NY99 E       GTGACTATCA TGTCTAAGGA CAAGCCTACC 120
WN02 E       GTGACTATCA TGTCTAAGGA CAAGCCTACC 120
DEF1         ---------- ---------- ---------- -
DEF3         ---------- ---------- ---------- -
DER3 rev     ---------- ---------- ---------- -
DER4 rev     ---------- ---------- ---------- -
Consensus    ---------- ---------- ----------
100%
Conservation
0%
```

Fig. 11A/17

```
     NY99 E  ATCGATGTGA AGATGATGAA TATGGAGGCG 150
     WN02 E  ATCGATGTGA AGATGATGAA TATGGAGGCG 150
       DEF1  --CGATGTGN -GANGANGAA TATGGAGGCG 27
       DEF3  ---------- ---------- ---------- -
   DER3 rev  ---------- ---------- ---------- -
   DER4 rev  ---------- ---------- ---------- -
  Consensus  --CGATGTG- -GA-GA-GAA TATGGAGGCG
       100%
Conservation
         0%
     NY99 E  GCCAACCTGG CAGAGGTCCG CAGTTATTGC 180
     WN02 E  GCCAACCTGG CAGAGGTCCG CAGTTATTGC 180
       DEF1  GCCAACCTGG CAGAGGTCCG CAGTTATTGC 57
       DEF3  ---------- ---------- ---------- -
   DER3 rev  ---------- ---------- ---------- -
   DER4 rev  ---------- ---------- ---------- -
  Consensus  GCCAACCTGG CAGAGGTCCG CAGTTATTGC
       100%
Conservation
         0%
     NY99 E  TATTTGGCTA CCGTCAGCGA TCTCTCCACC 210
     WN02 E  TATTTGGCTA CCGTCAGCGA TCTCTCCACC 210
       DEF1  TATTTGGCTA CCGTCAGCGA TCTCTCCACC 87
       DEF3  ---------- ---------- ---------- -
   DER3 rev  ---------- ---------- ---------- -
   DER4 rev  ---------- ---------- ---------- -
  Consensus  TATTTGGCTA CCGTCAGCGA TCTCTCCACC
       100%
Conservation
         0%
     NY99 E  AAAGCTGCGT GCCCGACCAT GGGAGAAGCT 240
     WN02 E  AAAGCTGCGT GCCCGACCAT GGGAGAAGCT 240
       DEF1  AAAGCTGCGT GCCCGACCAT GGGAGAAGCT 117
       DEF3  ---------- ---------- ---------- -
   DER3 rev  ---------- ---------- ---------- -
   DER4 rev  ---------- ---------- ---------- -
  Consensus  AAAGCTGCGT GCCCGACCAT GGGAGAAGCT
       100%
Conservation
         0%
```

Fig. 11B/17

```
     NY99 E  CACAATGACA  AACGTGCTGA  CCCAGCTTTT  270
     WN02 E  CACAATGACA  AACGTGCTGA  CCCAGCTTTT  270
       DEF1  CACAATGACA  AACGTGCTGA  CCCAGCTTTT  147
       DEF3  ----------  ----------  ----------  -
   DER3 rev  ----------  ----------  ----------  -
   DER4 rev  ----------  ----------  ----------  -
  Consensus  CACAATGACA  AACGTGCTGA  CCCAGCTTTT
       100%
Conservation
         0%
     NY99 E  GTGTGCAGAC  AAGGAGTGGT  GGACAGGGGC  300
     WN02 E  GTGTGCAGAC  AAGGAGTGGT  GGACAGGGGC  300
       DEF1  GTGTGCAGAC  AAGGAGTGGT  GGACAGGGGC  177
       DEF3  ----------  ----------  ----------  -
   DER3 rev  ----------  ----------  ----------  -
   DER4 rev  ----------  ----------  ----------  -
  Consensus  GTGTGCAGAC  AAGGAGTGGT  GGACAGGGGC
       100%
Conservation
         0%
     NY99 E  TGGGGCAACG  GCTGCGGACT  ATTTGGCAAA  330
     WN02 E  TGGGGCAACG  GCTGCGGACT  ATTTGGCAAA  330
       DEF1  TGGGGCAACG  GCTGCGGACT  ATTTGGCAAA  207
       DEF3  ----------  ----------  ----------  -
   DER3 rev  ----------  ----------  ----------  -
   DER4 rev  ----------  ----------  ----------  -
  Consensus  TGGGGCAACG  GCTGCGGACT  ATTTGGCAAA
       100%
Conservation
         0%
     NY99 E  GGAAGCATTG  ACACATGCGC  CAAATTTGCC  360
     WN02 E  GGAAGCATTG  ACACATGCGC  CAAATTTGCC  360
       DEF1  GGAAGCATTG  ACACATGCGC  CAAATTTGCC  237
       DEF3  ----------  ----------  ----------  -
   DER3 rev  ----------  ----------  ----------  -
   DER4 rev  ----------  ----------  ----------  -
  Consensus  GGAAGCATTG  ACACATGCGC  CAAATTTGCC
       100%
Conservation
         0%
```

Fig. 11C/17

| | | | | |
|---|---|---|---|---|
| NY99 E | TGCTCTACCA | AGGCAATAGG | AAGAACCATC | 390 |
| WN02 E | TGCTCTACCA | AGGCAATAGG | AAGAACCATC | 390 |
| DEF1 | TGCTCTACCA | AGGCAATAGG | AAGAACCATC | 267 |
| DEF3 | ---------- | ---------- | ---------- | - |
| DER3 rev | ---------- | ---------- | ---------- | - |
| DER4 rev | ---------- | ---------- | ---------- | - |
| Consensus | **TGCTCTACCA** | **AGGCAATAGG** | **AAGAACCATC** | |

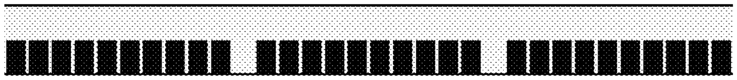

| | | | | |
|---|---|---|---|---|
| NY99 E | TTGAAAGAGA | ATATCAAGTA | CGAAGTGGCC | 420 |
| WN02 E | TTGAAAGAGA | ATATCAAGTA | CGAAGTGGCC | 420 |
| DEF1 | TTGAAAGAGA | ATATCAAGTA | CGAAGTGGCC | 297 |
| DEF3 | ---------- | ----CAAGTA | CGAAGTGGCC | 16 |
| DER3 rev | ---------- | ---------- | ---------- | - |
| DER4 rev | ---------- | ---------- | ---------- | - |
| Consensus | **TTGAAAGAGA** | **ATATCAAGTA** | **CGAAGTGGCC** | |

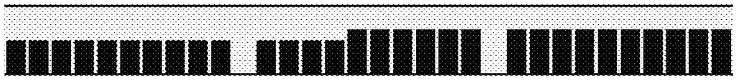

| | | | | |
|---|---|---|---|---|
| NY99 E | ATTTTTGTCC | ATGGACCAAC | TACTGTGGAG | 450 |
| WN02 E | ATTTTTGTCC | ATGGACCAAC | TACTGTGGAG | 450 |
| DEF1 | ATTTTTGTCC | ATGGACCAAC | TACTGTGGAG | 327 |
| DEF3 | ATTTTTGTCC | ATGGACCAAC | TACTGTGGAG | 46 |
| DER3 rev | ---------- | ---------- | ---------- | - |
| DER4 rev | ---------- | ---------- | ---------- | - |
| Consensus | **ATTTTTGTCC** | **ATGGACCAAC** | **TACTGTGGAG** | |

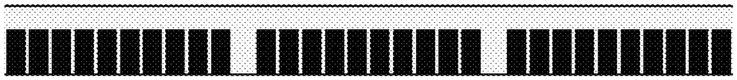

| | | | | |
|---|---|---|---|---|
| NY99 E | TCGCACGGAA | ACTACTCCAC | ACAGGTTGGA | 480 |
| WN02 E | TCGCACGGAA | ACTATTCCAC | ACAGGCTGGA | 480 |
| DEF1 | TCGCACGGAA | ACTACTCCAC | ACAGGCTGGA | 357 |
| DEF3 | TCGCACGGAA | ACTACTCCAC | ACAGGCTGGA | 76 |
| DER3 rev | ---------- | ---------- | ---------- | - |
| DER4 rev | ---------- | ---------- | ---------- | - |
| Consensus | **TCGCACGGAA** | **ACTACTCCAC** | **ACAGGCTGGA** | |

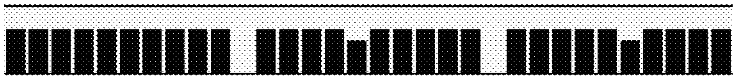

Fig. 11D/17

| | | | | |
|---|---|---|---|---|
| NY99 E | GCCACTCAGG | CAGGGAGATT | CAGCATCACT | 510 |
| WN02 E | GCCACTCAGG | CAGGGAGATT | CAGCATCACT | 510 |
| DEF1 | GCCACTCAGG | CAGGGAGATT | CAGCATCACT | 387 |
| DEF3 | GCCACTCAGG | CAGGGAGATT | CAGCATCACT | 106 |
| DER3 rev | ---------- | ---------- | ---------- | - |
| DER4 rev | ---------- | ---------- | ---------- | - |
| **Consensus** | **GCCACTCAGG** | **CAGGGAGATT** | **CAGCATCACT** | |

100%
Conservation
0%

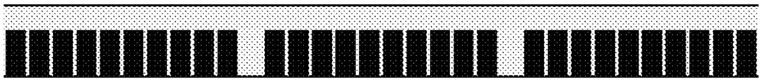

| | | | | |
|---|---|---|---|---|
| NY99 E | CCTGCGGCGC | CTTCACACAC | ACTAAAGCTT | 540 |
| WN02 E | CCTGCGGCGC | CTTCATACAC | ACTAAAGCTT | 540 |
| DEF1 | CCTGCGGCGC | CTTCATACAC | ACTAAAGCTT | 417 |
| DEF3 | CCTGCGGCGC | CTTCATACAC | ACTAAAGCTT | 136 |
| DER3 rev | ---------- | ---------- | ---------- | - |
| DER4 rev | ---------- | ---------- | ---------- | - |
| **Consensus** | **CCTGCGGCGC** | **CTTCATACAC** | **ACTAAAGCTT** | |

100%
Conservation
0%

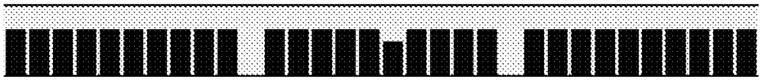

| | | | | |
|---|---|---|---|---|
| NY99 E | GGAGAATATG | GAGAGGTGAC | AGTGGACTGT | 570 |
| WN02 E | GGAGAATATG | GAGAGGTGAC | AGTGGACTGT | 570 |
| DEF1 | GGAGAATATG | GAGAGGTGAC | AGTGGACTGT | 447 |
| DEF3 | GGAGAATATG | GAGAGGTGAC | AGTGGACTGT | 166 |
| DER3 rev | ---------- | ---------- | ---------- | - |
| DER4 rev | ---------- | ---------- | ---------- | - |
| **Consensus** | **GGAGAATATG** | **GAGAGGTGAC** | **AGTGGACTGT** | |

100%
Conservation
0%

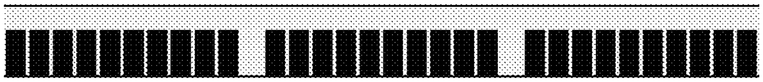

| | | | | |
|---|---|---|---|---|
| NY99 E | GAACCACGGT | CAGGGATTGA | CACCAATGCA | 600 |
| WN02 E | GAACCACGGT | CAGGGATTGA | CACCAATGCA | 600 |
| DEF1 | GAACCACGGT | CAGGGATTGA | CACCAATGCA | 477 |
| DEF3 | GAACCACGGT | CAGGGATTGA | CACCAATGCA | 196 |
| DER3 rev | ---------- | ---------- | -----ATGCN | 5 |
| DER4 rev | ---------- | ---------- | ---------- | - |
| **Consensus** | **GAACCACGGT** | **CAGGGATTGA** | **CACCAATGCA** | |

100%
Conservation
0%

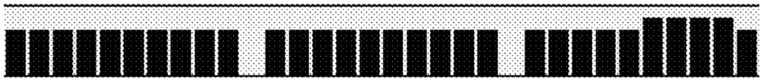

Fig. 11E/17

| | | | | |
|---|---|---|---|---|
| NY99 E | TACTACGTGA | TGACTGTTGG | AACAAAGACG | 630 |
| WN02 E | TACTACGTGA | TGACTGTTGG | AACAAAGACG | 630 |
| DEF1 | TACTACGTGA | TGACTGTTGG | AACAAAGACG | 507 |
| DEF3 | TACTACGTGA | TGACTGTTGG | AACAAAGACG | 226 |
| DER3 rev | NACTACGTGA | TGACTNNGAN | AAGANNNNNN | 35 |
| DER4 rev | ---------- | ---------- | ---------- | - |
| **Consensus** | **TACTACGTGA** | **TGACTGTTGG** | **AACAAAGACG** | |

100%
Conservation
0%

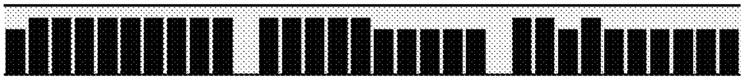

| | | | | |
|---|---|---|---|---|
| NY99 E | TTCTTGGTCC | ATCGTGAGTG | GTTCATGGAC | 660 |
| WN02 E | TTCTTGGTCC | ATCGTGAGTG | GTTCATGGAC | 660 |
| DEF1 | TTCTTGGTCC | ATCGTGAGTG | GTTCATGGAC | 537 |
| DEF3 | TTCTTGGTCC | ATCGTGAGTG | GTTCATGGAC | 256 |
| DER3 rev | T-------CC | ATCGTGAGNN | N--CATGGAN | 56 |
| DER4 rev | ---------- | ---------- | ---------- | - |
| **Consensus** | **TTCTTGGTCC** | **ATCGTGAGTG** | **GTTCATGGAC** | |

100%
Conservation
0%

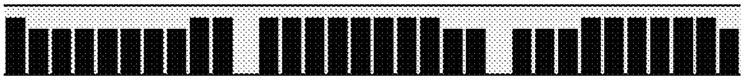

| | | | | |
|---|---|---|---|---|
| NY99 E | CTCAACCTCC | CTTGGAGCAG | TGCTGGAAGT | 690 |
| WN02 E | CTCAACCTCC | CTTGGAGCAG | TGCTGGAAGT | 690 |
| DEF1 | CTCAACCTCC | CTTGGAGCAG | TGCTGGAAGT | 567 |
| DEF3 | CTCAACCTCC | CTTGGAGCAG | TGCTGGAAGT | 286 |
| DER3 rev | CTCANCCTNC | CNNGGAGCAG | TGCTGGAAGT | 86 |
| DER4 rev | ---------- | ---------- | ---------- | - |
| **Consensus** | **CTCAACCTCC** | **CTTGGAGCAG** | **TGCTGGAAGT** | |

100%
Conservation
0%

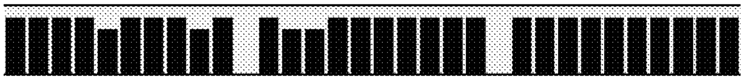

| | | | | |
|---|---|---|---|---|
| NY99 E | ACTGTGTGGA | GGAACAGAGA | GACGTTAATG | 720 |
| WN02 E | ACTGTGTGGA | GGAACAGAGA | GACGTTAATG | 720 |
| DEF1 | ACTGTGTGGA | GGAACAGAGA | GACGTTAATG | 597 |
| DEF3 | ACTGTGTGGA | GGAACAGAGA | GACGTTAATG | 316 |
| DER3 rev | ACTGNGTGGA | GGAACAGAGA | GACGTTAATG | 116 |
| DER4 rev | ---------- | ---------- | ---------- | - |
| **Consensus** | **ACTGTGTGGA** | **GGAACAGAGA** | **GACGTTAATG** | |

100%
Conservation
0%

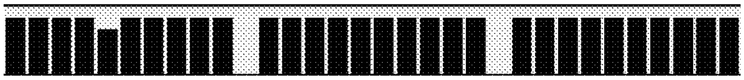

Fig. 11F/17

| | | | | |
|---|---|---|---|---|
| NY99 E | GAGTTTGAGG | AACCACACGC | CACGAAGCAG | 750 |
| WN02 E | GAGTTTGAGG | AACCACACGC | CACGAAGCAG | 750 |
| DEF1 | GAGTTTGAGG | AACCACACGC | CACGAAGCAG | 627 |
| DEF3 | GAGTTTGAGG | AACCACACGC | CACGAAGCAG | 346 |
| DER3 rev | GAGTTTGAGN | AACCNCNCGC | CACGAAGCAG | 146 |
| DER4 rev | ---------- | ---------- | -------CAG | 3 |
| **Consensus** | **GAGTTTGAGG** | **AACCACACGC** | **CACGAAGCAG** | |

100% Conservation 0%

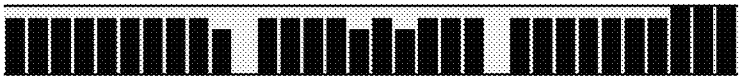

| | | | | |
|---|---|---|---|---|
| NY99 E | TCTGTGATAG | CATTGGGCTC | ACAAGAGGGA | 780 |
| WN02 E | TCTGTGATAG | CATTGGGCTC | ACAAGAGGGA | 780 |
| DEF1 | TCTGTGATAG | CATTGGGCTC | ACAAGAGGGA | 657 |
| DEF3 | TCTGTGATAG | CATTGGGCTC | ACAAGAGGGA | 376 |
| DER3 rev | TCTGTGATAG | CATTGGGCTC | ACAAGAGGGA | 176 |
| DER4 rev | TNNGTGATAN | CNTNGG-CTC | ANAN-AGGNA | 31 |
| **Consensus** | **TCTGTGATAG** | **CATTGGGCTC** | **ACAAGAGGGA** | |

100% Conservation 0%

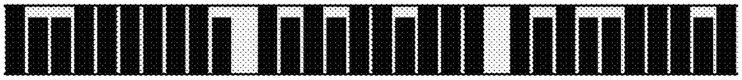

| | | | | |
|---|---|---|---|---|
| NY99 E | GCTCTGCAGC | AAGCTTTGGC | TGGAGCCATT | 810 |
| WN02 E | GCTCTGCATC | AAGCTTTGGC | TGGAGCCATT | 810 |
| DEF1 | GCTCTGCATC | AAGCTTTGGC | TGGAGCCATT | 687 |
| DEF3 | GCTCTGCATC | AAGCTTTGGC | TGGAGCCATT | 406 |
| DER3 rev | GCTNTGCATC | AAGCTTTGGC | NGGAGCCATT | 206 |
| DER4 rev | GNTNTGCATC | AAGCTTTGGC | NGGAGCCATT | 61 |
| **Consensus** | **GCTCTGCATC** | **AAGCTTTGGC** | **TGGAGCCATT** | |

100% Conservation 0%

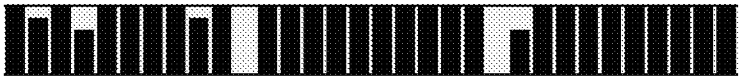

| | | | | |
|---|---|---|---|---|
| NY99 E | CCTGTGGAAT | TTTCAAGCAA | CACTGTCAAG | 840 |
| WN02 E | CCTGTGGAAT | TTTCAAGCAA | CACTGTCAAG | 840 |
| DEF1 | CCTGTGGAAT | TTTCAAGCAA | CACTGTCAAG | 717 |
| DEF3 | CCTGTGGAAT | TTTCAAGCAA | CACTGTCAAG | 436 |
| DER3 rev | CCTGTGGAAT | TTTCAAGCAA | CACTGTCAAG | 236 |
| DER4 rev | NCTGTGGAAT | TTTCAAGCAA | CACTGTCAAG | 91 |
| **Consensus** | **CCTGTGGAAT** | **TTTCAAGCAA** | **CACTGTCAAG** | |

100% Conservation 0%

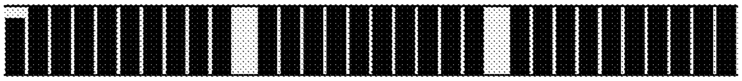

Fig. 11G/17

| | | | | |
|---|---|---|---|---|
| NY99 E | TTGACGTCGG | GTCATTTGAA | GTGTAGAGTG | 870 |
| WN02 E | TTGACGTCGG | GTCATTTGAA | GTGTAGAGTG | 870 |
| DEF1 | TTGACGTCGG | GTCATTTGAA | GTGTAGAGTG | 747 |
| DEF3 | TTGACGTCGG | GTCATTTGAA | GTGTAGAGTG | 466 |
| DER3 rev | TNGACGTCGG | NTCATTTGAA | GTGTAGAGTG | 266 |
| DER4 rev | TTGACGTCGG | GTCATTTGAA | GTGTAGAGTG | 121 |
| Consensus | **TTGACGTCGG** | **GTCATTTGAA** | **GTGTAGAGTG** | |

100%
Conservation
0%

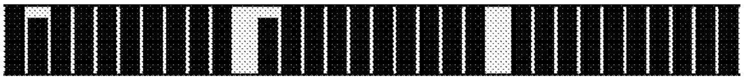

| | | | | |
|---|---|---|---|---|
| NY99 E | AAGATGGAAA | AATTGCAGTT | GAAGGGAACA | 900 |
| WN02 E | AAGATGGAAA | AATTGCAGTT | GAAGGGAACA | 900 |
| DEF1 | AAGATGGAAA | AATTGCAGTT | GAAGGGAACA | 777 |
| DEF3 | AAGATGGAAA | AATTGCAGTT | GAAGGGAACA | 496 |
| DER3 rev | AAGATGGAAA | AATTGCAGTT | GAAGGGAACA | 296 |
| DER4 rev | AAGATGGAAA | AATTGCAGTT | GAAGGGAACA | 151 |
| Consensus | **AAGATGGAAA** | **AATTGCAGTT** | **GAAGGGAACA** | |

100%
Conservation
0%

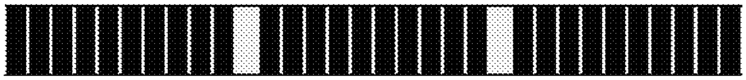

| | | | | |
|---|---|---|---|---|
| NY99 E | ACCTATGGCG | TCTGTTCAAA | GGCTTTCAAG | 930 |
| WN02 E | ACCTATGGCG | TCTGTTCAAA | GGCTTTCAAG | 930 |
| DEF1 | ACCTATGGCG | TCTGTTCAAA | GGCTTTCAAG | 807 |
| DEF3 | ACCTATGGCG | TCTGTTCAAA | GGCTTTCAAG | 526 |
| DER3 rev | ACNTATGGCG | TCTGTTCAAA | GGCTTTCAAG | 326 |
| DER4 rev | ACNTATGGCG | TCTGTTCAAA | GGCTTTCAAG | 181 |
| Consensus | **ACCTATGGCG** | **TCTGTTCAAA** | **GGCTTTCAAG** | |

100%
Conservation
0%

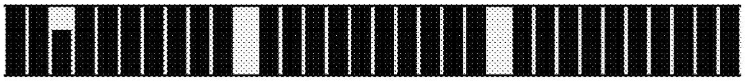

| | | | | |
|---|---|---|---|---|
| NY99 E | TTTCTTGGGA | CTCCCGCAGA | CACAGGTCAC | 960 |
| WN02 E | TTTCTTGGGA | CTCCCGCAGA | CACAGGTCAC | 960 |
| DEF1 | TTTCTTGGGA | CTCCCGCAGA | CACAGGTCAC | 837 |
| DEF3 | TTTCTTGGGA | CTCCCGCAGA | CACAGGTCAC | 556 |
| DER3 rev | TTTCTTGGGA | CTCCCGCAGA | CACAGGTCAC | 356 |
| DER4 rev | TTTCTTGGGA | CTCCCGCAGA | CACAGGTCAC | 211 |
| Consensus | **TTTCTTGGGA** | **CTCCCGCAGA** | **CACAGGTCAC** | |

100%
Conservation
0%

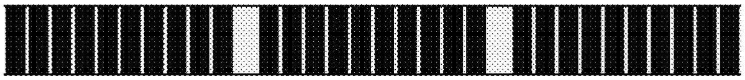

Fig. 11H/17

| | | | | |
|---|---|---|---|---|
| **NY99 E** | GGCACTGTGG | TGTTGGAATT | GCAGTACACT | **990** |
| **WN02 E** | GGCACTGTGG | TGTTGGAATT | GCAGTACACT | **990** |
| **DEF1** | GGCACTGTGG | TGTTGGAATT | GCAGTACACT | **867** |
| **DEF3** | GGCACTGTGG | TGTTGGAATT | GCAGTACACT | **586** |
| **DER3 rev** | GGCACTGTGG | TGTTGGAATT | GCAGTACACT | **386** |
| **DER4 rev** | GGCACTGTGG | TGTNGGAATT | GCAGTACACT | **241** |
| **Consensus** | **GGCACTGTGG** | **TGTTGGAATT** | **GCAGTACACT** | |

100%
Conservation
0%

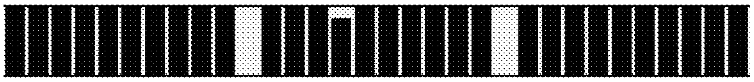

| | | | | |
|---|---|---|---|---|
| **NY99 E** | GGCACGGATG | GACCTTGCAA | AGTTCCTATC | **1020** |
| **WN02 E** | GGCACGGATG | GACCTTGCAA | AGTTCCTATC | **1020** |
| **DEF1** | GGCACGGATG | GACCTTGCNA | AGTTNCTATC | **897** |
| **DEF3** | GGCACGGATG | GACCTTGCAA | AGTTCCTATC | **616** |
| **DER3 rev** | GGCACGGATG | GACCTTGCAA | AGTTCCTATC | **416** |
| **DER4 rev** | GGCACGGATG | GACCTTGCAA | AGTTCCTATC | **271** |
| **Consensus** | **GGCACGGATG** | **GACCTTGCAA** | **AGTTCCTATC** | |

100%
Conservation
0%

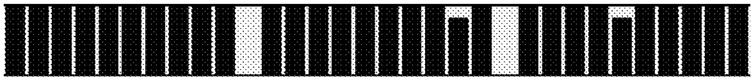

| | | | | |
|---|---|---|---|---|
| **NY99 E** | TCGTCAGTGG | CTTCATTGAA | CGACCTAACG | **1050** |
| **WN02 E** | TCGTCAGTGG | CTTCATTGAA | CGACCTAACG | **1050** |
| **DEF1** | TCGTCAGTGG | CTTCATTGAA | CGANCTAACG | **927** |
| **DEF3** | TCGTCAGTGG | CTTCATTGAA | CGACCTAACG | **646** |
| **DER3 rev** | TCGTCAGTGG | CTTCATTGAA | CGACCTAACG | **446** |
| **DER4 rev** | TCGTCAGTGG | CTTCATTGAA | CGACCTAACG | **301** |
| **Consensus** | **TCGTCAGTGG** | **CTTCATTGAA** | **CGACCTAACG** | |

100%
Conservation
0%

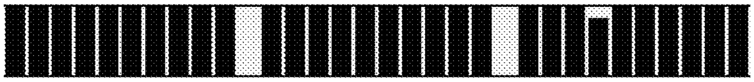

| | | | | |
|---|---|---|---|---|
| **NY99 E** | CCAGTGGGCA | GATTGGTCAC | TGTCAACCCT | **1080** |
| **WN02 E** | CCAGTGGGCA | GATTGGTCAC | TGTCAACCCT | **1080** |
| **DEF1** | CCAGTGNN-A | GANTGGNC-- | ---------- | **944** |
| **DEF3** | CCAGTGGGCA | GATTGGTCAC | TGTCAACCCT | **676** |
| **DER3 rev** | CCAGTGGGCA | GATTGGTCAC | TGTCAACCCT | **476** |
| **DER4 rev** | CCAGTGGGCA | GATTGGTCAC | TGTCAACCCT | **331** |
| **Consensus** | **CCAGTGGGCA** | **GATTGGTCAC** | **TGTCAACCCT** | |

100%
Conservation
0%

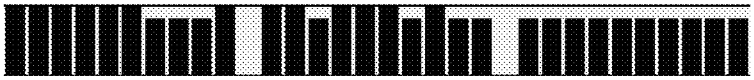

Fig. 11I/17

| | | | | |
|---|---|---|---|---|
| NY99 E | TTTGTTTCAG | TGGCCACGGC | CAACGCTAAG | 1110 |
| WN02 E | TTTGTTTCAG | TGGCCACGGC | CAACGCTAAG | 1110 |
| DEF1 | ---------- | ---------- | ---------- | 944 |
| DEF3 | TTTGTTTCAG | TGGCCACGGC | CAACGCTAAG | 706 |
| DER3 rev | TTTGTTTCAG | TGGCCACGGC | CAACGCTAAG | 506 |
| DER4 rev | TTTGTTTCAG | TGGCCACGGC | CAACGCTAAG | 361 |
| Consensus | **TTTGTTTCAG** | **TGGCCACGGC** | **CAACGCTAAG** | |

100%
Conservation
0%

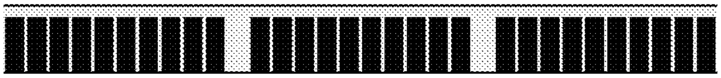

| | | | | |
|---|---|---|---|---|
| NY99 E | GTCCTGATTG | AATTGGAACC | ACCCTTTGGA | 1140 |
| WN02 E | GTCCTGATTG | AATTGGAACC | ACCCTTTGGA | 1140 |
| DEF1 | ---------- | ---------- | ---------- | 944 |
| DEF3 | GTCCTGATTG | AATTGGAACC | ACCCTTTGGA | 736 |
| DER3 rev | GTCCTGATTG | AATTGGAACC | ACCCTTTGGA | 536 |
| DER4 rev | GTCCTGATTG | AATTGGAACC | ACCCTTTGGA | 391 |
| Consensus | **GTCCTGATTG** | **AATTGGAACC** | **ACCCTTTGGA** | |

100%
Conservation
0%

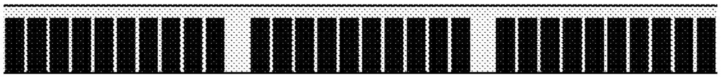

| | | | | |
|---|---|---|---|---|
| NY99 E | GACTCATACA | TAGTGGTGGG | CAGAGGAGAA | 1170 |
| WN02 E | GACTCATACA | TAGTGGTGGG | CAGAGGAGAA | 1170 |
| DEF1 | ---------- | ---------- | ---------- | 944 |
| DEF3 | GACTCATACA | TAGTGGTGGG | CAGAGGAGAA | 766 |
| DER3 rev | GACTCATACA | TAGTGGTGGG | CAGAGGAGAA | 566 |
| DER4 rev | GACTCATACA | TAGTGGTGGG | CAGAGGAGAA | 421 |
| Consensus | **GACTCATACA** | **TAGTGGTGGG** | **CAGAGGAGAA** | |

100%
Conservation
0%

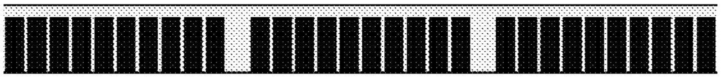

| | | | | |
|---|---|---|---|---|
| NY99 E | CAACAGATCA | ATCACCATTG | GCACAAGTCT | 1200 |
| WN02 E | CAACAGATCA | ATCACCATTG | GCACAAGTCT | 1200 |
| DEF1 | ---------- | ---------- | ---------- | 944 |
| DEF3 | CAACAGATCA | ATCACCATTG | GCACAAGTCT | 796 |
| DER3 rev | CAACAGATCA | ATCACCATTG | GCACAAGTCT | 596 |
| DER4 rev | CAACAGATCA | ATCACCATTG | GCACAAGTCT | 451 |
| Consensus | **CAACAGATCA** | **ATCACCATTG** | **GCACAAGTCT** | |

100%
Conservation
0%

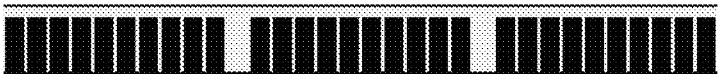

Fig. 11J/17

| | | | | |
|---|---|---|---|---|
| NY99 E | GGAAGCAGCA | TTGGCAAAGC | CTTTACAACC | 1230 |
| WN02 E | GGAAGTAGCA | TTGGCAAAGC | CTTTACAACC | 1230 |
| DEF1 | ---------- | ---------- | ---------- | 944 |
| DEF3 | GGAAGCAGCA | TTGGCAAAGC | CTTTACAACC | 826 |
| DER3 rev | GGAAGCAGCA | TTGGCAAAGC | CTTTACAACC | 626 |
| DER4 rev | GGAAGCAGCA | TTGGCAAAGC | CTTTACAACC | 481 |
| **Consensus** | **GGAAGCAGCA** | **TTGGCAAAGC** | **CTTTACAACC** | |

100%
Conservation
0%

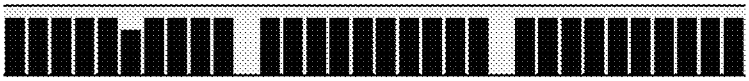

| | | | | |
|---|---|---|---|---|
| NY99 E | ACCCTCAAAG | GAGCGCAGAG | ACTAGCCGCT | 1260 |
| WN02 E | ACCCTCAAAG | GAGCGCAGAG | ACTAGCCGCT | 1260 |
| DEF1 | ---------- | ---------- | ---------- | 944 |
| DEF3 | ACCCTCAAAG | GANCGCAGAG | ACTAGCCGCT | 856 |
| DER3 rev | ACCCTCAAAG | GAGCGCAGAG | ACTAGCCGCT | 656 |
| DER4 rev | ACCCTCAAAG | GAGCGCAGAG | ACTAGCCGCT | 511 |
| **Consensus** | **ACCCTCAAAG** | **GAGCGCAGAG** | **ACTAGCCGCT** | |

100%
Conservation
0%

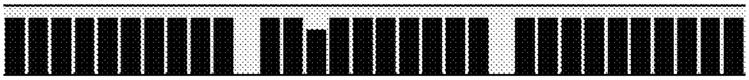

| | | | | |
|---|---|---|---|---|
| NY99 E | CTAGGAGACA | CAGCTTGGGA | CTTTGGATCA | 1290 |
| WN02 E | CTAGGAGACA | CAGCTTGGGA | CTTTGGATCA | 1290 |
| DEF1 | ---------- | ---------- | ---------- | 944 |
| DEF3 | CTAGGANACA | CAGCTTNGGA | CTTTGGATCA | 886 |
| DER3 rev | CTAGGAGACA | CAGCTTGGGA | CTTTGGATCA | 686 |
| DER4 rev | CTAGGAGACA | CAGCTTGGGA | CTTTGGATCA | 541 |
| **Consensus** | **CTAGGAGACA** | **CAGCTTGGGA** | **CTTTGGATCA** | |

100%
Conservation
0%

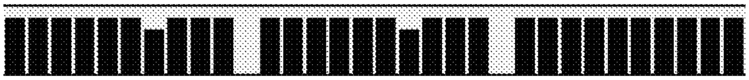

| | | | | |
|---|---|---|---|---|
| NY99 E | GTTGGAGGGG | TGTTCACCTC | AGTTGGGAA- | 1319 |
| WN02 E | GTTGGAGGGG | TGTTCACCTC | AGTTGGGAA- | 1319 |
| DEF1 | ---------- | ---------- | ---------- | 944 |
| DEF3 | GTTGGAGGGG | TGTTCACCTC | AGTTGGGAAN | 916 |
| DER3 rev | GTTGGAGGGG | TGTTCACCTC | AGTTGGGAA- | 715 |
| DER4 rev | GTTGGAGGGG | TGTTCACCTC | AGTTGGGAA- | 570 |
| **Consensus** | **GTTGGAGGGG** | **TGTTCACCTC** | **AGTTGGGAA-** | |

100%
Conservation
0%

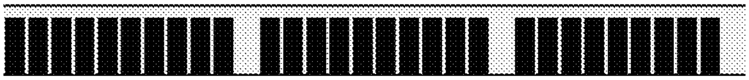

Fig. 11K/17

| | | | | |
|---|---|---|---|---|
| NY99 E | GGCTGTCCAT | CAAGTGTTCG | GAGGAGCATT | 1349 |
| WN02 E | GGCTGTCCAT | CAAGTGTTCG | GAGGAGCATT | 1349 |
| DEF1 | ---------- | ---------- | ---------- | 944 |
| DEF3 | GGNTGTCCAT | CAAGTGNTCG | GAGGAGCATT | 946 |
| DER3 rev | GGCTGTCCAT | CAAGTGTTCG | GAGGAGCATT | 745 |
| DER4 rev | GGCTGTCCAT | CAAGTGTTCG | GAGGAGCATT | 600 |
| Consensus | **GGCTGTCCAT** | **CAAGTGTTCG** | **GAGGAGCATT** | |

100%
Conservation
0%
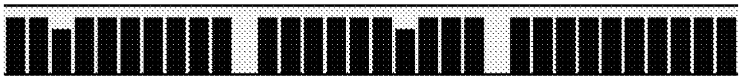

| | | | | |
|---|---|---|---|---|
| NY99 E | -CCGCTCACT | GTTCGGAGGC | ATGTCCTGGA | 1378 |
| WN02 E | -CCGCTCACT | GTTCGGAGGC | ATGTCCTGGA | 1378 |
| DEF1 | ---------- | ---------- | ---------- | 944 |
| DEF3 | NCCGCTCACT | GNTCGGAGGC | ATGTNCNGGN | 976 |
| DER3 rev | -CCGCTCACT | GTTCGGAGGC | ATGTCCTGGA | 774 |
| DER4 rev | -CCGCTCACT | GTTCGGAGGC | ATGTCCTGGA | 629 |
| Consensus | **-CCGCTCACT** | **GTTCGGAGGC** | **ATGTCCTGGA** | |

100%
Conservation
0%
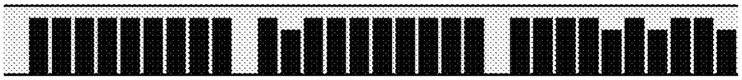

| | | | | |
|---|---|---|---|---|
| NY99 E | TAACGCAAGG | ATTGCTGGGG | GCTCTCCTGT | 1408 |
| WN02 E | TAACGCAAGG | ATTGCTGGGG | GCTCTCCTGT | 1408 |
| DEF1 | ---------- | ---------- | ---------- | 944 |
| DEF3 | NNACGCAAGG | NTNGNTGGGG | G--------- | 997 |
| DER3 rev | TAACGCAAGG | ATTGCTGGGG | GCTCTCCTGT | 804 |
| DER4 rev | TAACGCAAGG | ATTGCTGGGG | GCTCTCCTGT | 659 |
| Consensus | **TAACGCAAGG** | **ATTGCTGGGG** | **GCTCTCCTGT** | |

100%
Conservation
0%
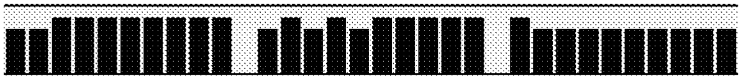

| | | | | |
|---|---|---|---|---|
| NY99 E | TGTGGATGGG | CATCAATGCT | CGTGATAGGT | 1438 |
| WN02 E | TGTGGATGGG | CATCAATGCT | CGTGATAGGT | 1438 |
| DEF1 | ---------- | ---------- | ---------- | 944 |
| DEF3 | ---------- | ---------- | ---------- | 997 |
| DER3 rev | TGTGGATGGG | CATCAATGCT | CGTGATAGGT | 834 |
| DER4 rev | TGTGGATGGG | CATCAATGCT | CGTGATAGGT | 689 |
| Consensus | **TGTGGATGGG** | **CATCAATGCT** | **CGTGATAGGT** | |

100%
Conservation
0%
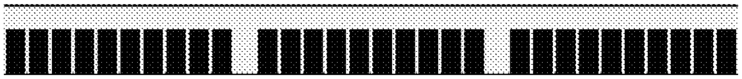

Fig. 11L/17

```
NY99 E     CCATAGCTCT CACGTTTCTC GCAGTTGGAG 1468
WN02 E     CCATAGCTCT CACGTTTCTC GCAGTTGGAG 1468
DEF1       ---------- ---------- ---------- 944
DEF3       ---------- ---------- ---------- 997
DER3 rev   CCATAGCTCT CACGTTTCTC GCAGTTGGAG 864
DER4 rev   CCATAGCTCT CACGTTTCTC GCAGTTGGAG 719
Consensus  CCATAGCTCT CACGTTTCTC GCAGTTGGAG
```

100%
Conservation
0%

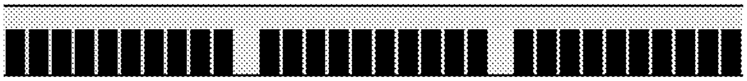

```
NY99 E     GAGTTCTGCT CTTCCTCTCC GTGAACGTGC 1498
WN02 E     GAGTTCTGCT CTTCCTCTCC GTGAACGTGC 1498
DEF1       ---------- ---------- ---------- 944
DEF3       ---------- ---------- ---------- 997
DER3 rev   GAGTTCTGCT CTTCCTCTCC GTGAACGTGC 894
DER4 rev   GAGTTCTGCT CTTCCTCTCC GTGAACGTGC 749
Consensus  GAGTTCTGCT CTTCCTCTCC GTGAACGTGC
```

100%
Conservation
0%

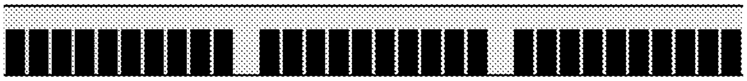

```
NY99 E     ACGCT----- ---------- ---------- 1503
WN02 E     ATGCT----- ---------- ---------- 1503
DEF1       ---------- ---------- ---------- 944
DEF3       ---------- ---------- ---------- 997
DER3 rev   ATGCTGACAC TGGGTGTGCC ATAGACATCA 924
DER4 rev   ATGCTGACAC TGGGTGTGCC ATAGACATCA 779
Consensus  ATGCT----- ---------- ----------
```

100%
Conservation
0%

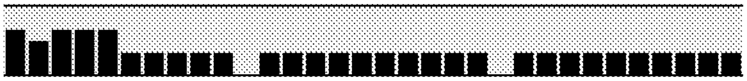

```
NY99 E     ---------- ---------- ---------- 1503
WN02 E     ---------- ---------- ---------- 1503
DEF1       ---------- ---------- ---------- 944
DEF3       ---------- ---------- ---------- 997
DER3 rev   GCCGGCAAGA GCTGAG---- ---------- 940
DER4 rev   GCCGGCAAGA GCTGAGATGT GGAAGTGGAG 809
Consensus  ---------- ---------- ----------
```

100%
Conservation
0%

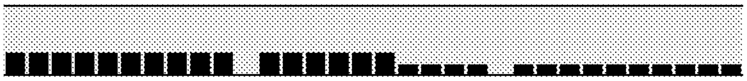

Fig. 11M/17

| | | | | |
|---|---|---|---|---|
| NY99 E | ---------- | ---------- | ---------- | 1503 |
| WN02 E | ---------- | ---------- | ---------- | 1503 |
| DEF1 | ---------- | ---------- | ---------- | 944 |
| DEF3 | ---------- | ---------- | ---------- | 997 |
| DER3 rev | ---------- | ---------- | ---------- | 940 |
| DER4 rev | TGTTCATACA | CAATGATGTG | GAGGCTTGGA | 839 |
| Consensus | ---------- | ---------- | ---------- | |
| 100% Conservation 0% | | | | |

| | | | | |
|---|---|---|---|---|
| NY99 E | ---------- | ---------- | ---------- | 1503 |
| WN02 E | ---------- | ---------- | ---------- | 1503 |
| DEF1 | ---------- | ---------- | ---------- | 944 |
| DEF3 | ---------- | ---------- | ---------- | 997 |
| DER3 rev | ---------- | ---------- | ---------- | 940 |
| DER4 rev | TGGACCGGTA | CAAGTATTAC | CCTGAAACGC | 869 |
| Consensus | ---------- | ---------- | ---------- | |
| 100% Conservation 0% | | | | |

| | | | | |
|---|---|---|---|---|
| NY99 E | ---------- | ---------- | ---------- | 1503 |
| WN02 E | ---------- | ---------- | ---------- | 1503 |
| DEF1 | ---------- | ---------- | ---------- | 944 |
| DEF3 | ---------- | ---------- | ---------- | 997 |
| DER3 rev | ---------- | ---------- | ---------- | 940 |
| DER4 rev | CACAAGGCCT | AGCCAAGATC | ATTCAGAAAG | 899 |
| Consensus | ---------- | ---------- | ---------- | |
| 100% Conservation 0% | | | | |

| | | | | |
|---|---|---|---|---|
| NY99 E | ---------- | ---------- | ---------- | 1503 |
| WN02 E | ---------- | ---------- | ---------- | 1503 |
| DEF1 | ---------- | ---------- | ---------- | 944 |
| DEF3 | ---------- | ---------- | ---------- | 997 |
| DER3 rev | ---------- | ---------- | ---------- | 940 |
| DER4 rev | CTCATAAGGA | AGGAGTGTGC | GGTCTACGAT | 929 |
| Consensus | ---------- | ---------- | ---------- | |
| 100% Conservation 0% | | | | |

Fig. 11N/17

| | | |
|---|---|---|
| NY99 E | - - | 1503 |
| WN02 E | - - | 1503 |
| DEF1 | - - | 944 |
| DEF3 | - - | 997 |
| DER3 rev | - A | 941 |
| DER4 rev | C A | 931 |
| Consensus | - - | |
100%
Conservation
0%
Fig. 11O/17

```
      NY99 NS5  ----------  ----------  ---------- -
      WN02 NS5  ----------  ----------  ---------- -
      D NS5F2   C---------  ----------  ---------- 1
      D NS5F5   TCTCNCGGAT  TCCNCGCACG  AGATGTATTG 30
  D NS5R3 rev   ----------  ----------  ---------- -
  D NS5R5 rev   ----------  ----------  ---------- -
     Consensus  ----------  ----------  ----------
          100%
  Conservation
            0%

      NY99 NS5  ----------  ----------  ---------- -
      WN02 NS5  ----------  ----------  ---------- -
      D NS5F2   ----------  ----------  ---------- 1
      D NS5F5   GGTGAGTCGA  GCTTCAGGCA  ATGTGGTACA 60
  D NS5R3 rev   ----------  ----------  ---------- -
  D NS5R5 rev   ----------  ----------  ---------- -
     Consensus  ----------  ----------  ----------
          100%
  Conservation
            0%

      NY99 NS5  ----------  ----------  ---------- -
      WN02 NS5  ----------  ----------  ---------- -
      D NS5F2   ----------  ----------  ---------- 1
      D NS5F5   TTCAGTGAAT  ATGACCAGCC  AGGTGCTCCT 90
  D NS5R3 rev   ----------  ----------  ---------- -
  D NS5R5 rev   ----------  ----------  ---------- -
     Consensus  ----------  ----------  ----------
          100%
  Conservation
            0%

      NY99 NS5  ----------  ----------  ---------- -
      WN02 NS5  ----------  ----------  ---------- -
      D NS5F2   ----------  ----------  ---------- 1
      D NS5F5   AGGAAGAATG  GAAAAAAGGA  CCTGGAAGGG 120
  D NS5R3 rev   ----------  ----------  ---------- -
  D NS5R5 rev   ----------  ----------  -------GGG 3
     Consensus  ----------  ----------  ----------
          100%
  Conservation
            0%
```

Fig. 12A/17

```
NY99 NS5      ----------  ----------  ----------  -
WN02 NS5      ----------  ----------  ----------  -
D NS5F2       ----------  ----------  ----------  1
D NS5F5       ACCCCAATAC  GAGGAAGATG  TAAACTTGGG  150
D NS5R3 rev   ----------  ----------  ----------  -
D NS5R5 rev   ACCCCAATAC  NNG-AAGATG  TAAACTTGGG  32
Consensus     ----------  ----------  ----------
```

100%
Conservation
0%

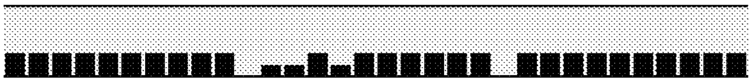

```
NY99 NS5      ----------  ----------  ----------  -
WN02 NS5      ----------  ----------  ----------  -
D NS5F2       ----------  ----------  ----------  1
D NS5F5       AAGTGGAACC  AGGGCGGTGG  GAAAACCCCT  180
D NS5R3 rev   ----------  ----------  ----------  -
D NS5R5 rev   AAGNN-ANCN  NGGGCGGTGG  GAAA--CCNN  59
Consensus     ----------  ----------  ----------
```

100%
Conservation
0%

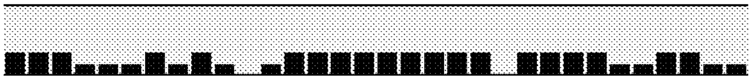

```
NY99 NS5      ----------  ----------  ----------  -
WN02 NS5      ----------  ----------  ----------  -
D NS5F2       ----------  ----------  ----------  1
D NS5F5       GCTCAACTCA  GACACCAGTA  AAATCAAGAA  210
D NS5R3 rev   ----------  ----------  ----------  -
D NS5R5 rev   GNTCAACTCA  GACNCCAGTA  AAATCAAGAN  89
Consensus     ----------  ----------  ----------
```

100%
Conservation
0%

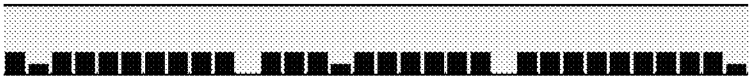

```
NY99 NS5      ----------  ----------  ----------  -
WN02 NS5      ----------  ----------  ----------  -
D NS5F2       ----------  ----------  ----------  1
D NS5F5       CAGGATTGAA  CGACTCAGGC  GTGAGTACAG  240
D NS5R3 rev   ----------  ----------  ----------  -
D NS5R5 rev   CAGGATTGAA  CGANTCAGGC  GTGAGTACAG  119
Consensus     ----------  ----------  ----------
```

100%
Conservation
0%

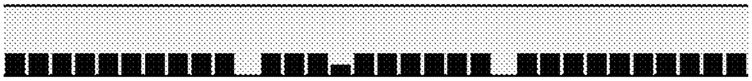

Fig. 12B/17

```
NY99 NS5      ----------  ----------  ----------  -
WN02 NS5      ----------  ----------  ----------  -
D NS5F2       ----------  ----------  ----------  1
D NS5F5       TTCGACGTGG  CACCACGATG  AGAACCACCC  270
D NS5R3 rev   ----------  ----------  ----------  -
D NS5R5 rev   TTCGACGTGG  CACCACGATG  AGAACCACCC  149
Consensus     ----------  ----------  ----------
```

100% Conservation 0%

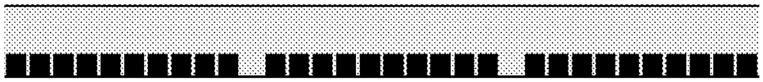

```
NY99 NS5      ----------  ----------  ----------  -
WN02 NS5      ----------  ----------  ----------  -
D NS5F2       ----------  ----------  ----------  1
D NS5F5       ATATAGAACC  TGGAACTATC  ACGGCAGTTA  300
D NS5R3 rev   ----------  ----------  ----------  -
D NS5R5 rev   ATATAGANCN  NGGAACTATC  ACGGCAGTTA  179
Consensus     ----------  ----------  ----------
```

100% Conservation 0%

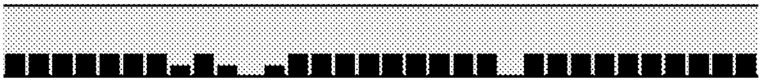

```
NY99 NS5      ----------  ----------  ----------  -
WN02 NS5      ----------  ----------  ----------  -
D NS5F2       ----------  ----------  ----------  1
D NS5F5       TGATGTGAAG  CCCACAGGCT  CCGCCAGTTC  330
D NS5R3 rev   ----------  ----------  -------TTC  3
D NS5R5 rev   TGATGTGAAG  CCCACAGGCT  CCGCCAGTTC  209
Consensus     ----------  ----------  -------TTC
```

100% Conservation 0%

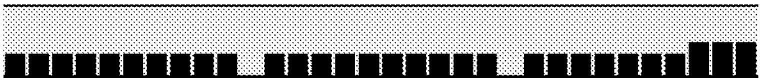

```
NY99 NS5      ----------  ----------  ----------  -
WN02 NS5      ----------  ----------  ----------  -
D NS5F2       ----------  ----------  ----------  1
D NS5F5       GCTGGTCAAT  GGAGTGGTCA  GGCTCCTCTC  360
D NS5R3 rev   GCTNGTCAAT  GGAGTNGTCA  GGCTCCTCTC  33
D NS5R5 rev   GCTGGTCAAT  GGAGTGGTCA  GGCTCCTCTC  239
Consensus     GCT-GTCAAT  GGAGT-GTCA  GGCTCCTCTC
```

100% Conservation 0%

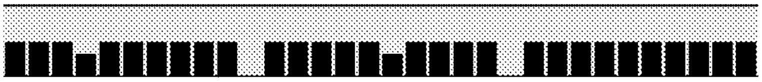

Fig. 12C/17

```
NY99 NS5      ----------  ----------  ----------  -
WN02 NS5      ----------  ----------  ----------  -
D NS5F2       ----------  ----------  ----------  1
D NS5F5       AAAACCATGG  GACACCATCA  CGAATGTTAC  390
D NS5R3 rev   AAAACCATGG  GACACCATCA  CGAATNNN-C  62
D NS5R5 rev   AAAACCATGG  GACACCATCA  CGAATGTTAC  269
Consensus     AAAACCATGG  GACACCATCA  CGAAT----C
100%
Conservation
0%
NY99 NS5      ----------  ----------  ----------  -
WN02 NS5      ----------  ----------  ----------  -
D NS5F2       ----------  ----------  ----------  1
D NS5F5       CACCATGGCC  ATGACTGACA  CTACTCCC-T  419
D NS5R3 rev   CACCATGGCC  ATGACTGACA  CTACTCCCNT  92
D NS5R5 rev   CACCATGGCC  ATGACTGACA  CTACTCCC-T  298
Consensus     CACCATGGCC  ATGACTGACA  CTACTCCC-T
100%
Conservation
0%
NY99 NS5      ----------  ----------  ----------  -
WN02 NS5      ----------  ----------  ----------  -
D NS5F2       ----------  ----------  ----------  1
D NS5F5       TCGGGCAGCA  GCGAGTGTTC  AAAGAGAAGG  449
D NS5R3 rev   TCGGGCAGCA  GCGAGTGTTC  AAAGAGAAGG  122
D NS5R5 rev   TCGGGCAGCA  GCGAGTGTTC  AAAGAGAAGG  328
Consensus     TCGGGCAGCA  GCGAGTGTTC  AAAGAGAAGG
100%
Conservation
0%
NY99 NS5      ----------  ----------  ----------  -
WN02 NS5      ----------  ----------  ----------  -
D NS5F2       ----------  ----------  ----------  1
D NS5F5       TGGACACGAA  AGCTCCTGAA  CCGCCAGAAG  479
D NS5R3 rev   TGGACACGAA  AGCTNNNGAA  CCGCCAGAAG  152
D NS5R5 rev   TGGACACGAA  AGCTCCTGAA  CCGCCAGAAG  358
Consensus     TGGACACGAA  AGCT---GAA  CCGCCAGAAG
100%
Conservation
0%
```

Fig. 12D/17

```
NY99 NS5       ----------  ----------  ---------- -
WN02 NS5       ----------  ----------  ---------- -
D NS5F2        ----------  ----------  ---------- 1
D NS5F5        GAGTGAAGTA  CGTGCTCAAC  GAGACCACCA 509
D NS5R3 rev    GAGTGAAGTA  CGTGCTCAAC  GAGACCACCA 182
D NS5R5 rev    GAGTGAAGTA  CGTGCTCAAC  GAGACCACCA 388
Consensus      GAGTGAAGTA  CGTGCTCAAC  GAGACCACCA
```

100%
Conservation
0%

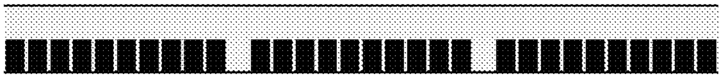

```
NY99 NS5       ----------  ----------  ---------- -
WN02 NS5       ----------  ----------  ---------- -
D NS5F2        ----------  ----------  ---------- 1
D NS5F5        ACTGGTTGTG  GGCGTTTTTG  GCCAGAGAAA 539
D NS5R3 rev    ACTGGTTGTG  GGCGTTTTTG  GCCAGAGAAA 212
D NS5R5 rev    ACTGGTTGTG  GGCGTTTTTG  GCCAGAGAAA 418
Consensus      ACTGGTTGTG  GGCGTTTTTG  GCCAGAGAAA
```

100%
Conservation
0%

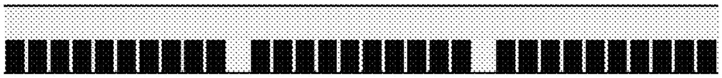

```
NY99 NS5       ----------  ----------  ---------- -
WN02 NS5       ----------  ----------  ---------- -
D NS5F2        ----------  ----------  ---------- 1
D NS5F5        AACGTCCCAG  AATGTGCTCT  CGAGAGGAAT 569
D NS5R3 rev    AACGTCCCAG  AATGTGCTCT  CGAGAGGAAT 242
D NS5R5 rev    AACGTCCCAG  AATGTGCTCT  CGAGAGGAAT 448
Consensus      AACGTCCCAG  AATGTGCTCT  CGAGAGGAAT
```

100%
Conservation
0%

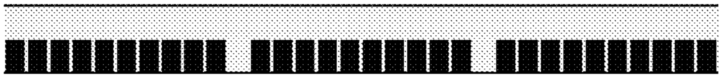

```
NY99 NS5       ----------  ----------  ---------- -
WN02 NS5       ----------  ----------  ---------- -
D NS5F2        ----------  -----ACAGC  AATGCAGCTT 16
D NS5F5        TCATAAGAAA  GGTCAACAGC  AATGCAGCTT 599
D NS5R3 rev    TCATNAGAAA  GGTCAACAGC  AATGCAGCTT 272
D NS5R5 rev    TCATAAGAAA  GGTCAACAGC  AATGCAGCTT 478
Consensus      TCAT-AGAAA  GGTCAACAGC  AATGCAGCTT
```

100%
Conservation
0%

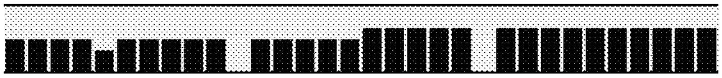

Fig. 12E/17

```
NY99 NS5      ---------- ---------- ---------- -
WN02 NS5      ---------- ---------- ---------- -
D NS5F2       TGGGTGCCNT GTTTGAAGAG CAGAATCAAT 46
D NS5F5       TGGGTGCCAT GTTTGAAGAG CAGAATCAAT 629
D NS5R3 rev   TGGGTGCCAT GTTTGAAGAG CAGAATCAAT 302
D NS5R5 rev   TGGGTGCCAT GTTTGAAGAG CAGAATCAAT 508
Consensus     TGGGTGCCAT GTTTGAAGAG CAGAATCAAT
```

100%
Conservation
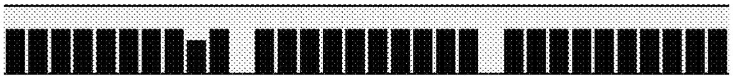
0%

```
NY99 NS5      ---------- ---------- ---------- -
WN02 NS5      ---------- ---------- ---------- -
D NS5F2       GGAGGAGCGC CAGAGAAGCA GTTGAAGATC 76
D NS5F5       GGAGGAGCGC CAGAGAAGCA GTTGAAGATC 659
D NS5R3 rev   GGAGGAGCGC CAGAGAAGCA GTTGAAGATC 332
D NS5R5 rev   GGAGGAGCGC CAGAGAAGCA GTTGAAGATC 538
Consensus     GGAGGAGCGC CAGAGAAGCA GTTGAAGATC
```

100%
Conservation
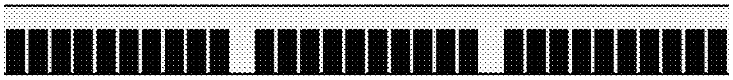
0%

```
NY99 NS5      ---------- ---------- ---------- -
WN02 NS5      ---------- ---------- ---------- -
D NS5F2       CAAAATTTTG GGAGATGGTG GATGAGGAGC 106
D NS5F5       CAAAATTTTG GGAGATGGTG GATGAGGAGC 689
D NS5R3 rev   CAAAATTTTG GGAGATGGTG GATGAGGAGC 362
D NS5R5 rev   CAAAATTTTG GGAGATGGTG GATGAGGAGC 568
Consensus     CAAAATTTTG GGAGATGGTG GATGAGGAGC
```

100%
Conservation
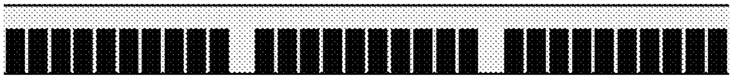
0%

```
NY99 NS5      ---------- ----CGGGGG GAATGTCACA 16
WN02 NS5      ---------- ----CGGGGG GAATGTCACA 16
D NS5F2       GCGAGGCACA TCTGCGGGGG GAATGTCACA 136
D NS5F5       GCGAGGCACA TCTGCGGGGG GAATGTCACA 719
D NS5R3 rev   GCGAGGCACA TCTGCGGGGG GAATGTCACA 392
D NS5R5 rev   GCGAGGCACA TCTGCGGGGG GAATGTCACA 598
Consensus     GCGAGGCACA TCTGCGGGGG GAATGTCACA
```

100%
Conservation
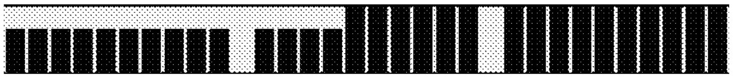
0%

Fig. 12F/17

| | | | | |
|---|---|---|---|---|
| NY99 NS5 | CTTGCATTTA | CAACATGATG | GGAAAGAGAG | 46 |
| WN02 NS5 | CTTGCATTTA | CAACATGATG | GGAAAGAGAG | 46 |
| D NS5F2 | CTTGCATTTA | CAACATGATG | GGAAAGAGAG | 166 |
| D NS5F5 | CTTGCATTTA | CAACATGATG | GGAAAGAGAG | 749 |
| D NS5R3 rev | CTTGCATTTA | CAACATGATG | GGAAAGAGAG | 422 |
| D NS5R5 rev | CTTGCATTTA | CAACATGATG | GGAAAGAGAG | 628 |
| **Consensus** | **CTTGCATTTA** | **CAACATGATG** | **GGAAAGAGAG** | |

100% Conservation 0%

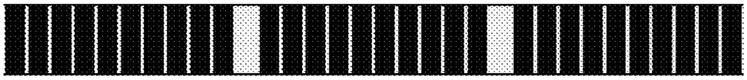

| | | | | |
|---|---|---|---|---|
| NY99 NS5 | AGAAAAAACC | CGGAGAATTC | GGAAAGGCCA | 76 |
| WN02 NS5 | AGAAAAAACC | CGGAGAGTTC | GGAAAGGCCA | 76 |
| D NS5F2 | AGAAAAAACC | CGGAGAGTTC | GGAAAGGCCA | 196 |
| D NS5F5 | AGAAAAAACC | CGGAGAGTTC | GGAAAGGCCA | 779 |
| D NS5R3 rev | AGAAAAAACC | CGGAGAGTTC | GGAAAGGCCA | 452 |
| D NS5R5 rev | AGAAAAAACC | CGGAGAGTTC | GGAAAGGCCA | 658 |
| **Consensus** | **AGAAAAAACC** | **CGGAGAGTTC** | **GGAAAGGCCA** | |

100% Conservation 0%

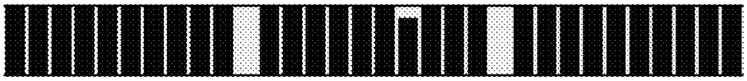

| | | | | |
|---|---|---|---|---|
| NY99 NS5 | AGGGAAGCAG | AGCCATTTGG | TTCATGTGGC | 106 |
| WN02 NS5 | AGGGAAGCAG | AGCCATTTGG | TTCATGTGGC | 106 |
| D NS5F2 | AGGGAAGCAG | AGCCATTTGG | TTCATGTGGC | 226 |
| D NS5F5 | AGGGAAGCAG | AGCCATTTGG | TTCATGTGGC | 809 |
| D NS5R3 rev | AGGGAAGCAG | AGCCATTTGG | TTCATGTGGC | 482 |
| D NS5R5 rev | AGGGAAGCAG | AGCCATTTGG | TTCATGTGGC | 688 |
| **Consensus** | **AGGGAAGCAG** | **AGCCATTTGG** | **TTCATGTGGC** | |

100% Conservation 0%

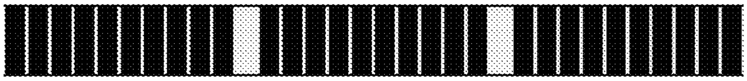

| | | | | |
|---|---|---|---|---|
| NY99 NS5 | TCGGAGCTCG | CTTTCTGGAG | TTCGAGGCTC | 136 |
| WN02 NS5 | TCGGAGCTCG | CTTTCTGGAG | TTCGAGGCTC | 136 |
| D NS5F2 | TCGGAGCTCG | CTTTCTGGAG | TTCGAGGCTC | 256 |
| D NS5F5 | TCGGANCTCG | CTTTCTGGAG | TTCGAGGCTC | 839 |
| D NS5R3 rev | TCGGAGCTCG | CTTTCTGGAG | TTCGAGGCTC | 512 |
| D NS5R5 rev | TCGGAGCTCG | CTTTCTGGAG | TTCGAGGCTC | 718 |
| **Consensus** | **TCGGAGCTCG** | **CTTTCTGGAG** | **TTCGAGGCTC** | |

100% Conservation 0%

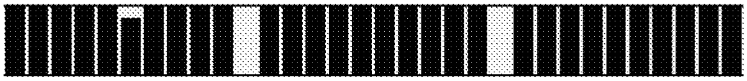

Fig. 12G/17

| | | | | |
|---|---|---|---|---|
| NY99 NS5 | TGGGTTTTCT | CAATGAAGAC | CACTGGCTTG | 166 |
| WN02 NS5 | TGGGTTTTCT | CAATGAAGAC | CACTGGCTTG | 166 |
| D NS5F2 | TGGGTTTTCT | CAATGAAGAC | CACTGGCTTG | 286 |
| D NS5F5 | TGGGTTTTCT | CAATGAAGAC | CACTGGCTTG | 869 |
| D NS5R3 rev | TGGGTTTTCT | CAATGAAGAC | CACTGGCTTG | 542 |
| D NS5R5 rev | TGGGTTTTCT | CAATGAAGAC | CACTGGCTTG | 748 |
| Consensus | **TGGGTTTTCT** | **CAATGAAGAC** | **CACTGGCTTG** | |

100% Conservation 0%

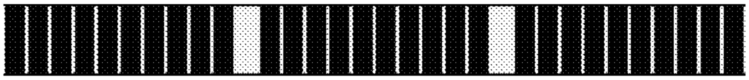

| | | | | |
|---|---|---|---|---|
| NY99 NS5 | GAAGAAAGAA | CTCAGGAGGA | GGTGTCGAGG | 196 |
| WN02 NS5 | GAAGAAAGAA | CTCAGGAGGA | GGTGTCGAGG | 196 |
| D NS5F2 | GAAGAAAGAA | CTCAGGAGGA | GGTGTCGAGG | 316 |
| D NS5F5 | GAAGNNN-AA | CTCNNNNNGA | GGTGTCGAGG | 898 |
| D NS5R3 rev | GAAGAAAGAA | CTCAGGAGGA | GGTGTCGAGG | 572 |
| D NS5R5 rev | GAAGAAAGAA | CTCAGGAGGA | GGTGTCGAGG | 778 |
| Consensus | **GAAGAAAGAA** | **CTCAGGAGGA** | **GGTGTCGAGG** | |

100% Conservation 0%

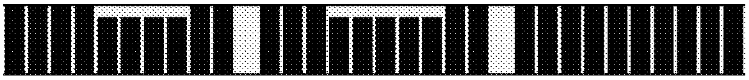

| | | | | |
|---|---|---|---|---|
| NY99 NS5 | GCTTGGGCCT | CCAAAAACTG | GGTTACATCC | 226 |
| WN02 NS5 | GCTTGGGCCT | CCAAAAACTG | GGTTACATCC | 226 |
| D NS5F2 | GCTTGGGCCT | CCAAAAACTG | GGTTACATCC | 346 |
| D NS5F5 | GCTTNNNC-T | CCAAAAACTG | GGTTACATCC | 927 |
| D NS5R3 rev | GCTTGGGCCT | CCAAAAACTG | GGTTACATCC | 602 |
| D NS5R5 rev | GCTTGGGCCT | CCAAAAACTG | GGTTACATCC | 808 |
| Consensus | **GCTTGGGCCT** | **CCAAAAACTG** | **GGTTACATCC** | |

100% Conservation 0%

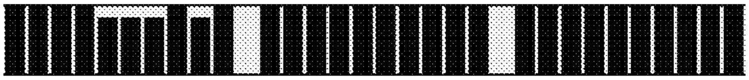

| | | | | |
|---|---|---|---|---|
| NY99 NS5 | TGCGTGAAGT | TGGCACCCGG | CCTGGGGGCA | 256 |
| WN02 NS5 | TGCGTGAAGT | TGGCACCCGG | CCTGGGGGCA | 256 |
| D NS5F2 | TGCGTGAAGT | TGGCACCCGG | CCTGGGGGCA | 376 |
| D NS5F5 | NGCGTGAAGT | NG-CACCCNG | NCTGGGGGC- | 955 |
| D NS5R3 rev | TGCGTGAAGT | TGGCACCCGG | CCTGGGGGCA | 632 |
| D NS5R5 rev | TGCGTGAAGT | TGGCACCCGG | CCTGGGGGCA | 838 |
| Consensus | **TGCGTGAAGT** | **TGGCACCCGG** | **CCTGGGGGCA** | |

100% Conservation 0%

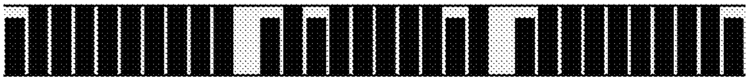

Fig. 12H/17

| | | | | |
|---|---|---|---|---|
| NY99 NS5 | AGATCTATGC | TGATGACACA | GCTGGCTGGG | 286 |
| WN02 NS5 | AGATCTATGC | TGATGACACA | GCTGGCTGGG | 286 |
| D NS5F2 | AGATCTATGC | TGATGACACA | GCTGGCTGGG | 406 |
| D NS5F5 | ---------- | ---------- | ---------- | 955 |
| D NS5R3 rev | AGATCTATGC | TGATGACACA | GCTGGCTGGG | 662 |
| D NS5R5 rev | AGATCTATGC | TGATGACACA | GCTGGCTGGG | 868 |
| **Consensus** | **AGATCTATGC** | **TGATGACACA** | **GCTGGCTGGG** | |

100%
Conservation
0%

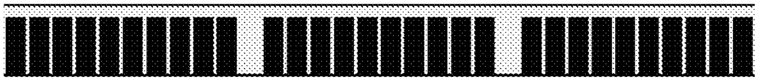

| | | | | |
|---|---|---|---|---|
| NY99 NS5 | ACACCCGCAT | CACGAGAGCT | GACTTGGAAA | 316 |
| WN02 NS5 | ACACCCGCAT | CACGAGTGCT | GACTTGGAAA | 316 |
| D NS5F2 | ACACCCGCAT | CACGAGAGCT | GACTTGGAAA | 436 |
| D NS5F5 | ---------- | ---------- | ---------- | 955 |
| D NS5R3 rev | ACACCCGCAT | CACGAGAGCT | GACTTGGAAA | 692 |
| D NS5R5 rev | ACACCCGCAT | CACGAGAGCT | GACTTGGAAA | 898 |
| **Consensus** | **ACACCCGCAT** | **CACGAGAGCT** | **GACTTGGAAA** | |

100%
Conservation
0%

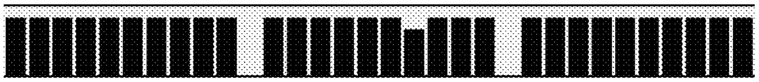

| | | | | |
|---|---|---|---|---|
| NY99 NS5 | ATGAAGCTAA | GGTGCTTGAG | CTGCTTGATG | 346 |
| WN02 NS5 | ATGAAGCTAA | GGTGCTTGAG | TTGCTTGATG | 346 |
| D NS5F2 | ATGAAGCTAA | GGTGCTTGAG | TTGCTTGATG | 466 |
| D NS5F5 | ---------- | ---------- | ---------- | 955 |
| D NS5R3 rev | ATGAAGCTAA | GGTGCTTGAG | TTGCTTGATG | 722 |
| D NS5R5 rev | ATGAAGCTAA | GGTGCTTGAG | TTGCTTGATG | 928 |
| **Consensus** | **ATGAAGCTAA** | **GGTGCTTGAG** | **TTGCTTGATG** | |

100%
Conservation
0%

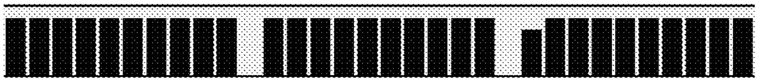

| | | | | |
|---|---|---|---|---|
| NY99 NS5 | GGGAACATCG | GCGTCTTGCC | AGGGCCATCA | 376 |
| WN02 NS5 | GGGAACATCG | GCGTCTTGCC | AGGGCCATCA | 376 |
| D NS5F2 | GGGAACATCG | GCGTCTTGCC | AGGGCCATCA | 496 |
| D NS5F5 | ---------- | ---------- | ---------- | 955 |
| D NS5R3 rev | GGGAACATCG | GCGTCTTGCC | AGGGCCATCA | 752 |
| D NS5R5 rev | GGGAACATCG | GCGTCTTGCC | AGGGCCATCA | 958 |
| **Consensus** | **GGGAACATCG** | **GCGTCTTGCC** | **AGGGCCATCA** | |

100%
Conservation
0%

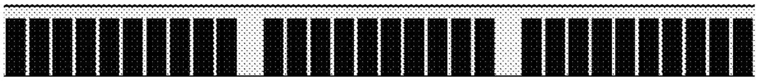

Fig. 12I/17

| | | | | |
|---|---|---|---|---|
| NY99 NS5 | TTGAGCTCAC | CTATCGTCAC | AAAGTTGTGA | 406 |
| WN02 NS5 | TTGAGCTCAC | CTATCGTCAC | AAAGTTGTGA | 406 |
| D NS5F2 | TTGAGCTCAC | CTATCGTCAC | AAAGTTGTGA | 526 |
| D NS5F5 | ---------- | ---------- | ---------- | 955 |
| D NS5R3 rev | TTGAGCTCAC | CTATCGTCAC | AAAGTTGTGA | 782 |
| D NS5R5 rev | TTGAGCTCAC | CNA------- | ---------- | 971 |
| **Consensus** | **TTGAGCTCAC** | **CTATCGTCAC** | **AAAGTTGTGA** | |

100%
Conservation
0%

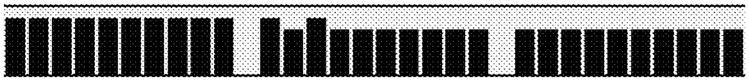

| | | | | |
|---|---|---|---|---|
| NY99 NS5 | AAGTGATGCG | CCCGGCTGCT | GATGGAAGAA | 436 |
| WN02 NS5 | AAGTGATGCG | CCCGGCTGCT | GATGGAAGAA | 436 |
| D NS5F2 | AAGTGATGCG | CCCGGCTGCT | GATGGAAGAA | 556 |
| D NS5F5 | ---------- | ---------- | ---------- | 955 |
| D NS5R3 rev | AAGTGATGCG | CCCGGCTGCT | GATGGAAGAA | 812 |
| D NS5R5 rev | ---------- | ---------- | ---------- | 971 |
| **Consensus** | **AAGTGATGCG** | **CCCGGCTGCT** | **GATGGAAGAA** | |

100%
Conservation
0%

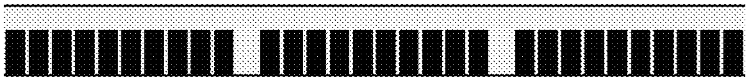

| | | | | |
|---|---|---|---|---|
| NY99 NS5 | CCGTCATGGA | TGTTATCTCC | AGAGAAGATC | 466 |
| WN02 NS5 | CCGTCATGGA | TGTTATCTCC | AGAGAAGATC | 466 |
| D NS5F2 | CCGTCATGGA | TGTTATCTCC | AGAGAAGATC | 586 |
| D NS5F5 | ---------- | ---------- | ---------- | 955 |
| D NS5R3 rev | CCGTCATGGA | TGTTATCTCC | AGAGAAGATC | 842 |
| D NS5R5 rev | ---------- | ---------- | ---------- | 971 |
| **Consensus** | **CCGTCATGGA** | **TGTTATCTCC** | **AGAGAAGATC** | |

100%
Conservation
0%

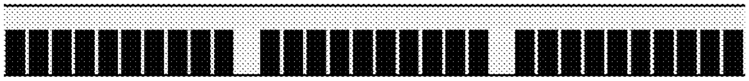

| | | | | |
|---|---|---|---|---|
| NY99 NS5 | AGAGGGGGAG | TGGACAAGTT | GTCACCTACG | 496 |
| WN02 NS5 | AGAGGGGGAG | TGGACAAGTT | GTCACCTACG | 496 |
| D NS5F2 | AGAGGGGGAG | TGGACAAGTT | GTCACCTACG | 616 |
| D NS5F5 | ---------- | ---------- | ---------- | 955 |
| D NS5R3 rev | AGAGGGGGAG | TGGACAAGTT | GTCACCTACG | 872 |
| D NS5R5 rev | ---------- | ---------- | ---------- | 971 |
| **Consensus** | **AGAGGGGGAG** | **TGGACAAGTT** | **GTCACCTACG** | |

100%
Conservation
0%

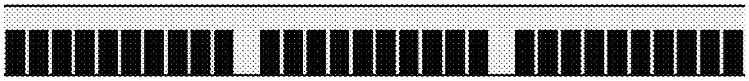

Fig. 12J/17

```
     NY99 NS5  CCCTAAACAC  TTTCACCAAC  CTGGCCGTCC  526
     WN02 NS5  CCCTAAACAC  TTTCACCAAC  CTGGCCGTCC  526
      D NS5F2  CCCTAAACAC  TTTCACCAAC  CTGGCCGTCC  646
      D NS5F5  ----------  ----------  ----------  955
  D NS5R3 rev  CCCTAAACAC  TTTCACCAAC  CTGGCCGTCC  902
  D NS5R5 rev  ----------  ----------  ----------  971
    Consensus  CCCTAAACAC  TTTCACCAAC  CTGGCCGTCC
```

100%
Conservation
0%

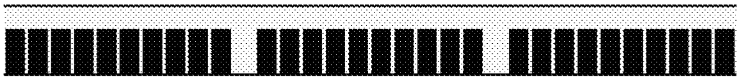

```
     NY99 NS5  AGCTGGTGAG  GATGATGGAA  GGGGAA-GGA  555
     WN02 NS5  AGCTGGTGAG  GATGATGGAA  GGGGAA-GGA  555
      D NS5F2  AGCTGGTGAG  GATGATGGAA  GGGGAANGGA  676
      D NS5F5  ----------  ----------  ----------  955
  D NS5R3 rev  AGCTGGTGAG  GATGATGGAA  GGGGAA-GGA  931
  D NS5R5 rev  ----------  ----------  ----------  971
    Consensus  AGCTGGTGAG  GATGATGGAA  GGGGAA-GGA
```

100%
Conservation
0%

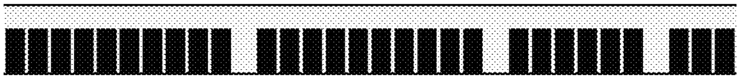

```
     NY99 NS5  GTGATTGGCC  CAGATGATGT  GGAGAAACTC  585
     WN02 NS5  GTGATTGGCC  CAGATGATGT  GGAGAAACTC  585
      D NS5F2  GTGATTGGCC  CAGATGATGT  GGAGAAACTC  706
      D NS5F5  ----------  ----------  ----------  955
  D NS5R3 rev  GTGATTGGCC  CAGATGATGT  GGAGAAACTC  961
  D NS5R5 rev  ----------  ----------  ----------  971
    Consensus  GTGATTGGCC  CAGATGATGT  GGAGAAACTC
```

100%
Conservation
0%

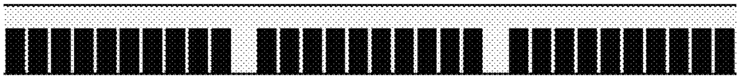

```
     NY99 NS5  ACAAAAGGGA  AAGGACCCAA  AGT-------  608
     WN02 NS5  ACAAAAGGGA  AAGGACCCAA  AGT-------  608
      D NS5F2  ACAAAAGGGA  AAGGACCCAA  AGTCAGGACC  736
      D NS5F5  ----------  ----------  ----------  955
  D NS5R3 rev  ACAAAAGG--  ----------  ----------  969
  D NS5R5 rev  ----------  ----------  ----------  971
    Consensus  ACAAAAGGGA  AAGGACCCAA  AGT-------
```

100%
Conservation
0%

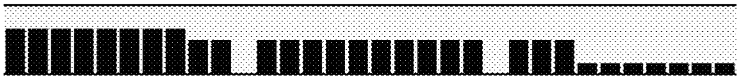

Fig. 12K/17

Figure 12L:
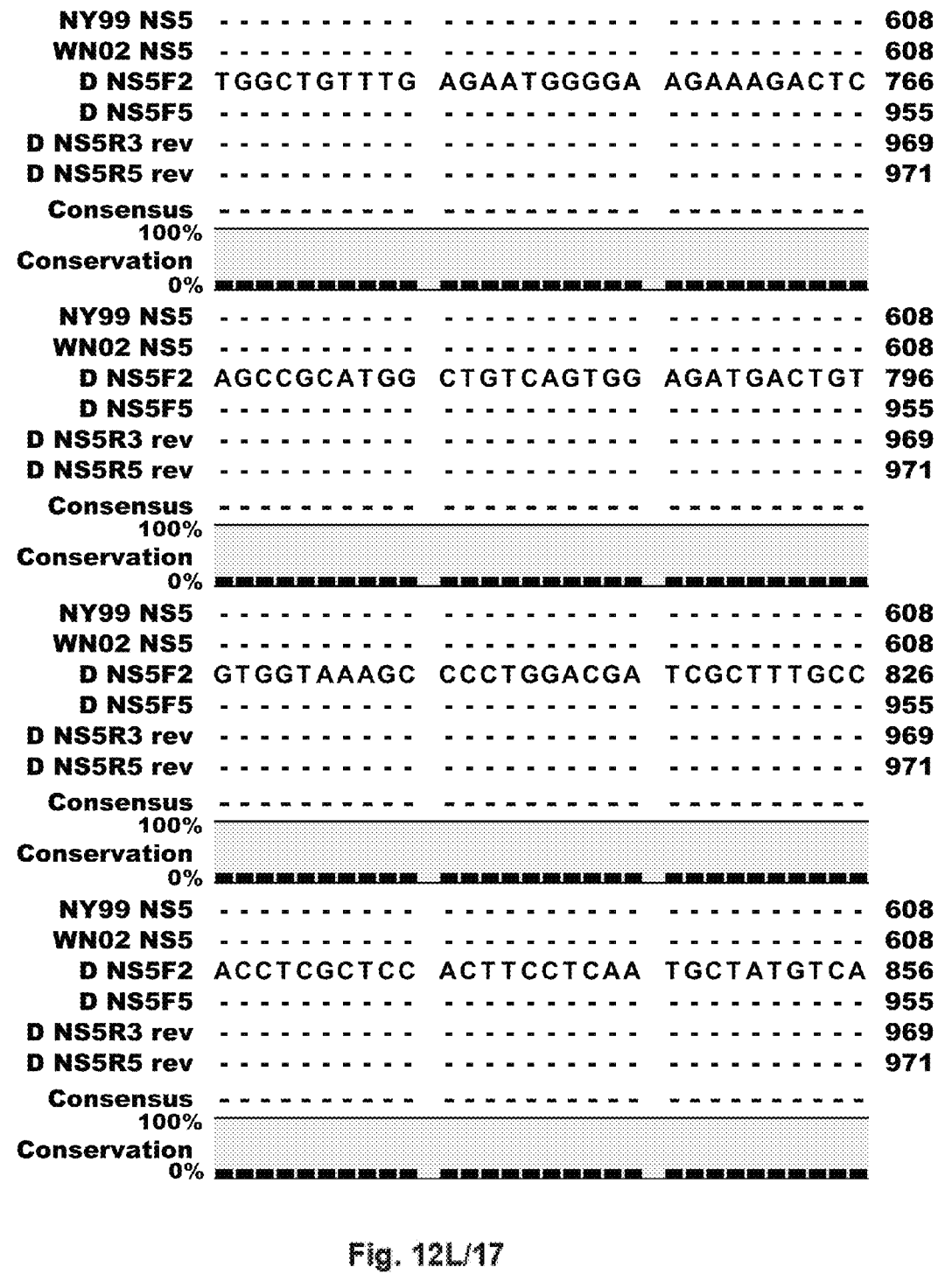

```
NY99 NS5     ----------  ----------  ----------  608
WN02 NS5     ----------  ----------  ----------  608
D NS5F2      TGGCTGTTTG  AGAATGGGGA  AGAAAGACTC  766
D NS5F5      ----------  ----------  ----------  955
D NS5R3 rev  ----------  ----------  ----------  969
D NS5R5 rev  ----------  ----------  ----------  971
Consensus    ----------  ----------  ----------
100%
Conservation
0%
NY99 NS5     ----------  ----------  ----------  608
WN02 NS5     ----------  ----------  ----------  608
D NS5F2      AGCCGCATGG  CTGTCAGTGG  AGATGACTGT  796
D NS5F5      ----------  ----------  ----------  955
D NS5R3 rev  ----------  ----------  ----------  969
D NS5R5 rev  ----------  ----------  ----------  971
Consensus    ----------  ----------  ----------
100%
Conservation
0%
NY99 NS5     ----------  ----------  ----------  608
WN02 NS5     ----------  ----------  ----------  608
D NS5F2      GTGGTAAAGC  CCCTGGACGA  TCGCTTTGCC  826
D NS5F5      ----------  ----------  ----------  955
D NS5R3 rev  ----------  ----------  ----------  969
D NS5R5 rev  ----------  ----------  ----------  971
Consensus    ----------  ----------  ----------
100%
Conservation
0%
NY99 NS5     ----------  ----------  ----------  608
WN02 NS5     ----------  ----------  ----------  608
D NS5F2      ACCTCGCTCC  ACTTCCTCAA  TGCTATGTCA  856
D NS5F5      ----------  ----------  ----------  955
D NS5R3 rev  ----------  ----------  ----------  969
D NS5R5 rev  ----------  ----------  ----------  971
Consensus    ----------  ----------  ----------
100%
Conservation
0%
```

Fig. 12L/17

Figure 12M:
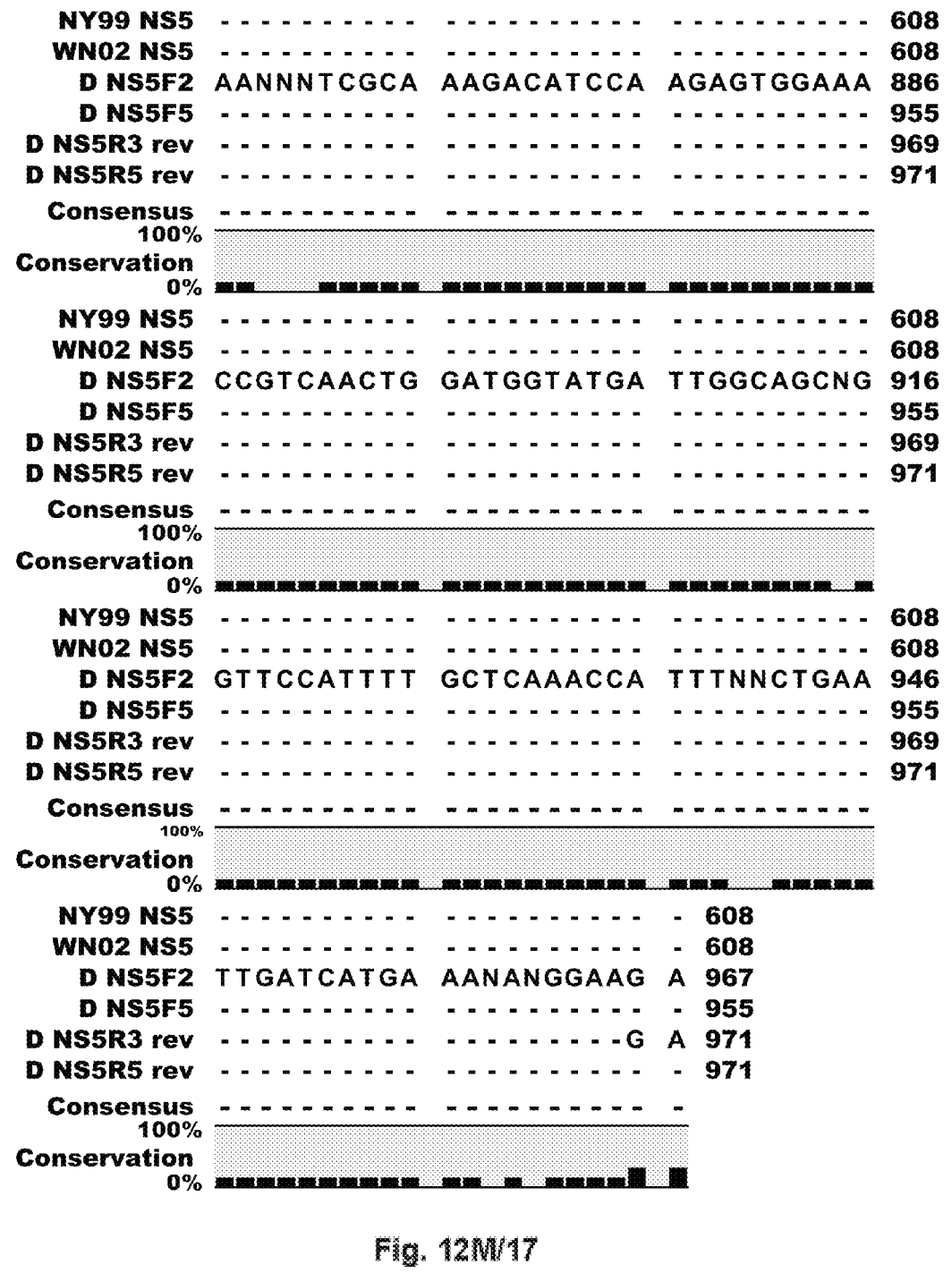

```
NY99 NS5      ----------  ----------  ----------  608
WN02 NS5      ----------  ----------  ----------  608
D NS5F2       AANNNTCGCA  AAGACATCCA  AGAGTGGAAA  886
D NS5F5       ----------  ----------  ----------  955
D NS5R3 rev   ----------  ----------  ----------  969
D NS5R5 rev   ----------  ----------  ----------  971

Consensus     ----------  ----------  ----------
100%
Conservation
0%
NY99 NS5      ----------  ----------  ----------  608
WN02 NS5      ----------  ----------  ----------  608
D NS5F2       CCGTCAACTG  GATGGTATGA  TTGGCAGCNG  916
D NS5F5       ----------  ----------  ----------  955
D NS5R3 rev   ----------  ----------  ----------  969
D NS5R5 rev   ----------  ----------  ----------  971

Consensus     ----------  ----------  ----------
100%
Conservation
0%
NY99 NS5      ----------  ----------  ----------  608
WN02 NS5      ----------  ----------  ----------  608
D NS5F2       GTTCCATTTT  GCTCAAACCA  TTTNNCTGAA  946
D NS5F5       ----------  ----------  ----------  955
D NS5R3 rev   ----------  ----------  ----------  969
D NS5R5 rev   ----------  ----------  ----------  971

Consensus     ----------  ----------  ----------
100%
Conservation
0%
NY99 NS5      ----------  ----------  -  608
WN02 NS5      ----------  ----------  -  608
D NS5F2       TTGATCATGA  AANANGGAAG  A  967
D NS5F5       ----------  ----------  -  955
D NS5R3 rev   ----------  ---------G  A  971
D NS5R5 rev   ----------  ----------  -  971

Consensus     ----------  ----------  -
100%
Conservation
0%
```

Fig. 12M/17

```
NY99 NS5      ----------  ----------  ----------  -
WN02 NS5      ----------  ----------  ----------  -
H NS5F2       ----------  ----------  ----------  -
H NS5F5       TCTCNCGGAT  TCCNCGCACG  AGATGTATTG  30
H NS5R3 rev   ----------  ----------  ----------  -
H NS5R5 rev   TGNCAN----  ----------  ----------  6
Consensus     ----------  ----------  ----------
100%
Conservation
0%
NY99 NS5      ----------  ----------  ----------  -
WN02 NS5      ----------  ----------  ----------  -
H NS5F2       ----------  ----------  ----------  -
H NS5F5       GGTGAGTCGA  GCTTCAGGCA  ATGTGGTACA  60
H NS5R3 rev   ----------  ----------  ----------  -
H NS5R5 rev   ----------  ----------  ----------  6
Consensus     ----------  ----------  ----------
100%
Conservation
0%
NY99 NS5      ----------  ----------  ----------  -
WN02 NS5      ----------  ----------  ----------  -
H NS5F2       ----------  ----------  ----------  -
H NS5F5       TTCAGTGAAT  ATGACCAGCC  AGGTGCTCCT  90
H NS5R3 rev   ----------  ----------  ----------  -
H NS5R5 rev   ----------  ---------C  NNGNGCTCNN  17
Consensus     ----------  ----------  ----------
100%
Conservation
0%
NY99 NS5      ----------  ----------  ----------  -
WN02 NS5      ----------  ----------  ----------  -
H NS5F2       ----------  ----------  ----------  -
H NS5F5       AGGAAGAATG  GAAAAAAGGA  CCTGGAAGGG  120
H NS5R3 rev   ----------  ----------  ----------  -
H NS5R5 rev   NGNN-GAATG  NAAAAAANNN  NNGGNANGGG  46
Consensus     ----------  ----------  ----------
100%
Conservation
0%
```

Fig. 13A/17

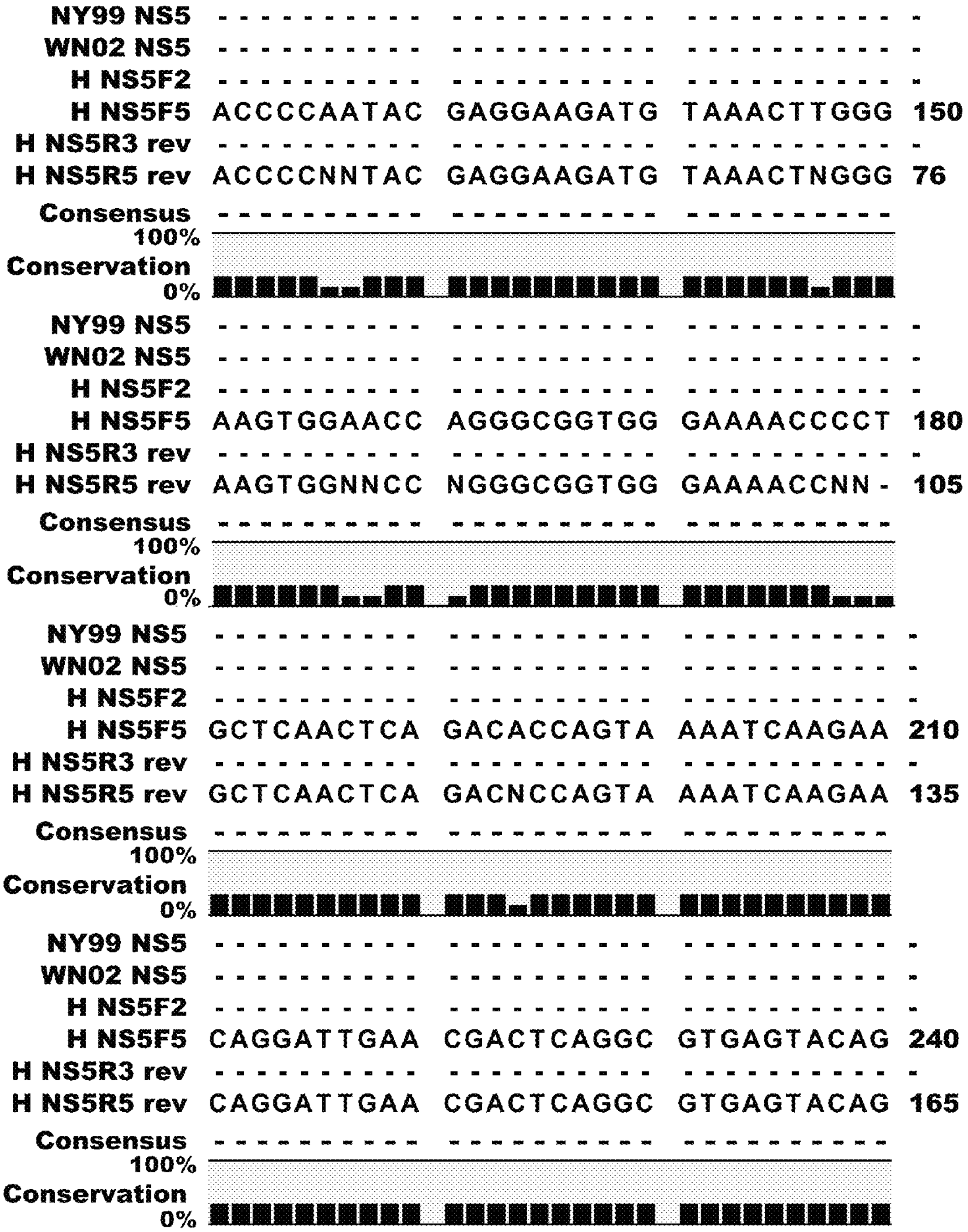
Fig. 13B/17

| | | | | |
|---|---|---|---|---|
| NY99 NS5 | ---------- | ---------- | ---------- | - |
| WN02 NS5 | ---------- | ---------- | ---------- | - |
| H NS5F2 | ---------- | ---------- | ---------- | - |
| H NS5F5 | TTCGACGTGG | CACCACGATG | AGAACCACCC | 270 |
| H NS5R3 rev | ---------- | ---------- | ---------- | - |
| H NS5R5 rev | TTCGACGTGG | CACCACGATG | AGAACCACCC | 195 |
| Consensus | ---------- | ---------- | ---------- | |

100%
Conservation
0%

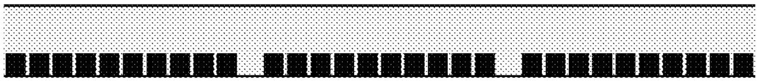

| | | | | |
|---|---|---|---|---|
| NY99 NS5 | ---------- | ---------- | ---------- | - |
| WN02 NS5 | ---------- | ---------- | ---------- | - |
| H NS5F2 | ---------- | ---------- | ---------- | - |
| H NS5F5 | ATATAGAACC | TGGAACTATC | ACGGCAGTTA | 300 |
| H NS5R3 rev | ---------- | -GGAACTATC | NCGGNAGTNA | 19 |
| H NS5R5 rev | ATATAGAACC | TGGAACTATC | ACGGCAGTTA | 225 |
| Consensus | ---------- | **-GGAACTATC** | **-CGG-AGT-A** | |

100%
Conservation
0%

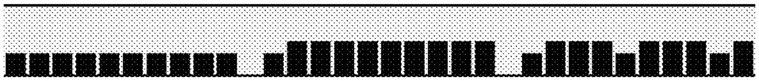

| | | | | |
|---|---|---|---|---|
| NY99 NS5 | ---------- | ---------- | ---------- | - |
| WN02 NS5 | ---------- | ---------- | ---------- | - |
| H NS5F2 | ---------- | ---------- | ---------- | - |
| H NS5F5 | TGATGTGAAG | CCCACAGGCT | CCGCCAGTTC | 330 |
| H NS5R3 rev | TGATGTGAAN | NNACNGGNTN | NNNCNNNNTC | 49 |
| H NS5R5 rev | TGATGTGAAG | CCCACAGGNT | CCGCCAGTTC | 255 |
| Consensus | **TGATGTGAA-** | **------G---** | **---C----TC** | |

100%
Conservation
0%

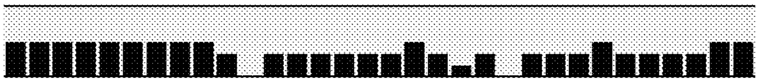

| | | | | |
|---|---|---|---|---|
| NY99 NS5 | ---------- | ---------- | ---------- | - |
| WN02 NS5 | ---------- | ---------- | ---------- | - |
| H NS5F2 | ---------- | ---------- | ---------- | - |
| H NS5F5 | GCTGGTCAAT | GGAGTGGTCA | GGCTCCTCTC | 360 |
| H NS5R3 rev | GCTGNTCAAT | GNAGTGNTCA | GGCTCNTNTC | 79 |
| H NS5R5 rev | GCTGGTCAAT | GGAGTGGTCA | GGCTCCTCTC | 285 |
| Consensus | **GCTG-TCAAT** | **G-AGTG-TCA** | **GGCTC-T-TC** | |

100%
Conservation
0%

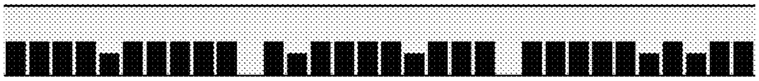

Fig. 13C/17

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| H NS5F2 | - - - - - - - - - - | - - - - - - - - - - | - - - - - - - - - - | - |
| H NS5F5 | AAAACC-ATG | GGACACCATC | ACGAATGTTA | 389 |
| H NS5R3 rev | AAAACCCNTG | GGACNCCATC | NCGAANNNNC | 109 |
| H NS5R5 rev | AAAACC-ATG | GGACACCATC | ACGAATGTTA | 314 |
| Consensus | AAAACC--TG | GGAC-CCATC | -CGAA----- | |

100%
Conservation
0%
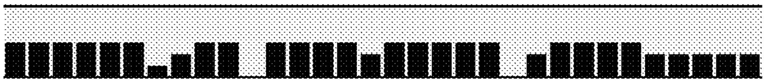

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| H NS5F2 | - - - - - - - - - - | - - - - - - - - - - | - - - - - - - - - - | - |
| H NS5F5 | CCACCATGGC | CATGACTGAC | ACTACTCCC- | 418 |
| H NS5R3 rev | CACCATNGNC | CATGACTGNC | ACTACTCCCN | 139 |
| H NS5R5 rev | CCACCATGGC | CATGACTGAC | ACTACTCCC- | 343 |
| Consensus | C--C---G-C | CATGACTG-C | ACTACTCCC- | |

100%
Conservation
0%
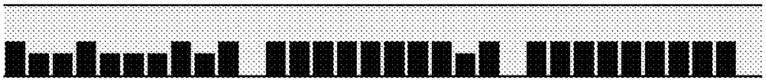

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| H NS5F2 | - - - - - - - - - - | - - - - - - - - - - | - - - - - - - - - - | - |
| H NS5F5 | TTCGGGCAGC | AGCGAGTGTT | CAAAGAGAAG | 448 |
| H NS5R3 rev | TTCGGGCAGC | AGCGAGTGTT | CAAAGAGAAG | 169 |
| H NS5R5 rev | TTCGGGCAGC | AGCGAGTGTT | CAAAGAGAAG | 373 |
| Consensus | TTCGGGCAGC | AGCGAGTGTT | CAAAGAGAAG | |

100%
Conservation
0%
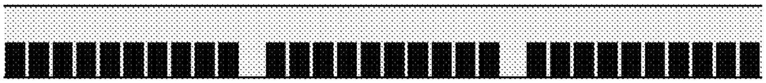

| | | | | |
|---|---|---|---|---|
| NY99 NS5 | - - - - - - - - - - | - - - - - - - - - - | - - - - - - - - - - | - |
| WN02 NS5 | - - - - - - - - - - | - - - - - - - - - - | - - - - - - - - - - | - |
| H NS5F2 | - - - - - - - - - - | - - - - - - - - - - | - - - - - - - - - - | - |
| H NS5F5 | GTGGACACGA | AAGCTCCTGA | ACCGCCAGAA | 478 |
| H NS5R3 rev | GTGGACACGA | AAGCTCNNGA | ACCGCCAGAA | 199 |
| H NS5R5 rev | GTGGACACGA | AAGCTCCTGA | ACCGCCAGAA | 403 |
| Consensus | GTGGACACGA | AAGCTC--GA | ACCGCCAGAA | |

100%
Conservation
0%
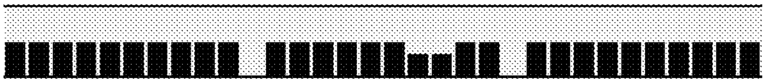

Fig. 13D/17

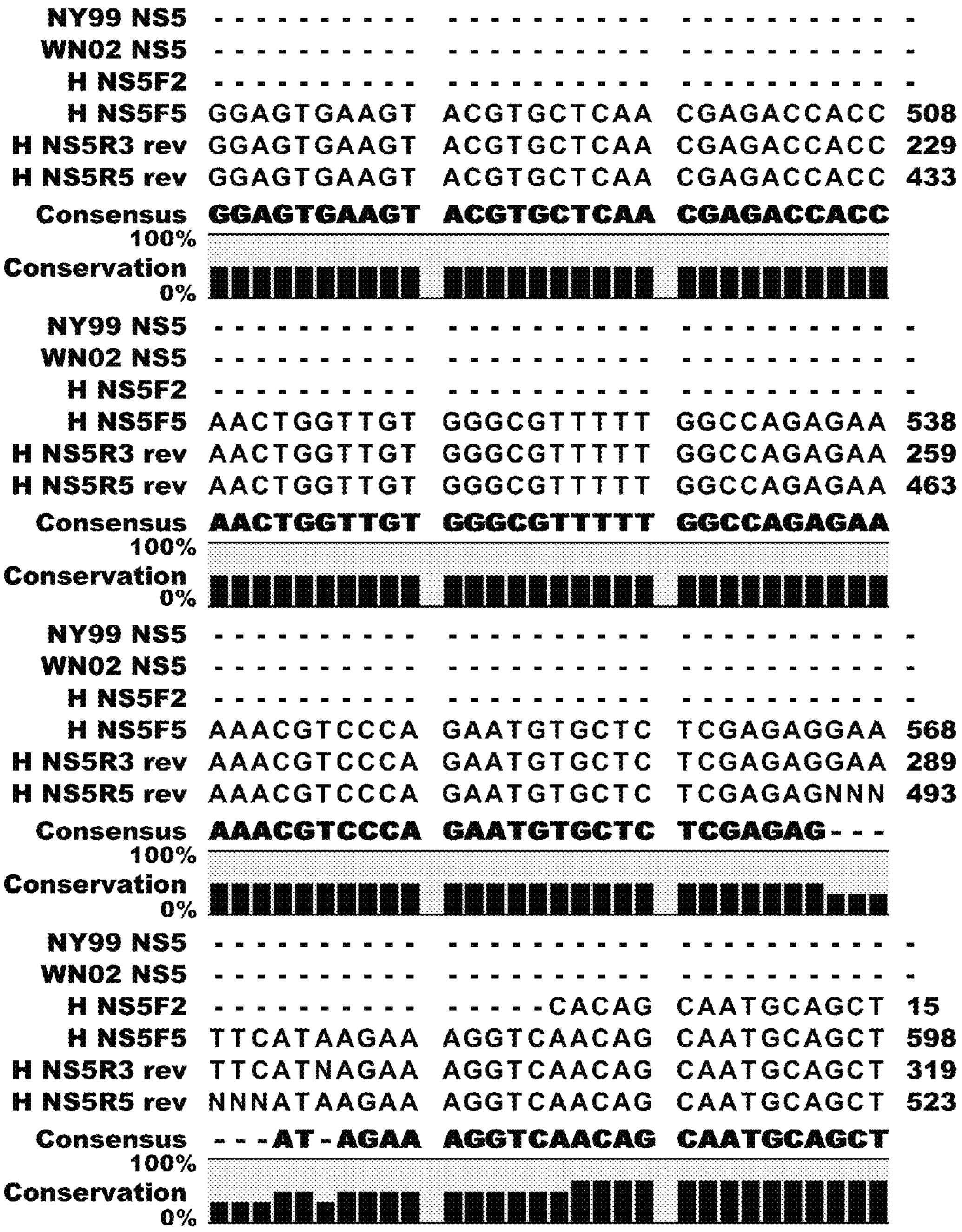

Fig. 13E/17

|              |            |            |            |     |
|---|---|---|---|---|
| NY99 NS5     | ----------  | ----------  | ----------  | -   |
| WN02 NS5     | ----------  | ----------  | ----------  | -   |
| H NS5F2      | ----------  | ----------  | ----------  | -   |
| H NS5F5      | GGAGTGAAGT | ACGTGCTCAA | CGAGACCACC | 508 |
| H NS5R3 rev  | GGAGTGAAGT | ACGTGCTCAA | CGAGACCACC | 229 |
| H NS5R5 rev  | GGAGTGAAGT | ACGTGCTCAA | CGAGACCACC | 433 |
| Consensus 100% | **GGAGTGAAGT** | **ACGTGCTCAA** | **CGAGACCACC** | |
| Conservation 0% | | | | |
| NY99 NS5     | ----------  | ----------  | ----------  | -   |
| WN02 NS5     | ----------  | ----------  | ----------  | -   |
| H NS5F2      | ----------  | ----------  | ----------  | -   |
| H NS5F5      | AACTGGTTGT | GGGCGTTTTT | GGCCAGAGAA | 538 |
| H NS5R3 rev  | AACTGGTTGT | GGGCGTTTTT | GGCCAGAGAA | 259 |
| H NS5R5 rev  | AACTGGTTGT | GGGCGTTTTT | GGCCAGAGAA | 463 |
| Consensus 100% | **AACTGGTTGT** | **GGGCGTTTTT** | **GGCCAGAGAA** | |
| Conservation 0% | | | | |
| NY99 NS5     | ----------  | ----------  | ----------  | -   |
| WN02 NS5     | ----------  | ----------  | ----------  | -   |
| H NS5F2      | ----------  | ----------  | ----------  | -   |
| H NS5F5      | AAACGTCCCA | GAATGTGCTC | TCGAGAGGAA | 568 |
| H NS5R3 rev  | AAACGTCCCA | GAATGTGCTC | TCGAGAGGAA | 289 |
| H NS5R5 rev  | AAACGTCCCA | GAATGTGCTC | TCGAGAGNNN | 493 |
| Consensus 100% | **AAACGTCCCA** | **GAATGTGCTC** | **TCGAGAG- - -** | |
| Conservation 0% | | | | |
| NY99 NS5     | ----------  | ----------  | ----------  | -   |
| WN02 NS5     | ----------  | ----------  | ----------  | -   |
| H NS5F2      | ----------  | - - - - -CACAG | CAATGCAGCT | 15  |
| H NS5F5      | TTCATAAGAA | AGGTCAACAG | CAATGCAGCT | 598 |
| H NS5R3 rev  | TTCATNAGAA | AGGTCAACAG | CAATGCAGCT | 319 |
| H NS5R5 rev  | NNNATAAGAA | AGGTCAACAG | CAATGCAGCT | 523 |
| Consensus 100% | **- - -AT-AGAA** | **AGGTCAACAG** | **CAATGCAGCT** | |
| Conservation 0% | | | | |

Fig. 13E/17

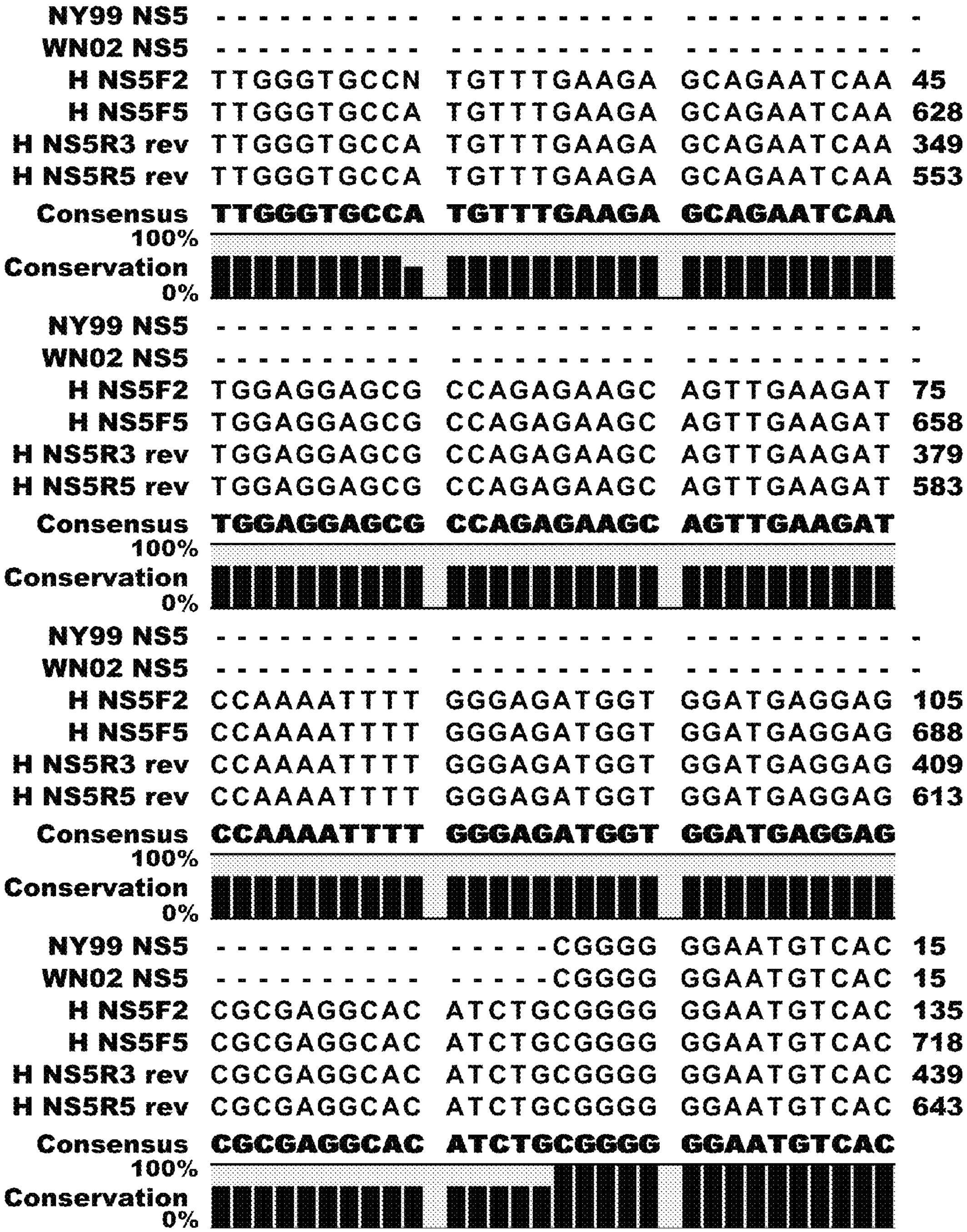
Fig. 13F/17

| | | | | |
|---|---|---|---|---|
| NY99 NS5 | ACTTGCATTT | ACAACATGAT | GGGAAAGAGA | 45 |
| WN02 NS5 | ACTTGCATTT | ACAACATGAT | GGGAAAGAGA | 45 |
| H NS5F2 | ACTTGCATTT | ACAACATGAT | GGGAAAGAGA | 165 |
| H NS5F5 | ACTTGCATTT | ACAACATGAT | GGGAAAGAGA | 748 |
| H NS5R3 rev | ACTTGCATTT | ACAACATGAT | GGGAAAGAGA | 469 |
| H NS5R5 rev | ACTTGCATTT | ACAACATGAT | GGGAAAGAGA | 673 |
| **Consensus** | **ACTTGCATTT** | **ACAACATGAT** | **GGGAAAGAGA** | |

100% Conservation 0%

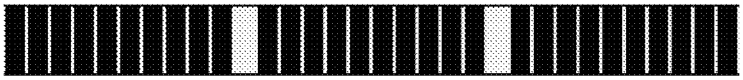

| | | | | |
|---|---|---|---|---|
| NY99 NS5 | GAGAAAAAAC | CCGGAGAATT | CGGAAAGGCC | 75 |
| WN02 NS5 | GAGAAAAAAC | CCGGAGAGTT | CGGAAAGGCC | 75 |
| H NS5F2 | GAGAAAAAAC | CCGGAGAGTT | CGGAAAGGCC | 195 |
| H NS5F5 | GAGAAAAAAC | CCGGAGAGTT | CGGAAAGGCC | 778 |
| H NS5R3 rev | GAGAAAAAAC | CCGGAGAGTT | CGGAAAGGCC | 499 |
| H NS5R5 rev | GAGAAAAAAC | CCGGAGAGTT | CGGAAAGGCC | 703 |
| **Consensus** | **GAGAAAAAAC** | **CCGGAGAGTT** | **CGGAAAGGCC** | |

100% Conservation 0%

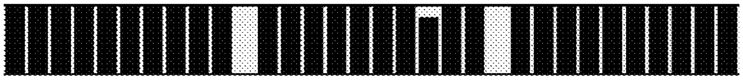

| | | | | |
|---|---|---|---|---|
| NY99 NS5 | AAGGGAAGCA | GAGCCATTTG | GTTCATGTGG | 105 |
| WN02 NS5 | AAGGGAAGCA | GAGCCATTTG | GTTCATGTGG | 105 |
| H NS5F2 | AAGGGAAGCA | GAGCCATTTG | GTTCATGTGG | 225 |
| H NS5F5 | AAGGGAAGCA | GAGCCATTTG | GTTCATGTGG | 808 |
| H NS5R3 rev | AAGGGAAGCA | GAGCCATTTG | GTTCATGTGG | 529 |
| H NS5R5 rev | AAGGGAAGCA | GAGCCATTTG | GTTCATGTGG | 733 |
| **Consensus** | **AAGGGAAGCA** | **GAGCCATTTG** | **GTTCATGTGG** | |

100% Conservation 0%

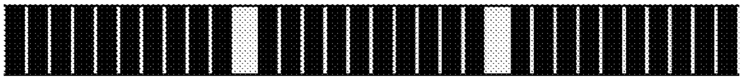

| | | | | |
|---|---|---|---|---|
| NY99 NS5 | CTCGGAGCTC | GCTTTCTGGA | GTTCGAGGCT | 135 |
| WN02 NS5 | CTCGGAGCTC | GCTTTCTGGA | GTTCGAGGCT | 135 |
| H NS5F2 | CTCGGAGCTC | GCTTTCTGGA | GTTCGAGGCT | 255 |
| H NS5F5 | CTCGGAGCTC | GCTTTCTGGA | GTTCGAGGCT | 838 |
| H NS5R3 rev | CTCGGAGCTC | GCTTTCTGGA | GTTCGAGGCT | 559 |
| H NS5R5 rev | CTCGGAGCTC | GCTTTCTGGA | GTTCGAGGCT | 763 |
| **Consensus** | **CTCGGAGCTC** | **GCTTTCTGGA** | **GTTCGAGGCT** | |

100% Conservation 0%

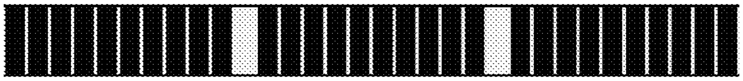

Fig. 13G/17

NY99 NS5 CTGGGTTTTC TCAATGAAGA CCACTGGCTT 165
WN02 NS5 CTGGGTTTTC TCAATGAAGA CCACTGGCTT 165
H NS5F2 CTGGGTTTTC TCAATGAAGA TCACTGGCTT 285
H NS5F5 CTNGGTTTTC TCAATGAAGA TCACTGGCTT 868
H NS5R3 rev CTGGGTTTTC TCAATGAAGA TCACTGGCTT 589
H NS5R5 rev CTGGGTTTTC TCAATGAAGA TCACTGGCTT 793
Consensus CTGGGTTTTC TCAATGAAGA TCACTGGCTT

100%
Conservation
0%
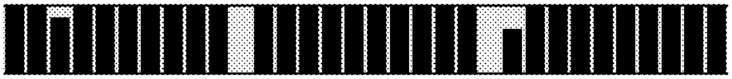

NY99 NS5 GGAAGAAAGA ACTCAGGAGG AGGTGTCGAG 195
WN02 NS5 GGAAGAAAGA ACTCAGGAGG AGGTGTCGAG 195
H NS5F2 GGAAGAAAGA ACTCAGGAGG AGGTGTCGAG 315
H NS5F5 GGAAGAAAGA ACTCNNNANG AGGTGTCGAG 898
H NS5R3 rev GGAAGAAAGA ACTCAGGAGG AGGTGTCGAG 619
H NS5R5 rev GGAAGAAAGA ACTCAGGAGG AGGTGTCGAG 823
Consensus GGAAGAAAGA ACTCAGGAGG AGGTGTCGAG

100%
Conservation
0%
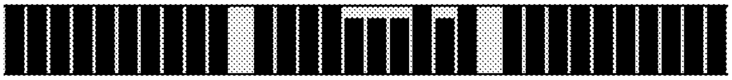

NY99 NS5 GGCTTGGGCC TCCAAAAACT GGGTTACATC 225
WN02 NS5 GGCTTGGGCC TCCAAAAACT GGGTTACATC 225
H NS5F2 GGCTTGGGCC TCCAAAAACT GGGTTACATC 345
H NS5F5 GGCTTGGGCC TCCAAAAACT GGGTTACATC 928
H NS5R3 rev GGCTTGGGCC TCCAAAAACT GGGTTACATC 649
H NS5R5 rev GGCTTGGGCC TCCAAAAACT GGGTTACATC 853
Consensus GGCTTGGGCC TCCAAAAACT GGGTTACATC

100%
Conservation
0%
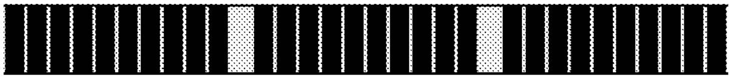

NY99 NS5 CTGCGTGAAG TTGGCACCCG G-CCTGGGGG 254
WN02 NS5 CTGCGTGAAG TTGGCACCCG G-CCTGGGGG 254
H NS5F2 CTGCGTGAAG TTGGCACCCG G-CCTGGGGG 374
H NS5F5 CTGCGTGAAG TTGGCACCCN GNCCTGGGGG 958
H NS5R3 rev CTGCGTGAAG TTGGCACCCG G-CCTGGGGG 678
H NS5R5 rev CTGCGTGAAG TTGGCACCCG G-CCTGGGGG 882
Consensus CTGCGTGAAG TTGGCACCCG G-CCTGGGGG

100%
Conservation
0%
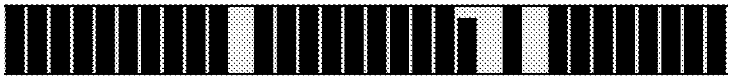

Fig. 13H/17

| | | | | |
|---|---|---|---|---|
| NY99 NS5 | CAAGATCTAT | GCTGATGACA | CAGCTGGCTG | 284 |
| WN02 NS5 | CAAGATCTAT | GCTGATGACA | CAGCTGGCTG | 284 |
| H NS5F2 | CAAGATCTAT | GCTGATGACA | CAGCTGGCTG | 404 |
| H NS5F5 | CAAGATCTAT | GCTGATGACN | CAGCTGNNTG | 988 |
| H NS5R3 rev | CAAGATCTAT | GCTGATGACA | CAGCTGGCTG | 708 |
| H NS5R5 rev | CAAGATCTAT | GCTGATGACA | CAGCTGGCTG | 912 |
| **Consensus** | **CAAGATCTAT** | **GCTGATGACA** | **CAGCTGGCTG** | |

100%
Conservation
0%

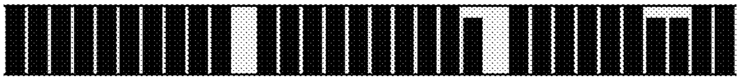

| | | | | |
|---|---|---|---|---|
| NY99 NS5 | GGACACCCGC | ATCACGAGAG | CTGACTTGGA | 314 |
| WN02 NS5 | GGACACCCGC | ATCACGAGTG | CTGACTTGGA | 314 |
| H NS5F2 | GGACACCCGC | ATCACGAGAG | CTGACTTGGA | 434 |
| H NS5F5 | GGNNACCCNC | ATCACGAGNG | CTGANTTNNN | 1018 |
| H NS5R3 rev | GGACACCCGC | ATCACGAGAG | CTGACTTGGA | 738 |
| H NS5R5 rev | GGACACCCGC | ATCACGAGAG | CTGACTTGGA | 942 |
| **Consensus** | **GGACACCCGC** | **ATCACGAGAG** | **CTGACTTGGA** | |

100%
Conservation
0%

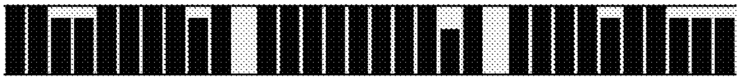

| | | | | |
|---|---|---|---|---|
| NY99 NS5 | AAATGAAGCT | AAGGTGCTTG | AGCTGCTTGA | 344 |
| WN02 NS5 | AAATGAAGCT | AAGGTGCTTG | AGTTGCTTGA | 344 |
| H NS5F2 | AAATGAAGCT | AAGGTGCTTG | AGCTGCTTGA | 464 |
| H NS5F5 | AAATGNAGC- | ---------- | ---------- | 1027 |
| H NS5R3 rev | AAATGAAGCT | AAGGTGCTTG | AGCTGCTTGA | 768 |
| H NS5R5 rev | AAATGAAGCT | AAGGTGCTTG | AGCTGCTTGA | 972 |
| **Consensus** | **AAATGAAGCT** | **AAGGTGCTTG** | **AGCTGCTTGA** | |

100%
Conservation
0%

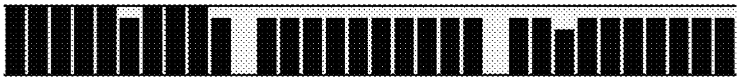

| | | | | |
|---|---|---|---|---|
| NY99 NS5 | TGGGGAACAT | CGGCGTCTTG | CCAGGGCCAT | 374 |
| WN02 NS5 | TGGGGAACAT | CGGCGTCTTG | CCAGGGCCAT | 374 |
| H NS5F2 | TGGGGAACAT | CGGCGTCTTG | CCAGGGCCAT | 494 |
| H NS5F5 | ---------- | ---------- | ---------- | 1027 |
| H NS5R3 rev | TGGGGAACAT | CGGCGTCTTG | CCAGGGCCAT | 798 |
| H NS5R5 rev | TGGGGAACAT | CGGCGTCTTG | CCAGGGCCAT | 1002 |
| **Consensus** | **TGGGGAACAT** | **CGGCGTCTTG** | **CCAGGGCCAT** | |

100%
Conservation
0%

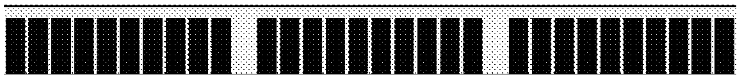

Fig. 13I/17

| | | | | |
|---|---|---|---|---|
| NY99 NS5 | CATTGAGCTC | ACCTATCGTC | ACAAAGTTGT | 404 |
| WN02 NS5 | CATTGAGCTC | ACCTATCGTC | ACAAAGTTGT | 404 |
| H NS5F2 | CATTGAGCTC | ACCTATCGTC | ACAAAGTTGT | 524 |
| H NS5F5 | ---------- | ---------- | ---------- | 1027 |
| H NS5R3 rev | CATTGAGCTC | ACCTATCGTC | ACAAAGTTGT | 828 |
| H NS5R5 rev | CATTGAGCTC | ACC------- | ---------- | 1015 |
| **Consensus** | **CATTGAGCTC** | **ACCTATCGTC** | **ACAAAGTTGT** | |

100%
Conservation
0%

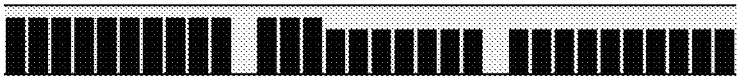

| | | | | |
|---|---|---|---|---|
| NY99 NS5 | GAAAGTGATG | CGCCCGGCTG | CTGATGGAAG | 434 |
| WN02 NS5 | GAAAGTGATG | CGCCCGGCTG | CTGATGGAAG | 434 |
| H NS5F2 | GAAAGTGATG | CGCCCGGCTG | CTGATGGAAG | 554 |
| H NS5F5 | ---------- | ---------- | ---------- | 1027 |
| H NS5R3 rev | GAAAGTGATG | CGCCCGGCTG | CTGATGGAAG | 858 |
| H NS5R5 rev | ---------- | ---------- | ---------- | 1015 |
| **Consensus** | **GAAAGTGATG** | **CGCCCGGCTG** | **CTGATGGAAG** | |

100%
Conservation
0%

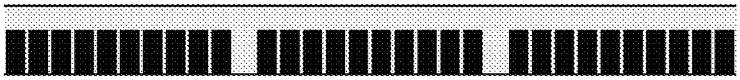

| | | | | |
|---|---|---|---|---|
| NY99 NS5 | AACCGTCATG | GATGTTATCT | CCAGAGAAGA | 464 |
| WN02 NS5 | AACCGTCATG | GATGTTATCT | CCAGAGAAGA | 464 |
| H NS5F2 | AACCGTCATG | GATGTTATCT | CCAGAGAAGA | 584 |
| H NS5F5 | ---------- | ---------- | ---------- | 1027 |
| H NS5R3 rev | AACCGTCATG | GATGTTATCT | CCAGAGAAGA | 888 |
| H NS5R5 rev | ---------- | ---------- | ---------- | 1015 |
| **Consensus** | **AACCGTCATG** | **GATGTTATCT** | **CCAGAGAAGA** | |

100%
Conservation
0%

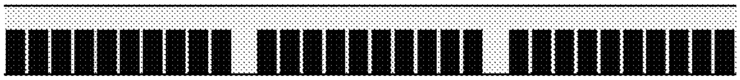

| | | | | |
|---|---|---|---|---|
| NY99 NS5 | TCAGAGGGGG | AGTGGACAAG | TTGTCACCTA | 494 |
| WN02 NS5 | TCAGAGGGGG | AGTGGACAAG | TTGTCACCTA | 494 |
| H NS5F2 | TCAGAGGGGG | AGTGGACAAG | TTGTCACCTA | 614 |
| H NS5F5 | ---------- | ---------- | ---------- | 1027 |
| H NS5R3 rev | TCAGAGGGGG | AGTGGACAAG | TTGTCACCTA | 918 |
| H NS5R5 rev | ---------- | ---------- | ---------- | 1015 |
| **Consensus** | **TCAGAGGGGG** | **AGTGGACAAG** | **TTGTCACCTA** | |

100%
Conservation
0%

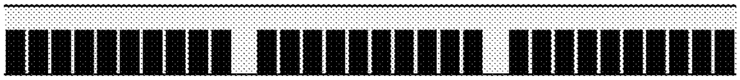

Fig. 13J/17

```
NY99 NS5      CGCCCTAAAC ACTTTCACCA ACCTGGCCGT  524
WN02 NS5      CGCCCTAAAC ACTTTCACCA ACCTGGCCGT  524
H NS5F2       CGCNCTAAAC ACTTTCACCA ACCTGGCCGT  644
H NS5F5       ---------- ---------- ----------  1027
H NS5R3 rev   CNCNCTAAAC ACTTTCACCA ACCTGGCCGT  948
H NS5R5 rev   ---------- ---------- ----------  1015
Consensus     CGCCCTAAAC ACTTTCACCA ACCTGGCCGT
```

100%
Conservation
0%

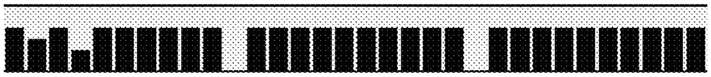

```
NY99 NS5      CCAGCTGGTG AGGATGATGG AAGGGGAA-G  553
WN02 NS5      CCAGCTGGTG AGGATGATGG AAGGGGAA-G  553
H NS5F2       CCAGCTGGTG AGGATGATGG AAGGGGAANG  674
H NS5F5       ---------- ---------- ----------  1027
H NS5R3 rev   CCAGCTGGTG AGGATGATGG AAGGGGAA-G  977
H NS5R5 rev   ---------- ---------- ----------  1015
Consensus     CCAGCTGGTG AGGATGATGG AAGGGGAA-G
```

100%
Conservation
0%

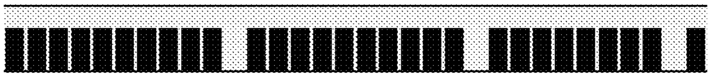

```
NY99 NS5      GAGTGATTGG CCCAGATGAT GTGGAGAAAC  583
WN02 NS5      GAGTGATTGG CCCAGATGAT GTGGAGAAAC  583
H NS5F2       GAGTGATTGG CCCAGATGAT GTGGAGAAAC  704
H NS5F5       ---------- ---------- ----------  1027
H NS5R3 rev   GAGTGATTGG CCCAGATGAT GTGGAGAAAC  1007
H NS5R5 rev   ---------- ---------- ----------  1015
Consensus     GAGTGATTGG CCCAGATGAT GTGGAGAAAC
```

100%
Conservation
0%

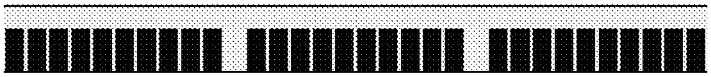

```
NY99 NS5      TCACAAAAGG GAAAGGACCC AAAGT-----  608
WN02 NS5      TCACAAAAGG GAAAGGACCC AAAGT-----  608
H NS5F2       TCACAAAAGG GAAAGGACCC AAAGTCAGGA  734
H NS5F5       ---------- ---------- ----------  1027
H NS5R3 rev   TCACAAAAGG GA-------- ----------  1019
H NS5R5 rev   ---------- ---------- ----------  1015
Consensus     TCACAAAAGG GAAAGGACCC AAAGT-----
```

100%
Conservation
0%

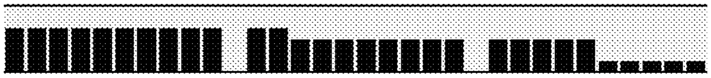

Fig. 13K/17

| | | | | |
|---|---|---|---|---|
| NY99 NS5 | ---------- | ---------- | ---------- | 608 |
| WN02 NS5 | ---------- | ---------- | ---------- | 608 |
| H NS5F2 | CCTGGCTGTT | TGAGAATGGG | GAAGAAAGAC | 764 |
| H NS5F5 | ---------- | ---------- | ---------- | 1027 |
| H NS5R3 rev | ---------- | ---------- | ---------- | 1019 |
| H NS5R5 rev | ---------- | ---------- | ---------- | 1015 |
| Consensus | ---------- | ---------- | ---------- | |

100%
Conservation
0%

| | | | | |
|---|---|---|---|---|
| NY99 NS5 | ---------- | ---------- | ---------- | 608 |
| WN02 NS5 | ---------- | ---------- | ---------- | 608 |
| H NS5F2 | TCAGCCGCAT | GGCTGTCAGT | GGAGATGACT | 794 |
| H NS5F5 | ---------- | ---------- | ---------- | 1027 |
| H NS5R3 rev | ---------- | ---------- | ---------- | 1019 |
| H NS5R5 rev | ---------- | ---------- | ---------- | 1015 |
| Consensus | ---------- | ---------- | ---------- | |

100%
Conservation
0%

| | | | | |
|---|---|---|---|---|
| NY99 NS5 | ---------- | ---------- | ---------- | 608 |
| WN02 NS5 | ---------- | ---------- | ---------- | 608 |
| H NS5F2 | GTGTGGTAAA | GCCCCTGGAC | GATCGCTTTG | 824 |
| H NS5F5 | ---------- | ---------- | ---------- | 1027 |
| H NS5R3 rev | ---------- | ---------- | ---------- | 1019 |
| H NS5R5 rev | ---------- | ---------- | ---------- | 1015 |
| Consensus | ---------- | ---------- | ---------- | |

100%
Conservation
0%

| | | | | |
|---|---|---|---|---|
| NY99 NS5 | ---------- | ---------- | ---------- | 608 |
| WN02 NS5 | ---------- | ---------- | ---------- | 608 |
| H NS5F2 | CCACCTCGCT | CCACTTCCTC | AATGCTATGT | 854 |
| H NS5F5 | ---------- | ---------- | ---------- | 1027 |
| H NS5R3 rev | ---------- | ---------- | ---------- | 1019 |
| H NS5R5 rev | ---------- | ---------- | ---------- | 1015 |
| Consensus | ---------- | ---------- | ---------- | |

100%
Conservation
0%

Fig. 13L/17

| | | | | |
|---|---|---|---|---|
| NY99 NS5 | - - - - - - - - - - | - - - - - - - - - - | - - - - - - - - - - | 608 |
| WN02 NS5 | - - - - - - - - - - | - - - - - - - - - - | - - - - - - - - - - | 608 |
| H NS5F2 | CAAANGTTCG | CAAAGACATC | CAAGAGTGGN | 884 |
| H NS5F5 | - - - - - - - - - - | - - - - - - - - - - | - - - - - - - - - - | 1027 |
| H NS5R3 rev | - - - - - - - - - - | - - - - - - - - - - | - - - - - - - - - - | 1019 |
| H NS5R5 rev | - - - - - - - - - - | - - - - - - - - - - | - - - - - - - - - - | 1015 |
| Consensus | - - - - - - - - - - | - - - - - - - - - - | - - - - - - - - - - | |

100%
Conservation
0%

| | | | | |
|---|---|---|---|---|
| NY99 NS5 | - - - - - - - - - - | - - - - - - - - - - | - - - - - - - - - - | 608 |
| WN02 NS5 | - - - - - - - - - - | - - - - - - - - - - | - - - - - - - - - - | 608 |
| H NS5F2 | AACCGTCAAC | TGGATGGTAT | GATTGGCAGC | 914 |
| H NS5F5 | - - - - - - - - - - | - - - - - - - - - - | - - - - - - - - - - | 1027 |
| H NS5R3 rev | - - - - - - - - - - | - - - - - - - - - - | - - - - - - - - - - | 1019 |
| H NS5R5 rev | - - - - - - - - - - | - - - - - - - - - - | - - - - - - - - - - | 1015 |
| Consensus | - - - - - - - - - - | - - - - - - - - - - | - - - - - - - - - - | |

100%
Conservation
0%

| | | | | |
|---|---|---|---|---|
| NY99 NS5 | - - - - - - - - - - | - - - - - - - - - - | - - - - - - - - - - | 608 |
| WN02 NS5 | - - - - - - - - - - | - - - - - - - - - - | - - - - - - - - - - | 608 |
| H NS5F2 | NNNTCCATTT | TGCTCAAACC | ATTTCACTGA | 944 |
| H NS5F5 | - - - - - - - - - - | - - - - - - - - - - | - - - - - - - - - - | 1027 |
| H NS5R3 rev | - - - - - - - - - - | - - - - - - - - - - | - - - - - - - - - - | 1019 |
| H NS5R5 rev | - - - - - - - - - - | - - - - - - - - - - | - - - - - - - - - - | 1015 |
| Consensus | - - - - - - - - - - | - - - - - - - - - - | - - - - - - - - - - | |

100%
Conservation
0%

| | | |
|---|---|---|
| NY99 NS5 | - | 608 |
| WN02 NS5 | - | 608 |
| H NS5F2 | A | 945 |
| H NS5F5 | - | 1027 |
| H NS5R3 rev | - | 1019 |
| H NS5R5 rev | - | 1015 |
| Consensus | - | |

100%
Conservation
0%

Fig. 13M/17

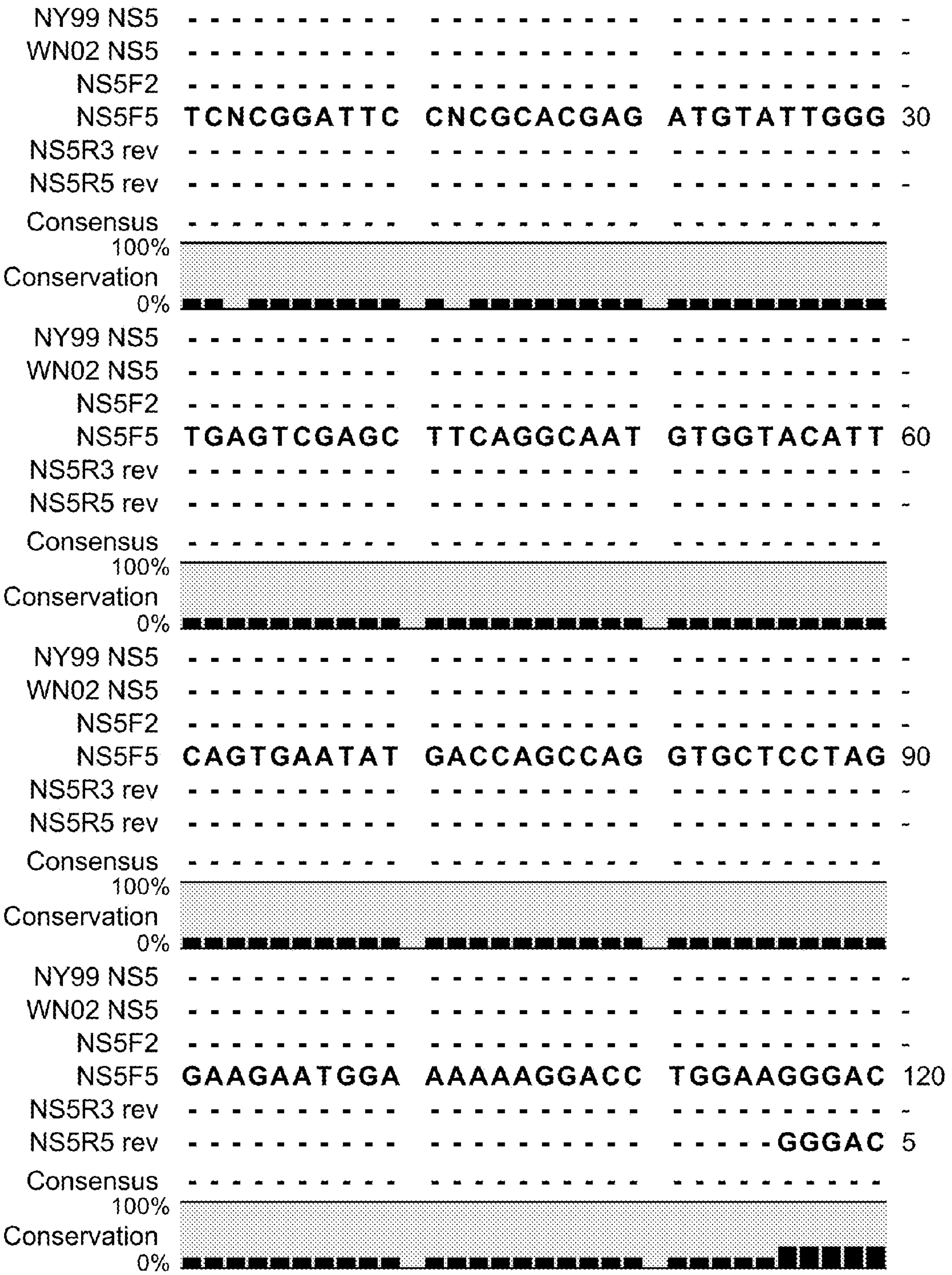
Fig. 14A/17
|              |              |              |              |     |
|---|---|---|---|---|
| NY99 NS5     | ----------   | ----------   | ----------   | -   |
| WN02 NS5     | ----------   | ----------   | ----------   | -   |
| NS5F2        | ----------   | ----------   | ----------   | -   |
| NS5F5        | TCNCGGATTC   | CNCGCACGAG   | ATGTATTGGG   | 30  |
| NS5R3 rev    | ----------   | ----------   | ----------   | -   |
| NS5R5 rev    | ----------   | ----------   | ----------   | -   |
| Consensus    | ----------   | ----------   | ----------   |     |
| NY99 NS5     | ----------   | ----------   | ----------   | -   |
|---|---|---|---|---|
| WN02 NS5     | ----------   | ----------   | ----------   | -   |
| NS5F2        | ----------   | ----------   | ----------   | -   |
| NS5F5        | TGAGTCGAGC   | TTCAGGCAAT   | GTGGTACATT   | 60  |
| NS5R3 rev    | ----------   | ----------   | ----------   | -   |
| NS5R5 rev    | ----------   | ----------   | ----------   | -   |
| Consensus    | ----------   | ----------   | ----------   |     |
| NY99 NS5     | ----------   | ----------   | ----------   | -   |
|---|---|---|---|---|
| WN02 NS5     | ----------   | ----------   | ----------   | -   |
| NS5F2        | ----------   | ----------   | ----------   | -   |
| NS5F5        | CAGTGAATAT   | GACCAGCCAG   | GTGCTCCTAG   | 90  |
| NS5R3 rev    | ----------   | ----------   | ----------   | -   |
| NS5R5 rev    | ----------   | ----------   | ----------   | -   |
| Consensus    | ----------   | ----------   | ----------   |     |
| NY99 NS5     | ----------   | ----------   | ----------   | -   |
|---|---|---|---|---|
| WN02 NS5     | ----------   | ----------   | ----------   | -   |
| NS5F2        | ----------   | ----------   | ----------   | -   |
| NS5F5        | GAAGAATGGA   | AAAAAGGACC   | TGGAAGGGAC   | 120 |
| NS5R3 rev    | ----------   | ----------   | ----------   | -   |
| NS5R5 rev    | ----------   | ----------   | -----GGGAC   | 5   |
| Consensus    | ----------   | ----------   | ----------   |     |
Fig. 14A/17

Figure 14B:
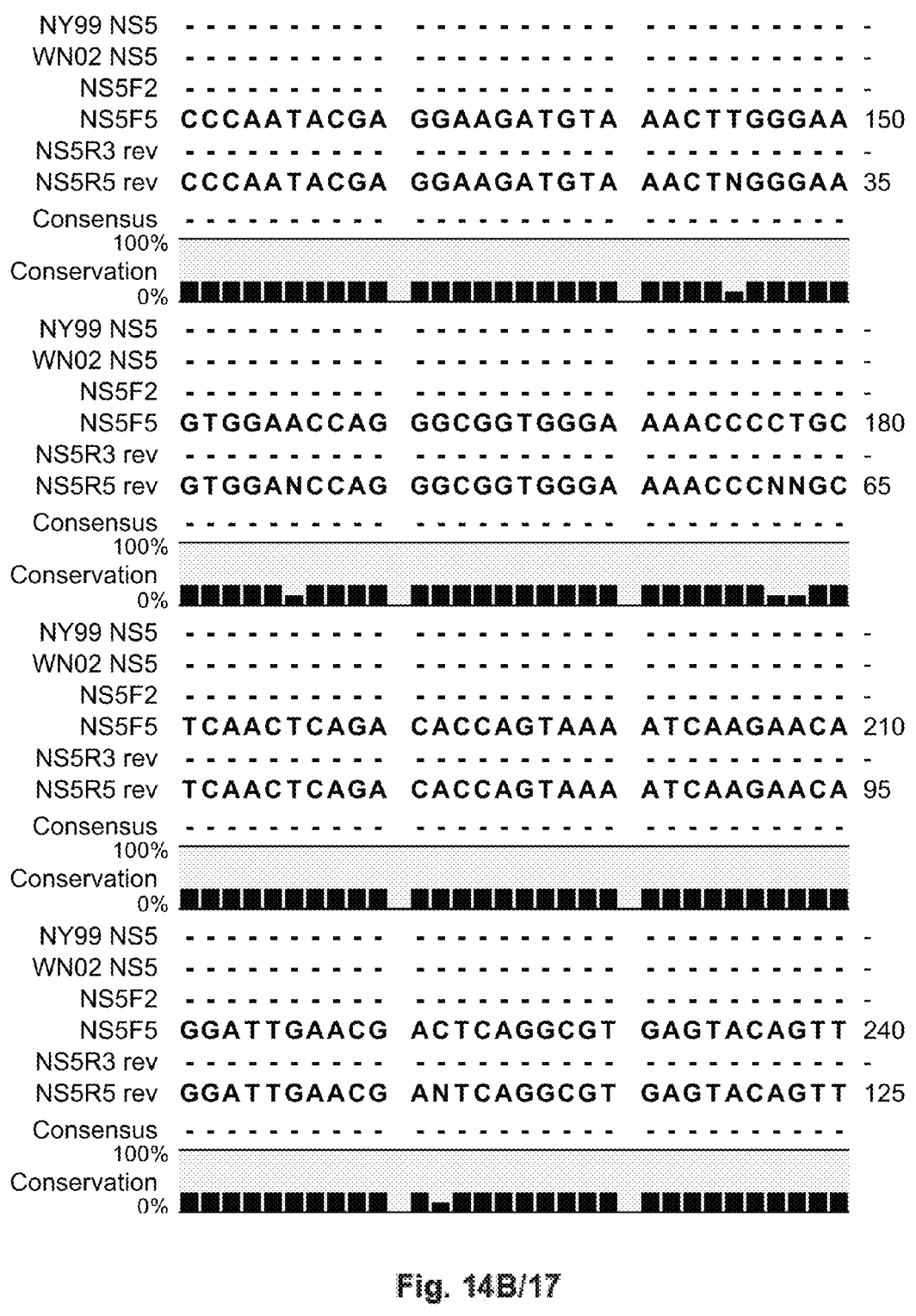

```
NY99 NS5     ----------  ----------  ---------- -
WN02 NS5     ----------  ----------  ---------- -
NS5F2        ----------  ----------  ---------- -
NS5F5        CCCAATACGA  GGAAGATGTA  AACTTGGGAA 150
NS5R3 rev    ----------  ----------  ---------- -
NS5R5 rev    CCCAATACGA  GGAAGATGTA  AACTNGGGAA 35
Consensus    ----------  ----------  ----------
100%
Conservation
0%
NY99 NS5     ----------  ----------  ---------- -
WN02 NS5     ----------  ----------  ---------- -
NS5F2        ----------  ----------  ---------- -
NS5F5        GTGGAACCAG  GGCGGTGGGA  AAACCCCTGC 180
NS5R3 rev    ----------  ----------  ---------- -
NS5R5 rev    GTGGANCCAG  GGCGGTGGGA  AAACCCNNGC 65
Consensus    ----------  ----------  ----------
100%
Conservation
0%
NY99 NS5     ----------  ----------  ---------- -
WN02 NS5     ----------  ----------  ---------- -
NS5F2        ----------  ----------  ---------- -
NS5F5        TCAACTCAGA  CACCAGTAAA  ATCAAGAACA 210
NS5R3 rev    ----------  ----------  ---------- -
NS5R5 rev    TCAACTCAGA  CACCAGTAAA  ATCAAGAACA 95
Consensus    ----------  ----------  ----------
100%
Conservation
0%
NY99 NS5     ----------  ----------  ---------- -
WN02 NS5     ----------  ----------  ---------- -
NS5F2        ----------  ----------  ---------- -
NS5F5        GGATTGAACG  ACTCAGGCGT  GAGTACAGTT 240
NS5R3 rev    ----------  ----------  ---------- -
NS5R5 rev    GGATTGAACG  ANTCAGGCGT  GAGTACAGTT 125
Consensus    ----------  ----------  ----------
100%
Conservation
0%
```

Fig. 14B/17

```
   NY99 NS5  - - - - - - - - - -   - - - - - - - - - -   - - - - - - - - - -   -
   WN02 NS5  - - - - - - - - - -   - - - - - - - - - -   - - - - - - - - - -   -
      NS5F2  - - - - - - - - - -   - - - - - - - - - -   - - - - - - - - - -   -
      NS5F5  CGACGTGGCA  CCACGATGAG  AACCACCCAT  270
 NS5R3 rev   - - - - - - - - - -   - - - - - - - - - -   - - - - - - - - - -   -
 NS5R5 rev   CGACGTGGCA  CCACGATGAG  AACCACCCAT  155
  Consensus  - - - - - - - - - -   - - - - - - - - - -   - - - - - - - - - -
       100%
Conservation
         0%
   NY99 NS5  - - - - - - - - - -   - - - - - - - - - -   - - - - - - - - - -   -
   WN02 NS5  - - - - - - - - - -   - - - - - - - - - -   - - - - - - - - - -   -
      NS5F2  - - - - - - - - - -   - - - - - - - - - -   - - - - - - - - - -   -
      NS5F5  ATAGAACCTG  GAACTATCAC  GGCAGTTATG  300
 NS5R3 rev   - - - - - - - - - -   - - - - - - - - - -   - - - - - - - - - -   -
 NS5R5 rev   ATAGAACCTG  GAACTATCAC  GGCAGTTATG  185
  Consensus  - - - - - - - - - -   - - - - - - - - - -   - - - - - - - - - -
       100%
Conservation
         0%
   NY99 NS5  - - - - - - - - - -   - - - - - - - - - -   - - - - - - - - - -   -
   WN02 NS5  - - - - - - - - - -   - - - - - - - - - -   - - - - - - - - - -   -
      NS5F2  - - - - - - - - - -   - - - - - - - - - -   - - - - - - - - - -   -
      NS5F5  ATGTGAAGCC  CACAGGCTCC  GCCAGTTCGC  330
 NS5R3 rev   - - - - - - - - - -   - - - - - - - - - -   - - - - - - - - - -   -
 NS5R5 rev   ATGTGAAGCC  CACAGGCTCC  GCCAGTTCGC  215
  Consensus  - - - - - - - - - -   - - - - - - - - - -   - - - - - - - - - -
       100%
Conservation
         0%
   NY99 NS5  - - - - - - - - - -   - - - - - - - - - -   - - - - - - - - - -   -
   WN02 NS5  - - - - - - - - - -   - - - - - - - - - -   - - - - - - - - - -   -
      NS5F2  - - - - - - - - - -   - - - - - - - - - -   - - - - - - - - - -   -
      NS5F5  TGGTTAATGG  AGTGGTCAGG  CTCCTCTCAA  360
 NS5R3 rev   -----AATGG  AGNGGTCAGG  CTCCTCTCAA  25
 NS5R5 rev   TGGTTAATGG  AGTGGTCAGG  CTCCTCTCAA  245
  Consensus  -----AATGG  AG-GGTCAGG  CTCCTCTCAA
       100%
Conservation
         0%
```

Fig. 14C/17

| | | | | |
|---|---|---|---|---|
| NY99 NS5 | ---------- | ---------- | ---------- | - |
| WN02 NS5 | ---------- | ---------- | ---------- | - |
| NS5F2 | ---------- | ---------- | ---------- | - |
| NS5F5 | AA-CCATGGG | ACACCATCAC | GAATGTTACC | 389 |
| NS5R3 rev | AACCCNTGGG | ACACCATCAC | GAATGNTACC | 55 |
| NS5R5 rev | AA-CCATGGG | ACACCATCAC | GAATGTTACC | 274 |
| Consensus | AA-CC-TGGG | ACACCATCAC | GAATG-TACC | |

100%
Conservation
0%
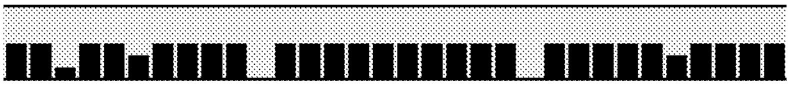

| | | | | |
|---|---|---|---|---|
| NY99 NS5 | ---------- | ---------- | ---------- | - |
| WN02 NS5 | ---------- | ---------- | ---------- | - |
| NS5F2 | ---------- | ---------- | ---------- | - |
| NS5F5 | ACCATGGCCA | TGACTGACAC | TACTCCC-TT | 418 |
| NS5R3 rev | ACCATGGCCA | TGACTGACAC | TACTCCCNTT | 85 |
| NS5R5 rev | ACCATGGCCA | TGACTGACAC | TACTCCC-TT | 303 |
| Consensus | ACCATGGCCA | TGACTGACAC | TACTCCC-TT | |

100%
Conservation
0%
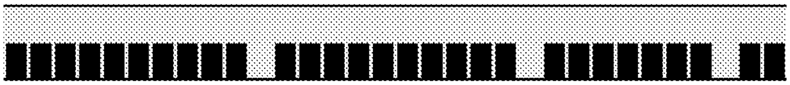

| | | | | |
|---|---|---|---|---|
| NY99 NS5 | ---------- | ---------- | ---------- | - |
| WN02 NS5 | ---------- | ---------- | ---------- | - |
| NS5F2 | ---------- | ---------- | ---------- | - |
| NS5F5 | CGGGCAGCAG | CGAGTGTTCA | AAGAGAAGGT | 448 |
| NS5R3 rev | CGGGCAGCAG | CGAGTGTTCA | AAGAGAAGGT | 115 |
| NS5R5 rev | CGGGCAGCAG | CGAGTGTTCA | AAGAGAAGGT | 333 |
| Consensus | CGGGCAGCAG | CGAGTGTTCA | AAGAGAAGGT | |

100%
Conservation
0%
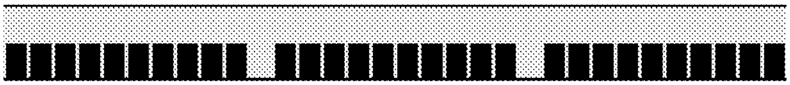

| | | | | |
|---|---|---|---|---|
| NY99 NS5 | ---------- | ---------- | ---------- | - |
| WN02 NS5 | ---------- | ---------- | ---------- | - |
| NS5F2 | ---------- | ---------- | ---------- | - |
| NS5F5 | GGACACGAAA | GCTCCTGAAC | CGCCAGAAGG | 478 |
| NS5R3 rev | GGACACGAAA | GCTCNTGAAC | CGCCAGAAGG | 145 |
| NS5R5 rev | GGACACGAAA | GCTCCTGAAC | CGCCAGAAGG | 363 |
| Consensus | GGACACGAAA | GCTC-TGAAC | CGCCAGAAGG | |

100%
Conservation
0%
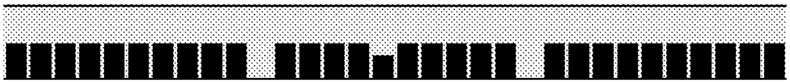

Fig. 14D/17

| | | | | |
|---|---|---|---|---|
| NY99 NS5 | ---------- | ---------- | ---------- | - |
| WN02 NS5 | ---------- | ---------- | ---------- | - |
| NS5F2 | ---------- | ---------- | ---------- | - |
| NS5F5 | AGTGAAGTAC | GTGCTCAACG | AGACCACCAA | 508 |
| NS5R3 rev | AGTGAAGTAC | GTGCTCAACG | AGACCACCAA | 175 |
| NS5R5 rev | AGTGAAGTAC | GTGCTCAACG | AGACCACCAA | 393 |
| Consensus | AGTGAAGTAC | GTGCTCAACG | AGACCACCAA | |

100%
Conservation
0%

| | | | | |
|---|---|---|---|---|
| NY99 NS5 | ---------- | ---------- | ---------- | - |
| WN02 NS5 | ---------- | ---------- | ---------- | - |
| NS5F2 | ---------- | ---------- | ---------- | - |
| NS5F5 | CTGGTTGTGG | GCGTTTTTGG | CCAGAGAAAA | 538 |
| NS5R3 rev | CTGGTTGTGG | GCGTTTTTGG | CCAGAGAAAA | 205 |
| NS5R5 rev | CTGGTTGTGG | GCGTTTTTGG | CCAGAGAAAA | 423 |
| Consensus | CTGGTTGTGG | GCGTTTTTGG | CCAGAGAAAA | |

100%
Conservation
0%

| | | | | |
|---|---|---|---|---|
| NY99 NS5 | ---------- | ---------- | ---------- | - |
| WN02 NS5 | ---------- | ---------- | ---------- | - |
| NS5F2 | ---------- | ---------- | ---------- | - |
| NS5F5 | ACGTCCCAGA | ATGTGCTCTC | GAGAGGAATT | 568 |
| NS5R3 rev | ACGTCCCAGA | ATGTGCTCTC | GAGAGGAATT | 235 |
| NS5R5 rev | ACGTCCCAGA | ATGTGCTCTC | GAGAGGAATT | 453 |
| Consensus | ACGTCCCAGA | ATGTGCTCTC | GAGAGGAATT | |

100%
Conservation
0%

| | | | | |
|---|---|---|---|---|
| NY99 NS5 | ---------- | ---------- | ---------- | - |
| WN02 NS5 | ---------- | ---------- | ---------- | - |
| NS5F2 | ---------- | -------GCA | ATGCAGCTTT | 13 |
| NS5F5 | CATAAGAAAG | GTCAACAGCA | ATGCAGCTTT | 598 |
| NS5R3 rev | CATAAGAAAG | GTCAACAGCA | ATGCAGCTTT | 265 |
| NS5R5 rev | CATAAGAAAG | GTCAACAGCA | ATGCAGCTTT | 483 |
| Consensus | CATAAGAAAG | GTCAACAGCA | ATGCAGCTTT | |

100%
Conservation
0%

Fig. 14E/17

| | | | | |
|---|---|---|---|---|
| NY99 NS5 | ---------- | ---------- | ---------- | - |
| WN02 NS5 | ---------- | ---------- | ---------- | - |
| NS5F2 | GGGTGCCATG | TTTGAAGAGC | AGAATCAATG | 43 |
| NS5F5 | GGGTGCCATG | TTTGAAGAGC | AGAATCAATG | 628 |
| NS5R3 rev | GGGTGCCATG | TTTGAAGAGC | AGAATCAATG | 295 |
| NS5R5 rev | GGGTGCCATG | TTTGAAGAGC | AGAATCAATG | 513 |
| Consensus | GGGTGCCATG | TTTGAAGAGC | AGAATCAATG | |

100%
Conservation
0%

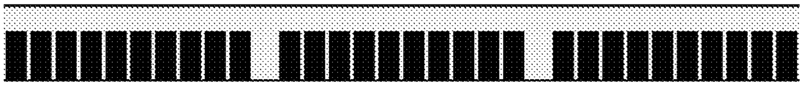

| | | | | |
|---|---|---|---|---|
| NY99 NS5 | ---------- | ---------- | ---------- | - |
| WN02 NS5 | ---------- | ---------- | ---------- | - |
| NS5F2 | GAGGAGCGCC | AGANAAGCAG | TTGAAGATCC | 73 |
| NS5F5 | GAGGAGCGCC | AGAGAAGCAG | TTGAAGATCC | 658 |
| NS5R3 rev | GAGGAGCGCC | AGAGAAGCAG | TTGAAGATCC | 325 |
| NS5R5 rev | GAGGAGCGCC | AGAGAAGCAG | TTGAAGATCC | 543 |
| Consensus | GAGGAGCGCC | AGAGAAGCAG | TTGAAGATCC | |

100%
Conservation
0%

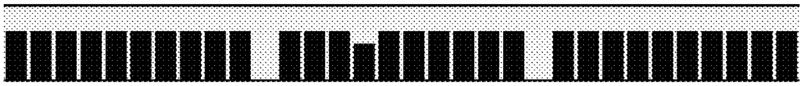

| | | | | |
|---|---|---|---|---|
| NY99 NS5 | ---------- | ---------- | ---------- | - |
| WN02 NS5 | ---------- | ---------- | ---------- | - |
| NS5F2 | AAAATTTTGG | GAGATGGTGG | ATGAGGAGCG | 103 |
| NS5F5 | AAAATTTTGG | GAGATGGTGG | ATGAGGAGCG | 688 |
| NS5R3 rev | AAAATTTTGG | GAGATGGTGG | ATGAGGAGCG | 355 |
| NS5R5 rev | AAAATTTTGG | GAGATGGTGG | ATGAGGAGCG | 573 |
| Consensus | AAAATTTTGG | GAGATGGTGG | ATGAGGAGCG | |

100%
Conservation
0%

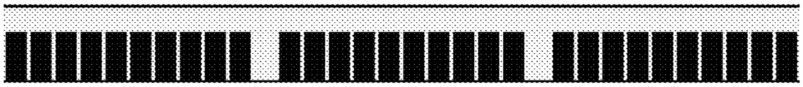

| | | | | |
|---|---|---|---|---|
| NY99 NS5 | ---------- | ---CGGGGGG | AATGTCACAC | 17 |
| WN02 NS5 | ---------- | ---CGGGGGG | AATGTCACAC | 17 |
| NS5F2 | CGAGGCACAT | CTGCGGGGGG | AATGTCACAC | 133 |
| NS5F5 | CGAGGCACAT | CTGCGGGGGG | AATGTCACAC | 718 |
| NS5R3 rev | CGAGGCACAT | CTGCGGGGGG | AATGTCACAC | 385 |
| NS5R5 rev | CGAGGCACAT | CTGCGGGGGG | AATGTCACAC | 603 |
| Consensus | CGAGGCACAT | CTGCGGGGGG | AATGTCACAC | |

100%
Conservation
0%

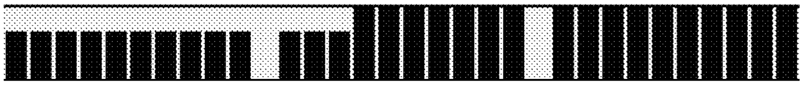

Fig. 14F/17

| | | | | |
|---|---|---|---|---|
| NY99 NS5 | TTGCATTTAC | AACATGATGG | GAAAGAGAGA | 47 |
| WN02 NS5 | TTGCATTTAC | AACATGATGG | GAAAGAGAGA | 47 |
| NS5F2 | TTGCATTTAC | AACATGATGG | GAAAGAGAGA | 163 |
| NS5F5 | TTGCATTTAC | AACATGATGG | GAAAGAGAGA | 748 |
| NS5R3 rev | TTGCATTTAC | AACATGATGG | GAAAGAGAGA | 415 |
| NS5R5 rev | TTGCATTTAC | AACATGATGG | GAAAGAGAGA | 633 |
| Consensus | TTGCATTTAC | AACATGATGG | GAAAGAGAGA | |

100%
Conservation
0%

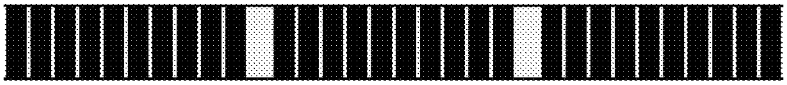

| | | | | |
|---|---|---|---|---|
| NY99 NS5 | GAAAAAACCC | GGAGAATTCG | GAAAGGCCAA | 77 |
| WN02 NS5 | GAAAAAACCC | GGAGAGTTCG | GAAAGGCCAA | 77 |
| NS5F2 | GAAAAAACCC | GGAGAGTTCG | GAAAGGCTAA | 193 |
| NS5F5 | GAAAAAACCC | GGAGAGTTCG | GAAAGGCTAA | 778 |
| NS5R3 rev | GAAAAAACCC | GGAGAGTTCG | GAAAGGCTAA | 445 |
| NS5R5 rev | GAAAAAACCC | GGAGAGTTCG | GAAAGGCTAA | 663 |
| Consensus | GAAAAAACCC | GGAGAGTTCG | GAAAGGCTAA | |

100%
Conservation
0%

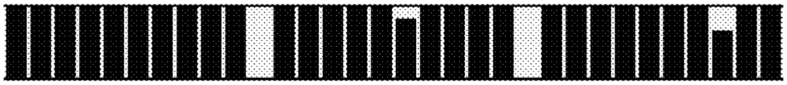

| | | | | |
|---|---|---|---|---|
| NY99 NS5 | GGGAAGCAGA | GCCATTTGGT | TCATGTGGCT | 107 |
| WN02 NS5 | GGGAAGCAGA | GCCATTTGGT | TCATGTGGCT | 107 |
| NS5F2 | GGGAAGCAGA | GCCATTTGGT | TCATGTGGCT | 223 |
| NS5F5 | GGGAAGCAGA | GCCATTTGGT | TCATGTGGCT | 808 |
| NS5R3 rev | GGGAAGCAGA | GCCATTTGGT | TCATGTGGCT | 475 |
| NS5R5 rev | GGGAAGCAGA | GCCATTTGGT | TCATGTGGCT | 693 |
| Consensus | GGGAAGCAGA | GCCATTTGGT | TCATGTGGCT | |

100%
Conservation
0%

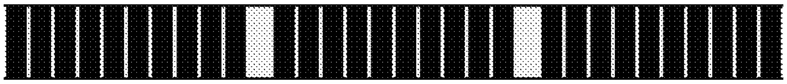

| | | | | |
|---|---|---|---|---|
| NY99 NS5 | CGGAGCTCGC | TTTCTGGAGT | TCGAGGCTCT | 137 |
| WN02 NS5 | CGGAGCTCGC | TTTCTGGAGT | TCGAGGCTCT | 137 |
| NS5F2 | CGGAGCTCGC | TTTCTGGAGT | TCGAGGCTCT | 253 |
| NS5F5 | CGGANCTCGC | TTTCTGGAGT | TCGAGGCTCT | 838 |
| NS5R3 rev | CGGAGCTCGC | TTTCTGGAGT | TCGAGGCTCT | 505 |
| NS5R5 rev | CGGAGCTCGC | TTTCTGGAGT | TCGAGGCTCT | 723 |
| Consensus | CGGAGCTCGC | TTTCTGGAGT | TCGAGGCTCT | |

100%
Conservation
0%

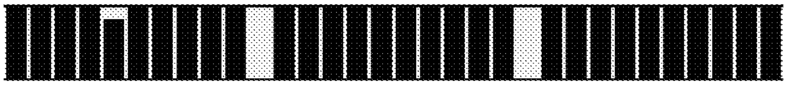

Fig. 14G/17

| | | | | |
|---|---|---|---|---|
| NY99 NS5 | GGGTTTTCTC | AATGAAGACC | ACTGGCTTGG | 167 |
| WN02 NS5 | GGGTTTTCTC | AATGAAGACC | ACTGGCTTGG | 167 |
| NS5F2 | GGGTTTTCTC | AATGAAGACC | ACTGGCTTGG | 283 |
| NS5F5 | GGGTTTTCTC | AATGAAGACC | ACTGGCTTGG | 868 |
| NS5R3 rev | GGGTTTTCTC | AATGAAGACC | ACTGGCTTGG | 535 |
| NS5R5 rev | GGGTTTTCTC | AATGAAGACC | ACTGGCTTGG | 753 |
| Consensus | GGGTTTTCTC | AATGAAGACC | ACTGGCTTGG | |

100%
Conservation
0%

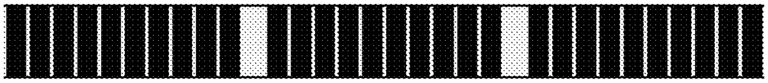

| | | | | |
|---|---|---|---|---|
| NY99 NS5 | AAGAAAGAAC | TCAGGAGGAG | GTGTCGAGGG | 197 |
| WN02 NS5 | AAGAAAGAAC | TCAGGAGGAG | GTGTCGAGGG | 197 |
| NS5F2 | AAGAAAGAAC | TCAGGAGGAG | GTGTCGAGGG | 313 |
| NS5F5 | AAGAAAGAAC | TCNNGAGGAG | GTGTCGAGGG | 898 |
| NS5R3 rev | AAGAAAGAAC | TCAGGAGGAG | GTGTCGAGGG | 565 |
| NS5R5 rev | AAGAAAGAAC | TCAGGAGGAG | GTGTCGAGGG | 783 |
| Consensus | AAGAAAGAAC | TCAGGAGGAG | GTGTCGAGGG | |

100%
Conservation
0%

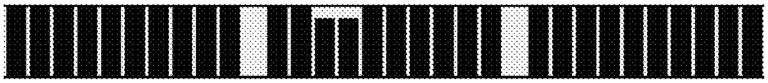

| | | | | |
|---|---|---|---|---|
| NY99 NS5 | CTTGGGCCTC | CAAAAACTGG | GTTACATCCT | 227 |
| WN02 NS5 | CTTGGGCCTC | CAAAAACTGG | GTTACATCCT | 227 |
| NS5F2 | CTTGGGCCTC | CAAAAACTGG | GTTACATCCT | 343 |
| NS5F5 | CTTGGGCCTC | CAAAAACTGG | GTTACATCCT | 928 |
| NS5R3 rev | CTTGGGCCTC | CAAAAACTGG | GTTACATCCT | 595 |
| NS5R5 rev | CTTGGGCCTC | CAAAAACTGG | GTTACATCCT | 813 |
| Consensus | CTTGGGCCTC | CAAAAACTGG | GTTACATCCT | |

100%
Conservation
0%

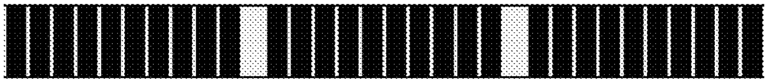

| | | | | |
|---|---|---|---|---|
| NY99 NS5 | GCGTGAAGTT | GGCACCCGGC | CTGGGGGCAA | 257 |
| WN02 NS5 | GCGTGAAGTT | GGCACCCGGC | CTGGGGGCAA | 257 |
| NS5F2 | GCGTGAAGTT | GGCACCCGAC | CTGGGGGCAA | 373 |
| NS5F5 | GCGTGAAGTT | GGCACCCGAC | CTGGGGGCAA | 958 |
| NS5R3 rev | GCGTGAAGTT | GGCACCCGAC | CTGGGGGCAA | 625 |
| NS5R5 rev | GCGTGAAGTT | GGCACCCGAC | CTGGGGGCAA | 843 |
| Consensus | GCGTGAAGTT | GGCACCCGAC | CTGGGGGCAA | |

100%
Conservation
0%

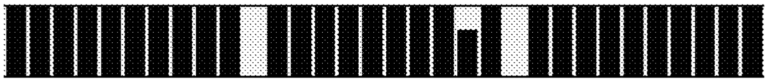

Fig. 14H/17

| | | | | |
|---|---|---|---|---|
| NY99 NS5 | GATCTATGCT | GATGACACAG | CTGGCTGGGA | 287 |
| WN02 NS5 | GATCTATGCT | GATGACACAG | CTGGCTGGGA | 287 |
| NS5F2 | GATCTATGCT | GATGACACAG | CCGGCTGGGA | 403 |
| NS5F5 | GATCTATGCT | GATGACA--- | ---------- | 975 |
| NS5R3 rev | GATCTATGCT | GATGACACAG | CCGGCTGGGA | 655 |
| NS5R5 rev | GATCTATGCT | GATGACACAG | CCGGCTGGGA | 873 |
| Consensus | GATCTATGCT | GATGACACAG | CCGGCTGGGA | |

100%
Conservation
0%

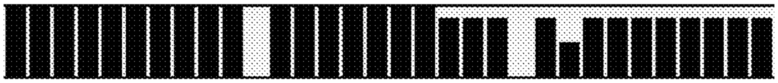

| | | | | |
|---|---|---|---|---|
| NY99 NS5 | CACCCGCATC | ACGAGAGCTG | ACTTGGAAAA | 317 |
| WN02 NS5 | CACCCGCATC | ACGAGTGCTG | ACTTGGAAAA | 317 |
| NS5F2 | CACCCGCATC | ACGAGAGCTG | ACTTGGAAAA | 433 |
| NS5F5 | ---------- | ---------- | ---------- | 975 |
| NS5R3 rev | CACCCGCATC | ACGAGAGCTG | ACTTGGAAAA | 685 |
| NS5R5 rev | CACCCGCATC | ACGAGAGCTG | ACTTGGAAAA | 903 |
| Consensus | CACCCGCATC | ACGAGAGCTG | ACTTGGAAAA | |

100%
Conservation
0%

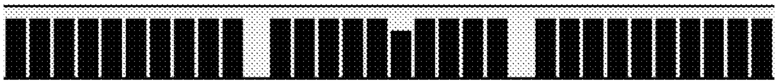

| | | | | |
|---|---|---|---|---|
| NY99 NS5 | TGAAGCTAAG | GTGCTTGAGC | TGCTTGATGG | 347 |
| WN02 NS5 | TGAAGCTAAG | GTGCTTGAGT | TGCTTGATGG | 347 |
| NS5F2 | TGAAGCTAAG | GTGCTTGAGT | TGCTTGATGG | 463 |
| NS5F5 | ---------- | ---------- | ---------- | 975 |
| NS5R3 rev | TGAAGCTAAG | GTGCTTGAGT | TGCTTGATGG | 715 |
| NS5R5 rev | TGAAGCTAAG | GTGCTTGAGT | TGCTTGATGG | 933 |
| Consensus | TGAAGCTAAG | GTGCTTGAGT | TGCTTGATGG | |

100%
Conservation
0%

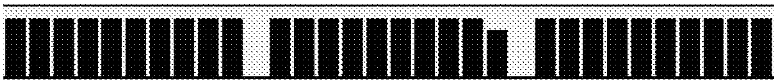

| | | | | |
|---|---|---|---|---|
| NY99 NS5 | GGAACATCGG | CGTCTTGCCA | GGGCCATCAT | 377 |
| WN02 NS5 | GGAACATCGG | CGTCTTGCCA | GGGCCATCAT | 377 |
| NS5F2 | GGAACATCGG | CGTCTTGCCA | GGGCCATCAT | 493 |
| NS5F5 | ---------- | ---------- | ---------- | 975 |
| NS5R3 rev | GGAACATCGG | CGTCTTGCCA | GGGCCATCAT | 745 |
| NS5R5 rev | GGAACATCGG | CGTCTTGCCA | GGGCCATC-- | 961 |
| Consensus | GGAACATCGG | CGTCTTGCCA | GGGCCATCAT | |

100%
Conservation
0%

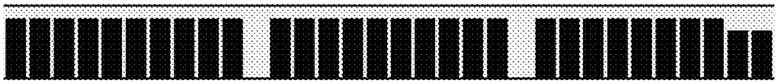

Fig. 14I/17

```
NY99 NS5    TGAGCTCACC TATCGTCACA AAGTTGTGAA 407
WN02 NS5    TGAGCTCACC TATCGTCACA AAGTTGTGAA 407
NS5F2       TGAGCTCACC TATCGTCACA AAGTTGTGAA 523
NS5F5       ---------- ---------- ---------- 975
NS5R3 rev   TGAGCTCACC TATCGTCACA AAGTTGTGAA 775
NS5R5 rev   ---------- ---------- ---------- 961
Consensus   TGAGCTCACC TATCGTCACA AAGTTGTGAA
```

100%
Conservation
0%

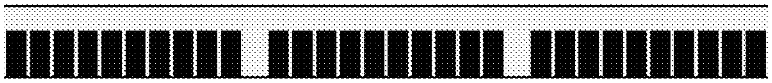

```
NY99 NS5    AGTGATGCGC CCGGCTGCTG ATGGAAGAAC 437
WN02 NS5    AGTGATGCGC CCGGCTGCTG ATGGAAGAAC 437
NS5F2       AGTGATGCGC CCGGCTGCTG ATGGAAGAAC 553
NS5F5       ---------- ---------- ---------- 975
NS5R3 rev   AGTGATGCGC CCGGCTGCTG ATGGAAGAAC 805
NS5R5 rev   ---------- ---------- ---------- 961
Consensus   AGTGATGCGC CCGGCTGCTG ATGGAAGAAC
```

100%
Conservation
0%

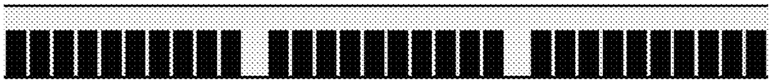

```
NY99 NS5    CGTCATGGAT GTTATCTCCA GAGAAGATCA 467
WN02 NS5    CGTCATGGAT GTTATCTCCA GAGAAGATCA 467
NS5F2       CGTCATGGAT GTTATCTCCA GAGAAGATCA 583
NS5F5       ---------- ---------- ---------- 975
NS5R3 rev   CGTCATGGAT GTTATCTCCA GAGAAGATCA 835
NS5R5 rev   ---------- ---------- ---------- 961
Consensus   CGTCATGGAT GTTATCTCCA GAGAAGATCA
```

100%
Conservation
0%

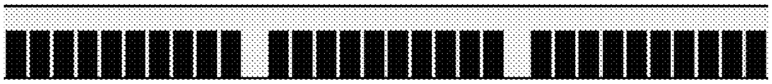

```
NY99 NS5    GAGGGGGAGT GGACAAGTTG TCACCTACGC 497
WN02 NS5    GAGGGGGAGT GGACAAGTTG TCACCTACGC 497
NS5F2       GAGGGGGAGT GGACAAGTTG TCACCTACGC 613
NS5F5       ---------- ---------- ---------- 975
NS5R3 rev   GAGGGGGAGT GGACAAGTTG TCACCTACGC 865
NS5R5 rev   ---------- ---------- ---------- 961
Consensus   GAGGGGGAGT GGACAAGTTG TCACCTACGC
```

100%
Conservation
0%

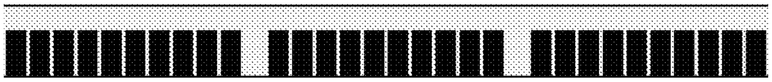

Fig. 14J/17

| | | | | |
|---|---|---|---|---|
| NY99 NS5 | CCTAAACACT | TTCACCAACC | TGGCCGTCCA | 527 |
| WN02 NS5 | CCTAAACACT | TTCACCAACC | TGGCCGTCCA | 527 |
| NS5F2 | CCTAAACACT | TTCACCAACC | TGGCCGTCCA | 643 |
| NS5F5 | ---------- | ---------- | ---------- | 975 |
| NS5R3 rev | CCTAAACACT | TTCACCAACC | TGGCCGTCCA | 895 |
| NS5R5 rev | ---------- | ---------- | ---------- | 961 |
| Consensus | CCTAAACACT | TTCACCAACC | TGGCCGTCCA | |

100%
Conservation
0%
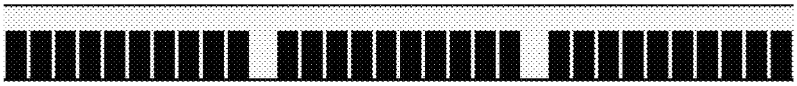

| | | | | |
|---|---|---|---|---|
| NY99 NS5 | GCTGGTGAGG | ATGATGGAAG | GGGAAGGAGT | 557 |
| WN02 NS5 | GCTGGTGAGG | ATGATGGAAG | GGGAAGGAGT | 557 |
| NS5F2 | GCTGGTGAGG | ATGATGGAAG | GGGAAGGAGT | 673 |
| NS5F5 | ---------- | ---------- | ---------- | 975 |
| NS5R3 rev | GCTGGTGAGG | ATGATGGAAG | GGGAAGGAGT | 925 |
| NS5R5 rev | ---------- | ---------- | ---------- | 961 |
| Consensus | GCTGGTGAGG | ATGATGGAAG | GGGAAGGAGT | |

100%
Conservation
0%
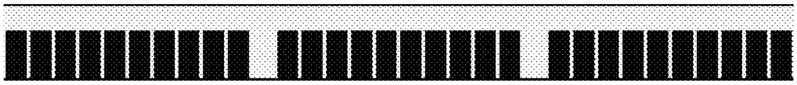

| | | | | |
|---|---|---|---|---|
| NY99 NS5 | GATTGGCCCA | GATGATGTGG | AGAAACTCAC | 587 |
| WN02 NS5 | GATTGGCCCA | GATGATGTGG | AGAAACTCAC | 587 |
| NS5F2 | GATTGGCCCA | GATGATGTGG | AGAAACTCAC | 703 |
| NS5F5 | ---------- | ---------- | ---------- | 975 |
| NS5R3 rev | GATTGGCCCA | GATGATGTGG | AGAAACTCAC | 955 |
| NS5R5 rev | ---------- | ---------- | ---------- | 961 |
| Consensus | GATTGGCCCA | GATGATGTGG | AGAAACTCAC | |

100%
Conservation
0%
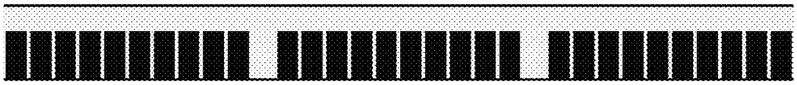

| | | | | |
|---|---|---|---|---|
| NY99 NS5 | AAAAGGGAAA | GGACCCAAAG | T--------- | 608 |
| WN02 NS5 | AAAAGGGAAA | GGACCCAAAG | T--------- | 608 |
| NS5F2 | AAAAGGGAAA | GGACCCAAAG | TCAGGACCTG | 733 |
| NS5F5 | ---------- | ---------- | ---------- | 975 |
| NS5R3 rev | AA-------- | ---------- | ---------- | 957 |
| NS5R5 rev | ---------- | ---------- | ---------- | 961 |
| Consensus | AAAAGGGAAA | GGACCCAAAG | T--------- | |

100%
Conservation
0%
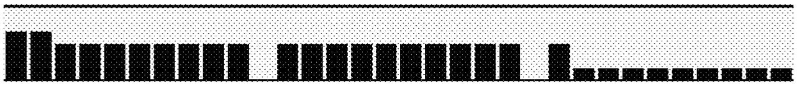

Fig. 14K/17

| | | | | |
|---|---|---|---|---|
| NY99 NS5 | ---------- | ---------- | ---------- | 608 |
| WN02 NS5 | ---------- | ---------- | ---------- | 608 |
| NS5F2 | **GCTGTTTGAG** | **AATGGGGAAG** | **AAAGACTCAG** | 763 |
| NS5F5 | ---------- | ---------- | ---------- | 975 |
| NS5R3 rev | ---------- | ---------- | ---------- | 957 |
| NS5R5 rev | ---------- | ---------- | ---------- | 961 |
| Consensus | ---------- | ---------- | ---------- | |
| 100% Conservation 0% | | | | |

| | | | | |
|---|---|---|---|---|
| NY99 NS5 | ---------- | ---------- | ---------- | 608 |
| WN02 NS5 | ---------- | ---------- | ---------- | 608 |
| NS5F2 | **CCGCATGGCT** | **GTCAGTGGAG** | **ATGACTGTGT** | 793 |
| NS5F5 | ---------- | ---------- | ---------- | 975 |
| NS5R3 rev | ---------- | ---------- | ---------- | 957 |
| NS5R5 rev | ---------- | ---------- | ---------- | 961 |
| Consensus | ---------- | ---------- | ---------- | |
| 100% Conservation 0% | | | | |

| | | | | |
|---|---|---|---|---|
| NY99 NS5 | ---------- | ---------- | ---------- | 608 |
| WN02 NS5 | ---------- | ---------- | ---------- | 608 |
| NS5F2 | **GGTAAAGCCC** | **CTGGACGATC** | **GCTTTGCCAC** | 823 |
| NS5F5 | ---------- | ---------- | ---------- | 975 |
| NS5R3 rev | ---------- | ---------- | ---------- | 957 |
| NS5R5 rev | ---------- | ---------- | ---------- | 961 |
| Consensus | ---------- | ---------- | ---------- | |
| 100% Conservation 0% | | | | |

| | | | | |
|---|---|---|---|---|
| NY99 NS5 | ---------- | ---------- | ---------- | 608 |
| WN02 NS5 | ---------- | ---------- | ---------- | 608 |
| NS5F2 | **CTCGCTCCAC** | **TTCCTCAATG** | **CTATGTCAAA** | 853 |
| NS5F5 | ---------- | ---------- | ---------- | 975 |
| NS5R3 rev | ---------- | ---------- | ---------- | 957 |
| NS5R5 rev | ---------- | ---------- | ---------- | 961 |
| Consensus | ---------- | ---------- | ---------- | |
| 100% Conservation 0% | | | | |

Fig. 14L/17

```
NY99 NS5     ----------  ----------  ----------  608
WN02 NS5     ----------  ----------  ----------  608
NS5F2        GGTTCGCAAA  GACATCCAAG  AGTGGAAACC  883
NS5F5        ----------  ----------  ----------  975
NS5R3 rev    ----------  ----------  ----------  957
NS5R5 rev    ----------  ----------  ----------  961

Consensus    ----------  ----------  ----------
100%
Conservation
0%

NY99 NS5     ----------  ----------  ------  608
WN02 NS5     ----------  ----------  ------  608
NS5F2        GTCAACTGGA  TGGTATGATT  GGCAGC  909
NS5F5        ----------  ----------  ------  975
NS5R3 rev    ----------  ----------  ------  957
NS5R5 rev    ----------  ----------  ------  961

Consensus    ----------  ----------  ------
100%
Conservation
0%
```

Fig. 14M/17

```
     NY99 E  TTCAACTGCC  TTGGAATGAG  CAACAGAGAC  30
     WN02 E  TTCAACTGCC  TTGGAATGAG  CAACAGAGAC  30
        EF1  ----------  ----------  ----------  -
        EF3  ----------  ----------  ----------  -
    ER3 rev  ----------  ----------  ----------  -
    ER4 rev  ----------  ----------  ----------  -
  Consensus  ----------  ----------  ----------
```

100%
Conservation
0%
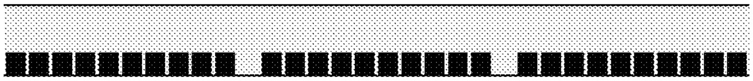

```
     NY99 E  TTCTTGGAAG  GAGTGTCTGG  AGCAACATGG  60
     WN02 E  TTCTTGGAAG  GAGTGTCTGG  AGCAACATGG  60
        EF1  ----------  ----------  ----------  -
        EF3  ----------  ----------  ----------  -
    ER3 rev  ----------  ----------  ----------  -
    ER4 rev  ----------  ----------  ----------  -
  Consensus  ----------  ----------  ----------
```

100%
Conservation
0%
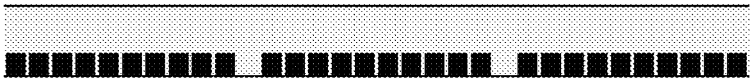

```
     NY99 E  GTGGATTTGG  TTCTCGAAGG  CGACAGCTGC  90
     WN02 E  GTGGATTTGG  TTCTCGAAGG  CGACAGCTGC  90
        EF1  ----------  ----------  ----------  -
        EF3  ----------  ----------  ----------  -
    ER3 rev  ----------  ----------  ----------  -
    ER4 rev  ----------  ----------  ----------  -
  Consensus  ----------  ----------  ----------
```

100%
Conservation
0%
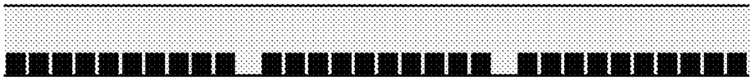

```
     NY99 E  GTGACTATCA  TGTCTAAGGA  CAAGCCTACC  120
     WN02 E  GTGACTATCA  TGTCTAAGGA  CAAGCCTACC  120
        EF1  ----------  ----------  ----------  -
        EF3  ----------  ----------  ----------  -
    ER3 rev  ----------  ----------  ----------  -
    ER4 rev  ----------  ----------  ----------  -
  Consensus  ----------  ----------  ----------
```

100%
Conservation
0%
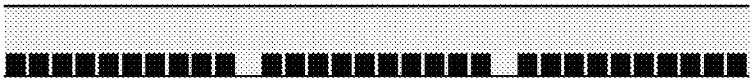

Fig. 15A/17

```
NY99 E     ATCGATGTGA AGATGATGAA TATGGAGGCG 150
WN02 E     ATCGATGTGA AGATGATGAA TATGGAGGCG 150
EF1        ---GATGTGN -GANGANGAA TATGGAGGCG 26
EF3        ---------- ---------- ---------- -
ER3 rev    ---------- ---------- ---------- -
ER4 rev    ---------- ---------- ---------- -
Consensus  ---GATGTG- -GA-GA-GAA TATGGAGGCG
```

100%
Conservation
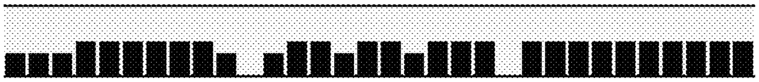
0%

```
NY99 E     GCCAACCTGG CAGAGGTCCG CAGTTATTGC 180
WN02 E     GCCAACCTGG CAGAGGTCCG CAGTTATTGC 180
EF1        GCCAACCTGG CAGAGGTCCG CAGTTATTGC 56
EF3        ---------- ---------- ---------- -
ER3 rev    ---------- ---------- ---------- -
ER4 rev    ---------- ---------- ---------- -
Consensus  GCCAACCTGG CAGAGGTCCG CAGTTATTGC
```

100%
Conservation
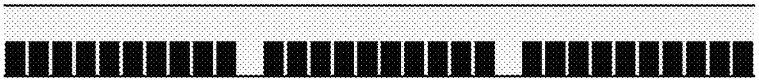
0%

```
NY99 E     TATTTGGCTA CCGTCAGCGA TCTCTCCACC 210
WN02 E     TATTTGGCTA CCGTCAGCGA TCTCTCCACC 210
EF1        TATTTGGCTA CCGTCAGCGA TCTCTCCACC 86
EF3        ---------- ---------- ---------- -
ER3 rev    ---------- ---------- ---------- -
ER4 rev    ---------- ---------- ---------- -
Consensus  TATTTGGCTA CCGTCAGCGA TCTCTCCACC
```

100%
Conservation
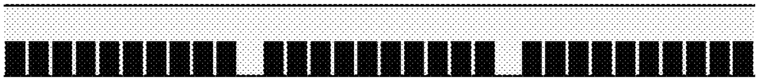
0%

```
NY99 E     AAAGCTGCGT GCCCGACCAT GGGAGAAGCT 240
WN02 E     AAAGCTGCGT GCCCGACCAT GGGAGAAGCT 240
EF1        AAAGCTGCGT GCCCGACCAT GGGAGAAGCT 116
EF3        ---------- ---------- ---------- -
ER3 rev    ---------- ---------- ---------- -
ER4 rev    ---------- ---------- ---------- -
Consensus  AAAGCTGCGT GCCCGACCAT GGGAGAAGCT
```

100%
Conservation
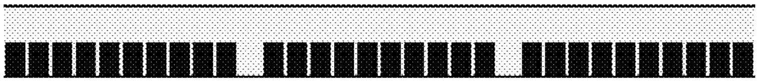
0%

Fig. 15B/17

| | | | | |
|---|---|---|---|---|
| NY99 E | CACAATGACA | AACGTGCTGA | CCCAGCTTTT | 270 |
| WN02 E | CACAATGACA | AACGTGCTGA | CCCAGCTTTT | 270 |
| EF1 | CACAATGACA | AACGTGCTGA | CCCAGCTTTT | 146 |
| EF3 | ---------- | ---------- | ---------- | - |
| ER3 rev | ---------- | ---------- | ---------- | - |
| ER4 rev | ---------- | ---------- | ---------- | - |
| **Consensus** | **CACAATGACA** | **AACGTGCTGA** | **CCCAGCTTTT** | |
| 100% Conservation 0% | | | | |
| NY99 E | GTGTGCAGAC | AAGGAGTGGT | GGACAGGGGC | 300 |
| WN02 E | GTGTGCAGAC | AAGGAGTGGT | GGACAGGGGC | 300 |
| EF1 | GTGTGCAGAC | AAGGAGTGGT | GGACAGGGGC | 176 |
| EF3 | ---------- | ---------- | ---------- | - |
| ER3 rev | ---------- | ---------- | ---------- | - |
| ER4 rev | ---------- | ---------- | ---------- | - |
| **Consensus** | **GTGTGCAGAC** | **AAGGAGTGGT** | **GGACAGGGGC** | |
| 100% Conservation 0% | | | | |
| NY99 E | TGGGGCAACG | GCTGCGGACT | ATTTGGCAAA | 330 |
| WN02 E | TGGGGCAACG | GCTGCGGACT | ATTTGGCAAA | 330 |
| EF1 | TGGGGCAACG | GCTGCGGACT | ATTTGGCAAA | 206 |
| EF3 | ---------- | ---------- | ---------- | - |
| ER3 rev | ---------- | ---------- | ---------- | - |
| ER4 rev | ---------- | ---------- | ---------- | - |
| **Consensus** | **TGGGGCAACG** | **GCTGCGGACT** | **ATTTGGCAAA** | |
| 100% Conservation 0% | | | | |
| NY99 E | GGAAGCATTG | ACACATGCGC | CAAATTTGCC | 360 |
| WN02 E | GGAAGCATTG | ACACATGCGC | CAAATTTGCC | 360 |
| EF1 | GGAAGCATTG | ACACATGCGC | CAAATTTGCC | 236 |
| EF3 | ---------- | ---------- | ---------- | - |
| ER3 rev | ---------- | ---------- | ---------- | - |
| ER4 rev | ---------- | ---------- | ---------- | - |
| **Consensus** | **GGAAGCATTG** | **ACACATGCGC** | **CAAATTTGCC** | |
| 100% Conservation 0% | | | | |

Fig. 15C/17

```
     NY99 E  TGCTCTACCA AGGCAATAGG AAGAACCATC 390
     WN02 E  TGCTCTACCA AGGCAATAGG AAGAACCATC 390
        EF1  TGCTCTACCA AGGCAATAGG AAGAACCATC 266
        EF3  ---------- ---------- ---------C 1
    ER3 rev  ---------- ---------- ---------- -
    ER4 rev  ---------- ---------- ---------- -
  Consensus  TGCTCTACCA AGGCAATAGG AAGAACCATC
```

100%
Conservation
0%

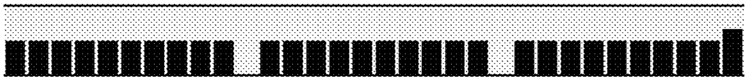

```
     NY99 E  TTGAAAGAGA ATATCAAGTA CGAAGTGGCC 420
     WN02 E  TTGAAAGAGA ATATCAAGTA CGAAGTGGCC 420
        EF1  TTGAAAGAGA ATATCAAGTA CGAAGTGGCC 296
        EF3  TTNANAGANA ---TCAAGTA CGAAGTGGCC 28
    ER3 rev  ---------- ---------- ---------- -
    ER4 rev  ---------- ---------- ---------- -
  Consensus  TTGAAAGAGA ATATCAAGTA CGAAGTGGCC
```

100%
Conservation
0%

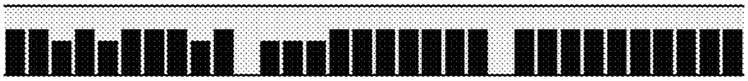

```
     NY99 E  ATTTTTGTCC ATGGACCAAC TACTGTGGAG 450
     WN02 E  ATTTTTGTCC ATGGACCAAC TACTGTGGAG 450
        EF1  ATTTTTGTCC ATGGACCAAC TACTGTGGAG 326
        EF3  ATTTTTGTCC ATGGACCAAC TACTGTGGAG 58
    ER3 rev  ---------- ---------- ---------- -
    ER4 rev  ---------- ---------- ---------- -
  Consensus  ATTTTTGTCC ATGGACCAAC TACTGTGGAG
```

100%
Conservation
0%

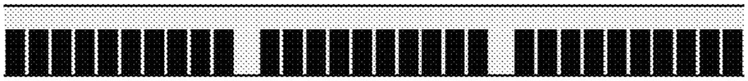

```
     NY99 E  TCGCACGGAA ACTACTCCAC ACAGGTTGGA 480
     WN02 E  TCGCACGGAA ACTATTCCAC ACAGGCTGGA 480
        EF1  TCGCACGGAA ACTACTCCAC ACAGGCTGGA 356
        EF3  TCGCACGGAA ACTACTCCAC ACAGGCTGGA 88
    ER3 rev  ---------- ---------- ---------- -
    ER4 rev  ---------- ---------- ---------- -
  Consensus  TCGCACGGAA ACTACTCCAC ACAGGCTGGA
```

100%
Conservation
0%

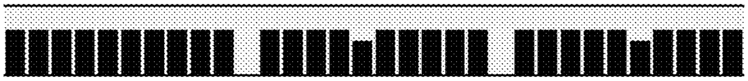

Fig. 15D/17

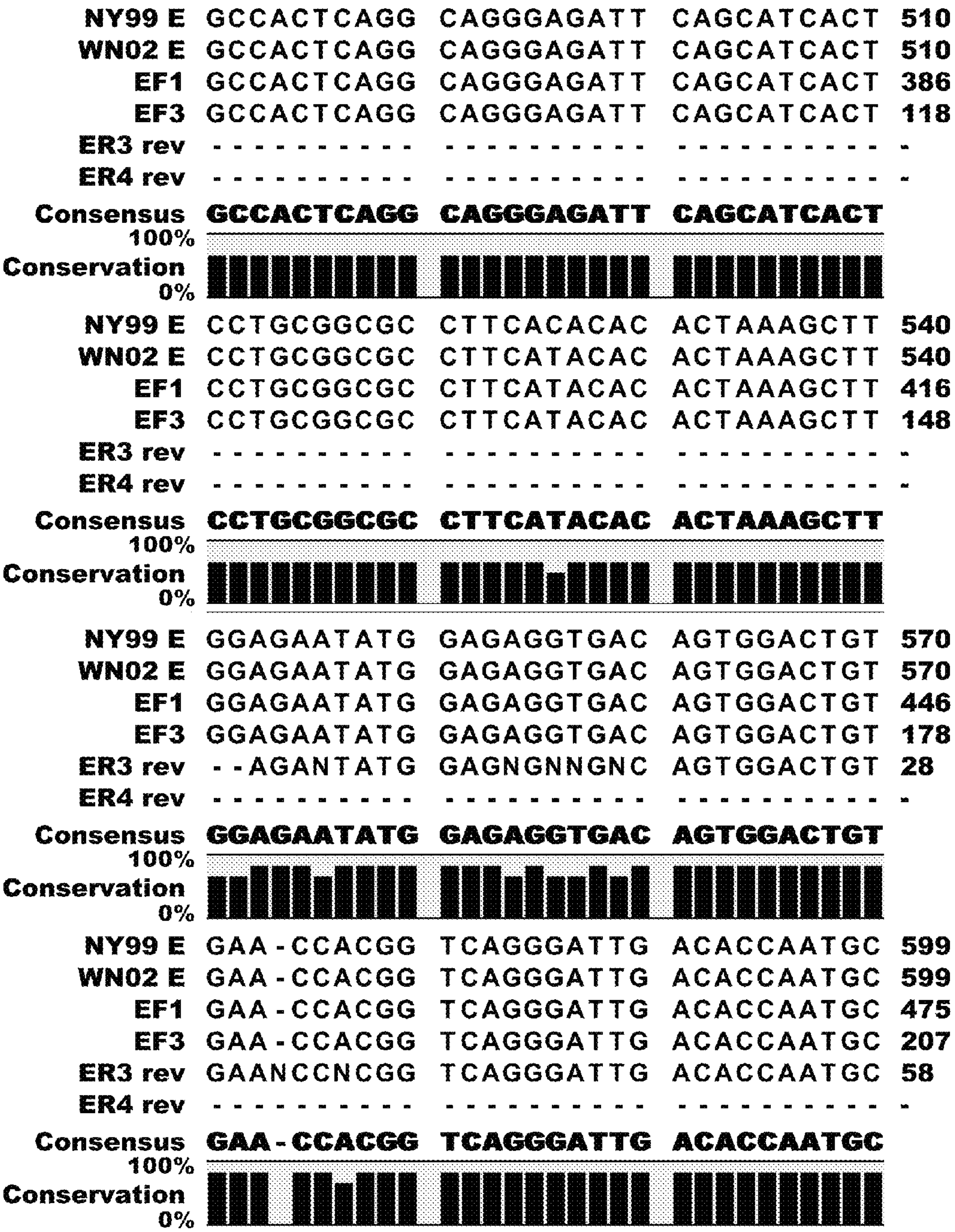
Fig. 15E/17

```
  NY99 E ATACTACGTG ATGACTGTTG GAACAAAGAC 629
  WN02 E ATACTACGTG ATGACTGTTG GAACAAAGAC 629
     EF1 ATACTACGTG ATGACTGTTG GAACAAAGAC 505
     EF3 ATACTACGTG ATGACTGTTG GAACAAAGAC 237
 ER3 rev ATACTACGTG ATGACTGTTG GAACAAAGAC 88
 ER4 rev ---------- ---------- ---------- -
Consensus ATACTACGTG ATGACTGTTG GAACAAAGAC
     100%
Conservation
       0%
  NY99 E GTTCTTGGTC CATCGTGAGT GGTTCATGGA 659
  WN02 E GTTCTTGGTC CATCGTGAGT GGTTCATGGA 659
     EF1 GTTCTTGGTC CATCGTGAGT GGTTCATGGA 535
     EF3 GTTCTTGGTC CATCGTGAGT GGTTCATGGA 267
 ER3 rev GTTCTTGGTC CATCGTGAGT GGTTCATGGA 118
 ER4 rev ---------- ---------- ---------- -
Consensus GTTCTTGGTC CATCGTGAGT GGTTCATGGA
     100%
Conservation
       0%
  NY99 E CCTCAACCTC CCTTGGAGCA GTGCTGGAAG 689
  WN02 E CCTCAACCTC CCTTGGAGCA GTGCTGGAAG 689
     EF1 CCTCAACCTC CCTTGGAGCA GTGCTGGAAG 565
     EF3 CCTCAACCTC CCTTGGAGCA GTGCTGGAAG 297
 ER3 rev CCTCAACCTC CCTTGGAGCA GTGCTGGAAG 148
 ER4 rev ---------- ------AGCA GTGCTGGAAG 14
Consensus CCTCAACCTC CCTTGGAGCA GTGCTGGAAG
     100%
Conservation
       0%
  NY99 E TACTGTGTGG AGG-AACAGA GAGACGTTAA 718
  WN02 E TACTGTGTGG AGG-AACAGA GAGACGTTAA 718
     EF1 TACTGTGTGG AGG-AACAGA GAGACGTTAA 594
     EF3 TACTGTGTGG AGG-AACAGA GAGACGTTAA 326
 ER3 rev TACTGTGTGG AGG-AACAGA GAGACGTTAA 177
 ER4 rev TACTGTGTGG AGGNAACAGA GAGACGTTAA 44
Consensus TACTGTGTGG AGG-AACAGA GAGACGTTAA
     100%
Conservation
       0%
```

Fig. 15F/17

| | | | | |
|---|---|---|---|---|
| NY99 E | TGGAGTTTGA | GGAACCACAC | GCCACGAAGC | 748 |
| WN02 E | TGGAGTTTGA | GGAACCACAC | GCCACGAAGC | 748 |
| EF1 | TGGAGTTTGA | GGAACCACAC | GCCACGAAGC | 624 |
| EF3 | TGGAGTTTGA | GGAACCACAC | GCCACGAAGC | 356 |
| ER3 rev | TGGAGTTTGA | GGAACCACAC | GCCACGAAGC | 207 |
| ER4 rev | TGGAGTTTGA | GGAACCACAC | GCCACGAAGC | 74 |
| **Consensus** | **TGGAGTTTGA** | **GGAACCACAC** | **GCCACGAAGC** | |

100%
Conservation
0%

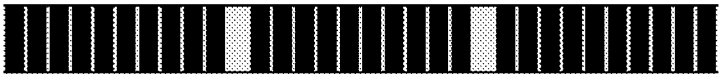

| | | | | |
|---|---|---|---|---|
| NY99 E | AGTCTGTGAT | AGCATTGGGC | TCACAAGAGG | 778 |
| WN02 E | AGTCTGTGAT | AGCATTGGGC | TCACAAGAGG | 778 |
| EF1 | AGTCTGTGAT | AGCATTGGGC | TCACAAGAGG | 654 |
| EF3 | AGTCTGTGAT | AGCATTGGGC | TCACAAGAGG | 386 |
| ER3 rev | AGTCTGTGAT | AGCATTGGGC | TCACAAGAGG | 237 |
| ER4 rev | AGTCTGTGAT | AGCATTGGGC | TCACAAGAGG | 104 |
| **Consensus** | **AGTCTGTGAT** | **AGCATTGGGC** | **TCACAAGAGG** | |

100%
Conservation
0%

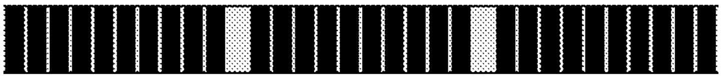

| | | | | |
|---|---|---|---|---|
| NY99 E | GAGCTCTGCA | GCAAGCTTTG | GCTGGAGCCA | 808 |
| WN02 E | GAGCTCTGCA | TCAAGCTTTG | GCTGGAGCCA | 808 |
| EF1 | GAGCTCTGCA | TCAAGCTTTG | GCTGGAGCCA | 684 |
| EF3 | GAGCTCTGCA | TCAAGCTTTG | GCTGGAGCCA | 416 |
| ER3 rev | GAGCTCTGCA | TCAAGCTTTG | GCTGGAGCCA | 267 |
| ER4 rev | GAGCTCTGCA | TCAAGCTTTG | GCTGGAGCCA | 134 |
| **Consensus** | **GAGCTCTGCA** | **TCAAGCTTTG** | **GCTGGAGCCA** | |

100%
Conservation
0%

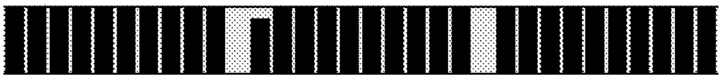

| | | | | |
|---|---|---|---|---|
| NY99 E | TTCCTGTGGA | ATTTTCAAGC | AACACTGTCA | 838 |
| WN02 E | TTCCTGTGGA | ATTTTCAAGC | AACACTGTCA | 838 |
| EF1 | TTCCTGTGGA | ATTTTCAAGC | AACACTGTCA | 714 |
| EF3 | TTCCTGTGGA | ATTTTCAAGC | AACACTGTCA | 446 |
| ER3 rev | TTCCTGTGGA | ATTTTCAAGC | AACACTGTCA | 297 |
| ER4 rev | TTCCTGTGGA | ATTTTCAAGC | AACACTGTCA | 164 |
| **Consensus** | **TTCCTGTGGA** | **ATTTTCAAGC** | **AACACTGTCA** | |

100%
Conservation
0%

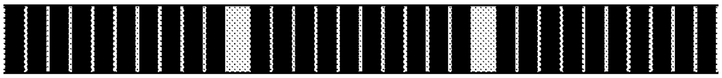

Fig. 15G/17

| | | | | |
|---|---|---|---|---|
| NY99 E | AGTTGACGTC | GGGTCATTTG | AAGTGTAGAG | 868 |
| WN02 E | AGTTGACGTC | GGGTCATTTG | AAGTGTAGAG | 868 |
| EF1 | AGTTGACGTC | GGGTCATTTG | AAGTGTAGAG | 744 |
| EF3 | AGTTGACGTC | GGGTCATTTG | AAGTGTAGAG | 476 |
| ER3 rev | AGTTGACGTC | GGGTCATTTG | AAGTGTAGAG | 327 |
| ER4 rev | AGTTGACGTC | GGGTCATTTG | AAGTGTAGAG | 194 |
| **Consensus** | **AGTTGACGTC** | **GGGTCATTTG** | **AAGTGTAGAG** | |

100%
Conservation
0%

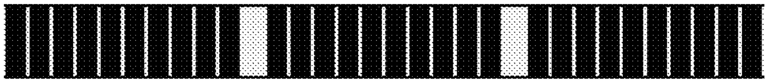

| | | | | |
|---|---|---|---|---|
| NY99 E | TGAAGATGGA | AAAATTGCAG | TTGAAGGGAA | 898 |
| WN02 E | TGAAGATGGA | AAAATTGCAG | TTGAAGGGAA | 898 |
| EF1 | TGAAGATGGA | AAAATTGCAG | TTGAAGGGAA | 774 |
| EF3 | TGAAGATGGA | AAAATTGCAG | TTGAAGGGAA | 506 |
| ER3 rev | TGAAGATGGA | AAAATTGCAG | TTGAAGGGAA | 357 |
| ER4 rev | TGAAGATGGA | AAAATTGCAG | TTGAAGGGAA | 224 |
| **Consensus** | **TGAAGATGGA** | **AAAATTGCAG** | **TTGAAGGGAA** | |

100%
Conservation
0%

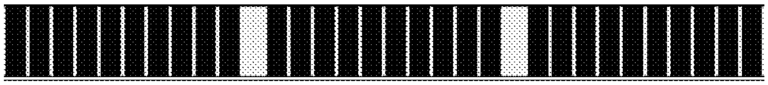

| | | | | |
|---|---|---|---|---|
| NY99 E | CAACCTATGG | CGTCTGTTCA | AAGGCTTTCA | 928 |
| WN02 E | CAACCTATGG | CGTCTGTTCA | AAGGCTTTCA | 928 |
| EF1 | CAACCTATGG | CGTCTGTTCA | AAGGCTTTCA | 804 |
| EF3 | CAACCTATGG | CGTCTGTTCA | AAGGCTTTCA | 536 |
| ER3 rev | CAACCTATGG | CGTCTGTTCA | AAGGCTTTCA | 387 |
| ER4 rev | CAACCTATGG | CGTCTGTTCA | AAGGCTTTCA | 254 |
| **Consensus** | **CAACCTATGG** | **CGTCTGTTCA** | **AAGGCTTTCA** | |

100%
Conservation
0%

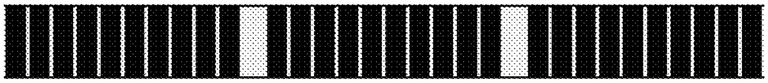

| | | | | |
|---|---|---|---|---|
| NY99 E | AGTTTCTTGG | GACTCCCGCA | GACACAGGTC | 958 |
| WN02 E | AGTTTCTTGG | GACTCCCGCA | GACACAGGTC | 958 |
| EF1 | AGTTTCTTGG | GACTCCCGCA | GACACAGGTC | 834 |
| EF3 | AGTTTCTTGG | GACTCCCGCA | GACACAGGTC | 566 |
| ER3 rev | AGTTTCTTGG | GACTCCCGCA | GACACAGGTC | 417 |
| ER4 rev | AGTTTCTTGG | GACTCCCGCA | GACACAGGTC | 284 |
| **Consensus** | **AGTTTCTTGG** | **GACTCCCGCA** | **GACACAGGTC** | |

100%
Conservation
0%

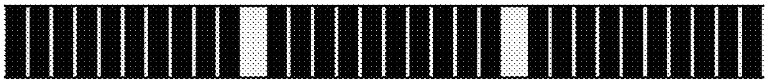

Fig. 15H/17

| | | | | |
|---|---|---|---|---|
| NY99 E | ACGGCACTGT | GGTGTTGGAA | TTGCAGTACA | 988 |
| WN02 E | ACGGCACTGT | GGTGTTGGAA | TTGCAGTACA | 988 |
| EF1 | ACGGCACTGT | GGTGTTGGAA | TTGCAGTACA | 864 |
| EF3 | ACGGCACTGT | GGTGTTGGAA | TTGCAGTACA | 596 |
| ER3 rev | ACGGCACTGT | GGTGTTGGAA | TTGCAGTACA | 447 |
| ER4 rev | ACGGCACTGT | GGTGTTGGAA | TTGCAGTACA | 314 |
| **Consensus** | **ACGGCACTGT** | **GGTGTTGGAA** | **TTGCAGTACA** | |

100%
Conservation
0%

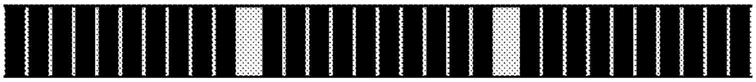

| | | | | |
|---|---|---|---|---|
| NY99 E | CTGGCACGGA | TGGACCTTGC | AAAGTTCCTA | 1018 |
| WN02 E | CTGGCACGGA | TGGACCTTGC | AAAGTTCCTA | 1018 |
| EF1 | CTGGCACGGA | TGGACCTTGC | AAAGTTCCTA | 894 |
| EF3 | CTGGCACGGA | TGGACCTTGC | AAAGTTCCTA | 626 |
| ER3 rev | CTGGCACGGA | TGGACCTTGC | AAAGTTCCTA | 477 |
| ER4 rev | CTGGCACGGA | TGGACCTTGC | AAAGTTCCTA | 344 |
| **Consensus** | **CTGGCACGGA** | **TGGACCTTGC** | **AAAGTTCCTA** | |

100%
Conservation
0%

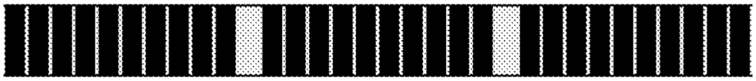

| | | | | |
|---|---|---|---|---|
| NY99 E | TCTCGTCAGT | GGCTTCATTG | AACGACCTAA | 1048 |
| WN02 E | TCTCGTCAGT | GGCTTCATTG | AACGACCTAA | 1048 |
| EF1 | TCTCGTCAGT | GGCTTCATTG | AACGATCTAA | 924 |
| EF3 | TCTCGTCAGT | GGCTTCATTG | AACGATCTAA | 656 |
| ER3 rev | TCTCGTCAGT | GGCTTCATTG | AACGATCTAA | 507 |
| ER4 rev | TCTCGTCAGT | GGCTTCATTG | AACGATCTAA | 374 |
| **Consensus** | **TCTCGTCAGT** | **GGCTTCATTG** | **AACGATCTAA** | |

100%
Conservation
0%

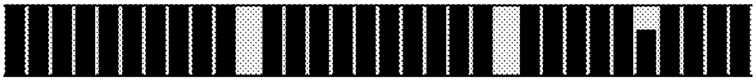

| | | | | |
|---|---|---|---|---|
| NY99 E | CGCCAGTGGG | CAGATTGGTC | ACTGTCAACC | 1078 |
| WN02 E | CGCCAGTGGG | CAGATTGGTC | ACTGTCAACC | 1078 |
| EF1 | CGCCAGTGGG | CAGATTNNTC | ACTGTCAACC | 954 |
| EF3 | CGCCAGTGGG | CAGATTGGTC | ACTGTCAACC | 686 |
| ER3 rev | CGCCAGTGGG | CAGATTGGTC | ACTGTCAACC | 537 |
| ER4 rev | CGCCAGTGGG | CAGATTGGTC | ACTGTCAACC | 404 |
| **Consensus** | **CGCCAGTGGG** | **CAGATTGGTC** | **ACTGTCAACC** | |

100%
Conservation
0%

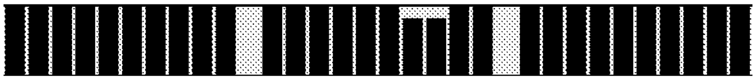

Fig. 15I/17

```
NY99 E     CTTTTGTTTC AGTGGCCACG GCCAACGCTA 1108
WN02 E     CTTTTGTTTC AGTGGCCACG GCCAACGCTA 1108
EF1        CTTTTGTTTC AGTG------ ---------- 968
EF3        CTTTTGTTTC AGTGGCCACG GCCAACGCTA 716
ER3 rev    CTTTTGTTTC AGTGGCCACG GCCAACGCTA 567
ER4 rev    CTTTTGTTTC AGTGGCCACG GCCAACGCTA 434
Consensus  CTTTTGTTTC AGTGGCCACG GCCAACGCTA
```

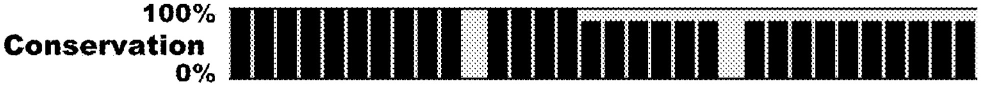

```
NY99 E     AGGTCCTGAT TGAATTGGAA CCACCCTTTG 1138
WN02 E     AGGTCCTGAT TGAATTGGAA CCACCCTTTG 1138
EF1        ---------- ---------- ---------- 968
EF3        AGGTCCTGAT TGAATTGGAA CCACCCTTTG 746
ER3 rev    AGGTCCTGAT TGAATTGGAA CCACCCTTTG 597
ER4 rev    AGGTCCTGAT TGAATTGGAA CCACCCTTTG 464
Consensus  AGGTCCTGAT TGAATTGGAA CCACCCTTTG
```

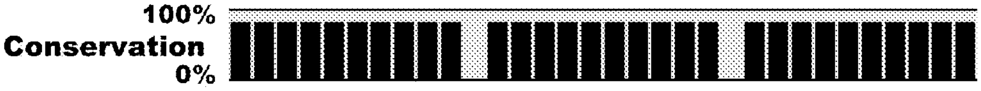

```
NY99 E     GAGACTCATA CATAGTGGTG GGCAGAGGAG 1168
WN02 E     GAGACTCATA CATAGTGGTG GGCAGAGGAG 1168
EF1        ---------- ---------- ---------- 968
EF3        GAGACTCATA CATAGTGGTG GGCAGAGGAG 776
ER3 rev    GAGACTCATA CATAGTGGTG GGCAGAGGAG 627
ER4 rev    GAGACTCATA CATAGTGGTG GGCAGAGGAG 494
Consensus  GAGACTCATA CATAGTGGTG GGCAGAGGAG
```

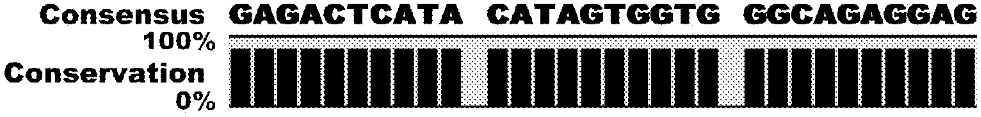

```
NY99 E     AACAACAGAT CAATCACCAT TGGCACAAGT 1198
WN02 E     AACAACAGAT CAATCACCAT TGGCACAAGT 1198
EF1        ---------- ---------- ---------- 968
EF3        AACAACAGAT CAATCACCAT TGGCACAAGT 806
ER3 rev    AACAACAGAT CAATCACCAT TGGCACAAGT 657
ER4 rev    AACAACAGAT CAATCACCAT TGGCACAAGT 524
Consensus  AACAACAGAT CAATCACCAT TGGCACAAGT
```

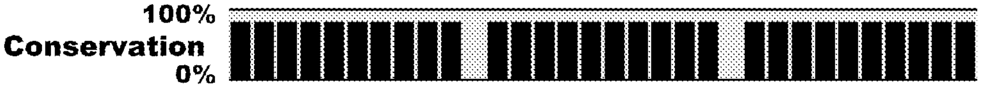

Fig. 15J/17

| | | | | |
|---|---|---|---|---|
| NY99 E | CTGGAAGCAG | CATTGGCAAA | GCCTTTACAA | 1228 |
| WN02 E | CTGGAAGTAG | CATTGGCAAA | GCCTTTACAA | 1228 |
| EF1 | ---------- | ---------- | ---------- | 968 |
| EF3 | CTGGAAGCAG | CATTGGCAAA | GCCTTTACAA | 836 |
| ER3 rev | CTGGAAGCAG | CATTGGCAAA | GCCTTTACAA | 687 |
| ER4 rev | CTGGAAGCAG | CATTGGCAAA | GCCTTTACAA | 554 |
| **Consensus** | **CTGGAAGCAG** | **CATTGGCAAA** | **GCCTTTACAA** | |

100%
Conservation
0%

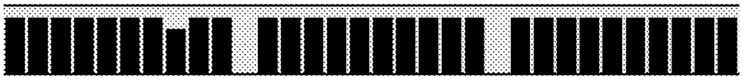

| | | | | |
|---|---|---|---|---|
| NY99 E | CCACCCTCAA | AGGAGCGCAG | AGACTAGCCG | 1258 |
| WN02 E | CCACCCTCAA | AGGAGCGCAG | AGACTAGCCG | 1258 |
| EF1 | ---------- | ---------- | ---------- | 968 |
| EF3 | CCACCCTCAA | AGGAGCGCAG | AGACTAGCCG | 866 |
| ER3 rev | CCACCCTCAA | AGGAGCGCAG | AGACTAGCCG | 717 |
| ER4 rev | CCACCCTCAA | AGGAGCGCAG | AGACTAGCCG | 584 |
| **Consensus** | **CCACCCTCAA** | **AGGAGCGCAG** | **AGACTAGCCG** | |

100%
Conservation
0%

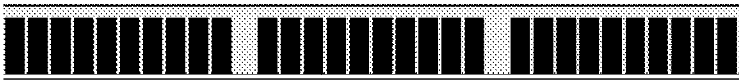

| | | | | |
|---|---|---|---|---|
| NY99 E | CTCTAGGAGA | CACAGCTTGG | GACTTTGGAT | 1288 |
| WN02 E | CTCTAGGAGA | CACAGCTTGG | GACTTTGGAT | 1288 |
| EF1 | ---------- | ---------- | ---------- | 968 |
| EF3 | CTCTAGGAGA | CACAGCTTGG | GACTTTGGAT | 896 |
| ER3 rev | CTCTAGGAGA | CACAGCTTGG | GACTTTGGAT | 747 |
| ER4 rev | CTCTAGGAGA | CACAGCTTGG | GACTTTGGAT | 614 |
| **Consensus** | **CTCTAGGAGA** | **CACAGCTTGG** | **GACTTTGGAT** | |

100%
Conservation
0%

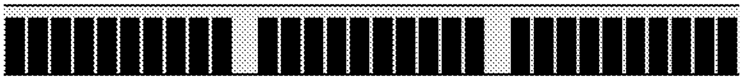

| | | | | |
|---|---|---|---|---|
| NY99 E | CAGTTGGAGG | GGTGTTCACC | TCAGTTGGGA | 1318 |
| WN02 E | CAGTTGGAGG | GGTGTTCACC | TCAGTTGGGA | 1318 |
| EF1 | ---------- | ---------- | ---------- | 968 |
| EF3 | CAGTTGGAGG | GGTGTTCACC | TCAGTTGGGA | 926 |
| ER3 rev | CAGTTGGAGG | GGTGTTCACC | TCAGTTGGGA | 777 |
| ER4 rev | CAGTTGGAGG | GGTGTTCACC | TCAGTTGGGA | 644 |
| **Consensus** | **CAGTTGGAGG** | **GGTGTTCACC** | **TCAGTTGGGA** | |

100%
Conservation
0%

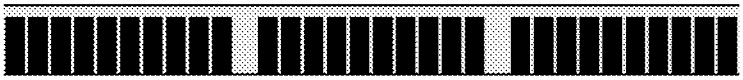

Fig. 15K/17

Figure 15L:
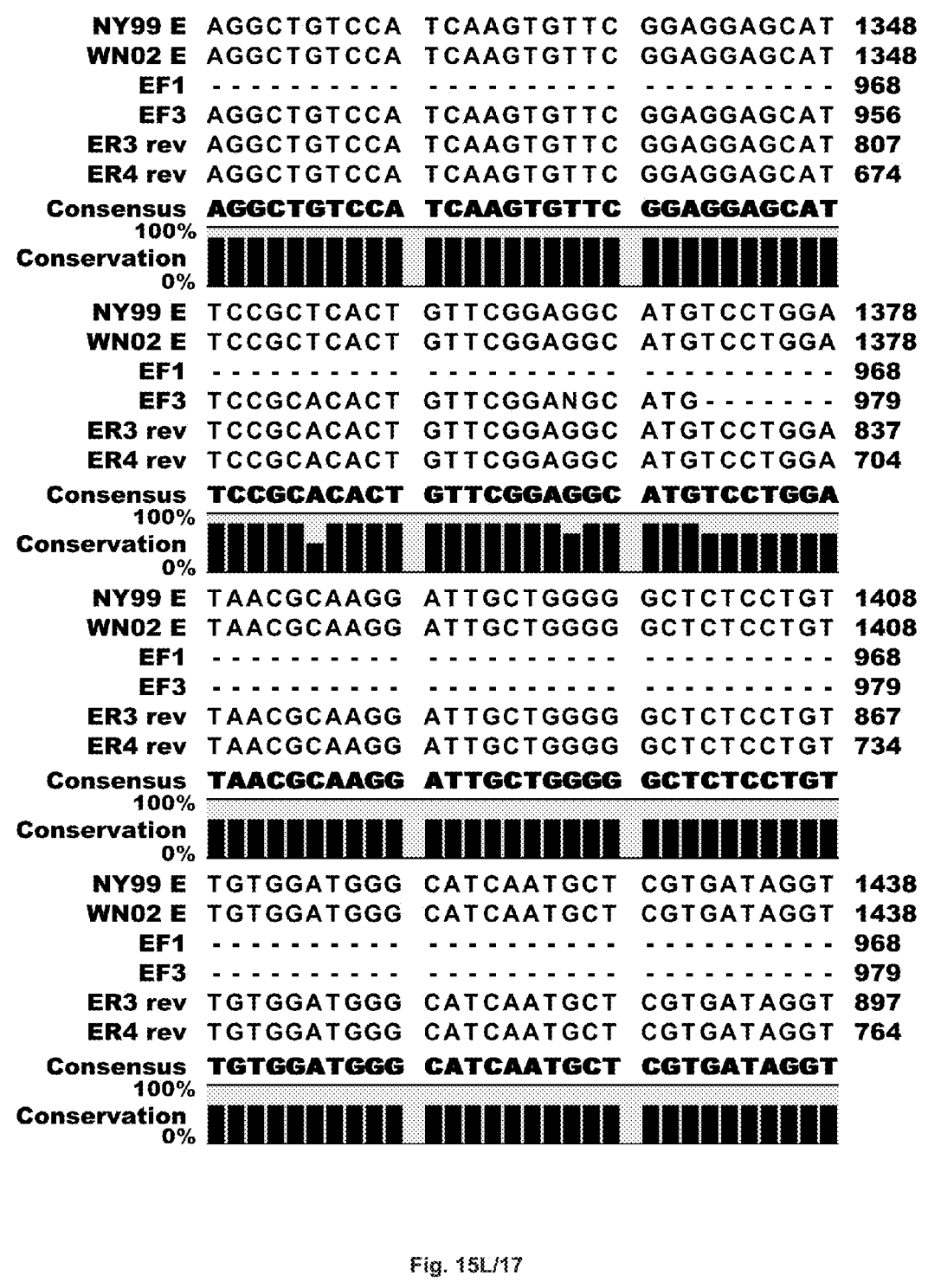

| | | | | |
|---|---|---|---|---|
| NY99 E | AGGCTGTCCA | TCAAGTGTTC | GGAGGAGCAT | 1348 |
| WN02 E | AGGCTGTCCA | TCAAGTGTTC | GGAGGAGCAT | 1348 |
| EF1 | - - - - - - - - - - | - - - - - - - - - - | - - - - - - - - - - | 968 |
| EF3 | AGGCTGTCCA | TCAAGTGTTC | GGAGGAGCAT | 956 |
| ER3 rev | AGGCTGTCCA | TCAAGTGTTC | GGAGGAGCAT | 807 |
| ER4 rev | AGGCTGTCCA | TCAAGTGTTC | GGAGGAGCAT | 674 |
| **Consensus** | **AGGCTGTCCA** | **TCAAGTGTTC** | **GGAGGAGCAT** | |
| 100% Conservation 0% | | | | |
| NY99 E | TCCGCTCACT | GTTCGGAGGC | ATGTCCTGGA | 1378 |
| WN02 E | TCCGCTCACT | GTTCGGAGGC | ATGTCCTGGA | 1378 |
| EF1 | - - - - - - - - - - | - - - - - - - - - - | - - - - - - - - - - | 968 |
| EF3 | TCCGCACACT | GTTCGGANGC | ATG- - - - - - - | 979 |
| ER3 rev | TCCGCACACT | GTTCGGAGGC | ATGTCCTGGA | 837 |
| ER4 rev | TCCGCACACT | GTTCGGAGGC | ATGTCCTGGA | 704 |
| **Consensus** | **TCCGCACACT** | **GTTCGGAGGC** | **ATGTCCTGGA** | |
| 100% Conservation 0% | | | | |
| NY99 E | TAACGCAAGG | ATTGCTGGGG | GCTCTCCTGT | 1408 |
| WN02 E | TAACGCAAGG | ATTGCTGGGG | GCTCTCCTGT | 1408 |
| EF1 | - - - - - - - - - - | - - - - - - - - - - | - - - - - - - - - - | 968 |
| EF3 | - - - - - - - - - - | - - - - - - - - - - | - - - - - - - - - - | 979 |
| ER3 rev | TAACGCAAGG | ATTGCTGGGG | GCTCTCCTGT | 867 |
| ER4 rev | TAACGCAAGG | ATTGCTGGGG | GCTCTCCTGT | 734 |
| **Consensus** | **TAACGCAAGG** | **ATTGCTGGGG** | **GCTCTCCTGT** | |
| 100% Conservation 0% | | | | |
| NY99 E | TGTGGATGGG | CATCAATGCT | CGTGATAGGT | 1438 |
| WN02 E | TGTGGATGGG | CATCAATGCT | CGTGATAGGT | 1438 |
| EF1 | - - - - - - - - - - | - - - - - - - - - - | - - - - - - - - - - | 968 |
| EF3 | - - - - - - - - - - | - - - - - - - - - - | - - - - - - - - - - | 979 |
| ER3 rev | TGTGGATGGG | CATCAATGCT | CGTGATAGGT | 897 |
| ER4 rev | TGTGGATGGG | CATCAATGCT | CGTGATAGGT | 764 |
| **Consensus** | **TGTGGATGGG** | **CATCAATGCT** | **CGTGATAGGT** | |
| 100% Conservation 0% | | | | |

Fig. 15L/17

```
NY99 E       CCATAGCTCT  CACGTTTCTC  GCAGTTGGAG  1468
WN02 E       CCATAGCTCT  CACGTTTCTC  GCAGTTGGAG  1468
EF1          ----------  ----------  ----------  968
EF3          ----------  ----------  ----------  979
ER3 rev      CCATAGCTCT  CACGTTTCTC  GCAGTTGGAG  927
ER4 rev      CCATAGCTCT  CACGTTTCTC  GCAGTTGGAG  794
Consensus    CCATAGCTCT  CACGTTTCTC  GCAGTTGGAG
```

100%
Conservation
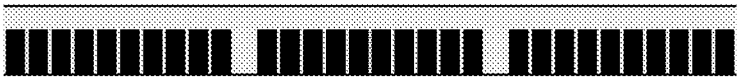
0%

```
NY99 E       GAGTTCTGCT  CTTCCTCTCC  GTGAACGTGC  1498
WN02 E       GAGTTCTGCT  CTTCCTCTCC  GTGAACGTGC  1498
EF1          ----------  ----------  ----------  968
EF3          ----------  ----------  ----------  979
ER3 rev      GAGTTCTGCT  CTTCCTCTCC  GTGAACGTGC  957
ER4 rev      GAGTTCTGCT  CTTCCTCTCC  GTGAACGTGC  824
Consensus    GAGTTCTGCT  CTTCCTCTCC  GTGAACGTGC
```

100%
Conservation
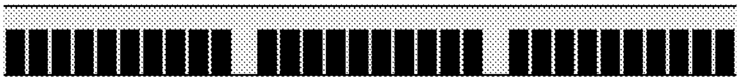
0%

```
NY99 E       ACGCT-----  ----------  ----------  1503
WN02 E       ATGCT-----  ----------  ----------  1503
EF1          ----------  ----------  ----------  968
EF3          ----------  ----------  ----------  979
ER3 rev      ATGCTGACAC  TGGGTGTGCC  ATAGACATCA  987
ER4 rev      ATGCTGACAC  TGGGTGTGCC  ATAGACATCA  854
Consensus    ATGCT-----  ----------  ----------
```

100%
Conservation
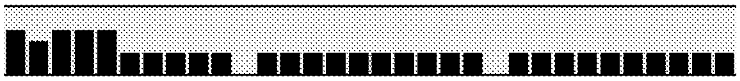
0%

```
NY99 E       ----------  ----------  ----------  1503
WN02 E       ----------  ----------  ----------  1503
EF1          ----------  ----------  ----------  968
EF3          ----------  ----------  ----------  979
ER3 rev      GCCGGCAAGA  GCTGAG----  ----------  1003
ER4 rev      GCCGGCAAGA  GCTGAGATGT  GGAAGTGGAG  884
Consensus    ----------  ----------  ----------
```

100%
Conservation
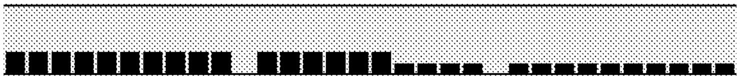
0%

Fig. 15M/17

| | | | | |
|---|---|---|---|---|
| NY99 E | ---------- | ---------- | ---------- | 1503 |
| WN02 E | ---------- | ---------- | ---------- | 1503 |
| EF1 | ---------- | ---------- | ---------- | 968 |
| EF3 | ---------- | ---------- | ---------- | 979 |
| ER3 rev | ---------- | ---------- | ---------- | 1003 |
| ER4 rev | TGTTCATACA | CAATGATGTG | GAGGCTTGGA | 914 |
| Consensus | ---------- | ---------- | ---------- | |

100%
Conservation
0%

| | | | | |
|---|---|---|---|---|
| NY99 E | ---------- | ---------- | ---------- | 1503 |
| WN02 E | ---------- | ---------- | ---------- | 1503 |
| EF1 | ---------- | ---------- | ---------- | 968 |
| EF3 | ---------- | ---------- | ---------- | 979 |
| ER3 rev | ---------- | ---------- | ---------- | 1003 |
| ER4 rev | TGGACCGGTA | CAAGTATTAC | CCTGAAACGC | 944 |
| Consensus | ---------- | ---------- | ---------- | |

100%
Conservation
0%

| | | | | |
|---|---|---|---|---|
| NY99 E | ---------- | ---------- | ---------- | 1503 |
| WN02 E | ---------- | ---------- | ---------- | 1503 |
| EF1 | ---------- | ---------- | ---------- | 968 |
| EF3 | ---------- | ---------- | ---------- | 979 |
| ER3 rev | ---------- | ---------- | ---------- | 1003 |
| ER4 rev | CACAAGGCCT | AGCCAAGATC | ATTCAGAAAG | 974 |
| Consensus | ---------- | ---------- | ---------- | |

100%
Conservation
0%

| | | | | |
|---|---|---|---|---|
| NY99 E | ---------- | ---------- | ---------- | 1503 |
| WN02 E | ---------- | ---------- | ---------- | 1503 |
| EF1 | ---------- | ---------- | ---------- | 968 |
| EF3 | ---------- | ---------- | ---------- | 979 |
| ER3 rev | ---------- | ---------- | ---------- | 1003 |
| ER4 rev | CTCATAAGGA | AGGAGTGTGC | GNTCTACGAN | 1004 |
| Consensus | ---------- | ---------- | ---------- | |

100%
Conservation
0%

Fig. 15N/17

| | | |
|---|---|---|
| NY99 E | - - | 1503 |
| WN02 E | - - | 1503 |
| EF1 | - - | 968 |
| EF3 | - - | 979 |
| ER3 rev | - A | 1004 |
| ER4 rev | C A | 1006 |
| Consensus | - - | |
100%
Conservation
0%
Fig. 15O/17

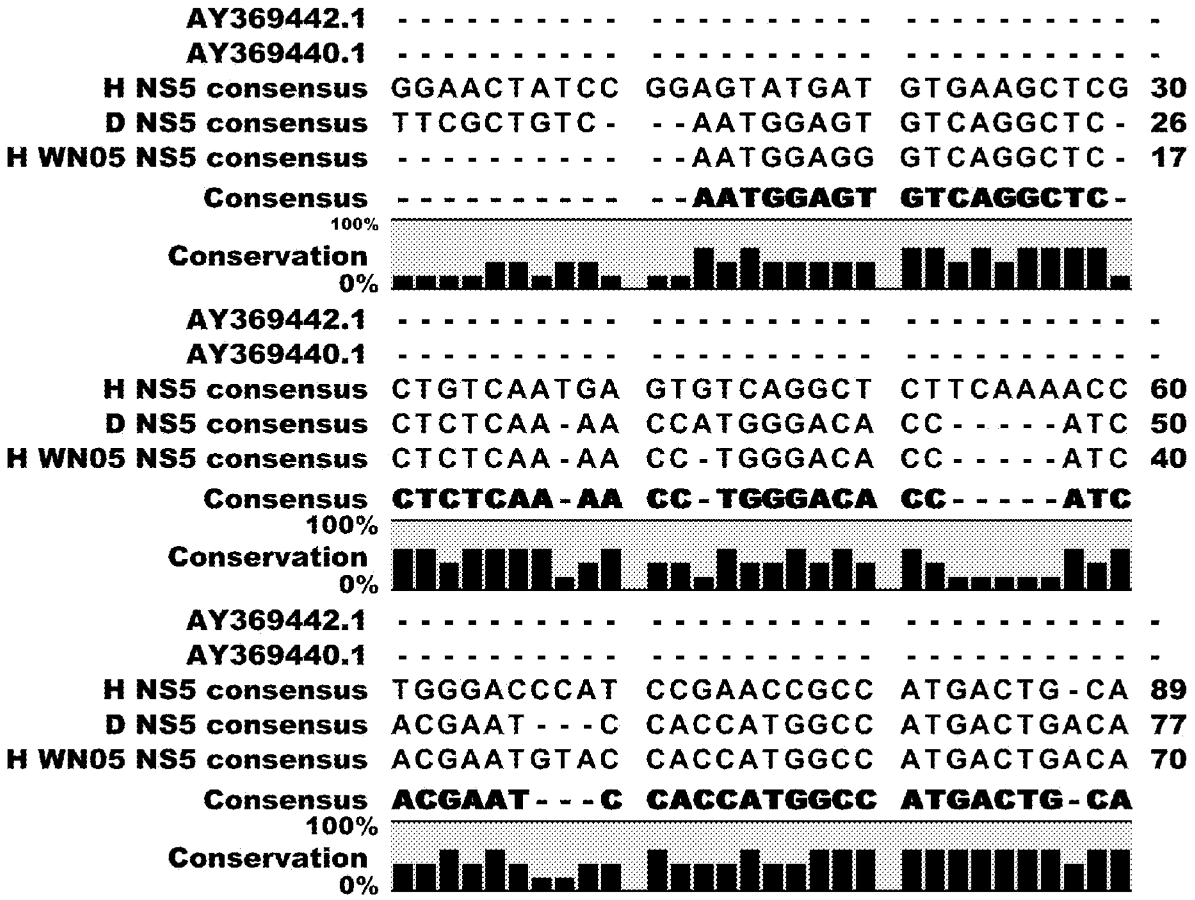
Fig. 16A/17

```
AY369442.1           ----------  ----------  ----------  -
AY369440.1           ----------  ----------  ----------  -
H NS5 consensus      CTACTCCCTT  CGGGCAGCAG  CGAGTGTTCA  119
D NS5 consensus      CTACTCCCTT  CGGGCAGCAG  CGAGTGTTCA  107
H WN05 NS5 consensus CTACTCCCTT  CGGGCAGCAG  CGAGTGTTCA  100
Consensus            CTACTCCCTT  CGGGCAGCAG  CGAGTGTTCA
100%
Conservation
0%
AY369442.1           ----------  ----------  ----------  -
AY369440.1           ----------  ----------  ----------  -
H NS5 consensus      AAGAGAAGGT  GGACACGAAA  GCTC-GAACC  148
D NS5 consensus      AAGAGAAGGT  GGACACGAAA  GCT--GAACC  135
H WN05 NS5 consensus AAGAGAAGGT  GGACACGAAA  GCTCTGAACC  130
Consensus            AAGAGAAGGT  GGACACGAAA  GCT--GAACC
100%
Conservation
0%
AY369442.1           ----------  ----------  ----------  -
AY369440.1           ----------  ----------  ----------  -
H NS5 consensus      GCCAGAAGGA  GTGAAGTACG  TGCTCAACGA  178
D NS5 consensus      GCCAGAAGGA  GTGAAGTACG  TGCTCAACGA  165
H WN05 NS5 consensus GCCAGAAGGA  GTGAAGTACG  TGCTCAACGA  160
Consensus            GCCAGAAGGA  GTGAAGTACG  TGCTCAACGA
100%
Conservation
0%
```

Fig. 16B/17

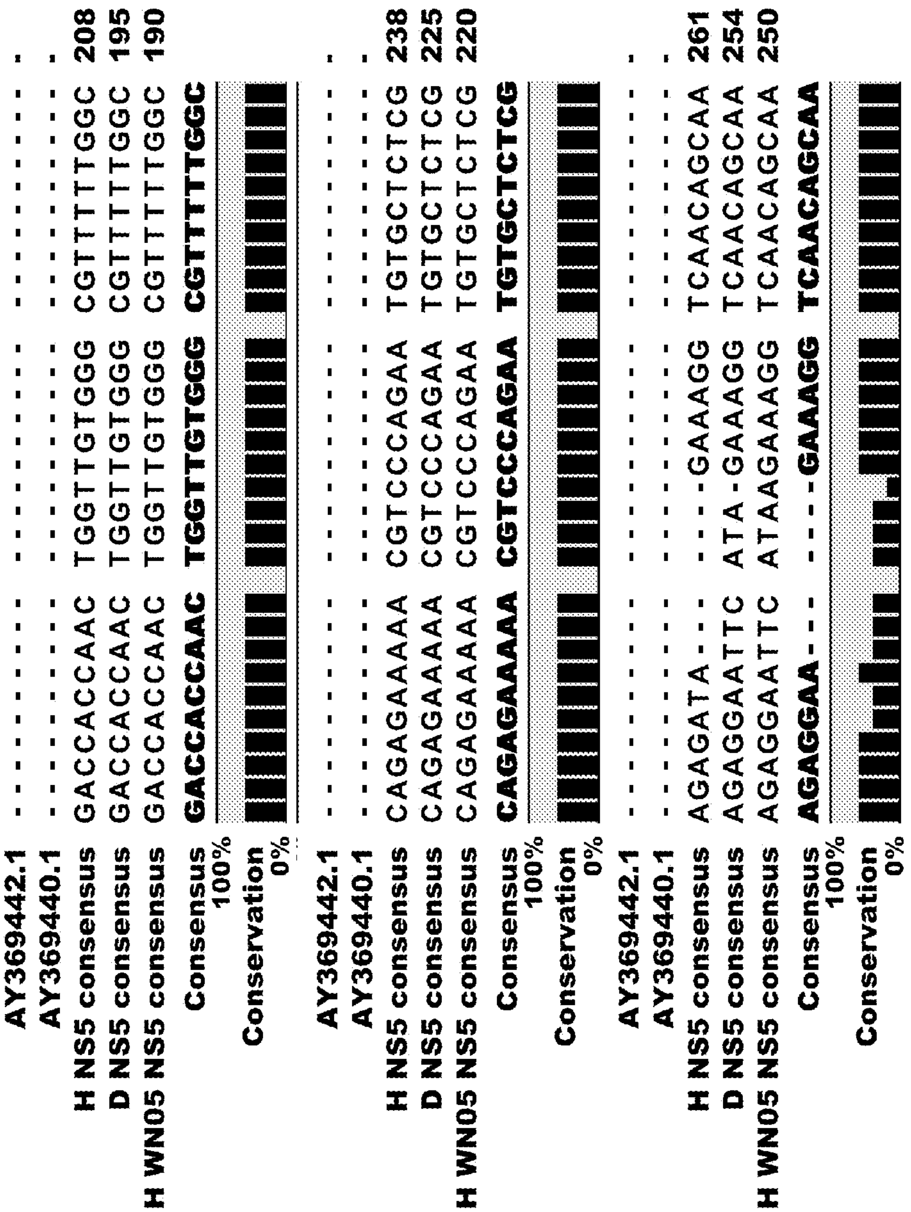
Fig. 16C/17

| | | | | |
|---|---|---|---|---|
| AY369442.1 | ---------- | ---------- | ---------- | - |
| AY369440.1 | ---------- | ---------- | ---------- | - |
| H NS5 consensus | TGCAGCTTTG | GGTGCCATGT | TTGAAGAGCA | 291 |
| D NS5 consensus | TGCAGCTTTG | GGTGCCATGT | TTGAAGAGCA | 284 |
| H WN05 NS5 consensus | TGCAGCTTTG | GGTGCCATGT | TTGAAGAGCA | 280 |
| Consensus | **TGCAGCTTTG** | **GGTGCCATGT** | **TTGAAGAGCA** | |
| 100% Conservation 0% | | | | |
| AY369442.1 | ---------- | ---------- | ---------- | - |
| AY369440.1 | ---------- | ---------- | ---------- | - |
| H NS5 consensus | GAATCAATGG | AGGAGCGCCA | GAGAAGCAGT | 321 |
| D NS5 consensus | GAATCAATGG | AGGAGCGCCA | GAGAAGCAGT | 314 |
| H WN05 NS5 consensus | GAATCAATGG | AGGAGCGCCA | GAGAAGCAGT | 310 |
| Consensus | **GAATCAATGG** | **AGGAGCGCCA** | **GAGAAGCAGT** | |
| 100% Conservation 0% | | | | |
| AY369442.1 | ---------- | ---------- | ---------- | - |
| AY369440.1 | ---------- | ---------- | ---------- | - |
| H NS5 consensus | TGAAGATCCA | AAATTTTGGG | AGATGGTGGA | 351 |
| D NS5 consensus | TGAAGATCCA | AAATTTTGGG | AGATGGTGGA | 344 |
| H WN05 NS5 consensus | TGAAGATCCA | AAATTTTGGG | AGATGGTGGA | 340 |
| Consensus | **TGAAGATCCA** | **AAATTTTGGG** | **AGATGGTGGA** | |
| 100% Conservation 0% | | | | |

Fig. 16D/17

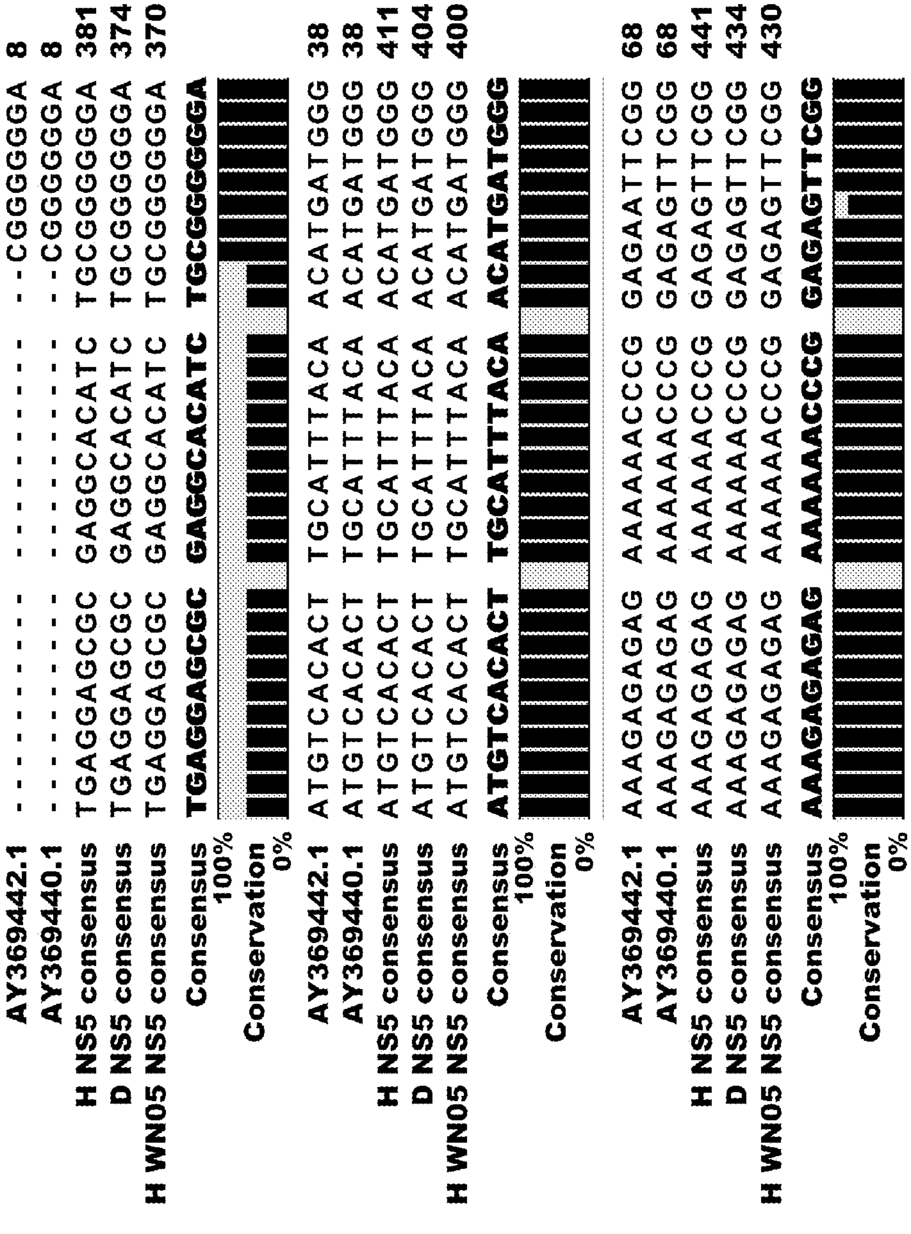
Fig. 16E/17

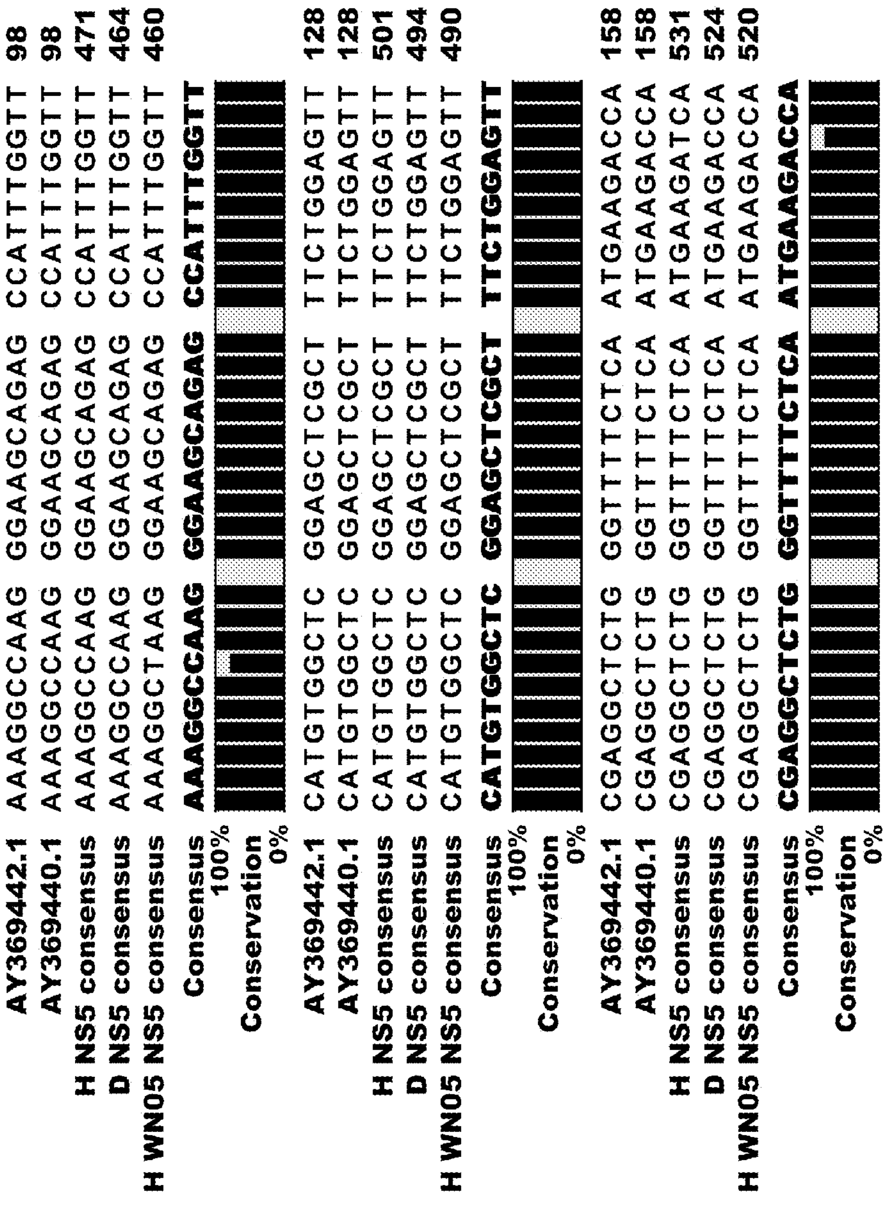
Fig. 16F/17

```
AY369442.1             CTGGCTTGGA  AGAAAGAACT  CAGGAGGAGG  188
AY369440.1             CTGGCTTGGA  AGAAAGAACT  CAGGAGGAGG  188
H NS5 consensus        CTGGCTTGGA  AGAAAGAACT  CAGGAGGAGG  561
D NS5 consensus        CTGGCTTGGA  AGAAAGAACT  CAGGAGGAGG  554
H WN05 NS5 consensus   CTGGCTTGGA  AGAAAGAACT  CAGGAGGAGG  550
Consensus              CTGGCTTGGA  AGAAAGAACT  CAGGAGGAGG
100%
Conservation
0%
AY369442.1             TGTCGAGGGC  TTGGGCCTCC  AAAAACTGGG  218
AY369440.1             TGTCGAGGGC  TTGGGCCTCC  AAAAACTGGG  218
H NS5 consensus        TGTCGAGGGC  TTGGGCCTCC  AAAAACTGGG  591
D NS5 consensus        TGTCGAGGGC  TTGGGCCTCC  AAAAACTGGG  584
H WN05 NS5 consensus   TGTCGAGGGC  TTGGGCCTCC  AAAAACTGGG  580
Consensus              TGTCGAGGGC  TTGGGCCTCC  AAAAACTGGG
100%
Conservation
0%
AY369442.1             TTACATCCTG  CGTGAAGTTG  GCACCCGGCC  248
AY369440.1             TTACATCCTG  CGTGAAGTTG  GCACCCGGCC  248
H NS5 consensus        TTACATCCTG  CGTGAAGTTG  GCACCCGGCC  621
D NS5 consensus        TTACATCCTG  CGTGAAGTTG  GCACCCGGCC  614
H WN05 NS5 consensus   TTACATCCTG  CGTGAAGTTG  GCACCCGACC  610
Consensus              TTACATCCTG  CGTGAAGTTG  GCACCCGGCC
100%
Conservation
0%
```

Fig. 16G/17

| | | | | |
|---|---|---|---|---|
| AY369442.1 | TGGGGGCAAG | ATCTATGCTG | ATGACACAGC | 278 |
| AY369440.1 | TGGGGGCAAG | ATCTATGCTG | ATGACACAGC | 278 |
| H NS5 consensus | TGGGGGCAAG | ATCTATGCTG | ATGACACAGC | 651 |
| D NS5 consensus | TGGGGGCAAG | ATCTATGCTG | ATGACACAGC | 644 |
| H WN05 NS5 consensus | TGGGGGCAAG | ATCTATGCTG | ATGACACAGC | 640 |
| **Consensus** | **TGGGGGCAAG** | **ATCTATGCTG** | **ATGACACAGC** | |

100%
Conservation
0%

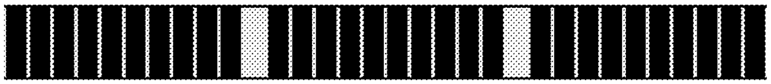

| | | | | |
|---|---|---|---|---|
| AY369442.1 | TGGCTGGGAC | ACCCGCATCA | CGAGAGCTGA | 308 |
| AY369440.1 | TGGCTGGGAC | ACCCGCATCA | CGAGTGCTGA | 308 |
| H NS5 consensus | TGGCTGGGAC | ACCCGCATCA | CGAGAGCTGA | 681 |
| D NS5 consensus | TGGCTGGGAC | ACCCGCATCA | CGAGAGCTGA | 674 |
| H WN05 NS5 consensus | CGGCTGGGAC | ACCCGCATCA | CGAGAGCTGA | 670 |
| **Consensus** | **TGGCTGGGAC** | **ACCCGCATCA** | **CGAGAGCTGA** | |

100%
Conservation
0%

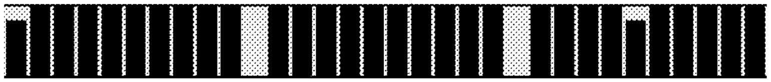

| | | | | |
|---|---|---|---|---|
| AY369442.1 | CTTGGAAAAT | GAAGCTAAGG | TGCTTGAGCT | 338 |
| AY369440.1 | CTTGGAAAAT | GAAGCTAAGG | TGCTTGAGTT | 338 |
| H NS5 consensus | CTTGGAAAAT | GAAGCTAAGG | TGCTTGAGCT | 711 |
| D NS5 consensus | CTTGGAAAAT | GAAGCTAAGG | TGCTTGAGTT | 704 |
| H WN05 NS5 consensus | CTTGGAAAAT | GAAGCTAAGG | TGCTTGAGTT | 700 |
| **Consensus** | **CTTGGAAAAT** | **GAAGCTAAGG** | **TGCTTGAGTT** | |

100%
Conservation
0%

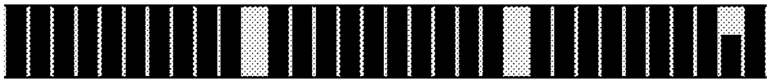

Fig. 16H/17

| | | | | |
|---|---|---|---|---|
| AY369442.1 | GCTTGATGGG | GAACATCGGC | GTCTTGCCAG | 368 |
| AY369440.1 | GCTTGATGGG | GAACATCGGC | GTCTTGCCAG | 368 |
| H NS5 consensus | GCTTGATGGG | GAACATCGGC | GTCTTGCCAG | 741 |
| D NS5 consensus | GCTTGATGGG | GAACATCGGC | GTCTTGCCAG | 734 |
| H WN05 NS5 consensus | GCTTGATGGG | GAACATCGGC | GTCTTGCCAG | 730 |
| **Consensus** | **GCTTGATGGG** | **GAACATCGGC** | **GTCTTGCCAG** | |

100%
Conservation
0%

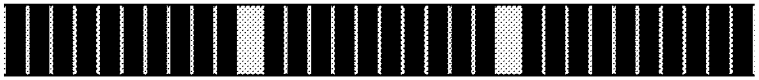

| | | | | |
|---|---|---|---|---|
| AY369442.1 | GGCCATCATT | GAGCTCACCT | ATCGTCACAA | 398 |
| AY369440.1 | GGCCATCATT | GAGCTCACCT | ATCGTCACAA | 398 |
| H NS5 consensus | GGCCATCATT | GAGCTCACCT | ATCGTCACAA | 771 |
| D NS5 consensus | GGCCATCATT | GAGCTCACCT | ATCGTCACAA | 764 |
| H WN05 NS5 consensus | GGCCATCATT | GAGCTCACCT | ATCGTCACAA | 760 |
| **Consensus** | **GGCCATCATT** | **GAGCTCACCT** | **ATCGTCACAA** | |

100%
Conservation
0%

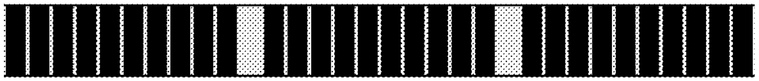

| | | | | |
|---|---|---|---|---|
| AY369442.1 | AGTTGTGAAA | GTGATGCGCC | CGGCTGCTGA | 428 |
| AY369440.1 | AGTTGTGAAA | GTGATGCGCC | CGGCTGCTGA | 428 |
| H NS5 consensus | AGTTGTGAAA | GTGATGCGCC | CGGCTGCTGA | 801 |
| D NS5 consensus | AGTTGTGAAA | GTGATGCGCC | CGGCTGCTGA | 794 |
| H WN05 NS5 consensus | AGTTGTGAAA | GTGATGCGCC | CGGCTGCTGA | 790 |
| **Consensus** | **AGTTGTGAAA** | **GTGATGCGCC** | **CGGCTGCTGA** | |

100%
Conservation
0%

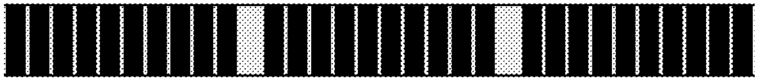

Fig. 16I/17

```
AY369442.1            TGGAAGAACC GTCATGGATG TTATCTCCAG 458
AY369440.1            TGGAAGAACC GTCATGGATG TTATCTCCAG 458
H NS5 consensus       TGGAAGAACC GTCATGGATG TTATCTCCAG 831
D NS5 consensus       TGGAAGAACC GTCATGGATG TTATCTCCAG 824
H WN05 NS5 consensus  TGGAAGAACC GTCATGGATG TTATCTCCAG 820
Consensus             TGGAAGAACC GTCATGGATG TTATCTCCAG
```

100%
Conservation
0%

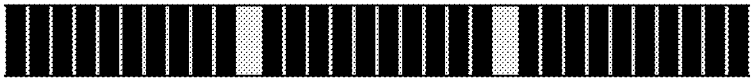

```
AY369442.1            AGAAGATCAG AGGGGGAGTG GACAAGTTGT 488
AY369440.1            AGAAGATCAG AGGGGGAGTG GACAAGTTGT 488
H NS5 consensus       AGAAGATCAG AGGGGGAGTG GACAAGTTGT 861
D NS5 consensus       AGAAGATCAG AGGGGGAGTG GACAAGTTGT 854
H WN05 NS5 consensus  AGAAGATCAG AGGGGGAGTG GACAAGTTGT 850
Consensus             AGAAGATCAG AGGGGGAGTG GACAAGTTGT
```

100%
Conservation
0%

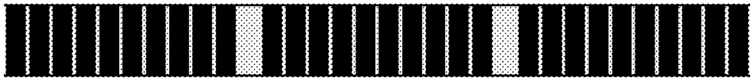

```
AY369442.1            CACCTACGCC CTAAACACTT TCACCAACCT 518
AY369440.1            CACCTACGCC CTAAACACTT TCACCAACCT 518
H NS5 consensus       CACCTACGCC CTAAACACTT TCACCAACCT 891
D NS5 consensus       CACCTACGCC CTAAACACTT TCACCAACCT 884
H WN05 NS5 consensus  CACCTACGCC CTAAACACTT TCACCAACCT 880
Consensus             CACCTACGCC CTAAACACTT TCACCAACCT
```

100%
Conservation
0%

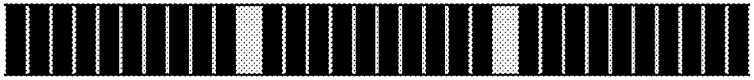

Fig. 16J/17

AY369442.1 GGCCGTCCAG CTGGTGAGGA TGATGGAAGG 548
AY369440.1 GGCCGTCCAG CTGGTGAGGA TGATGGAAGG 548
H NS5 consensus GGCCGTCCAG CTGGTGAGGA TGATGGAAGG 921
D NS5 consensus GGCCGTCCAG CTGGTGAGGA TGATGGAAGG 914
H WN05 NS5 consensus GGCCGTCCAG CTGGTGAGGA TGATGGAAGG 910
Consensus GGCCGTCCAG CTGGTGAGGA TGATGGAAGG
100%
Conservation
0%
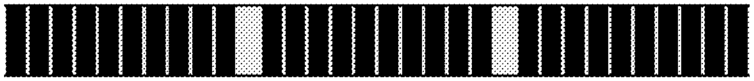

AY369442.1 GGAAGGAGTG ATTGGCCCAG ATGATGTGGA 578
AY369440.1 GGAAGGAGTG ATTGGCCCAG ATGATGTGGA 578
H NS5 consensus GGAAGGAGTG ATTGGCCCAG ATGATGTGGA 951
D NS5 consensus GGAAGGAGTG ATTGGCCCAG ATGATGTGGA 944
H WN05 NS5 consensus GGAAGGAGTG ATTGGCCCAG ATGATGTGGA 940
Consensus GGAAGGAGTG ATTGGCCCAG ATGATGTGGA
100%
Conservation
0%
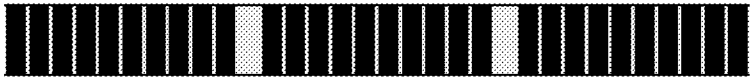

AY369442.1 GAAACTCACA AAAGGGAAAG GACCCAAAGT 608
AY369440.1 GAAACTCACA AAAGGGAAAG GACCCAAAGT 608
H NS5 consensus GAAACTCACA AAAGGGAAAG GACCCAAAGT 981
D NS5 consensus GAAACTCACA AAAGGGAAAG GACCCAAAGT 974
H WN05 NS5 consensus GAAACTCACA AAAGGGAAAG GACCCAAAGT 970
Consensus GAAACTCACA AAAGGGAAAG GACCCAAAGT
100%
Conservation
0%
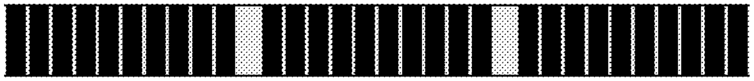

Fig. 16K/17

```
AY590210.1          TTCAACTGCC TTGGAATGAG CAACAGAGAC 30
AY590223.1          TTCAACTGCC TTGGAATGAG CAACAGAGAC 30
H E consensus       ---------- ---------- ---------- -
D E consensus       ---------- ---------- ---------- -
H WN05 E consensus  ---------- ---------- ---------- -
Consensus           ---------- ---------- ----------
```

100%
Conservation
0%

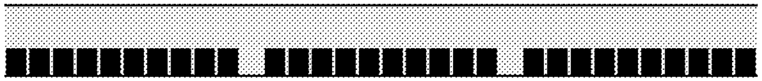

```
AY590210.1          TTCTTGGAAG GAGTGTCTGG AGCAACATGG 60
AY590223.1          TTCTTGGAAG GAGTGTCTGG AGCAACATGG 60
H E consensus       ---------- ---------- ---------- -
D E consensus       ---------- ---------- ---------- -
H WN05 E consensus  ---------- ---------- ---------- -
Consensus           ---------- ---------- ----------
```

100%
Conservation
0%

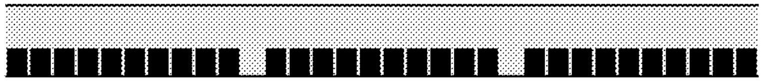

```
AY590210.1          GTGGATTTGG TTCTCGAAGG CGACAGCTGC 90
AY590223.1          GTGGATTTGG TTCTCGAAGG CGACAGCTGC 90
H E consensus       ---------- ---------- ---------- -
D E consensus       ---------- ---------- ---------- -
H WN05 E consensus  ---------- ---------- ---------- -
Consensus           ---------- ---------- ----------
```

100%
Conservation
0%

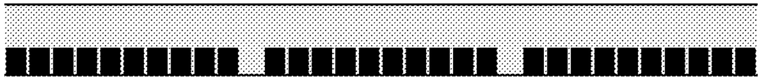

Fig. 17A/17

| | | | | |
|---|---|---|---|---|
| AY590210.1 | GTGACTATCA | TGTCTAAGGA | CAAGCCTACC | 120 |
| AY590223.1 | GTGACTATCA | TGTCTAAGGA | CAAGCCTACC | 120 |
| H E consensus | ---------- | ---------- | ---------- | - |
| D E consensus | ---------- | ---------- | ---------- | - |
| H WN05 E consensus | ---------- | ---------- | ---------- | - |
| Consensus | ---------- | ---------- | ---------- | |
| 100% Conservation 0% | | | | |
| AY590210.1 | ATCGATGTGA | AGATGATGAA | TATGGAGGCG | 150 |
| AY590223.1 | ATCGATGTGA | AGATGATGAA | TATGGAGGCG | 150 |
| H E consensus | ---GATGTGG | AGA----GAA | TATGGAGGCG | 23 |
| D E consensus | ---GATGTGG | AGA----GAA | TATGGAGGCG | 23 |
| H WN05 E consensus | ---GATGTGG | AGA----GAA | TATGGAGGCG | 23 |
| Consensus | **---GATGTGG** | **AGA----GAA** | **TATGGAGGCG** | |
| 100% Conservation 0% | | | | |
| AY590210.1 | GCCAACCTGG | CAGAGGTCCG | CAGTTATTGC | 180 |
| AY590223.1 | GCCAACCTGG | CAGAGGTCCG | CAGTTATTGC | 180 |
| H E consensus | GCCAACCTGG | CAGAGGTCCG | CAGTTATTGC | 53 |
| D E consensus | GCCAACCTGG | CAGAGGTCCG | CAGTTATTGC | 53 |
| H WN05 E consensus | GCCAACCTGG | CAGAGGTCCG | CAGTTATTGC | 53 |
| Consensus | **GCCAACCTGG** | **CAGAGGTCCG** | **CAGTTATTGC** | |
| 100% Conservation 0% | | | | |

Fig. 17B/17

| | | | | |
|---|---|---|---|---|
| **AY590210.1** | TATTTGGCTA | CCGTCAGCGA | TCTCTCCACC | **210** |
| **AY590223.1** | TATTTGGCTA | CCGTCAGCGA | TCTCTCCACC | **210** |
| **H E consensus** | TATTTGGCTA | CCGTCAGCGA | TCTCTCCACC | **83** |
| **D E consensus** | TATTTGGCTA | CCGTCAGCGA | TCTCTCCACC | **83** |
| **H WN05 E consensus** | TATTTGGCTA | CCGTCAGCGA | TCTCTCCACC | **83** |
| **Consensus** | **TATTTGGCTA** | **CCGTCAGCGA** | **TCTCTCCACC** | |
| **100% Conservation 0%** | | | | |
| **AY590210.1** | AAAGCTGCGT | GCCCGACCAT | GGGAGAAGCT | **240** |
| **AY590223.1** | AAAGCTGCGT | GCCCGACCAT | GGGAGAAGCT | **240** |
| **H E consensus** | AAAGCTGCGT | GCCCGACCAT | GGGAGAAGCT | **113** |
| **D E consensus** | AAAGCTGCGT | GCCCGACCAT | GGGAGAAGCT | **113** |
| **H WN05 E consensus** | AAAGCTGCGT | GCCCGACCAT | GGGAGAAGCT | **113** |
| **Consensus** | **AAAGCTGCGT** | **GCCCGACCAT** | **GGGAGAAGCT** | |
| **100% Conservation 0%** | | | | |
| **AY590210.1** | CACAATGACA | AACGTGCTGA | CCCAGCTTTT | **270** |
| **AY590223.1** | CACAATGACA | AACGTGCTGA | CCCAGCTTTT | **270** |
| **H E consensus** | CACAATGACA | AACGTGCTGA | CCCAGCTTTT | **143** |
| **D E consensus** | CACAATGACA | AACGTGCTGA | CCCAGCTTTT | **143** |
| **H WN05 E consensus** | CACAATGACA | AACGTGCTGA | CCCAGCTTTT | **143** |
| **Consensus** | **CACAATGACA** | **AACGTGCTGA** | **CCCAGCTTTT** | |
| **100% Conservation 0%** | | | | |

Fig. 17C/17

| | | | | |
|---|---|---|---|---|
| AY590210.1 | GTGTGCAGAC | AAGGAGTGGT | GGACAGGGGC | 300 |
| AY590223.1 | GTGTGCAGAC | AAGGAGTGGT | GGACAGGGGC | 300 |
| H E consensus | GTGTGCAGAC | AAGGAGTGGT | GGACAGGGGC | 173 |
| D E consensus | GTGTGCAGAC | AAGGAGTGGT | GGACAGGGGC | 173 |
| H WN05 E consensus | GTGTGCAGAC | AAGGAGTGGT | GGACAGGGGC | 173 |
| Consensus | **GTGTGCAGAC** | **AAGGAGTGGT** | **GGACAGGGGC** | |

100%
Conservation
0%

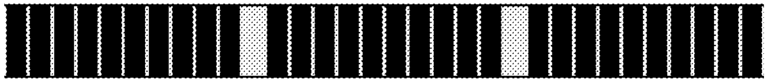

| | | | | |
|---|---|---|---|---|
| AY590210.1 | TGGGGCAACG | GCTGCGGACT | ATTTGGCAAA | 330 |
| AY590223.1 | TGGGGCAACG | GCTGCGGACT | ATTTGGCAAA | 330 |
| H E consensus | TGGGGCAACG | GCTGCGGACT | ATTTGGCAAA | 203 |
| D E consensus | TGGGGCAACG | GCTGCGGACT | ATTTGGCAAA | 203 |
| H WN05 E consensus | TGGGGCAACG | GCTGCGGACT | ATTTGGCAAA | 203 |
| Consensus | **TGGGGCAACG** | **GCTGCGGACT** | **ATTTGGCAAA** | |

100%
Conservation
0%

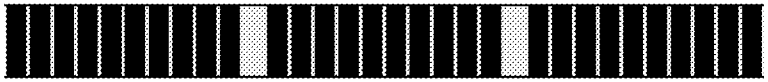

| | | | | |
|---|---|---|---|---|
| AY590210.1 | GGAAGCATTG | ACACATGCGC | CAAATTTGCC | 360 |
| AY590223.1 | GGAAGCATTG | ACACATGCGC | CAAATTTGCC | 360 |
| H E consensus | GGAAGCATTG | ACACATGCGC | CAAATTTGCC | 233 |
| D E consensus | GGAAGCATTG | ACACATGCGC | CAAATTTGCC | 233 |
| H WN05 E consensus | GGAAGCATTG | ACACATGCGC | CAAATTTGCC | 233 |
| Consensus | **GGAAGCATTG** | **ACACATGCGC** | **CAAATTTGCC** | |

100%
Conservation
0%

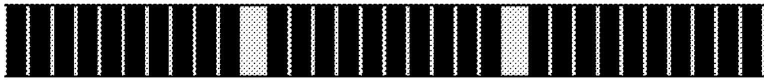

Fig. 17D/17

| | | | | |
|---|---|---|---|---|
| AY590210.1 | TGCTCTACCA | AGGCAATAGG | AAGAACCATC | 390 |
| AY590223.1 | TGCTCTACCA | AGGCAATAGG | AAGAACCATC | 390 |
| H E consensus | TGCTCTACCA | AGGCAATAGG | AAGAACCATC | 263 |
| D E consensus | TGCTCTACCA | AGGCAATAGG | AAGAACCATC | 263 |
| H WN05 E consensus | TGCTCTACCA | AGGCAATAGG | AAGAACCATC | 263 |
| Consensus | **TGCTCTACCA** | **AGGCAATAGG** | **AAGAACCATC** | |
| 100% Conservation 0% | | | | |
| AY590210.1 | TTGAAAGAGA | ATATCAAGTA | CGAAGTGGCC | 420 |
| AY590223.1 | TTGAAAGAGA | ATATCAAGTA | CGAAGTGGCC | 420 |
| H E consensus | TTGAAAGAGA | ATATCAAGTA | CGAAGTGGCC | 293 |
| D E consensus | TTGAAAGAGA | ATATCAAGTA | CGAAGTGGCC | 293 |
| H WN05 E consensus | TTGAAAGAGA | ATATCAAGTA | CGAAGTGGCC | 293 |
| Consensus | **TTGAAAGAGA** | **ATATCAAGTA** | **CGAAGTGGCC** | |
| 100% Conservation 0% | | | | |
| AY590210.1 | ATTTTTGTCC | ATGGACCAAC | TACTGTGGAG | 450 |
| AY590223.1 | ATTTTTGTCC | ATGGACCAAC | TACTGTGGAG | 450 |
| H E consensus | ATTTTTGTCC | ATGGACCAAC | TACTGTGGAG | 323 |
| D E consensus | ATTTTTGTCC | ATGGACCAAC | TACTGTGGAG | 323 |
| H WN05 E consensus | ATTTTTGTCC | ATGGACCAAC | TACTGTGGAG | 323 |
| Consensus | **ATTTTTGTCC** | **ATGGACCAAC** | **TACTGTGGAG** | |
| 100% Conservation 0% | | | | |

Fig. 17E/17

| | | | | |
|---|---|---|---|---|
| AY590210.1 | TCGCACGGAA | ACTACTCCAC | ACAGGTTGGA | 480 |
| AY590223.1 | TCGCACGGAA | ACTATTCCAC | ACAGGCTGGA | 480 |
| H E consensus | TCGCACGGAA | ACTACTCCAC | ACAGGTTGGA | 353 |
| D E consensus | TCGCACGGAA | ACTACTCCAC | ACAGGCTGGA | 353 |
| H WN05 E consensus | TCGCACGGAA | ACTACTCCAC | ACAGGCTGGA | 353 |
| **Consensus** | **TCGCACGGAA** | **ACTACTCCAC** | **ACAGGCTGGA** | |

100% Conservation 0%

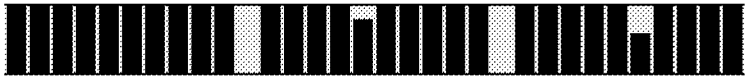

| | | | | |
|---|---|---|---|---|
| AY590210.1 | GCCACTCAGG | CAGGGAGATT | CAGCATCACT | 510 |
| AY590223.1 | GCCACTCAGG | CAGGGAGATT | CAGCATCACT | 510 |
| H E consensus | GCCACTCAGG | CAGGGAGATT | CAGCATCACT | 383 |
| D E consensus | GCCACTCAGG | CAGGGAGATT | CAGCATCACT | 383 |
| H WN05 E consensus | GCCACTCAGG | CAGGGAGATT | CAGCATCACT | 383 |
| **Consensus** | **GCCACTCAGG** | **CAGGGAGATT** | **CAGCATCACT** | |

100% Conservation 0%

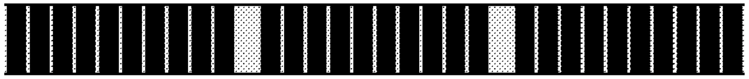

| | | | | |
|---|---|---|---|---|
| AY590210.1 | CCTGCGGCGC | CTTCACACAC | ACTAAAGCTT | 540 |
| AY590223.1 | CCTGCGGCGC | CTTCATACAC | ACTAAAGCTT | 540 |
| H E consensus | CCTGCGGCGC | CTTCATACAC | ACTAAAGCTT | 413 |
| D E consensus | CCTGCGGCGC | CTTCATACAC | ACTAAAGCTT | 413 |
| H WN05 E consensus | CCTGCGGCGC | CTTCATACAC | ACTAAAGCTT | 413 |
| **Consensus** | **CCTGCGGCGC** | **CTTCATACAC** | **ACTAAAGCTT** | |

100% Conservation 0%

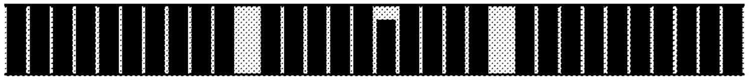

Fig. 17F/17

| | | | | |
|---|---|---|---|---|
| AY590210.1 | GGAGAATATG | GAGAGGTGAC | AGTGGACTGT | 570 |
| AY590223.1 | GGAGAATATG | GAGAGGTGAC | AGTGGACTGT | 570 |
| H E consensus | GGAGAATATG | GAGAGGTGAC | AGTGGACTGT | 443 |
| D E consensus | GGAGAATATG | GAGAGGTGAC | AGTGGACTGT | 443 |
| H WN05 E consensus | GGAGAATATG | GAGAGGTGAC | AGTGGACTGT | 443 |
| **Consensus** | **GGAGAATATG** | **GAGAGGTGAC** | **AGTGGACTGT** | |

100%
Conservation
0%

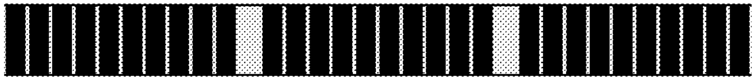

| | | | | |
|---|---|---|---|---|
| AY590210.1 | GAACCACGGT | CAGGGATTGA | CACCAATGCA | 600 |
| AY590223.1 | GAACCACGGT | CAGGGATTGA | CACCAATGCA | 600 |
| H E consensus | GAACCACGGT | CAGGGATTGA | CACCAATGCA | 473 |
| D E consensus | GAACCACGGT | CAGGGATTGA | CACCAATGCA | 473 |
| H WN05 E consensus | GAACCACGGT | CAGGGATTGA | CACCAATGCA | 473 |
| **Consensus** | **GAACCACGGT** | **CAGGGATTGA** | **CACCAATGCA** | |

100%
Conservation
0%

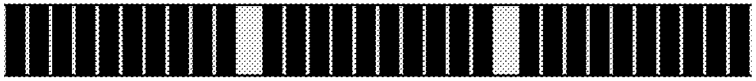

| | | | | |
|---|---|---|---|---|
| AY590210.1 | TACTACGTGA | TGACTGTTGG | AACAAAGACG | 630 |
| AY590223.1 | TACTACGTGA | TGACTGTTGG | AACAAAGACG | 630 |
| H E consensus | TACTATGTGA | TGACTGTTGG | AACAAAGACG | 503 |
| D E consensus | TACTACGTGA | TGACTGTTGG | AACAAAGACG | 503 |
| H WN05 E consensus | TACTACGTGA | TGACTGTTGG | AACAAAGACG | 503 |
| **Consensus** | **TACTACGTGA** | **TGACTGTTGG** | **AACAAAGACG** | |

100%
Conservation
0%

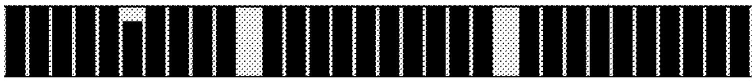

Fig. 17G/17

| | | | | |
|---|---|---|---|---|
| AY590210.1 | TTCTTGGTCC | ATCGTGAGTG | GTTCATGGAC | 660 |
| AY590223.1 | TTCTTGGTCC | ATCGTGAGTG | GTTCATGGAC | 660 |
| H E consensus | TTCTTGGTCC | ATCGTGAGTG | GTTCATGGAC | 533 |
| D E consensus | TTCTTGGTCC | ATCGTGAGTG | GTTCATGGAC | 533 |
| H WN05 E consensus | TTCTTGGTCC | ATCGTGAGTG | GTTCATGGAC | 533 |
| Consensus | **TTCTTGGTCC** | **ATCGTGAGTG** | **GTTCATGGAC** | |
| 100% Conservation 0% | | | | |
| AY590210.1 | CTCAACCTCC | CTTGGAGCAG | TGCTGGAAGT | 690 |
| AY590223.1 | CTCAACCTCC | CTTGGAGCAG | TGCTGGAAGT | 690 |
| H E consensus | CTCAACCTCC | CTTGGAGCAG | TGCTGGAAGT | 563 |
| D E consensus | CTCAACCTCC | CTTGGAGCAG | TGCTGGAAGT | 563 |
| H WN05 E consensus | CTCAACCTCC | CTTGGAGCAG | TGCTGGAAGT | 563 |
| Consensus | **CTCAACCTCC** | **CTTGGAGCAG** | **TGCTGGAAGT** | |
| 100% Conservation 0% | | | | |
| AY590210.1 | ACTGTGTGGA | GGAACAGAGA | GACGTTAATG | 720 |
| AY590223.1 | ACTGTGTGGA | GGAACAGAGA | GACGTTAATG | 720 |
| H E consensus | ACTGTGTGGA | GGAACAGAGA | GACGTTAATG | 593 |
| D E consensus | ACTGTGTGGA | GGAACAGAGA | GACGTTAATG | 593 |
| H WN05 E consensus | ACTGTGTGGA | GGAACAGAGA | GACGTTAATG | 593 |
| Consensus | **ACTGTGTGGA** | **GGAACAGAGA** | **GACGTTAATG** | |
| 100% Conservation 0% | | | | |

Fig. 17H/17

```
AY590210.1          GAGTTTGAGG  AACCACACGC  CACGAAGCAG  750
AY590223.1          GAGTTTGAGG  AACCACACGC  CACGAAGCAG  750
H E consensus       GAGTTTGAGG  AACCACACGC  CACGAAGCAG  623
D E consensus       GAGTTTGAGG  AACCACACGC  CACGAAGCAG  623
H WN05 E consensus  GAGTTTGAGG  AACCACACGC  CACGAAGCAG  623
Consensus           GAGTTTGAGG  AACCACACGC  CACGAAGCAG
```

100%
Conservation
0%

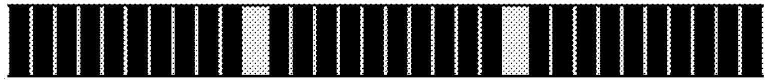

```
AY590210.1          TCTGTGATAG  CATTGGGCTC  ACAAGAGGGA  780
AY590223.1          TCTGTGATAG  CATTGGGCTC  ACAAGAGGGA  780
H E consensus       TCTGTGATAG  CATTGGGCTC  ACAAGAGGGA  653
D E consensus       TCTGTGATAG  CATTGGGCTC  ACAAGAGGGA  653
H WN05 E consensus  TCTGTGATAG  CATTGGGCTC  ACAAGAGGGA  653
Consensus           TCTGTGATAG  CATTGGGCTC  ACAAGAGGGA
```

100%
Conservation
0%

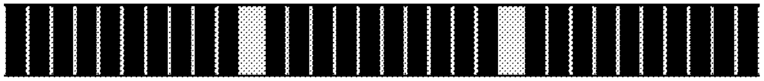

```
AY590210.1          GCTCTGCAGC  AAGCTTTGGC  TGGAGCCATT  810
AY590223.1          GCTCTGCATC  AAGCTTTGGC  TGGAGCCATT  810
H E consensus       GCTCTGCATC  AAGCTTTGGC  TGGAGCCATT  683
D E consensus       GCTCTGCATC  AAGCTTTGGC  TGGAGCCATT  683
H WN05 E consensus  GCTCTGCATC  AAGCTTTGGC  TGGAGCCATT  683
Consensus           GCTCTGCATC  AAGCTTTGGC  TGGAGCCATT
```

100%
Conservation
0%

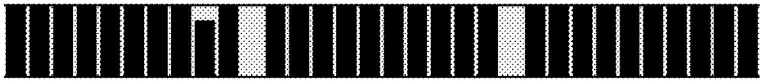

Fig. 17I/17

| | | | | |
|---|---|---|---|---|
| AY590210.1 | CCTGTGGAAT | TTTCAAGCAA | CACTGTCAAG | 840 |
| AY590223.1 | CCTGTGGAAT | TTTCAAGCAA | CACTGTCAAG | 840 |
| H E consensus | CCTGTGGAAT | TTTCAAGCAA | CACTGTCAAG | 713 |
| D E consensus | CCTGTGGAAT | TTTCAAGCAA | CACTGTCAAG | 713 |
| H WN05 E consensus | CCTGTGGAAT | TTTCAAGCAA | CACTGTCAAG | 713 |
| Consensus | **CCTGTGGAAT** | **TTTCAAGCAA** | **CACTGTCAAG** | |

100%
Conservation
0%

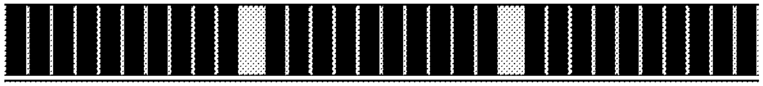

| | | | | |
|---|---|---|---|---|
| AY590210.1 | TTGACGTCGG | GTCATTTGAA | GTGTAGAGTG | 870 |
| AY590223.1 | TTGACGTCGG | GTCATTTGAA | GTGTAGAGTG | 870 |
| H E consensus | TTGACGTCGG | GTCATTTGAA | GTGTAGAGTG | 743 |
| D E consensus | TTGACGTCGG | GTCATTTGAA | GTGTAGAGTG | 743 |
| H WN05 E consensus | TTGACGTCGG | GTCATTTGAA | GTGTAGAGTG | 743 |
| Consensus | **TTGACGTCGG** | **GTCATTTGAA** | **GTGTAGAGTG** | |

100%
Conservation
0%

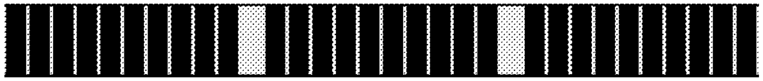

| | | | | |
|---|---|---|---|---|
| AY590210.1 | AAGATGGAAA | AATTGCAGTT | GAAGGGAACA | 900 |
| AY590223.1 | AAGATGGAAA | AATTGCAGTT | GAAGGGAACA | 900 |
| H E consensus | AAGATGGAAA | AATTGCAGTT | GAAGGGAACA | 773 |
| D E consensus | AAGATGGAAA | AATTGCAGTT | GAAGGGAACA | 773 |
| H WN05 E consensus | AAGATGGAAA | AATTGCAGTT | GAAGGGAACA | 773 |
| Consensus | **AAGATGGAAA** | **AATTGCAGTT** | **GAAGGGAACA** | |

100%
Conservation
0%

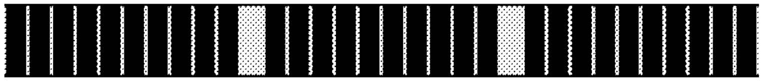

Fig. 17J/17

| | | | | |
|---|---|---|---|---|
| AY590210.1 | ACCTATGGCG | TCTGTTCAAA | GGCTTTCAAG | 930 |
| AY590223.1 | ACCTATGGCG | TCTGTTCAAA | GGCTTTCAAG | 930 |
| H E consensus | ACCTATGGCG | TCTGTTCAAA | GGCTTTCAAG | 803 |
| D E consensus | ACCTATGGCG | TCTGTTCAAA | GGCTTTCAAG | 803 |
| H WN05 E consensus | ACCTATGGCG | TCTGTTCAAA | GGCTTTCAAG | 803 |
| Consensus | **ACCTATGGCG** | **TCTGTTCAAA** | **GGCTTTCAAG** | |

100%
Conservation
0%

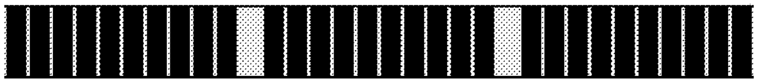

| | | | | |
|---|---|---|---|---|
| AY590210.1 | TTTCTTGGGA | CTCCCGCAGA | CACAGGTCAC | 960 |
| AY590223.1 | TTTCTTGGGA | CTCCCGCAGA | CACAGGTCAC | 960 |
| H E consensus | TTTCTTGGGA | CTCCCGCAGA | CACAGGTCAC | 833 |
| D E consensus | TTTCTTGGGA | CTCCCGCAGA | CACAGGTCAC | 833 |
| H WN05 E consensus | TTTCTTGGGA | CTCCCGCAGA | CACAGGTCAC | 833 |
| Consensus | **TTTCTTGGGA** | **CTCCCGCAGA** | **CACAGGTCAC** | |

100%
Conservation
0%

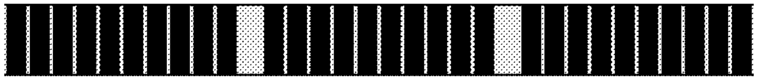

| | | | | |
|---|---|---|---|---|
| AY590210.1 | GGCACTGTGG | TGTTGGAATT | GCAGTACACT | 990 |
| AY590223.1 | GGCACTGTGG | TGTTGGAATT | GCAGTACACT | 990 |
| H E consensus | GGCACTGTGG | TGTTGGAATT | GCAGTACACT | 863 |
| D E consensus | GGCACTGTGG | TGTTGGAATT | GCAGTACACT | 863 |
| H WN05 E consensus | GGCACTGTGG | TGTTGGAATT | GCAGTACACT | 863 |
| Consensus | **GGCACTGTGG** | **TGTTGGAATT** | **GCAGTACACT** | |

100%
Conservation
0%

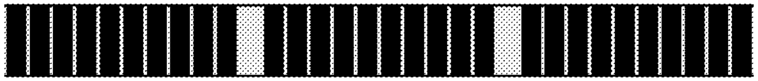

Fig. 17K/17

| | | | | |
|---|---|---|---|---|
| AY590210.1 | GGCACGGATG | GACCTTGCAA | AGTTCCTATC | 1020 |
| AY590223.1 | GGCACGGATG | GACCTTGCAA | AGTTCCTATC | 1020 |
| H E consensus | GGCACGGATG | GACCTTGCAA | AGTTCCTATC | 893 |
| D E consensus | GGCACGGATG | GACCTTGCAA | AGTTCCTATC | 893 |
| H WN05 E consensus | GGCACGGATG | GACCTTGCAA | AGTTCCTATC | 893 |
| Consensus | **GGCACGGATG** | **GACCTTGCAA** | **AGTTCCTATC** | |

100%
Conservation
0%

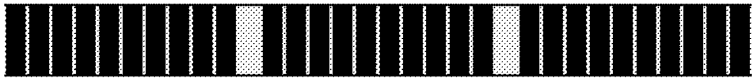

| | | | | |
|---|---|---|---|---|
| AY590210.1 | TCGTCAGTGG | CTTCATTGAA | CGACCTAACG | 1050 |
| AY590223.1 | TCGTCAGTGG | CTTCATTGAA | CGACCTAACG | 1050 |
| H E consensus | TCGTCAGTGG | CTTCATTGAA | CGACCTAACG | 923 |
| D E consensus | TCGTCAGTGG | CTTCATTGAA | CGACCTAACG | 923 |
| H WN05 E consensus | TCGTCAGTGG | CTTCATTGAA | CGATCTAACG | 923 |
| Consensus | **TCGTCAGTGG** | **CTTCATTGAA** | **CGACCTAACG** | |

100%
Conservation
0%

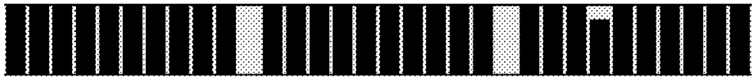

| | | | | |
|---|---|---|---|---|
| AY590210.1 | CCAGTGGGCA | GATTGGTCAC | TGTCAACCCT | 1080 |
| AY590223.1 | CCAGTGGGCA | GATTGGTCAC | TGTCAACCCT | 1080 |
| H E consensus | CCAGTGGGCA | GATTGGTCAC | TGTCAACCCT | 953 |
| D E consensus | CCAGTGGGCA | GATTGGTCAC | TGTCAACCCT | 953 |
| H WN05 E consensus | CCAGTGGGCA | GATTGGTCAC | TGTCAACCCT | 953 |
| Consensus | **CCAGTGGGCA** | **GATTGGTCAC** | **TGTCAACCCT** | |

100%
Conservation
0%

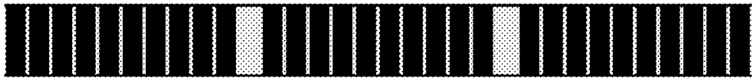

Fig. 17L/17

```
AY590210.1          TTTGTTTCAG TGGCCACGGC CAACGCTAAG 1110
AY590223.1          TTTGTTTCAG TGGCCACGGC CAACGCTAAG 1110
H E consensus       TTTGTTTCAG TGGCCACGGC CAACGCTAAG 983
D E consensus       TTTGTTTCAG TGGCCACGGC CAACGCTAAG 983
H WN05 E consensus  TTTGTTTCAG TGGCCACGGC CAACGCTAAG 983
Consensus           TTTGTTTCAG TGGCCACGGC CAACGCTAAG
```

100%
Conservation
0%

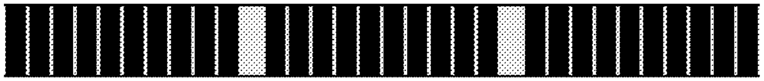

```
AY590210.1          GTCCTGATTG AATTGGAACC ACCCTTTGGA 1140
AY590223.1          GTCCTGATTG AATTGGAACC ACCCTTTGGA 1140
H E consensus       GTCCTGATTG AATTGGAACC ACCCTTTGGA 1013
D E consensus       GTCCTGATTG AATTGGAACC ACCCTTTGGA 1013
H WN05 E consensus  GTCCTGATTG AATTGGAACC ACCCTTTGGA 1013
Consensus           GTCCTGATTG AATTGGAACC ACCCTTTGGA
```

100%
Conservation
0%

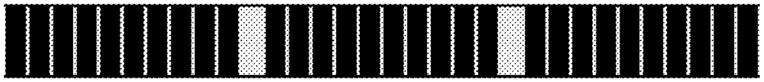

```
AY590210.1          GACTCATACA TAGTGGTGGG CAGAGGAGAA 1170
AY590223.1          GACTCATACA TAGTGGTGGG CAGAGGAGAA 1170
H E consensus       GACTCATACA TAGTGGTGGG CAGAGGAGAA 1043
D E consensus       GACTCATACA TAGTGGTGGG CAGAGGAGAA 1043
H WN05 E consensus  GACTCATACA TAGTGGTGGG CAGAGGAGAA 1043
Consensus           GACTCATACA TAGTGGTGGG CAGAGGAGAA
```

100%
Conservation
0%

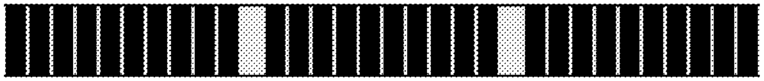

Fig. 17M/17

```
AY590210.1         CAACAGATCA  ATCACCATTG  GCACAAGTCT  1200
AY590223.1         CAACAGATCA  ATCACCATTG  GCACAAGTCT  1200
H E consensus      CAACAGATCA  ATCACCATTG  GCACAAGTCT  1073
D E consensus      CAACAGATCA  ATCACCATTG  GCACAAGTCT  1073
H WN05 E consensus CAACAGATCA  ATCACCATTG  GCACAAGTCT  1073
Consensus          CAACAGATCA  ATCACCATTG  GCACAAGTCT
```

100% Conservation 0%

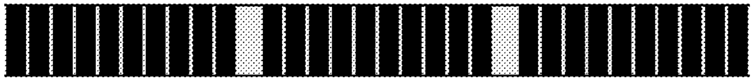

```
AY590210.1         GGAAGCAGCA  TTGGCAAAGC  CTTTACAACC  1230
AY590223.1         GGAAGTAGCA  TTGGCAAAGC  CTTTACAACC  1230
H E consensus      GGAAGCAGCA  TTGGCAAAGC  CTTTACAACC  1103
D E consensus      GGAAGCAGCA  TTGGCAAAGC  CTTTACAACC  1103
H WN05 E consensus GGAAGCAGCA  TTGGCAAAGC  CTTTACAACC  1103
Consensus          GGAAGCAGCA  TTGGCAAAGC  CTTTACAACC
```

100% Conservation 0%

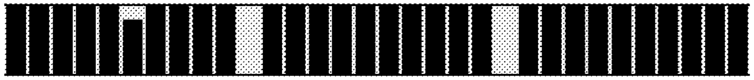

```
AY590210.1         ACCCTCAAAG  GAGCGCAGAG  ACTAGCCGCT  1260
AY590223.1         ACCCTCAAAG  GAGCGCAGAG  ACTAGCCGCT  1260
H E consensus      ACCCTCAAAG  GAGCGCAGAG  ACTAGCCGCT  1133
D E consensus      ACCCTCAAAG  GAGCGCAGAG  ACTAGCCGCT  1133
H WN05 E consensus ACCCTCAAAG  GAGCGCAGAG  ACTAGCCGCT  1133
Consensus          ACCCTCAAAG  GAGCGCAGAG  ACTAGCCGCT
```

100% Conservation 0%

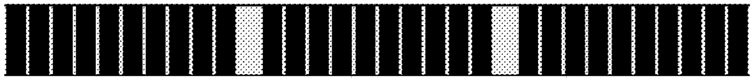

Fig. 17N/17

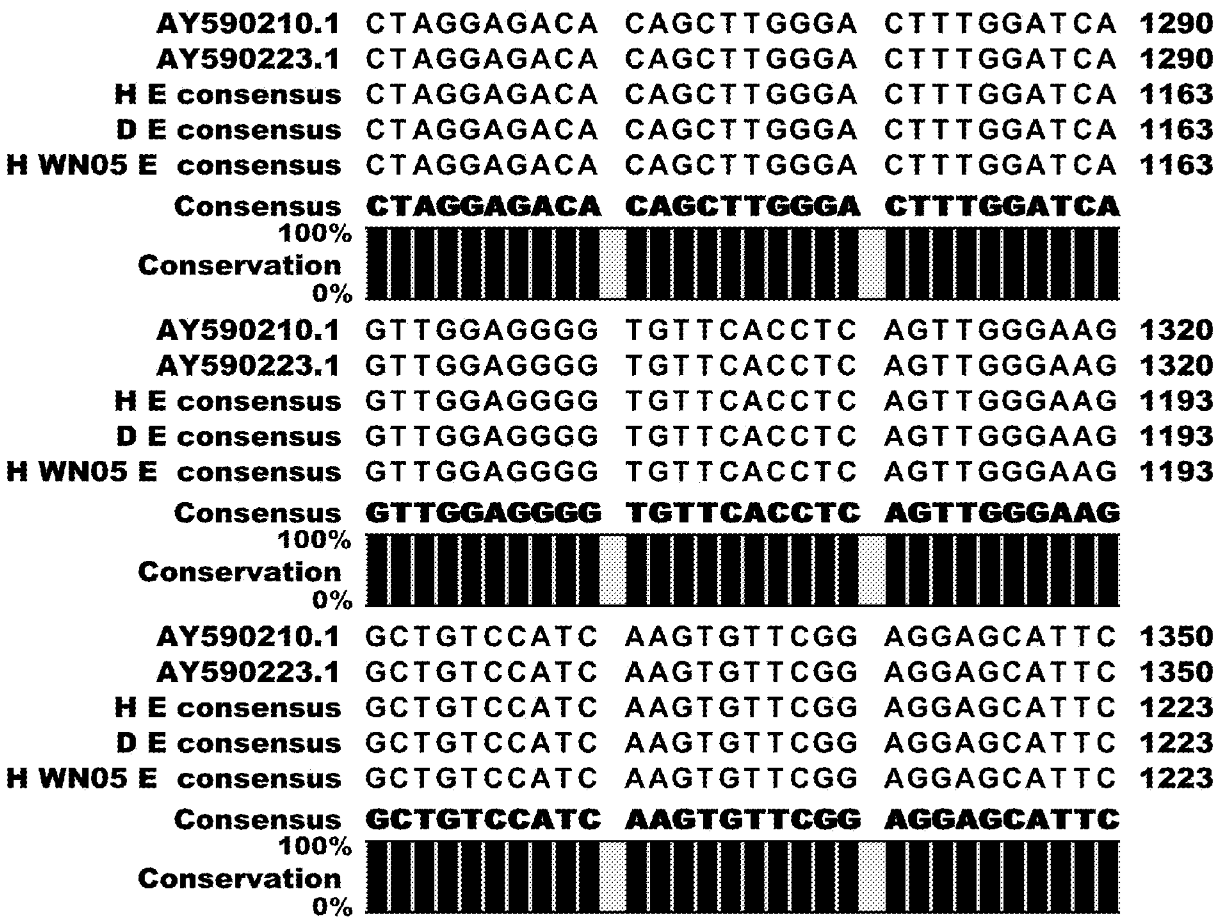
Fig. 17O/17

| | | | | |
|---|---|---|---|---|
| **AY590210.1** | CGCTCACTGT | TCGGAGGCAT | GTCCTGGATA | **1380** |
| **AY590223.1** | CGCTCACTGT | TCGGAGGCAT | GTCCTGGATA | **1380** |
| **H E consensus** | CGCTCACTGT | TCGGAGGCAT | GTCCTGGATA | **1253** |
| **D E consensus** | CGCTCACTGT | TCGGAGGCAT | GTCCTGGATA | **1253** |
| **H WN05 E consensus** | CGCACACTGT | TCGGAGGCAT | GTCCTGGATA | **1253** |
| **Consensus** | **CGCTCACTGT** | **TCGGAGGCAT** | **GTCCTGGATA** | |
| **100% Conservation 0%** | | | | |
| **AY590210.1** | ACGCAAGGAT | TGCTGGGGGC | TCTCCTGTTG | **1410** |
| **AY590223.1** | ACGCAAGGAT | TGCTGGGGGC | TCTCCTGTTG | **1410** |
| **H E consensus** | ACGCAAGGAT | TGCTGGGGGC | TCTCCTGTTG | **1283** |
| **D E consensus** | ACGCAAGGAT | TGCTGGGGGC | TCTCCTGTTG | **1283** |
| **H WN05 E consensus** | ACGCAAGGAT | TGCTGGGGGC | TCTCCTGTTG | **1283** |
| **Consensus** | **ACGCAAGGAT** | **TGCTGGGGGC** | **TCTCCTGTTG** | |
| **100% Conservation 0%** | | | | |
| **AY590210.1** | TGGATGGGCA | TCAATGCTCG | TGATAGGTCC | **1440** |
| **AY590223.1** | TGGATGGGCA | TCAATGCTCG | TGATAGGTCC | **1440** |
| **H E consensus** | TGGATGGGCA | TCAATGCTCG | TGATAGGTCC | **1313** |
| **D E consensus** | TGGATGGGCA | TCAATGCTCG | TGATAGGTCC | **1313** |
| **H WN05 E consensus** | TGGATGGGCA | TCAATGCTCG | TGATAGGTCC | **1313** |
| **Consensus** | **TGGATGGGCA** | **TCAATGCTCG** | **TGATAGGTCC** | |
| **100% Conservation 0%** | | | | |

Fig. 17P/17

```
AY590210.1          ATAGCTCTCA  CGTTTCTCGC  AGTTGGAGGA  1470
AY590223.1          ATAGCTCTCA  CGTTTCTCGC  AGTTGGAGGA  1470
H E consensus       ATAGCTCTCA  CGTTTCTCGC  AGTTGGAGGA  1343
D E consensus       ATAGCTCTCA  CGTTTCTCGC  AGTTGGAGGA  1343
H WN05 E consensus  ATAGCTCTCA  CGTTTCTCGC  AGTTGGAGGA  1343

Consensus           ATAGCTCTCA  CGTTTCTCGC  AGTTGGAGGA
100%
Conservation
0%

AY590210.1          GTTCTGCTCT  TCCTCTCCGT  GAACGTGCAC  1500
AY590223.1          GTTCTGCTCT  TCCTCTCCGT  GAACGTGCAT  1500
H E consensus       GTTCTGCTCT  TCCTNTCCGT  GAACGTGCAC  1373
D E consensus       GTTCTGCTCT  TCCTCTCCGT  GAACGTGCAT  1373
H WN05 E consensus  GTTCTGCTCT  TCCTCTCCGT  GAACGTGCAT  1373

Consensus           GTTCTGCTCT  TCCTCTCCGT  GAACGTGCAT
100%
Conservation
0%

AY590210.1          GCT-  1503
AY590223.1          GCT-  1503
H E consensus       GCT-  1376
D E consensus       GCT-  1376
H WN05 E consensus  GCT-  1376

Consensus           GCT-
100%
Conservation
0%
```

Fig. 17Q/17

WEST NILE VIRUS VACCINE

SEQUENCE LISTING

This application contains a sequence listing in accordance with 37 C.F.R. 1.821-1.825. The sequence listing accompanying this application has been submitted electronically in ASCII format and is hereby incorporated by reference in its entirety. Said ASCII copy, created on Dec. 14, 2015, is named 10-0111-US-4-SEQ-UP.txt and is 117,841 bytes in size.

BACKGROUND

West Nile Virus ("WNV") is in the family Flaviviridae. Infection is usually contracted through a mosquito vector transferred through the insect's bite. West Nile infects all types of animals and birds across the globe. This virus was first discovered in the North American region in 1999 with the first diagnosis occurring in Canadian horses. Presently, West Nile Virus has become endemic in the United States affecting birds, humans, and animals of all types. In 2002, over 14,700 confirmed cases of West Nile Virus were reported in 43 states.

The spread of WNV has been influenced by several factors. Since the mosquito is the vector for the virus and perpetuates WNV, the ecological conditions conducive to growth and development of mosquito populations have had an impact of the spread of the WNV. There are several tactics that have been utilized to control populations of mosquitoes in an effort to prevent the spread of WNV. These tactics include the use of pesticides, repellants, physical barriers preventing contact between mosquitoes and animals, eliminating environments that perpetuate breeding of mosquitoes, and the use of immunizations. Typical signs of WNV include various symptoms affecting the central nervous system. Symptoms of encephalitis are often seen and include viremia, histopathologic lesions of the central nervous system, anorexia, depression, fever, weakness, abnormal gait, paralysis of hind limbs, impaired vision, ataxia, aimless wandering, convulsions, inability to swallow, coma, and death.

A few vaccines directed towards WNV have been introduced which are undesirable for various reasons. For example, one vaccine was produced from a canarypox-vectored West Nile Virus. Another set of vaccines were produced from a recombinant chimeric protein of West Nile Virus, wherein the chimeric protein vaccine was designed by fusing a modified version of bacterial flagellin (STF2 Delta) to the EIII domain of the WNV envelope protein. Another vaccine included an inactivated early North American West Nile strain that required a metabolizable oil as an adjuvant. Finally, a live, attenuated chimeric vaccine was produced from an infectious clone of yellow fever 17D virus in which the pre-membrane and envelope proteins have been replaced by the corresponding genes of WN(4).

There are several problems inherent in vaccines described above. Vaccines containing live viral organisms have the risk of infecting an animal with the virus through vaccination leading to sickness and even death. Chimeric protein vaccines, recombinantly expressed vaccines, and some subunit vaccines have the problem of limited immunological activity and effect related to the number of proteins included in the vaccine composition. The efficacy of these types of vaccines is usually limited and the risk of infection by the virus or reversion to wild type virus is prevalent. In addition, some of the adjuvants utilized in common vaccines are comprised of metabolizable oils which are removed relatively rapidly from the body and limit the duration during which the immune system of the vaccinated animal may respond to the immunogenically active composition. Other adjuvants can cause allergic reactions and unfavorable effects in the vaccinated animals. Additionally, these vaccines do not include antigens for stimulating immunity to other pathogens besides WNV, so they fail to protect animals against several diseases with both convenience and safety. Also, all previous vaccines were derived from an early isolate of WNV that is no longer present in the environment, and hence, can no longer infect animals and cause disease.

Accordingly, what is needed in the art is a vaccine that is safe for administration to animals of all ages, including pregnant animals, that includes adjuvants suitable for aiding the immunogenic effect and duration of the vaccine, and that is prepared from contemporary or dominant isolates of WNV that remain present in the natural environment and cause disease against which such vaccines would afford protection. What is further needed is a vaccine that reduces the incidence and/or severity of up to and including the elimination or prevention of clinical signs associated with the disease or infection by West Nile Virus. Additionally what is needed is a vaccine against West Nile virus, which includes West Nile Virus antigens in combination with antigens from other equine pathogens, thereby providing further protection by reducing the incidence of or severity of clinical signs of disease from both West Nile Virus and the other pathogen(s).

SUMMARY OF INVENTION

The present invention overcomes the problems inherent in the prior art and provides a distinct advance in the state of the art. More particularly, the present invention provides for a vaccine or immunogenic composition comprising an immunogenically active antigenic component comprised of one or more strains or isolates of West Nile Virus. In some preferred embodiments, the composition further comprises an adjuvant, preferably a carbomer, and a pharmaceutically acceptable carrier. Preferably, the West Nile Virus antigen is killed or inactivated. This composition induces an immunogenic response in animals susceptible to contraction of West Nile Virus and provides for a safe vaccine for animals of any age.

The present invention additionally provides for a vaccine composition, which is immunogenically active, and which overcomes the limitations of those previously described. The present invention provides an inactivated vaccine thereby providing unique safety for the vaccinated animals, including pregnant females. Additionally, the immunogenic composition of the present invention overcomes interference from passively acquired maternal immunity and stimulates active immunity in vaccinated animals. Advantageously, the present invention provides a broad and effective immunogenically active composition containing many or all relevant antigenic components and proteins of pathogenic WNV. The immunogenic composition of the present invention is unique in that it includes antigens of contemporary isolates or epidemiologically dominant isolates of WNV in the composition, providing protective immunogenic responses by reducing the incidence of and/or severity of clinical signs of WNV infection up to and including immunity against the most prevalent isolates seen in animals, including horses, today. In a preferred embodiment, those contemporary isolates of WNV include those isolates that are part of the North American West Nile Virus isolates or North American Dominant West Nile Virus isolates For purposes of the present invention, WN02 is a representative example of a WNV strain that can be referred to as a North American Dominant West Nile Virus strain or isolate. Specifically, North American Dominant strains and isolates are those having at least 1 nucleotide change resulting in an amino acid change from the WN99 isolates. Strain NY99 (GenBank accession no. AF196835) serves as a reference strain for determining if a strain or isolate is North American Dominant. In addition, these strains or isolates may have one or more silent amino acid changes. In a preferred embodiment, the nucleotide change results in an amino acid change in an envelope protein of the strain or isolate and, more preferably, the nucleotide change results in an amino acid change from valine to alanine. Preferably, this amino acid change is associated with a greater ability to replicate in the intermediate host, namely, the mosquito. More preferably, North American Dominant strains include either (and preferably both) a U to C mutation and a C to U mutation at positions 1442 and 2466 (in comparison to a North American strain, e.g. NY 99 and SEQ ID NO.23), respectively. Still more preferably, North American Dominant strains or isolates further include a mutation in the nucleotide sequence encoding the E protein and the C to U mutation at position 9352 in the sequence encoding the NS5 protein (again in comparison to a North American strain, e.g. NY 99 and SEQ ID NO. 23). These preferred mutations are shown in Example 10 and in Phylogenetic Analysis of North American West Nile Virus Isolates, 2001-2004: Evidence For the Emergence of a Dominant Genotype, C. Todd Davis, et. al, Virology 342, p. 252-265 (2005), the teaching and content of which is hereby incorporated by reference herein.

The present invention also provides for a method of making the immunogenic composition of the present invention. The method generally comprises the steps of combining a West Nile Virus antigen and an excipient or pharmaceutically or veterinary acceptable carrier. A preferred embodiment further comprises the step of adding one or more additional equine antigens. In another embodiment, the method further comprises the step of adding a suitable adjuvant to the composition.

In one preferred embodiment, the present invention includes WNV antigens and a non-metabolizable oil adjuvant, preferably mineral oil, to extend the duration during which the immune system of the vaccinated animal may respond to the immunogenically active composition. The non-metabolizable oil is understood to be an oil that, when administered with an antigen, does not metabolize in the body after administration. A preferred non-metabolizable oil is mineral oil. In other preferred forms, both a carbomer adjuvant and non-metabolizable oil (preferably mineral oil) are present in addition to the WNV antigens. The adjuvant(s) can be used in any of the compositions described herein.

In an additional embodiment, the composition of the present invention contains WNV antigens, preferably an inactivated or killed WNV from a North American dominant strain, and essentially no oil or oil-based adjuvants. In such an embodiment, other adjuvants, preferably carbomer, can be included.

In another embodiment, a vaccine composition comprised of WNV antigens in combination with other antigens from equine microbial pathogens is provided in order to confer a broad scope of protection to the animal. In such embodiments, the WNV antigens are in any form as described above.

In one preferred embodiment, the present invention provides a vaccine composition comprising WNV antigens as described above in combination with one or more immunologically effective amounts of antigenic components selected from the group consisting of Venezuelan Equine Encephalomyelitis (VEE), Eastern Equine Encephalomyelitis (EEE), Western Equine Encephalomyelitis (WEE), Tetanus toxoid (T), Equine herpes viruses (EHV) including types 1 and 4, Equine influenza viruses (EIV), and combinations thereof, along with a pharmaceutically acceptable carrier. Preferably such embodiments will include an adjuvant, preferably carbomer, and a pharmaceutically acceptable carrier. Additionally, a non-metabolizable oil, preferably mineral oil, may be present, however, such an oil is not required.

Preferred embodiments also include WNV antigens, as described above, in combination with: Eastern Equine Encephalomyelitis; Western Equine Encephalomyelitis; Venezuelan Equine Encephalomyelitis; Tetanus Toxoid; Eastern Equine Encephalomyelitis and Western Equine Encephalomyelitis; Eastern Equine Encephalomyelitis and Venezuelan Equine Encephalomyelitis; Eastern Equine Encephalomyelitis and Tetanus Toxoid; Eastern Equine Encephalomyelitis, Western Equine Encephalomyelitis, and Venezuelan Equine Encephalomyelitis; Eastern Equine Encephalomyelitis, Western Equine Encephalomyelitis, and Tetanus Toxoid; Eastern Equine Encephalomyelitis, Western Equine Encephalomyelitis, Venezuelan Equine Encephalomyelitis and Tetanus Toxoid; Western Equine Encephalomyelitis and Venezuelan Equine Encephalomyelitis; Western Equine Encephalomyelitis and Tetanus Toxoid; Western Equine Encephalomyelitis, Venezuelan Equine Encephalomyelitis, and Tetanus Toxoid; Venezuelan Equine Encephalomyelitis and Tetanus Toxoid; and Eastern Equine Encephalomyelitis, Venezuelan Equine Encephalomyelitis and Tetanus Toxoid. The most preferred combination of these specified combinations includes WNV antigens in combination with antigens or antigenic components of Eastern Equine Encephalomyelitis, Western Equine Encephalomyelitis, Venezuelan Equine Encephalomyelitis, and Tetanus Toxoid. In each such specified combination, an adjuvant or combination of adjuvants can be used, with carbomer, and even more preferably carbopol, being particularly preferred. In the most preferred forms of the combination of WNV and Eastern Equine Encephalomyelitis, Western Equine Encephalomyelitis, Venezuelan Equine Encephalomyelitis and Tetanus Toxoid, no oil (metabolizable or non-metabolizable) is present. The NJO strain of Eastern Equine Encephalomyelitis, the Fleming strain of Western Equine Encephalomyelitis strain, and the TC-83 strain of Venezuelan Equine Encephalomyelitis strain are all representative strains of these vaccine components.

Further preferred embodiments of the present invention can be made using each of the specified combination vaccines listed above and adding in antigens from Equine Herpesvirus, preferably type 1, type 4, (EHV1 and/or EHV4) or combinations thereof.

Still further variations of each of the specified combination vaccines listed above, including those that include EHV1 and/or EHV4 can be made by adding in antigens from Equine influenza virus (EIV). Preferred embodiments incorporating Equine influenza virus include: West Nile Virus, at least one strain of Equine Influenza Virus, and Tetanus Toxoid; West Nile Virus, at least one strain of Equine Influenza Virus, Tetanus Toxoid, and Eastern Equine Encephalomyelitis; West Nile Virus, at least one strain of Equine Influenza Virus, Tetanus Toxoid, Eastern Equine Encephalomyelitis, and Western Equine Encephalomyelitis; West Nile Virus, at least one strain of Equine Influenza Virus, Tetanus Toxoid, Eastern Equine Encephalomyelitis, Western Equine Encephalomyelitis; and Venezuelan Equine Encephalomyelitis; West Nile Virus, at least one strain of Equine Influenza Virus, and Eastern Equine Encephalomyelitis; West Nile Virus, at least one strain of Equine Influenza Virus, and Western Equine Encephalomyelitis; West Nile Virus, at least one strain of Equine Influenza Virus, and Venezuelan Equine Encephalomyelitis; West Nile Virus, at least one strain of Equine Influenza Virus, Eastern Equine Encephalomyelitis, and Western Equine Encephalomyelitis; West Nile Virus, at least one strain of Equine Influenza Virus, Eastern Equine Encephalomyelitis, and Venezuelan Equine Encephalomyelitis; West Nile Virus, at least one strain of Equine Influenza Virus, Western Equine Encephalomyelitis, and Venezuelan Equine Encephalomyelitis; West Nile Virus, at least one strain of Equine Influenza Virus, Western Equine Encephalomyelitis, and tetanus toxoid; West Nile Virus, at least one strain of Equine Influenza Virus, Venezuelan Equine Encephalomyelitis, and tetanus toxoid; West Nile Virus, at least one strain of Equine Influenza Virus, Venezuelan Equine Encephalomyelitis, Western Equine Encephalomyelitis, and tetanus toxoid; and West Nile Virus, at least one strain of Equine Influenza Virus, Venezuelan Equine Encephalomyelitis, Eastern Equine Encephalomyelitis, and tetanus toxoid. In each specified embodiment any one or more strains or isolates of Equine Influenza may be present. Preferred strains of Equine Influenza virus include Influenza A/equine-2/Ohio/03, Influenza A/equine-2/New Market/2/93, Influenza A/equine-2/Kentucky/95, and combinations thereof. In all of the combinations listed above, it is preferred to use at least two strains of Equine Influenza and still more preferred to use at least 3 strains of Equine Influenza. Preferred embodiments incorporating Equine Herpes Virus include: West Nile Virus, at least one strain of Equine Influenza Virus, Tetanus Toxoid, and Equine Herpes Virus; West Nile Virus, at least one strain of Equine Influenza Virus, Tetanus Toxoid, Eastern Equine Encephalomyelitis, and Equine Herpes Virus; West Nile Virus, at least one strain of Equine Influenza Virus, Tetanus Toxoid, Eastern Equine Encephalomyelitis, Western Equine Encephalomyelitis, and Equine Herpes Virus; West Nile Virus, at least one strain of Equine Influenza Virus, Tetanus Toxoid, Eastern Equine Encephalomyelitis, Western Equine Encephalomyelitis; Venezuelan Equine Encephalomyelitis, and Equine Herpes Virus; West Nile Virus, at least one strain of Equine Influenza Virus, and Eastern Equine Encephalomyelitis; West Nile Virus, at least one strain of Equine Influenza Virus, Western Equine Encephalomyelitis and Equine Herpes Virus; West Nile Virus, at least one strain of Equine Influenza Virus, Venezuelan Equine Encephalomyelitis, and Equine Herpes Virus; West Nile Virus, at least one strain of Equine Influenza Virus, Eastern Equine Encephalomyelitis, Western Equine Encephalomyelitis, and Equine Herpes Virus; West Nile Virus, at least one strain of Equine Influenza Virus, Eastern Equine Encephalomyelitis, Venezuelan Equine Encephalomyelitis, and Equine Herpes Virus; West Nile Virus, at least one strain of Equine Influenza Virus, Western Equine Encephalomyelitis, Venezuelan Equine Encephalomyelitis, and Equine Herpes Virus; West Nile Virus, at least one strain of Equine Influenza Virus, Western Equine Encephalomyelitis, Tetanus Toxoid, and Equine Herpes Virus; West Nile Virus, at least one strain of Equine Influenza Virus, Venezuelan Equine Encephalomyelitis, tetanus toxoid, and Equine Herpes Virus; West Nile Virus, at least one strain of Equine Influenza Virus, Venezuelan Equine Encephalomyelitis, Western Equine Encephalomyelitis, Tetanus Toxoid, and Equine Herpes Virus; and West Nile Virus, at least one strain of Equine Influenza Virus, Venezuelan Equine Encephalomyelitis, Eastern Equine Encephalomyelitis, Tetanus Toxoid, and Equine Herpes Virus. In all of the combinations listed above, it is preferred to use at least two strains of Equine Influenza and still more preferred to use at least 3 strains of Equine Influenza. Additionally, in all combinations above, the "at least one" strain of Equine Herpesvirus is preferred to be selected from the group consisting of EHV-1 and EHV-4. In some preferred forms, both strains, EHV-1 and EHV-4, will be included in the immunogenic composition. In other preferred forms, just EHV-1 will be included. The WNV component of the combination will preferably be an inactivated or killed North American dominant strain as described herein.

The vaccine composition can be administered in any immunogenically effective dose. In a preferred embodiment, the vaccine composition is administered as a single dose. Preferably, the dose has a total volume between about 0.5 ml and 2.5 ml, more preferably between about 0.6 ml and 2.0 ml, even more preferably between about 0.7 ml and 1.75 ml, still more preferably between about 0.8 ml and 1.5 ml, even more preferably between about 0.9 ml and 1.25 ml, with a single 1.0 ml dose being the most preferred.

In another embodiment, the vaccine is administered with a first dose being administered prior to the administration of a second (booster) dose. Preferably, the second dose is administered at least 15 days after the first dose. More preferably, the second dose is administered between 15 and 28 days after the first dose. Even more preferably, the second dose is administered at least 17 days after the first dose. Still more preferably, the second dose is administered between 17 and 25 days after the first dose. Even more preferably, the second dose is administered at least 19 days after the first dose. Still more preferably, the second dose is administered between 19 and 23 days after the first dose. Most preferably the second dose is administered at least 21 days after the first dose. In a preferred embodiment, both the first and second doses of the vaccine are in the same amount. Preferably, each dose is in the preferred amounts specified above, with a dose of 1 ml for the first and second dose being most preferred. In addition to the first and second dose regimen, an alternate embodiment comprises further subsequent doses. For example, a third, fourth, or fifth dose could be administered in these embodiments. Preferably, subsequent third, fourth, and fifth dose regimens are administered in the same amount as the first dose, with the time frame between the doses being consistent with the timing between the first and second doses mentioned above.

In an additional preferred embodiment, in each dose of the composition of the present invention, the WNV antigen comprises at least $10^{2.0}$ $TCID_{50}$/dose. More preferably, the WNV antigen comprises between about $10^{2.0}$ $TCID_{50}$/dose to $10^{10.0}$ $TCID_{50}$/dose. Still more preferably, the WNV antigen comprises at least $10^{2.5}$ $TCID_{50}$/dose. Even more preferably, the WNV antigen comprises between about $10^{2.5}$ $TCID_{50}$/dose to about $10^{9.5}$ $TCID_{50}$/dose. Still more preferably, the WNV antigen comprises at least $10^{3.0}$ $TCID_{50}$/dose. Even more preferably, the WNV antigen comprises between about $10^{3.0}$ $TCID_{50}$/dose to about $10^{9.0}$ $TCID_{50}$/dose. Still more preferably, the WNV antigen comprises at least $10^{3.5}$ $TCID_{50}$/dose. Even more preferably, the WNV antigen comprises between about $10^{3.5}$ $TCID_{50}$/dose to about $10^{9.0}$ $TCID_{50}$/dose. Most preferably, the WNV antigen comprises between $10^{7.0}$ $TCID_{50}$/dose and $10^{9.0}$ $TCID_{50}$/dose. The $TCID_{50}$ values of an inactivated WNV vaccine or any other inactivated vaccine refer in general to the antigen content in the final vaccine that however is equivalent to the antigen content calculated for the vaccine composition prior to the inactivation of its antigen. Preferably, the immunogenic composition of the present invention stimulates serum neutralizing antibodies to WNV at a titer of 1:4 or higher when determined in a commercial available detection assay or using the procedures known to those of skill in the art with a representative example provided herein. In a preferred embodiment, in each dose of an embodiment of the present invention that comprises additional equine antigen, the amount of Eastern Equine Encephalomyelitis or Venezuelan Equine Encephalomyelitis in any dose is preferably at least $10^{5.5}TCID_{50}$/dose. Even more preferably, the dose is between about $10^{5.5}TCID_{50}$/dose and $10^{9.5}TCID_{50}$/dose. Still more preferably, the dose is at least $10^{6.0}TCID_{50}$/dose. Still more preferably, the dose is between about $10^{6.0}TCID_{50}$/dose and $10^{9.0}TCID_{50}$/dose. Even more preferably, the dose is at least $10^{6.5}TCID_{50}$/dose. Still more preferably, the dose is between about $10^{6.5}TCID_{50}$/dose and $10^{9.5}TCID_{50}$/dose. Even more preferably, the dose is at least $10^{7.0}TCID_{50}$/dose. Most preferably, the dose is between $10^{6.7}TCID_{50}$ and $10^{9.2}TCID_{50}$/dose.

Preferably, the Western Equine Encephalomyelitis antigen, when present in the composition of the present invention, is in an amount of at least $10^{6.2}$ PFU/ml. Even more preferably, the amount is between $10^{6.2}$ PFU/ml and $10^{10.2}$ PFU/ml. Still more preferably, the amount is at least $10^{6.7}$ PFU/ml. Even more preferably, the amount is between $10^{6.5}$ PFU/ml and $10^{9.7}$ PFU/ml. Still more preferably, the amount is at least $10^{7.2}$ PFU/ml. Even more preferably, the amount is between about $10^{7.2}$ PFU/ml and $10^{9.2}$ PFU/ml. Still more preferably, the amount is at least $10^{7.7}$ PFU/ml with at between $10^{6.5}$ PFU/dose and $10^{9.0}$ PFU/ml being the most preferred.

In another preferred embodiment, the amount of tetanus toxoid, if present in the composition of the present invention, is in an amount of at least 3 CPU, more preferably, between about 3 CPU and 20 CPU, still more preferably, at least 4 CPU, and most preferably, at least 5 CPU but not more than 20 CPU.

In an alternate embodiment, where one or more strains of Equine Influenza Virus is present, the amount of Equine Influenza present in the composition is in an amount of at least $10^{5.0}TCID_{50}$/mL. More preferably, the Equine Influenza is in an amount of between about $10^{5.0}TCID_{50}$/mL to $10^{9.0}TCID_{50}$/mL, and, more preferably, at least $10^{6.0}TCID_{50}$/mL. Still more preferably, the amount is between about $10^{6.0}TCID_{50}$/mL to $10^{8.0}TCID_{50}$/mL and, more preferably, the amount is at least $10^{6.5}TCID_{50}$/mL. Still more preferably, the amount is between about $10^{6.5}TCID_{50}$/mL to $10^{7.0}TCID_{50}$/mL, with the most preferred amount being between about $10^{6.7}TCID_{50}$/mL to $10^{7.0}$.

In an embodiment that comprises Equine Herpes Virus, the amount of Equine Herpes Virus in each dose is at least $10^{6.0}TCID_{50}$/mL. More preferably, Equine Herpes Virus is present in the composition in an amount of between $10^{6.0}TCID_{50}$/mL to $10^{9.5}TCID_{50}$/mL and, more preferably, in an amount of about $10^{7.0}TCID_{50}$/mL. Still more preferably, Equine Herpes Virus is present in an amount between $10^{7.5}TCID_{50}$/mL to $10^{9.0}TCID_{50}$/mL and, more preferably, in an amount of about $10^{8.0}TCID_{50}$/mL. Still more preferably, Equine Herpes Virus is present in an amount of between $10^{8.0}TCID_{50}$/mL to $10^{9.0}TCID_{50}$/mL and, most preferably, in an amount of about $10^{8.50}TCID_{50}$/mL.

In yet another preferred embodiment, a vaccine composition comprising the chronologically contemporary and epidemiologically prevalent strains of WNV is provided. Such a composition will generally improve the efficacy of the composition. Preferably, such a prevalent strain is isolated from the tissues of a horse. Such a source is a preferred source of WNV for preparing vaccine seed virus for an immunological composition for a species for which a comprehensively safe and effective WNV vaccine is particularly needed, namely, the horse. Further, the present invention discloses a vaccine composition comprising an inactivated low passage strain of WNV from the tissues of a horse, thereby overcoming the limitations of previous vaccines with the inappropriate limited repertoire of protein antigens found in either high passage attenuated vaccines, subunit vaccines, or other compositions produced by recombinant technology that express less than the full complement of proteins. This inactivated low passage WNV strain, isolated from horse tissues, overcomes deficiencies inherent in previous vaccines and provides a broad number of immunogenic proteins of most relevance by virtue of being produced from a highly virulent equine strain of low passage, thereby comprising a uniquely and comprehensively effective, yet safe, immunogenic composition not previously available for vaccination of the horse. Additionally, preferred chronologically contemporary and epidemiologically prevalent strains of WNV are North American dominant WNV strains, as defined herein.

The present invention provides for a broader scope of protection than traditional immunogenic or vaccine compositions, as the present invention provides protection against a broad range of isolates of a particular antigen. The challenge model used to evaluate the efficacy of the composition of the present invention utilized a heterologous challenge strain, evidencing the composition's ability to provide protection to isolates and strains outside of the particular strain or isolate used to vaccinate the animal. This is a unique feature of the present invention.

The present invention additionally provides for a method of reduction of the incidence and/or severity of clinical signs associated with West Nile Virus infection in an animal, preferably a horse, when compared to wild type infection. Such methods generally comprise the step of administering a vaccine composition comprising a killed or inactivated isolate of West Nile virus, preferably a North American dominant WNV strain, and a pharmaceutically acceptable carrier. In some preferred embodiments of the present application, an adjuvant is added to the composition, and in other preferred forms, no adjuvant is provided. In an alternate preferred embodiment, the method comprises administering a vaccine composition comprising one or more killed or inactivated isolate(s) of West Nile virus in combination with immunologically effective amounts of antigenic components from other equine pathogens. Preferably those isolates are selected from the group consisting of Eastern Equine Encephalomyelitis antigen, Western Equine Encephalomyelitis antigen, Venezuelan Equine Encephalomyelitis antigen, tetanus toxoid, and combinations thereof, and more preferably being those combinations described above. In another preferred embodiment, the vaccine of the present invention is combined with a suitable adjuvant, diluent, or pharmaceutically acceptable carrier.

The present invention provides for reduction of the incidence and/or severity of clinical symptoms associated with West Nile Virus infection in a herd, when compared to wild type infection. Preferably, the severity and/or incidence of clinical symptoms in animals receiving the immunogenic composition of the present invention are reduced at least 10% in comparison to animals not receiving such an administration when both groups (animals receiving and animals not receiving the composition) are challenged with or exposed to wild type infection by WNV. More preferably, the incidence or severity is reduced at least 20%, even more preferably, at least 30%, still more preferably, at least 40%, even more preferably, at least 50%, still more preferably, at least 60%, even more preferably, at least 70%, still more preferably, at least 80%, even more preferably, at least 90%, still more preferably, at least 95%, and most preferably, at least 100%, wherein the animals receiving the composition of the present invention exhibit no clinical symptoms. Preferably, the WNV strain is a North American dominant strain of WNV. Advantageously, the present invention also provides protection from heterologous strains (relative to the strain used in the composition) of pathogens.

The present invention further provides a method of stimulating serum neutralizing or serum hemagglutination antibodies to a pathogen selected from the group consisting of WNV, WEE, VEE, EEE, EHV, EIV, and combinations thereof by administering a composition in accordance with the present invention described herein. Preferably the compositions of the present invention stimulate serum neutralizing antibodies to WNV at a titer of 1:4 or higher, thereby preventing or reducing WNV viremia.

The immunogenic composition of the present invention provides an extended duration of immunity against all antigens present in the vaccine. Preferably, the duration of immunity against West Nile is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against EIV is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against EHV is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Western Equine Encephalomyelitis is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Eastern Equine Encephalomyelitis is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Venezuelan Equine Encephalomyelitis is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Tetanus Toxoid is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity of at least 12 months further relates to any combination of antigens forming the immunogenic composition of the present invention.

In another preferred embodiment comprising EIV and/or EHV antigen, as described above, the immunogenic composition ameliorates shedding of infectious EIV or EHV to prevent spread of the virus to other susceptible animals.

In yet another preferred embodiment, compositions in accordance with the present invention described herein overcome interference from passively acquired maternal immunity and stimulates active immunity and a reduction in the incidence of or severity of clinical signs of EIV infection in vaccinated animals against EIV.

In another preferred embodiment of the present invention, an immunogenic composition comprising VEE, WEE, EEE, tetanus, WNV, equine rhinopneumonitis and equine influenza, all as described herein, demonstrates efficacy against VEE, WEE, EEE, tetanus, WNV, equine rhinopneumonitis and equine influenza after administration in accordance with the present invention. Preferably, such a composition will further include an adjuvant, preferably mineral oil and/or a carbomer, and a veterinary acceptable carrier. In preferred forms, the composition will be administered in a single, 1 ml dose.

Each of the immunogenic compositions described herein that include WNV antigen can be administered as described such that they reduce the incidence of or lessen the severity of clinical symptoms associated with West Nile Virus.

Each of the immunogenic compositions described herein that include EIV antigen can be administered as described such that they reduce the incidence of or lessen the severity of clinical symptoms associated with Equine Influenza.

The present invention also provides a method for reducing the incidence of or lessening the severity of clinical symptoms associated with Equine Herpes virus comprising the step of administering any one of the immunogenic compositions described above, that includes an Equine Herpes virus antigen, to an animal.

The present invention also provides a method for reducing the incidence of clinical symptoms associated with West Nile Virus comprising the step of administering any one of the immunogenic compositions that includes West Nile Virus antigen, as described herein, to an animal.

The present invention also provides a method for reducing the incidence of clinical symptoms associated with Equine Influenza Virus comprising the step of administering any one of the immunogenic compositions described above, that includes an Equine Influenza antigen, to an animal.

The present invention further provides a method for reducing the incidence of clinical symptoms associated with Equine Herpes Virus comprising the step of administering any one of the immunogenic compositions described above that includes an Equine Herpes virus antigen, to an animal.

The present invention also provides a method of reducing the incidence of clinical symptoms associated with Equine Influenza Virus comprising the step of administering any one of the immunogenic compositions described above to an animal, wherein the reduction in clinical signs, compared to animals not receiving the immunogenic composition, is at least a 10% reduction in clinical signs.

The present invention provides a method of reducing the incidence of infection in a herd comprising the step of administering any one of the immunogenic compositions described above to an animal.

The present invention provides a method of reducing the incidence of infection in a herd comprising the step of administering any one of the immunogenic compositions described above to an animal, wherein the reduction of incidence of infection, compared to herds not receiving the immunogenic composition, is from about 10%-50% reduction.

The present invention provides a method of reducing the incidence and severity of clinical symptoms of EHV in a herd, wherein the clinical symptoms are selected from the group consisting of respiratory disease, abortion, reproductive complications, neurological disease, central nervous system disease, and combinations thereof.

The present invention provides a method for reducing the incidence of or lessening the severity of clinical symptoms associated with Equine Herpes Virus comprising the step of administering any one of the immunogenic compositions described above, that includes an Equine Herpes Virus antigen, to an animal.

The present invention provides a method for reducing the severity of or lessening the severity of clinical symptoms associated with Equine Influenza in a herd, comprising the step of administering any one of the immunogenic compositions described above, that includes an Equine Influenza antigen, to an animal.

The present invention provides a method for reducing the incidence of or lessening the severity of clinical symptoms associated with West Nile Virus in a herd, comprising the step of administering any one of the immunogenic compositions described above, that includes a West Nile Virus antigen, to an animal.

The present invention provides a method for reducing the incidence of or lessening the severity of clinical symptoms associated with Eastern Equine Encephalomyelitis in a herd, comprising the step of administering any one of the immunogenic compositions described above that includes an Eastern Equine Encephalomyelitis antigen to an animal.

The present invention further provides a method for reducing the incidence of or lessening the severity of clinical symptoms associated with Western Equine Encephalomyelitis in a herd, comprising the step of administering any one of the immunogenic compositions described above, that includes an Western Equine Encephalomyelitis antigen, to an animal.

The present invention further provides a method for reducing the incidence of or lessening the severity of clinical symptoms associated with Venezuelan Equine Encephalomyelitis in a herd, comprising the step of administering any one of the immunogenic compositions described above, that includes a Venezuelan Equine Encephalomyelitis antigen, to an animal.

The present invention also provides a method of making any one of the immunogenic composition of the present invention as described above and herein, comprising the steps of combining a West Nile Virus antigen with a suitable excipient or pharmaceutical carrier. In preferred forms, this method further comprises the step of adding one or more equine antigens. A preferred group of equine antigens are selected from the group consisting of Western Equine Encephalomyelitis, Eastern Equine Encephalomyelitis, Venezuelan Equine Encephalomyelitis, Tetanus Toxoid, EHV, EIV, and combinations thereof. In some preferred forms, the methods described herein can further comprise a filtration step, wherein the final product is in a purified form.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), non-metabolizable oil, mineral and/or plant/vegetable and/or animal oils, polymers, carbomers, surfactants, natural organic compounds, plant extracts, carbohydrates, cholesterol, lipids, water-in-oil emulsion, oil-in-water emulsion, water-in-oil-in-water emulsion. The emulsion can be based in particular on light liquid paraffin oil (European Pharmacopeia type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997). In a preferred embodiment the adjuvant is at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product. Of the possible adjuvants used in combination with the present invention, it is preferred to not use a metabolizable oil. In a preferred embodiment, the adjuvant is at least a non-metabolizable oil, preferably mineral oil. In an alternate preferred embodiment, the vaccine composition contains essentially no oil-based adjuvants. In a most preferred embodiment the vaccine composition contains both a non-metabolizable oil, preferably mineral oil, and carbomer as adjuvants.

In addition, the immunogenic and vaccine compositions of the present invention can include one or more veterinary-acceptable carriers. As used herein, "a veterinary-acceptable carrier" includes any and all solvents, dispersion media, coatings, adjuvants, stabilizing agents, diluents, preservatives, excipients, antibacterial and antifungal agents, antimicrobic agents, isotonic agents, adsorption delaying agents, and the like. In some preferred embodiments, and especially those that include lyophilized immunogenic compositions, stabilizing agents for use in the present invention include stabilizers for lyophilization or freeze-drying.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In a preferred embodiment, the immunogenic composition of the present invention is prepared comprising a preservative and a stabilizer; and, more preferably, the immunogenic composition of the present invention is prepared comprising gentamycin, EDTA, Glycerol, and combinations thereof.

An "immunogenic or immunological composition" refers to a composition of matter that comprises at least one antigen, which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of clinical signs normally displayed by an infected host, a quicker recovery time and/or a lowered duration or bacterial titer in the tissues or body fluids or excretions of the infected host.

The term "in need of such administration" or "in need of such administration treatment", as used herein means that the administration/treatment is associated with the boosting or improvement in health or any other positive medicinal effect on health of the animals which receive the immunogenic composition in accordance with the present invention.

The term "West Nile Virus" antigen means, but is not limited to the components of the WNV virion that are immunogenic when present in an animal, and most particularly protein components, such as envelope and non-structural proteins, of the WNV that provoke humoral or cellular immune responses when present in an animal. Such antigens can include DNA, protein subunits, modified live virus, and killed or inactivated virus. In preferred forms of the invention, the WNV antigen or antigens comprise inactivated or killed, and even more preferably, North American dominant, WNV strains.

The term "North American West Nile Virus (strains)" refers to, but is not limited to any West Nile Virus strain or isolate that has ever been discovered on the North American continent. Preferably, a North American West Nile Virus strain has a sequence identity to the NY99 strain (GenBank accession no. AF196835 or NCBI reference sequence NC 00942.1 (SEQ ID No. 23) of at least 97%, even more preferably, at least 98%, still more preferably, at least 98.5%, more preferably, at least 99%, even more preferably, at least 99.2%, and, most preferably of at least 99.4%.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% “sequence identity” to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The term “North American Dominant West Nile Virus” strains and isolates refers to those strains or isolates defined as such in *Phylogenetic Analysis of North American West Nile Virus Isolates,* 2001-2004*: Evidence For the Emergence of a Dominant Genotype*, C. Todd Davis, et. al, Virology 342, p. 252-265 (2005), the teaching and content of which is hereby incorporated by reference herein. As noted therein, North American Dominant WNV strains or isolates have at least 1 nucleotide change resulting in an amino acid change from the WN99 isolates. Strain NY99 (GenBank accession no. AF196835), an example of which is provided in SEQ ID. NO. 23, serves as a reference strain for determining if a strain or isolate is North American Dominant. In a preferred embodiment, the nucleotide change results in an amino acid change in an envelope protein of the strain or isolate and, more preferably, the nucleotide change results in an amino acid change from valine to alanine at position 159 in the critical envelope protein or “E159”. Preferably, this amino acid change is associated with a greater ability to replicate in the intermediate host, namely, the mosquito. In addition, these strains or isolates may have one or more silent amino acid changes. Preferably, North American Dominant strains also include either (and preferably both) a U to C mutation and a C to U mutation at positions 1442 and 2466 (in comparison to a North American strain, e.g. NY 99 and SEQ ID NO.23), respectively. Still more preferably, North American Dominant strains or isolates further include a mutation in the nucleotide sequence encoding the E protein and the C to U mutation at position 9352 in the sequence encoding the NS5 protein (again in comparison to a North American strain, e.g. NY 99 and SEQ ID NO. 23). These preferred mutations are shown in detail for specific regions in Example 10 and FIGS. 10-17. Representative North American Dominant WNV strains are listed in this application. Additionally, for purposes of the present invention North American Dominant and WN02 are used interchangeably.

For purposes of the present invention, Horse Origin 2005 strain North American Equine E159, E159 (Horse Origin), NAEE159, United States Department of Agriculture Isolate 405330 (USDA 2005) Horse Origin, and E159 strain are used interchangeably. For purposes of the present invention, Donkey Origin 2004 strain, United States Department of Agricultures Isolate 292206 (USDA 2004) Donkey Origin, E159 (Donkey Origin), and North American Donkey E159 (NADE159) are used interchangeably. E159 indicates that the amino acid change in the envelope protein from valine to alanine occurs at position 159, as described above.

West Nile Virus strains or isolates, for purposes of the present invention, are not limited to horse and equine West Nile Virus strains but encompass, while not being limited to, those West Nile Virus strains of bird origin, donkey origin, pig origin, human origin, mammal origin, and equine origin.

For purposes of the present invention the terms “strain” and “isolate” have the same meaning and are used interchangeably.

As used herein, “a pharmaceutically” or “veterinary acceptable carrier” or “pharmaceutical carrier” includes any and all solvents, growth media, dispersion media, coatings, adjuvants, stabilizing agents, diluents, preservatives, antibacterial and antifungal agents, isotonic agents, adsorption delaying agents, and the like.

An “immunogenic or immunological composition” refers to a composition of matter that comprises at least one antigen which elicits an immunological response in the host of a cellular and/or antibody-mediated immune response to the composition or vaccine of interest. Usually, an “immunological response” includes but is not limited to one or more of the following effects: the production or activation of antibodies, B cells, helper T cells, suppressor T cells, and/or cytotoxic T cells and/or gamma-delta T cells, and/or virus neutralizing antibodies directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of clinical signs normally displayed by an infected host, a quicker recovery time and/or a lowered duration of clinical disease or higher viral antibody titer in the tissues or body fluids or excretions of the infected host, or lessened viremia in the blood, or lessened gross or histopathological lesions due to infection.

In addition, the immunogenic and vaccine compositions of the present invention can include one or more veterinary-acceptable carriers. As used herein, "a veterinary-acceptable carrier" includes any and all solvents, dispersion media, cell culture media and cell culture constituents, coatings, adjuvants, stabilizing agents, diluents, preservatives, antibacterial and antifungal agents, isotonic agents, adsorption delaying agents, and the like. "Diluents" can include water, saline, buffered saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Clinical signs" of West Nile Virus, for purposes of this invention, include, but are not limited to, symptoms or lesions associated with encephalitis, viremia, anorexia, depression, fever, weakness, abnormal gait, paralysis of hind limbs, impaired vision, ataxia, aimless wandering, convulsions, inability to swallow, coma, posterior weakness, paralysis, poor coordination, depression and related behavior, tremors, convulsions, paddling of the limbs, neurological problems, swelling of the central nervous system, death, and combinations thereof. The clinical signs exhibited by an infected animal vary depending on the severity of infection "Clinical Signs" of Equine Herpes virus, for purposes of this invention include, but are not limited to, abortion, neurological deficiencies, respiratory disease, reproductive system deficiencies and failure, and symptoms relating to the central nervous system. Additionally, clinical symptoms of EHV 1 include, but are not limited to, the phenomenon of foals infected with EHV1, exhibiting respiratory complications, passing the virus to the older members of the herd who then exhibit reproductive deficiencies, including abortion, and neurological deficiencies, normally exhibited in the central nervous system.

"Clinical Signs" of Eastern Equine Encephalomyelitis, Western Equine Encephalomyelitis, and Venezuelan Equine Encephalomyelitis, for purposes of the present invention are those symptoms normally known to be associated with encephalomyelitis, including, but are not limited to fever, nervous signs such as sensitivity to sound, periods of excitement, and restlessness, brain lesions, drowsiness, drooping ears, circling, abnormal gait, paralysis, loss of appetite, depression, head pressing, lack of coordination, long-term disability, brain damage, death, and combinations thereof.

"Safety" as used herein, refers to the absence of adverse consequences in the vaccinated animal following vaccination, including but not limited to, potential reversion of vaccine virus to virulence and clinically significant side effects, such as persistent systemic illness or unacceptable inflammation at the site of vaccine administration.

"Reduction of the incidence and/or severity of clinical signs" or "reduction in the incidence and/or severity of clinical symptoms", as referred to herein, means reducing the number of infected animals in a group, reducing or eliminating the number of animals exhibiting clinical signs of infection, or reducing the severity of any clinical signs that are present in the animals, in comparison to wild-type infection. For example, in the experiments herein, such clinical signs included viremia, fever, antibody response, and histopathology. Preferably, these are reduced in animals receiving the composition of the present invention by at least 10% in comparison to animals not receiving the vaccination which may become infected. More preferably, clinical signs are reduced in animals receiving the composition of the present invention by at least 20%, more preferably by at least 30%, even more preferably by at least 40%, and even more preferably by at least 50%.

"Duration of Immunity," as used herein, refers to the minimum number of days during which an animal produces an immunogenic response such that the animal will be relatively immune from contracting a virus and/or benefit from reduction of incidence and/or severity of clinical signs, as described herein.

The terms "strain" and "isolate", when used herein, are meant to be used interchangeably.

The terms "vaccine" and "immunogenic composition", when used herein, are meant to be used interchangeably.

Any West Nile Virus strain(s) or isolate(s) can be used in accordance with the present invention. In a preferred embodiment, the isolate is selected from one or more of the following: New York (Northeastern North American) Isolate (WN-NY 99), Horse Origin, 1999, New York (Northeastern North American) Isolate (WN-NY 99), Crow Origin, 1999, United States Department of Agricultures Isolate 292206 (USDA 2004), Donkey Origin, United States Department of Agriculture Isolate 405330 (USDA 2005), Horse Origin, North American Isolate (WN-Texas-2002/2003), Southeast Texas Coastal Isolate 2002, Mexico (Tabasco) Isolate 2003, and combinations thereof, and in a more preferred embodiment the isolate is selected from one or more of the following: United States Department of Agricultures Isolate 292206 (USDA 2004), Donkey Origin, United States Department of Agriculture Isolate 405330 (USDA 2005), Horse Origin, North American Isolate (WN-Texas-2002/2003), Southeast Texas Coastal Isolate 2002, Mexico (Tabasco) Isolate 2003, and combinations thereof. In a most preferred embodiment, the isolate is United States Department of Agriculture Isolate 405330 (USDA 2005), Horse Origin singularly or in combination with one or more isolates as listed above. In an additionally preferred embodiment, those isolates which are part of the North American West Nile Virus isolates are included. In yet another preferred embodiment North American Dominant West Nile Virus isolates are included. In addition to those listed above, specific isolates include, but are not limited to, WN02 and isolates which have at least 1, preferably at least 2, and even more preferably at least 3 nucleotide changes resulting in at least one amino acid change from the WN NY99 isolates, and most preferred are strains with the amino acid change from valine to alanine at position 159 of the envelope protein. Most preferred North American Dominant strains include, but are not limited to: NY2002Nassau, NY2002Clinton, NY2002Queens, GA20021, GA20022, TX20021, TX20022, IN2002, NY2003Albany, N.Y. 2003Suffolk, NY2003Chatauqua, CO20031, CO20032, TX2003, TX2003Harris4, TX2003Harris6, TX2003Harris7, TX2003Harris10, AZ2004, and TX2004Harris4, and combinations thereof. The strains of West Nile Virus useful in the vaccine or immunogenic composition of the present invention can be any strain or isolate. In a preferred embodiment, the North American Dominant West Nile Virus strain used is either E-159 (Horse Origin) or E-159 (Donkey Origin). A representative strain of such a North American Dominant WNV strain includes the Horse Origin 2005 strain deposited with the ATCC (ATCC Accession No. PTA-9409), located at 10801 University Boulevard, Manassas, Va., 20110-2209, on Aug. 14, 2008, under the provisions of the Budapest Treaty. Equine Influenza strains useful in the vaccine or immunogenic composition of the present invention can be any strain or isolate. Representative strains include Equi-2/Ohio/03, deposited as ATCC Accession No. PTA-9522, Equi-2/Kentucky/95, deposited as ATCC Accession No. PTA-9523, and Equi-2/New Market/2/93, deposited as ATCC Accession No. PTA-9524. Representative strains ATCC Accession Nos. PTA-9522, PTA-9523, and PTA-9524 were each deposited with the ATCC at 10801 University Boulevard, Manassas, Va., 20110-2209 on Sep. 23, 2008, under the provisions of the Budapest Treaty.

Equine Herpes Virus ("EHV") strains useful in the vaccine or immunogenic composition of the present invention can be any strain or isolate. Representative strains include EHV Subtype 1, deposited as ATCC Accession No. PTA-9525, and EHV Subtype 4, deposited as ATCC Accession No. PTA-9526. Representative strains ATCC Accession Nos. PTA-9525 and PTA-9526 were each deposited with the ATCC at 10801 University Boulevard, Manassas, Va., 20110-2209 on Sep. 23, 2008, under the provisions of the Budapest Treaty.

Western Equine Encephalomyelitis strains useful in the vaccine or immunogenic composition of the present invention can be any strain or isolate. A representative strain includes the Fleming Strain, deposited with the ATCC (ATCC Accession No. PTA-9410), located at 10801 University Boulevard, Manassas, Va., 20110-2209, on Aug. 14, 2008, under the provisions of the Budapest Treaty.

Venezuelan Equine Encephalomyelitis strains useful in the vaccine or immunogenic composition of the present invention can be any strain or isolate. A representative strain includes the TC-83 strain, deposited with the ATCC (ATCC Accession No. PTA-9411), located at 10801 University Boulevard, Manassas, Va., 20110-2209, on Aug. 14, 2008, under the provisions of the Budapest Treaty.

Eastern Equine Encephalomyelitis strains useful in the vaccine or immunogenic composition of the present invention can be any strain or isolate. A representative strain includes the NJO strain, deposited with the ATCC (ATCC Accession No. PTA-9412), located at 10801 University Boulevard, Manassas, Va., 20110-2209, on Aug. 14, 2008, under the provisions of the Budapest Treaty.

Tetanus toxoid strains useful in the vaccine or immunogenic composition of the present invention can be any strain or isolate. A representative strain is that taken from a master seed of *Clostridium tetani* from The Massachusetts Department of Public Health Institute of Laboratories in Boston, Mass.

The vaccine of the present invention is safe for administration in WNV susceptible species, particularly equidae, at any age and at any stage of reproduction, including pregnant females. In a preferred embodiment, the present invention is safe for administration to foals 12 months of age or older, more preferably, it is safe for administration to foals 10 months of age or older, more preferably, it is safe for administration to foals 8 months or older, more preferably, it is safe for administration to foals 6 months of age or older, more preferably, is safe for administration to foals 4 months of age or older, more preferably, it is safe for administration to foals 2 months of age or older, more preferably, it is safe for administration to foals 1 month of age or older, even more preferably, it is safe for administration to foals between 1 day and 1 month of age, and, most preferably, it is safe for administration to foals 1 day of age or older.

The composition of the present invention can be administered in any conventional manner. Examples of administration methods include any that afford access by cells of the immune system to the immunogenic composition including oral, transdermal/intradermal, intravenous, subcutaneous, intramuscular, intraocular, intraperitoneal, intrarectal, intravaginal, intranasal, intragastrical, intratracheal, intrapulmonarial, or any combination thereof. In a preferred embodiment, the vaccine is administered parenterally, preferably intranasally, subcutaneously, or intramuscularly, and in the most preferred embodiment the vaccine is administered intramuscularly.

BRIEF DESCRIPTION OF THE DRAWINGS

FIG. 1 is a graphical representation of the Mean Total Clinical Scores;

FIG. 2 is a graphical representation of the Proportion Shedding;

FIG. 3 is a graphical representation of the Nasal Discharge Score;

FIG. 4 is a graphical representation of Proportion Virus Shedding;

FIG. 5 is a graphical representation of Conjunctivitis Score;

FIG. 6 is a graphical representation of Serum Neutralization Titers;

FIG. 7 is a graphical representation of Proportion Positive for EHV-1;

FIG. 8 is a graphical representation of Mean White Blood Cell Count;

FIG. 9 is a graphical representation of Proportion Positive (pyrexic);

FIG. 10A through 10N is a nucleotide alignment of the HE region of WNV isolates (SEQ ID NOS 17-18 and 25-28, respectively, in order of appearance);

FIG. 11A through 110 is a nucleotide alignment of the DE region of WNV isolates (SEQ ID NOS 17-18 and 29-32, respectively, in order of appearance);

FIG. 12A through 12M is a nucleotide alignment of the D NS5 region of WNV isolates (SEQ ID NOS 1-2 and 33-36, respectively, in order of appearance);

FIG. 13A through 13M is a nucleotide alignment of the H NS5 region of WNV isolates (SEQ ID NOS 1-2 and 37-40, respectively, in order of appearance);

FIG. 14A through 14M is a nucleotide alignment of the H WN05 E NS5 region of WNV isolates (SEQ ID NOS 1-6, respectively, in order of appearance);

FIG. 15A through 150 is a nucleotide alignment of the H WN05 region of WNV isolates (SEQ ID NOS 17-22, respectively, in order of appearance);

FIG. 16A through 16K is a nucleotide alignment of the NS5 region of WNV isolates (SEQ ID NOS 12-16, respectively, in order of appearance); and FIG. 17A through 17Q is a nucleotide alignment of the E region of WNV isolates (SEQ ID NOS 7-11, respectively, in order of appearance).

DETAILED DESCRIPTION

Examples

The following examples are set forth below to illustrate specific embodiments of the present invention. These examples are merely illustrative and are understood not to limit the scope or the underlying principles of the present invention.

Example 1

This example illustrates a preferred vaccine composition in accordance with the present invention.

Materials and Methods

For preparation of working cell stock, the Master Cell Stock (MCS), consisting of the Vero Cell Line known to propagate West Nile Virus, which was tested for purity, identity, and karyology, was thawed and used to inoculate a range of T25 up to T150 $cm^2$ vessels or 1050 $cm^2$ roller bottles, or bioreactors or other suitable sterile vessels. Thawed cells were suspended in growth medium at a rate of 0.0015 mL to 5.0 L per vessel, depending on vessel volume. Cells were then incubated at 36-38° C. for up to seven days. Cultures planted from frozen stock were re-fed with medium, if needed, within thirty-six hours after planting to remove residual DMSO. Cultures were re-fed with medium, if needed, during the growth period to remove excessive debris, or to stimulate the growth of cultures which have not reached confluence, or to maintain viability of confluent cultures.

Cells were passaged 1-20 times by decanting the spent medium and then by adding 5-500 mL of 0.25% Trypsin-EDTA Solution to each vessel, depending upon vessel volume. The vessels were agitated gently until the cells slough from the surface. The cells were then removed from the vessels by rinsing with growth medium and pooled together. Prior to inoculation, cell growth medium was decanted from Vero Working Cells that are at least 55% confluent. Virus growth medium described was added to each vessel at 0.15 to 0.4 mL per $cm^2$ surface area. A Multiplicity of Infection (MOI) of 0.000001-0.0002 was used for infection as determined by performing a cell count of at least two representative vessels. Roller bottle cultures infected were incubated at 36-38° C. for two to five days at 0.1-0.8 rpm.

During the growth period, cultures were checked for typical CPE microscopically and for gross contamination macroscopically. Unsuitable cultures were discarded after sterilization. Cultures may be attenuated using standard techniques or may be used without attenuation.

The microorganisms were then harvested for production purposes. Virus fluids were harvested when CPE reached 85% or greater. Roller bottles were swirled to remove loose cells, and fluids and then pooled into sterile 2-20 L glass, plastic, or PETG bottles, 20 L sterile polypropylene containers or 2-500 L sterile stainless steel tanks containers appropriate for clarification.

Next, the product was prepared. Clarified fluids were inactivated with Formaldehyde Solution, USP, 0.2% by volume, or another effective inactivating agent, transferred to a secondary container, and held at 20-25° C. (room temperature) with agitation for forty-eight hours. A sample of at least 12 mL of the inactivated fluids was taken for inactivation assurance testing (described below) prior to concentration. After inactivation was completed, inactivated lot material was held at 2-7° C. for up to sixty days prior to concentration. A number of suitable adjuvants may be added to the vaccine formulation, most preferably a non-metabolizable oil, preferably mineral oil, and/or a carbomer. Typical processing steps may be employed such as mixing, blending, microfluidization, and emulsification, of the adjuvant and/or the harvested virus antigens with other ingredients.

The product was then standardized. Sufficient volumes of clarified, inactivated, concentrated (optional) lots were combined to provide a calculated titer of at least $10^{4.0}$ $TCID_{50}$ per dose of each strain in the final product. Multiple lots may be blended to achieve the titer requirements per dose.

The product was then assembled to final formulation. Based on the desired final serial volume, the amounts of antigenic components, adjuvant, stabilizer and diluent were calculated as follows:

a. West Nile Virus, Horse Origin 2005 (ATCC No. PTA-9409): minimum $10^{4.0}$ $TCID_{50}$/dose
b. Adjuvant: The total adjuvant concentration, preferably a non metabolizable oil, and more preferably mineral oil and/or a carbomer, in a serial is at least 10% v/v and is added at time of serial batching/assembly.
c. Diluent: An appropriate volume of phosphate buffered saline (PBS) is added to bring the final volume to the desired volume.
d. Additional Formalin: An appropriate volume of 37% Formalin is added to maintain an appropriate level.
e. Gentamicin Sulfate The required amounts of adjuvant and PBS were combined in a sterile vessel. The pH of this mixture was adjusted to approximately 4.9-5.1 with 10N NaOH or 5N HCl if necessary. Clarified, killed, concentrated West Nile Virus, as well as Gentamicin, and Formalin were added and the pH adjusted to 6.9 to 7.1. This was mixed at 2-6° C. for at least 8 hours, not to exceed 48 hours.

The vaccine was given by typical hypodermic injection, with booster vaccinations if desired. Most preferably, the initial dose and the booster doses were 1 mL volume administered intramuscularly at 21-day intervals. The vaccination regimen of initial and booster dose was given at the most preferred 1 mL dose volume to horses, other equidae, and other WNV susceptible species to reduce the incidence of and or severity of clinical signs of WNV infection, and preferably to prevent infection by WNV as well as to prevent disease due to West Nile Virus infection for a sustained period following vaccination.

Results and Discussion

The vaccine was given by various appropriate parenteral routes, dose volumes, and dosing regimens to animals of varying immunological status for WNV, including naive and those with passive antibody, and provided for long duration of immunity up to and exceeding at least 2 years following vaccination. The vaccine was safe for administration in WNV susceptible species, particularly equidae, at any age and at any stage of reproduction, including pregnant females.

Example 2

This investigation was carried out to obtain an efficacy evaluation of a vaccine to protect horses from challenge with West Nile Virus (WNV).

Materials and Methods

A total of 30 horses were randomly divided into groups of 15 horses each. A total of 20 horses received 2 doses of vaccine at 21-day intervals and 10 horses were used for control. Each group of horses, Block 1 and Block 2, contained 10 vaccinated horses and 5 control horses. The vaccine was a combination including WNV antigen, specifically an inactivated or killed North American Dominant Strain of WNV, Horse Origin 2005 (ATCC Deposit No. PTA-9409) as well as antigenic components of Venezuelan Equine Encephalomyelitis, TC-83 strain (ATCC Deposit No. PTA-9411) Eastern Equine Encephalomyelitis, NJO strain (ATCC Deposit No. PTA-9412) Western Equine Encephalomyelitis, Fleming strain (ATCC Deposit No. PTA-9410) and Tetanus toxoid formulated approximately as follows:

| | |
|---|---|
| Eastern Equine Encephalomyelitis | $10^{6.7}$-$10^{9.2}$ $TCID_{50}$/mL |
| Western Equine Encephalomyelitis | $10^{6.7}$-$10^{9.2}$ PFU/mL |

-continued

| | |
|---|---|
| Venezuelan Equine Encephalomyelitis | $10^{6.7}$-$10^{9.2}$ $TCID_{50}$/mL |
| West Nile Virus | $10^{7.0}$-$10^{9.}$ $TCID_{50}$/mL |
| Tetanus Toxoid | 5-10 CPU/mL |
| Adjuvant | 100-200 µl/mL |
| Diluent - DMEM containing | q.s. |
| Gentamycin (30 µg/mL of diluent volume) | |
| Formaldehyde (0.1% of diluent volume) | |

All groups were challenged with intrathecal inoculation of 1 ml PBS containing approximately $10^5$ pfu of a heterologous strain of WNV (NY99, 4132, crow isolate). The challenge was conducted under ketamine-xylazine anesthesia.

Horses were monitored for a maximum of 14 days, then humanely euthanized. Those that developed severe disease prior to 14 days were euthanized prematurely.

The following data were collected to assess the effectiveness of the vaccine:

- Basic clinical evaluation
- Body temperature
- Assay for viremia
- Histopathology: two sections of brainstem were evaluated by a board-certified veterinary pathologist.

Sera collected on appropriate days were evaluated for characterization of serologic responses to challenge.

Results and Discussion

Viremia after challenge and serum neutralization titers were considered the primary outcome variables in this study. The first block of horses that had been vaccinated were 100% protected from viremia after challenge in this study. In comparison, 4 of the 5 control horses demonstrated viremia for 4-5 days post-challenge and 1 of 5 control horses demonstrated viremia for 1 timepoint. In addition, serum neutralization titers of vaccinated horses were statistically significantly higher than those of control horses at each time point examined after vaccination. Furthermore, the data establish that a WNV vaccine that provides a serum neutralization titer of 1:4 or higher is effective in preventing WNV viremia. The serum titers and viremia after challenge for Block 1 is summarized in Table 1 below:

TABLE 1

Serum Titers and Viremia for Block 1

| Horse Number | Treatment | Serum Titer Day of Challenge | Viremia After Challenge Highest Titer |
|---|---|---|---|
| 1 | Control | <2 | 390 |
| 2 | Vaccinate | 12 | <5 |
| 3 | Vaccinate | 12 | <5 |
| 4 | Control | <2 | 65 |
| 5 | Control | <2 | 1475 |
| 6 | Vaccinate | 6 | <5 |
| 7 | Vaccinate | 97 | <5 |
| 8 | Vaccinate | 10 | <5 |
| 9 | Vaccinate | 21 | <5 |
| 10 | Vaccinate | 35 | <5 |
| 11 | Vaccinate | 10 | <5 |
| 12 | Vaccinate | 24 | <5 |
| 13 | Vaccinate | 4 | <5 |
| 14 | Control | <2 | 235 |
| 15 | Control | <2 | 165 |

Viremia after challenge and serum neutralization titers were also considered the primary outcome variables in the second block of horses in this study. In the second block of horses only one vaccinate group horse displayed any timepoints of viremia throughout the challenge period. That horse had 3 separate timepoints on 3 mornings (not those same evenings) with minimal value readings of 5 (where <5 is negative). All control horses in the study (with the exception of one horse which exited the study prematurely but displayed definitive WNV histopathology and was excluded from evaluation) showed high levels of viremia for 1-8 timepoints after challenge.

Since viremia is a prerequisite before virus can cross the blood-brain barrier to cause WNV encephalitis, viremia is well justified as the primary parameter for evaluation of protection in an experimental study of this type.

This study demonstrated that 2 doses of the experimental combination vaccine administered to foals 4 to 5 months of age reliably and effectively stimulated protective serological serum neutralization titers. In addition the data confirm that post vaccination SN titers as low as 1:4 resulting from vaccination using an effectively batched antigen amount of West Nile Virus in this experimental combination vaccine protected vaccinated horses from viremia, clinical disease, and histopathology after a severe intrathecal challenge with a heterologous strain of West Nile Virus.

Histopathology also was different between the two groups with the likelihood of lesions in vaccinates being 40% less in Block 2 and 100% less in Block 1 than the likelihood of lesions in control animals challenged with virulent West Nile virus.

In addition a Control Group horse became weak on his hind legs on Day 9 post-challenge and got progressively worse until he was no longer able to stand. Histopathology of the pons and medulla from this horse showed severe encephalitis and myelitis consistent with WNV pathology that was more prevalent than signs of disease from any other horse in this study.

Two Block 2 control horses in this study displayed 3 days each of clinical signs relating to infection with West Nile Virus. One other control horse had a single timepoint of weakness due to disease. Another control horse did not display any timepoints of clinical signs, although it had multiple days of viremia. Although several vaccinated Block 2 horses in the study had mild to moderate histopathological changes in tissue as a result of the intrathecal challenge of WNV, only very mild clinical disease (mild head tremors) was noted for one vaccinate on one day of the study as compared to multiple days of clinical disease in 2 control horses and a single day of clinical disease in a third control horse.

The results demonstrated that the vaccine is effective and that an immunogenic reaction is induced in the animals that were administered the vaccine. The effectiveness of the vaccine was evidenced in this example by reduction in WNV viremia, by stimulation of high serum neutralization titers to WNV, and by prevention of WNV related clinical signs and histopathology in the brain and meninges. Because this vaccine is comprised of unique constituents, including a long lasting non-metabolizable adjuvant, it was formulated in a low 1 mL dose volume to provide a high degree of safety as a highly immunogenic low passage whole inactivated virus WNV isolate of recent origin and high epidemiological prevalence, and a WNV isolated from the tissues of an infected horse, it provides more comprehensive safety and effectiveness than other vaccines currently available. Additionally, it has the effect of providing a safe vaccine when administered to animals.

Example 3

This example illustrates the efficacy of the immunogenic composition of the present invention against infection by EHV-4

Materials and Methods

Thirty-seven (37) horses, 4-5 months of age, were used in this study. Horses were randomly assigned to either vaccinate or control groups by random number generator and then vaccinated. Twenty-four (24) horses served as vaccinates and thirteen (13) horses were mock-vaccinated control horses. All horses had low (≤1:14, avg.=1:7) EHV-4 serum neutralization (SN) titers prior to initiation of the study, indicative of horses susceptible to infection. The vaccine used was an experimental vaccine and had the following components:

The final formulated vaccine contains the following ingredients per 1 mL dose:

| | |
|---|---|
| EHV-1 (PTA-9525) | $10^{7.0-9.0}$ $TCID_{50}$/mL |
| Influenza A2/Ohio/03 (PTA-9522) | $10^{6.0-9.5}$ $TCID_{50}$/mL |
| Influenza A2/KY/95 (PTA-9523 | $10^{6.0-9.5}$ $TCID_{50}$/mL |
| Influenza A2/NewMarket/2/93 (PTA-9524) | $10^{6.0-9.5}$ $TCID_{50}$/mL |
| Tetanus Toxoid | 5-10 CPU |
| Eastern Equine Encephalomyelitis, (ATCC Deposit No. PTA-9412) | $10^{6.7-9.2}$ $TCID_{50}$/mL |
| Western Equine Encephalomyelitis, (ATCC Deposit No. PTA-9410) | $10^{6.7-9.2}$ PFU/mL |
| Venezuelan Equine Encephalomyelitis, (ATCC Deposit No. PTA-9411) | $10^{6.7-9.2}$ $TCID_{50}$/mL |
| West Nile Virus, Horse Origin 2005 (ATCC Deposit No. PTA-9409) | $10^{7.0-9.0}$ $TCID_{50}$/mL |
| Adjuvant | 100-200 μl |
| Glycerol | 100-200 μl |
| EDTA 240 mM solution | 10-20 μl |
| Diluent - DMEM containing Gentamicin (30 μg/mL of diluent volume) Formaldehyde (0.1-0.2% of diluent volume) | q.s. |

The Experimental Vaccine was administered intramuscularly in a 1 mL dose volume to each of 24 horses in the vaccinate group. Thirteen horses in the control group received a 1 mL dose of adjuvanted DMEM (Lot 004) containing excipients used in the 9-way vaccine (Gentamicin and formaldehyde) but no antigens. Challenge inoculation of virulent EHV-4 HRA005 strain virus was performed 15 days post-booster vaccination.

Each of the vaccinated and control horses was challenged with an EHV-4 strain of virus (HRA005). The titer of the dilute challenge virus was sufficient to provoke disease due to EHV infection in the non-vaccinated horses.

SEDIVET® (romifidine hydrochloride), a sedative and analgesic, was administered intravenously to each horse prior to challenge at a dosage of 50 μg/kg of body weight. Each horse was then challenged with the EHV-4 strain HRA005 virus. The challenge virus was administered intranasally as an aerosol produced by a nebulizer into an Equine AeroMask (Trudell Medical International, Ontario, Canada).

Daily morning rectal temperatures were recorded for each of the 37 vaccinated and control horses on Day of Challenge and for 14 days post challenge by means of a calibrated, electronic thermometer (GSA Electronics) probe. The daily rectal temperatures were recorded in degrees Fahrenheit (° F.).

Complete Blood Cell Counts

Venous blood from each of the 37 vaccinated and control horses was collected daily on the Day of Challenge and for 14 days post-challenge directly into a Vacutainer Disodium EDTA tube for Complete Blood Counts.

Nasal Exudate Evaluation

All nasal exudate observations were made prior to collection of nasopharyngeal swabs. On the Day of Challenge and for 14 days post challenge, the nasal passages and muzzle of each of the 37 vaccinated and control horses were examined and graded using the grading and scoring description listed below.

The scoring grades of 0 through 6 were assigned on the basis of the severity of the disease indicated by each of the following classifications:

TABLE 2

Scores for Clinical Symptoms

| Score | Description of symptoms | Score sheet designation |
|---|---|---|
| 0 | Essentially normal indicates the horse was clean and essentially free of nasal exudate | EN |
| 1 | Slight clear serous discharge that may be frequently observed in both diseased and normal horses | C-1 |
| 2 | Moderate clear serous discharge is indicative of a definite increase in volume over that normally observed | C-2 |
| 3 | Copious clear serous discharge that is generally observed only in diseased horses | C-3 |
| 1.5 | Very slight mucopurulent discharge indicates that mucus was definitely present in small amounts in either one or both nostrils | VSM |
| 2 | Slightly mucopurulent is a discharge easily observed in one or both nostrils | SM |
| 4 | Moderately mucopurulent indicates that mucoid discharges were present in large quantities in both nostrils | MM |
| 6 | Heavy mucopurulent indicates that copious amounts of a mucoid discharge filled both nostrils | HM |

Nasopharyngeal Viral Isolation Methods

On each observation test day each nasal passage of each vaccinated and control was sampled deeply by means of sterile swabs. On collection, each of two swabs were immediately placed in a single tube containing 4 mL of chilled transport medium (Dulbecco's Minimal Essential Medium (DMEM) supplemented with 2% FBS, 2× Pen/Strep, 2× Gentamicin, and 2× Amphotericin B).

For isolation of virus, the tubes were mixed, the swabs aseptically removed, and the medium centrifuged at 1500 rpm for 10 minutes to remove particulates. Medium was filtered through a 0.2μ syringe filter prior to inoculation on tissue culture cells. One mL of the clarified transport medium was used to inoculate a 2 $cm^2$ one day old monolayer of ED cells grown in a 24 well tissue culture plate from which the growth medium had been aseptically removed. Following inoculation, the inoculum was allowed to adsorb on the cell monolayer for one hour at 37° C. in a humidified incubator containing a 5% $CO_2$ atmosphere. After the adsorption period, an additional 1 mL of re-feed medium (DMEM containing 2-5% fetal bovine serum (FBS), 2 mM L-glutamine and 3× Gentamicin and 2× Amphotericin B) was added to each well. Following addition of re-feed media the plates were then incubated at 37° C. in a $CO_2$ incubator. Each test and control tissue culture well was examined microscopically for 7 days for signs of cytopathic effect (CPE) typical of the EHV-4 challenge virus. Wells that were negative at the end of the 7 day observation period were subcultured onto fresh cells and observed for an additional 7 days.

Serum Neutralization Testing Procedure

A standard microtiter serum neutralization test was employed in this study. All sera were tested in sterile flat bottom microtiter plates using 5 wells per dilution and an 8 well dilution series for each of the 5 test wells. Each of the 5 test wells contained 25 μl of serum dilution mixed with 25 μl of the indicator virus and 150 μl of a freshly planted ED cell suspension containing approximately $5\times10^4$ cells. The test indicator virus used was EHV-4 HRA005 Lot 033106 SN Stock Virus. In all tests the indicator virus back titration titers ranged between 68-149 $TCID_{50}$/25 μl. Serum neutralizing antibody titers are expressed as Reed-Muench $ID_{50}$ titers.

For performance of the test, two-fold dilutions of each test serum was made in a sterile flat bottom microtiter plate using five replicate wells per test serum and an 8 well dilution series. Dilutions were made with an adjustable volume single or multi-channel pipetting instrument using sterile microtiter tips. The volume of serum added each of 5 wells of the first row was 50 μl. All other wells contained 25 μl of DMEM (no FBS). Following serial dilution down the plate, 25 μl was discarded from the last row. 25 μl of a pre-determined dilution of the indicator virus was added to each test well. Plates were then mixed and incubated for one hour at 37° C. in 5% $CO_2$. On conclusion of the incubation period, 150 μl of a suspension containing $5\times10^4$ ED cells was added to each test and cell control well. The plates were incubated at 37° C. in a $CO_2$ incubator for 5-7 days, at which time plates were microscopically examined for CPE typical of EHV-4. However, any other commercial available test or any test described in the prior art could be used for this purpose.

Results and Conclusion

Nasal Exudate Evaluation

The vaccination group by day interaction was statistically significant for the nasal discharge scores (P<0.05, Table 1). Statistically significant group effects were seen on Days 6-10 and Day 14 post-challenge (lower nasal scores in the vaccinated group).

When the daily scores were summed over the post-challenge period, horses in the vaccinated group had lower total scores than those in the control group (P<0.05, Table 1). The mitigated fraction was estimated to be 0.824 (95% ASE CI: 0.629, 1.000).

TABLE 3

| Nasal Discharge Score | | | | |
|---|---|---|---|---|
| | Control | Vaccinate | P-value | Mitigated fraction (95% ASE CI) |
| Cumulative nasal discharge score | 28.9 | 13.6 | <0.0001 | 0.824 (0.629, 1.000) |

Conjunctivitis

The vaccination group by day interaction was statistically significant for the conjunctivitis scores. Statistically significant group effects were seen on Days 6, 7, 9, 10, 13 and 14 post-challenge (lower scores in the vaccinated group on 5 of the 6 days, P<0.05, FIG. 2).

Serological Studies

Titers were log transformed prior to the statistical analysis. The vaccination group by day interaction was statistically significant for SN titers. Statistically significant group effects were seen on Day 0 (pre-vaccination; control group titers>vaccinated group titers), Days 35 (the day of challenge) and 7 and 14 days post-challenge (study days 42 and 49). Horses in the vaccinated group had higher titers on Days 35, 42 and 49 than those in the control group (P<0.05, Table 4).

TABLE 4

| | Titers | | |
|---|---|---|---|
| Study day | Control | Vaccinated | P-value |
| 0 | 8.31 | 5.74 | 0.0303 |
| 21 | 8.25 | 6.51 | 0.1639 |
| 35 (day of challenge) | 6.12 | 8.56 | 0.0495 |
| 42 | 4.57 | 7.27 | 0.0069 |
| 49 | 4.87 | 13.12 | <0.0001 |

White Blood Cell Counts (WBC) and Lymphocyte Counts

The vaccination group by day interaction was statistically significant for WBC and lymphocyte counts. Statistically significant group effects were seen on Days 4-6 (WBC) and Days 4 and 5 (lymphocytes) post-challenge. Horses in the vaccinated group were protected from leucopenia due to EHV4 disease and had higher WBC and lymphocyte counts than those in the control group (P<0.05).

Discussion and Conclusions

In this study, moderate and adequate clinical signs of EHV-4 infection were seen after challenge. Significantly fewer clinical signs of nasal exudate were seen in vaccinated horses on Days 6-10 and Day 14 post-challenge. Conjunctivitis scores were significantly lower in vaccinated horses on Days 7, 9, 10, 13, and 14 post-challenge. Despite the adequate display of clinical signs following challenge, virus shedding in nasal swab samples was infrequent following this EHV-4 challenge. Nasal swabs were examined by virus isolation in cell culture.

Significant group effects for WBCs and lymphocytes were seen on Days 4-6 (WBC) and Days 4-5 (lymphocytes) with vaccinated animals showing higher WBC and lymphocyte counts than control horses. These values establish that control horses did succumb to the immunosuppression brought on by infection with Herpesvirus, and also demonstrate that vaccination with a cross-protective strain of EHV-1 allowed vaccinated horses to be more refractive to the immunosuppressive properties of Herpesvirus infection. Additionally, horses in the vaccinated group had higher serum neutralization titers on Days 35, 42 and 49 than those in the control group Data from this study confirm that horses vaccinated with a multi-component vaccine containing EHV-1 demonstrate cross-protective immunity when challenged with a heterologous EHV-4 challenge organism.

Example 4

This example is to illustrate the efficacy of the combination vaccine of the present invention as well as duration of immunity.

Materials and Methods

The influenza viral antigen used in the vaccine evaluated in this study was produced on Madin Darby Canine Kidney (MDCK) cells. Following growth, viral fluids were filtered, formalin inactivated, and concentrated. The inactivated viral fluids were tested for residual live virus after inactivation. On completion of satisfactory residual live virus testing the inactivated viral fluids were then used to formulate a vaccine which also contained inactivated Venezuelan, TC-83 strain (ATCC Accession No. PTA-9411), Eastern, NJO strain (ATCC Accession No. PTA-9412), and Western, Fleming strain (ATCC Accession No. PTA-9410), equine encephalomyelitis viruses, inactivated EHV-1 (ATCC Accession No. PTA-9525), inactivated influenza A/equine-2/Kentucky/95 (ATCC Accession No. PTA-9523) and influenza A/equine-2/NewMarket/2/93 (ATCC Accession No. PTA-9524) viruses, inactivated West Nile Virus, Horse Origin 2005 (ATCC Accession No. PTA-9409), and tetanus toxoid.

Vaccine was formulated to appropriate specifications for all antigens included in the product. Influenza A/equi-2/Ohio/03 (ATCC Accession No. PTA-9522) antigen was added to the vaccine at a pre-inactivation titer of $10^{6.7}$ $TCID_{50}$/mL.

The final formulated vaccine contains the following ingredients per 1 mL dose:

| | | |
|---|---|---|
| EHV-1 | $10^{7.0\text{-}9.0}$ | $TCID_{50}$/mL |
| Influenza A2/Ohio/03 | $10^{6.7\text{-}9.5}$ | $TCID_{50}$/mL |
| Influenza A2/KY/95 | $10^{6.7\text{-}9.5}$ | $TCID_{50}$/mL |
| Influenza A2/NewMarket/2/93 | $10^{6.7\text{-}9.5}$ | $TCID_{50}$/mL |
| Tetanus Toxoid | 5-10 | CPU |
| Eastern Equine Encephalomyelitis | $10^{6.7\text{-}9.2}$ | $TCID_{50}$/mL |
| Western Equine Encephalomyelitis | $10^{6.7\text{-}9.2}$ | PFU/mL |
| Venezuelan Equine Encephalomyelitis | $10^{6.7\text{-}9.2}$ | $TCID_{50}$/mL |
| West Nile Virus | $10^{7.0\text{--}9.0}$ | $TCID_{50}$/mL |
| Adjuvant (preferably mineral oil) | 100-200 | μl |
| Glycerol | 100-200 | μl |
| EDTA 240 mM solution | 10-20 | μl |
| Diluent - DMEM containing | q.s. | |
| Gentamicin (30 μg/mL of diluent volume) | | |
| Formaldehyde (0.1-0.2% of diluent volume) | | |

Twenty-six (26) horses, 4-5 months of age, were used in this study. Fifteen horses served as vaccinates and eleven horses were mock-vaccinated control horses.

Vaccine was administered intramuscularly in a 1 mL dose volume to each of 15 horses in the vaccinate group. Eleven horses in the control group received a 1 mL dose of adjuvanted DMEM (Lot 004) containing excipients used in the 9-way vaccine (Gentamicin and formaldehyde) but no antigens. Challenge inoculation of virulent influenza A/equi-2/Ohio/03 strain virus was performed 4 months post-booster vaccination.

Serum samples for serological evaluation were collected from the vaccinated and control horses prior to initial vaccination, at 21 days post first dose vaccination (day of booster vaccination), on the day of challenge, and at 7 and 14 days post challenge. Body temperature, whole blood samples, and nasal swabs were obtained from each horse on the day of challenge, and daily throughout the 10 day post-challenge observation period for a total of 11 observation days. Clinical data was also recorded daily for each horse for the 11-day observation period.

Challenge

The challenge virus seed of Influenza A/equi-2/Ohio/03 was produced in eggs. Challenge virus was diluted on the morning of challenge 1:20 with tissue culture media to affect a titer sufficient to cause clinical influenza in the non-vaccinated challenged horses.

SEDIVET® (romifidine hydrochloride), a sedative and analgesic, was administered intravenously to each horse prior to challenge at a dosage of 50 μg/kg of body weight. Each horse was then challenged with influenza A/equi-2/Ohio/03 virus. The challenge virus was administered intranasally as an aerosol produced by a nebulizer into an Equine AeroMask (Trudell Medical International, Ontario, Canada) by the following method:

Four milliliters of challenge virus were placed into the nebulizer cup in the AeroMask device. A pressure hose was fitted from an air compressor to the inlet port of the nebulizer. The outlet tube was then inserted into the AeroMask attached to the head of the horse being challenged and air pressure was applied to the inlet port. During this time approximately two milliliters of challenge virus fluid was aerosolized directly into the nostrils of the horse being challenged.

Temperature

Daily rectal temperatures were recorded for each of the 26 vaccinated and control horses on Day of Challenge and for 10 days post challenge by means of a calibrated, electronic thermometer (GSA Electronics) probe. The daily rectal temperatures were recorded in degrees Fahrenheit (° F.).

White Blood Cell Counts

Venous blood from each of the 26 vaccinated and control horses was collected daily on the Day of Challenge and for 10 days post-challenge directly into a vacutainer Disodium EDTA tube for WBC counts.

Nasal Exudate Evaluation

All nasal exudate observations were made prior to collection of nasopharyngeal swabs. On the Day of Challenge and for 10 days post challenge, the nasal passages and muzzle of each of the 26 vaccinated and control horses were examined and graded using the grading and scoring description listed below.

The scoring grades of 0 through 6 were assigned on the basis of the severity of the disease indicated by each of the following classification:

TABLE 5

Scoring Grades

| Score | Description of symptoms | Score sheet designation |
|---|---|---|
| 0 | Essentially normal indicates the horse was clean and essentially free of nasal exudate | EN |

TABLE 5-continued

| Scoring Grades | | |
|---|---|---|
| Score | Description of symptoms | Score sheet designation |
| 1 | Slight clear serous discharge that may be frequently observed in both diseased and normal horses | C-1 |
| 2 | Moderate clear serous discharge is indicative of a definite increase in volume over that normally observed | C-2 |
| 3 | Copious clear serous discharge that is generally observed only in diseased horses | C-3 |
| 1.5 | Very slight mucopurulent discharge indicates that mucus was definitely present in small amounts in either one or both nostrils | VSM |
| 2 | Slightly mucopurulent is a discharge easily observed in one or both nostrils | SM |
| 4 | Moderately mucopurulent indicates that mucoid discharges were present in large quantities in both nostrils | MM |
| 6 | Heavy mucopurulent indicates that copious amounts of a mucoid discharge filled both nostrils | HM |

Coughing

Episodes of coughing on each observation day were counted for each horse during the entirety of the observation period, whether or not the individual animal was being examined by the investigator at that time. Observers other than the investigator recorded the number of episodes of coughing of each individual horse during the observation period. Scoring of coughing episodes was actual counts of coughing episodes per horse.

Conjunctivitis

Conjunctivitis was evaluated daily at the time of nasal exudate evaluation. Conjunctivitis scores were recorded as 0=normal; 1=mild to moderate conjunctivitis and 2=severe conjunctivitis.

Nasopharyngeal Viral Isolation/Hemagglutination (Ha) Methods

On each observation test day each nasal passage of each vaccinated and control was sampled deeply by means of sterile swabs. On collection, each of two swabs was immediately placed in a single tube containing 4 mL of chilled transport medium (Dulbecco's Minimal Essential Medium (DMEM) supplemented with 2% FBS, 2× Pen/Strep, 2× Amphotericin B).

For isolation of virus, the tubes were mixed, the swabs aseptically removed, and the medium centrifuged at 1500 rpm for 10 to 15 minutes to remove particulates. Medium was filtered through a 0.2μ syringe filter prior to inoculation on tissue culture cells. After filtration, 4-6% of sterile 85% sucrose solution was added to each sample for freezing at −80° C. in order for all samples to be tested concurrently.

All samples were tested in sterile flat bottom microtiter plates using five wells per dilution and a 4 well dilution series for each of the 5 test wells. Upon thawing, 22 μL of the clarified sample medium was used to inoculate one day old monolayer of MDCK-S cells from which the growth medium had been aseptically removed and replaced with 200 μl of influenza growth medium (DMEM containing 5-10 units/mL of 10,000 U stock solution Porcine Trypsin, 2 mM L-glutamine, 1× Pen-Strep and 1× Amphotericin B). The plates were then incubated at 35° C. in a $CO_2$ incubator for 5-7 days. After the 5-7 day incubation period, 500 from all wells of the titration plates were transferred directly into a labeled 96 well vinyl HA plate. Chicken red blood cells were added to each well and allowed to settle for 30-90 minutes at room temperature. Wells were read for positive agglutination as evidence of presence of equine influenza virus.

Hemagglutination Inhibition (Hi) Testing Procedure

Serum samples were prepared by dispensing 0.15 ml of each sample into a test tube and extracting with 0.3 mL of 0.01M Sodium Periodate Solution at room temperature for 15 minutes. Glycerol Solution 3% (0.125 mL) was added to each tube, mixed and incubated at room temperature for 15 minutes. All samples were then heat-inactivated at 56° C. for 30 minutes.

A 0.5% solution of chicken red blood cells was prepared in PBS (SAFC catalog number 59321C) and standardized to an optical density of 0.5 at 550 nm.

Extracted serum samples were tested in duplicate in U bottom polystyrene plates using a 2-fold dilution scheme in PBS ranging from 1:4 to 1:256, 25 ul per well. Influenza A/Equi2/Ohio03 stock virus (25 μL) was added to serum sample dilution. Plates were gently tapped to mix, and incubated at room temperature for 30 minutes. After incubation, chicken red blood cells were added to each well and incubated undisturbed at room temperature for 1 to 1.5 hours. Results were read by observing plates for presence or absence of agglutinated red blood cells in each well. Antibody titer was determined as the highest dilution of serum at which agglutination did not occur.

Results and Conclusions

When pooled across all timepoints post-challenge, vaccinated animals had lower total clinical scores than the control animals. When the total daily scores were summed over the post-challenge period, horses in the vaccinated group had lower total scores than those in the control group ($P<0.05$). The mitigated fraction was estimated to be 0.6485 (95% ASE CI: 0.3258, 0.9712).

TABLE 6

| Total Clinical Score | | | |
|---|---|---|---|
| Outcome variable | Vaccination group | Day | Group by day interaction |
| Total clinical score[1] | **<0.0001** | <0.0001 | 0.1321 |

[1]The GLIMMIX procedure would not converge, thus an ANOVA approach was used to evaluate the effect of vaccination over time after challenge. Results were interpreted through the bolded values.

TABLE 7

| Mitigated fraction - total cumulative clinical score | | | | |
|---|---|---|---|---|
| | Control | Vaccinate | P-value[1] | Mitigated fraction[2] (95% ASE CI) |
| Total cumulative clinical score[2] | 18.36[3] | 9.93 | 0.0055 | 0.6485 (0.3258, 0.9712) |

[1]P-value from Wilcoxon's rank sum test

[2]Nasal discharge score, conjunctivitis score and coughing score were summed with day and across all time points for each animal then ranked for the estimation of the mitigated fraction.

[3]Mean rank

Nasal Discharge

The main effect of vaccination was statistically significant and reduced nasal discharge due to the influenza challenge. When pooled across all time points post-challenge, vaccinated animals had lower nasal discharge scores than the control animals.

TABLE 8

| Nasal Discharge Score | | | |
|---|---|---|---|
| Outcome variable | Vaccination group | Day | Group by day interaction |
| Nasal discharge score[1] | **0.0012** | <0.0001 | 0.4627 |

[1]The GLIMMIX procedure would not converge, thus an ANOVA approach was used to evaluate the effect of vaccination over time after challenge. Results were interpreted through the bolded values.

Conjunctivitis

For conjunctivitis, the main effect of vaccination was statistically significant. When pooled across all time points post-challenge, vaccinated animals had reduced conjunctivitis due to influenza infection as demonstrated by lower conjunctivitis scores than the control animals.

TABLE 9

| Conjunctivitis Score | | | |
|---|---|---|---|
| Outcome variable | Vaccination group | Day | Group by day interaction |
| Conjunctivitis score[1] | **0.0187** | 0.0001 | 0.2498 |

[1]The GLIMMIX procedure would not converge, thus an ANOVA approach was used to evaluate the effect of vaccination over time after challenge. Results were interpreted through the bolded values.

Coughing

Vaccine also protected against the cough resulting from equine influenza infection. Vaccinated animals had lower scores (P<0.05,) on Days 3, 5, 7, 8, and 9 post-challenge than control animals.

TABLE 10

| Coughing Score | | | |
|---|---|---|---|
| Outcome variable | Vaccination group | Day | Group by day interaction |
| Coughing score[1] | 0.0004 | 0.0009 | **0.0275** |

[1]The GLIMMIX procedure would not converge, thus an ANOVA approach was used to evaluate the effect of vaccination over time after challenge. Results were interpreted through the bolded values.

Virus Shedding (Nasal Swabs)

The vaccination also reduced the percent of horses shedding virus (P<0.05). The figure below represents that the percentage of vaccinated animals shedding virus was lower (P<0.05) on Days 3, 4, and 5 post-challenge than control animals.

TABLE 11

| Mitigated fraction - days virus shedding | | | | |
|---|---|---|---|---|
| | Control | Vaccinate | P-value[1] | Mitigated fraction[2] (95% ASE CI) |
| Days virus positive[2,3] | 2[3] | 0 | 0.0004 | 0.7939 (0.5343, 1.0000) |

[1]P-value from Wilcoxon's rank sum test

[2]The number of days of viral shedding was calculated then ranked for the estimation of the mitigated fraction. Asymptotic standard errors (ASE) were used to estimate the 95% confidence intervals (CI).

[3]The median number of days positive results was obtained from the virus isolation assay.

Hi Titers

The vaccine was also effective in eliciting protective antibody titers to equine influenza virus. Statistically significant higher titers in the vaccinated horses were seen on Day 36 (relative to vaccination), Day 154 (the day of challenge), 159 and 164. Horses in the vaccinated group had higher titers on each of these days than those in the control group (P<0.05).

WBC and Lymphocyte Counts

The vaccination also protected horses from reduction in white blood cell counts seen following influenza virus challenge. (P<0.05). Vaccination with the combination vaccine provided statistically significant protection that was seen on Days 2 and 7 for WBC counts, and Days 2, 6, 7, and 8 post-challenge. Horses in the vaccinated group had higher WBC and lymphocyte counts than those in the control group (P<0.05). A four month Duration of Immunity challenge was performed to demonstrate efficacy of the influenza virus fractions of a multi-component vaccine that included West Nile Virus vaccine (Encephalomyelitis-Rhinopneumonitis-Influenza-West Nile Virus Vaccine, Eastern, Western & Venezuelan, Killed Virus, Tetanus Toxoid) containing 3 Equine influenza A/equi-2 virus strains, ATCC Accession Nos. PTA-9522, PTA-9523, and PTA-9524, each of which is currently relevant in the equine population of the Americas, Europe and Asia. Twenty-six horses (15 vaccinates and 11 controls) were vaccinated twice in 3 week intervals with a 1 mL dose of vaccine, or were mock vaccinated with adjuvanted media components of the vaccine without viral antigen. Four months post-booster vaccination, horses were challenged with a virulent live Equine Influenza A/equi-2/Ohio03 virus. This virulent virus is the current Equine Influenza A/equi-2 strain recommended for inclusion into vaccines by OIE and is currently recognized as the most pertinent strain involved in outbreaks in the United States.

Results from this 4-month DOI challenge study show significant protective effects from challenge by vaccination with the test vaccine, a combination West Nile Virus vaccine with flu and other pertinent equine antigens. Importantly, vaccinated horses displayed statistically lower total clinical signs of influenza virus (nasal discharge, conjunctivitis, and coughing, P=0.0055) with a mitigated fraction estimated to be 0.6485 (95% ASE CI: 0.3258, 0.9712). Additionally, viral shedding was statistically lower in vaccinated horses than control horses (P=0.0004) with a mitigated fraction estimated to be 0.7939 (95% ASE CI: 0.5343, 1.0000). Hemagglutination inhibition titers were significantly higher in vaccinated horses than control horses, and white blood cell and lymphocyte counts remained significantly higher in vaccinated horses on multiple days of the study over those of control horses. No differences in rectal temperature were determined between the two groups.

In conclusion, the data from this study demonstrate that administration of 2×1 mL intramuscular doses of this West Nile Virus combination vaccine administered at a 21 day interval to foals 4 to 5 months of age protected against virulent challenge with the Equine Influenza A/equi-2/Ohio03 virus and provided a duration of immunity of at least 4 months for this product.

Example 5

This example illustrates the efficacy of an immunogenic composition of the present invention when challenged with (Equine Herpes Virus Type 1) EHV-1.

Materials and Methods

The EHV-1 viral antigen used in the vaccine evaluated in this study was produced on Madin Darby Bovine Kidney (MDBK) cells. Following growth, viral fluids were filtered, BPL inactivated, and concentrated. The inactivated viral fluids were tested for residual live virus after inactivation. On completion of satisfactory residual live virus testing, the inactivated viral fluids were then used to formulate a vaccine which also contained inactivated Venezuelan Equine Encephalomyelitis, TC-83 strain (ATCC Accession No. PTA-9411) Eastern Equine Encephalomyelitis, NJO strain (ATCC Accession No. PTA-9412) and Western Equine Encephalomyelitis, Fleming strain (ATCC Accession No. PTA-9410) viruses, inactivated influenza A/equine-2/Kentucky/95 (ATCC Accession No. PTA-9523), influenza A/equine-2/NewMarket/2/93 (ATCC Accession No. PTA-9524) and influenza A/equine-2/Ohio/03 (ATCC Accession No. PTA-9522) viruses, inactivated West Nile Virus (ATCC Accession No. PTA-9409) and tetanus toxoid.

Vaccine was formulated to minimum specifications for all antigens included in the product. EHV-1 antigen was added to the vaccine at a pre-inactivation titer of $10^{7.0}$ $TCID_{50}$/mL.

The final formulated vaccine contains the following ingredients per 1 mL dose:

| | |
|---|---|
| EHV-1 | $10^{7.0-9.0}$ $TCID_{50}$/mL |
| Influenza A2/Ohio/03 | $10^{6.7-9.5}$ $TCID_{50}$/mL |
| Influenza A2/KY/95 | $10^{6.7-9.5}$ $TCID_{50}$/mL |
| Influenza A2/NewMarket/2/93 | $10^{6.7-9.5}$ $TCID_{50}$/mL |
| Tetanus Toxoid | 5-10 CPU |
| Eastern Equine Encephalomyelitis | $10^{6.7-9.2}$ $TCID_{50}$/mL |
| Western Equine Encephalomyelitis | $10^{6.7-9.2}$ PFU/mL |
| Venezuelan Equine Encephalomyelitis | $10^{6.7-9.2}$ $TCID_{50}$/mL |
| West Nile Virus | $10^{7.0-9.0}$ $TCID_{50}$/mL |
| Adjuvant (preferably mineral oil) | 100-200 μl |
| Glycerol | 100-200 μl |
| EDTA 240 mM solution | 10-20 μl |
| Diluent - DMEM containing | q.s. |
| Gentamicin (30 μg/mL of diluent volume) | |
| Formaldehyde (0.1-0.2% of diluent volume) | |

Forty (40) horses, 4-5 months of age, were used in this study. Horses were randomly assigned to either vaccinate or control groups and were micro-chipped and then vaccinated. Twenty horses served as vaccinates and twenty horses were mock-vaccinated control horses. All horses had negative to low (<1:6) EHV-1 serum neutralization (SN) titers prior to initiation of the study, indicative of horses susceptible to infection.

Vaccine was administered intramuscularly in a 1 mL dose volume to each of 20 horses in the vaccinate group. Twenty horses in the control group received a 1 mL dose of adjuvanted DMEM (Lot 004) containing excipients used in the 9-way vaccine (Gentamycin and formaldehyde) but no antigens. Challenge inoculation of virulent EHV-1 A183 strain virus was performed 15 days post-booster vaccination.

Serum samples for serological evaluation were collected from the vaccinated and control horses prior to initial vaccination, at 21 days post first dose vaccination (day of booster vaccination), on the day of challenge, and at 7 and 14 days post challenge. Body temperature, whole blood samples, and nasal swabs were obtained from each horse on the day of challenge, and daily throughout the 14 day post-challenge observation period for a total of 15 observation days. Clinical data was also recorded daily for each horse for the 15-day observation period.

Challenge Procedure

Challenge Virus

The original challenge virus seed used in this challenge study was the first passage of the original seed virus on Equine Dermal (ED) cells. This challenge virus was harvested and frozen at a titer of $10^{6.2}$ $TCID_{50}$/mL.

Intranasal Challenge Method

SEDIVET® (romifidine hydrochloride), a sedative and analgesic, was administered intravenously to each horse prior to challenge at a dosage of 50 μg/kg of body weight. Each horse was then challenged with approximately $10^{6.5}$ $TCID_{50}$ of EHV-1 strain. The challenge virus was administered intranasally as an aerosol produced by a nebulizer into an Equine AeroMask (Trudell Medical International, Ontario, Canada) by the following method:

A pressure hose was fitted from an air compressor to the inlet port of the nebulizer. The outlet tube was then inserted into the AeroMask attached to the head of the horse being challenged and approximately 10 psi of air pressure was applied to the inlet port for four minutes. During this time approximately two milliliters of a $10^{62}$ $TCID_{50}$/mL challenge virus fluid was aerosolized directly into the nostrils of the horse being challenged.

Pre and Post Challenge Evaluation Parameters

Temperature

Daily morning rectal temperatures were recorded for each of the 40 vaccinated and control horses on Day of Challenge and for 14 days post challenge by means of a calibrated, electronic thermometer (GSA Electronics) probe. The daily rectal temperatures were recorded in degrees Fahrenheit (° F.).

White Blood Cell Counts

Venous blood from each of the 40 vaccinated and control horses was collected daily on the Day of Challenge and for 14 days post-challenge directly into a vacutainer Disodium EDTA tube for WBC counts.

Nasal Exudate Evaluation

All nasal exudate observations were made prior to collection of nasopharyngeal swabs. On the Day of Challenge and for 14 days post challenge, the nasal passages and muzzle of each of the 40 vaccinated and control horses were examined and graded using the grading and scoring description listed below.

The scoring grades of 0 through 6 were assigned on the basis of the severity of the disease indicated by each of the following classification:

(EN) Essentially normal indicates the horse was clean and essentially free of nasal exudate, score, 0;

(C-1) Slight clear serous discharge that may be frequently observed in both diseased and normal horses, score 1;

(C-2) Moderate clear serous discharge is indicative of a definite increase in volume over that normally observed, score 2;

(C-3) Copious clear serous discharge that is generally observed only in diseased horses, score 3;

(VSM) Very slight mucopurulent discharge indicates that mucus was definitely present in small amounts in either one or both nostrils, score 1.5;

(SM) Slightly mucopurulent is a discharge easily observed in one or both nostrils, score 2;

(MM) Moderately mucopurulent indicates that mucoid discharges were present in large quantities in both nostrils, score 4; and (HM) Heavy mucopurulent indicates that copious amounts of a mucoid discharge filled both nostrils, score 6.

Nasopharyngeal Viral Isolation Methods

On each observation test day each nasal passage of each vaccinated and control was sampled deeply by means of a sterile swabs. On collection, each of two swabs were immediately placed in a single tube containing 4 mL of chilled transport medium (Dulbecco's Minimal Essential Medium (DMEM) supplemented with 2% FBS, 2× Pen/Strep, 2× Gentamicin, and 2× Amphotericin B).

For isolation of virus, the tubes were mixed, the swabs aseptically removed, and the medium centrifuged at 1500 rpm for 10 minutes to remove particulates. Medium was filtered through a 0.2μ syringe filter prior to inoculation on tissue culture cells. One mL of the clarified transport medium was used to inoculate a 2 $cm^2$ one day old monolayer of ED cells grown in a 24 well tissue culture plate from which the growth medium had been aseptically removed. Following inoculation, the inoculum was allowed to adsorb on the cell monolayer for one hour at 37° C. in a humidified incubator containing a 5% $CO_2$ atmosphere. After the absorption period, an additional 1 mL of re-feed medium (DMEM containing 2-5% fetal bovine serum (FBS), 2 mM L-glutamine and 3× Gentamicin and 2× Amphotericin B) was added to each well. Following addition of re-feed media the plates were then incubated at 37° C. in a $CO_2$ incubator. Each test and control tissue culture well was examined microscopically for 7 days for signs of cytopathic effect (CPE) typical of the EHV-1 A183 challenge virus. Wells that were negative at the end of the 7 day observation period were subcultured onto fresh cells and observed for an additional 7 days.

WBC Buffy Coat Virus Isolation

Venous blood from each of the 40 vaccinated and control horses was collected on the Day of Challenge and daily for 14 days post-challenge by vacutainer into a Disodium EDTA tube. After permitting gravity sedimentation of the erythrocytes in the tube of EDTA anti-coagulated blood, the plasma and white blood cells were pipetted off and placed in a sterile 5 mL snap-cap tube. The plasma and white blood cell mixture was centrifuged at 1500 RPM for 10-15 minutes to pellet the white blood cells. The pellet was washed twice with 3 mL of phosphate buffered saline (PBS) containing 2× Pen/Strep, 2× Gentamicin, and 2× Amphotericin B. Cells were then suspended in 4 mL of DMEM supplemented with 2% fetal bovine serum (FBS) and 2× Pen/Strep, 2× Gentamicin, and 2× Amphotericin B. One mL buffy coat suspension was used to inoculate a 2 $cm^2$ one day old monolayer of ED cells grown in a 24 well tissue culture plate from which the growth medium had been aseptically removed. Following inoculation, the inoculum was allowed to adsorb on the cell monolayer for one hour at 37° C. in a humidified incubator containing a 5% $CO_2$ atmosphere. After the adsorption period, an additional 1 mL of re-feed medium (DMEM containing 5-7% fetal bovine serum (FBS), 2 mM L-glutamine and 1× Gentamicin was added to each well. Following addition of re-feed media the plates were then incubated at 37° C. in a $CO_2$ incubator. Wells could not be observed microscopically due to large volume of white blood cells settled on the monolayer. Therefore, at the end of 7 days, all wells were subcultured onto fresh ED cells using 0.5 ml of the $1^{st}$ passage as inoculum. The subculture was observed for 7 days for CPE typical of challenge virus infection.

Serum Neutralization Testing Procedure

A standard microtiter serum neutralization test was employed in this study. All sera were tested in sterile flat bottom microtiter plates using five wells per dilution and an 8 well dilution series for each of the 5 test wells. Each of the 5 test wells contained 25 μl of serum dilution mixed with 25 μl of the indicator virus and 150 μl of a freshly planted ED cell suspension containing approximately $5\times10^4$ cells. The test indicator virus used was EHV-1 subtype 1 strain A183. In all tests the indicator virus back titration titers ranged between 109 to 263 $TCID_{50}$/25 μl. Serum neutralizing antibody titers are expressed as Reed-Muench $ID_{50}$ titers.

For performance of the test, two-fold dilutions of each test serum was made in a sterile flat bottom microtiter plate using five replicate wells per test serum and an 8 well dilution series. Dilutions were made with an adjustable volume single or multi-channel pipetting instrument using sterile microtiter tips. The volume of serum added each of 5 wells of the first row was 50 μl. All other wells contained 25 μl of DMEM (no FBS). Following serial dilution down the plate, 25 μl was discarded from the last row. 25 μl of a predetermined dilution of the indicator virus was added to each test well. Plates were then mixed and incubated for one hour at 37° C. in 5% $CO_2$. On conclusion of the incubation period, 150 μl of a suspension containing $5\times10^4$ ED cells was added to each test and cell control well. The plates were incubated at 37° C. in a $CO_2$ incubator for 3 days, at which time plates were microscopically examined for CPE typical of EHV-1. Alternatively, any conventional or commercial available assay can be used or those of skill in the art would be able to follow the guidance herein.

Results and Conclusion

Nasal discharge scores, nasal shedding of EHV-1 and conjunctivitis scores were considered the primary outcome variables. All other outcomes were considered secondary.

TABLE 12

| Summary of the statistical analysis (P-values) | | | |
|---|---|---|---|
| Outcome variable | Vaccination group | Day | Group by day interaction |
| Nasal discharge score[1] | 0.0001 | <.0001 | **<0.0001** |
| Virus shedding[1] | **0.0028** | <0.0001 | 0.0863 |
| Conjunctivitis score[1] | 0.0020 | <0.0001 | **0.0017** |
| SN Titers | <0.0001 | <0.0001 | **<0.0001** |
| WBC | 0.3064 | <0.0001 | **<0.0001** |

[1]The GLIMMIX procedure would not converge, thus an ANOVA approach was used to evaluate the effect of vaccination over time after challenge. Results were interpreted through the bolded values.

Nasal Exudate Evaluation

The vaccination group by day interaction was statistically significant for the nasal discharge scores (P<0.05). Statistically significant group effects were seen on Days 4, 5 and on Days 7-11 post-challenge (lower nasal scores in the vaccinated group, P<0.05,). When the daily scores were summed over the post-challenge period, horses in the vaccinated group had lower total scores than those in the control group (P<0.05). The mitigated fraction was estimated to be 0.7250 (95% ASE CI: 0.4886, 0.9614).

TABLE 13

| Mitigated fraction - nasal discharge and conjunctivitis scores, nasal virus shedding (mean ranks) | | | | |
|---|---|---|---|---|
| | Control | Vaccinate | P-value[1] | Mitigated fraction[2] (95% ASE CI) |
| Nasal discharge | 27.75 | 13.25 | <0.0001 | 0.7250 (0.4886, 0.9614) |
| Days shedding virus[2] | 24.43 | 15.78 | 0.0068 | 0.4925 (0.1896, 0.7954) |
| Conjunctivitis | 25.80 | 15.20 | 0.0038 | 0.5300 (0.2463, 0.8137) |

[1]P-value from Wilcoxon's rank sum test

[2]Nasal discharge and conjunctivitis scores were summed across all time points then ranked for the estimation of the mitigated fraction. The number of days of viral shedding was calculated then ranked for the estimation of the mitigated fraction. Asymptotic standard errors (ASE) were used to estimate the 95% confidence intervals (CI).

TABLE 14

| Mean nasal discharge score (N = 20 horses per group) | | | |
|---|---|---|---|
| Days post-challenge | Control | Vaccinated | P-value[1] |
| 0 | 0.00 | 0.00 | 1.0000 |
| 1 | 0.00 | 0.00 | 1.0000 |
| 2 | 0.15 | 0.00 | 0.6029 |
| 3 | 0.33 | 0.48 | 0.6029 |
| 4 | 1.08 | 0.23 | **0.0033** |
| 5 | 1.43 | 0.40 | **0.0004** |
| 6 | 1.05 | 0.55 | 0.0833 |
| 7 | 1.50 | 0.68 | **0.0044** |
| 8 | 1.68 | 0.63 | **0.0003** |
| 9 | 2.13 | 0.50 | **<.0001** |
| 10 | 1.58 | 0.80 | **0.0074** |
| 11 | 0.98 | 0.23 | **0.0095** |
| 12 | 0.90 | 0.35 | 0.0568 |
| 13 | 1.23 | 0.90 | 0.2599 |
| 14 | 0.93 | 0.43 | 0.0833 |

[1]The GLIMMIX procedure would not converge, thus an ANOVA approach was used to evaluate the effect of vaccination over time on the nasal discharge score.

Conjunctivitis

The vaccination group, by day interaction, was statistically significant for the conjunctivitis scores (P<0.05). Statistically significant group effects were seen on Days 5 and 6, and on Days 9-14 post-challenge (lower scores in the vaccinated group, P<0.05). When the daily scores were summed over the post-challenge period, horses in the vaccinated group had lower total scores than those in the control group (P<0.05). The mitigated fraction was estimated to be 0.5300 (95% ASE CI: 0.2463, 0.8137).

TABLE 15

| Mean conjunctivitis score (N = 20 horses per group) | | | |
|---|---|---|---|
| Days post-challenge | Control | Vaccinated | P-value[1] |
| 0 | 0.00 | 0.00 | 1.0000 |
| 1 | 0.00 | 0.00 | 1.0000 |
| 2 | 0.00 | 0.00 | 1.0000 |
| 3 | 0.05 | 0.00 | 0.7321 |
| 4 | 0.15 | 0.15 | 1.0000 |
| 5 | 0.70 | 0.25 | **0.0022** |
| 6 | 0.85 | 0.25 | **<.0001** |
| 7 | 0.75 | 0.65 | 0.4936 |
| 8 | 0.45 | 0.35 | 0.4936 |
| 9 | 0.50 | 0.15 | **0.0168** |
| 10 | 0.45 | 0.15 | **0.0403** |
| 11 | 0.50 | 0.05 | **0.0022** |

TABLE 15-continued

| Mean conjunctivitis score (N = 20 horses per group) | | | |
|---|---|---|---|
| Days post-challenge | Control | Vaccinated | P-value[1] |
| 12 | 0.45 | 0.00 | **0.0022** |
| 13 | 0.45 | 0.05 | **0.0063** |
| 14 | 0.35 | 0.05 | **0.0403** |

[1]The GLIMMIX procedure would not converge, thus an ANOVA approach was used to evaluate the effect of vaccination over time.

Virus Isolation from Nasopharyngeal Swabs

The main effect of vaccination group was statistically significant (fewer animals shedding in the vaccinated group, P<0.05). When the number of days shedding was evaluated, horses in the vaccinated group had fewer days of virus shedding than those in the control group (P<0.05, Table 2). The mitigated fraction was estimated to be 0.4925 (95% ASE CI: 0.1896, 0.7954).

TABLE 16

| Proportion virus shedding (nasal swab, N = 20 horses per group) | | |
|---|---|---|
| Days post-challenge | Control | Vaccinated |
| 0 | 0.00 | 0.00 |
| 1 | 0.00 | 0.00 |
| 2 | 0.05 | 0.05 |
| 3 | 0.05 | 0.10 |

TABLE 16-continued

| Proportion virus shedding (nasal swab, N = 20 horses per group) | | |
|---|---|---|
| Days post-challenge | Control | Vaccinated |
| 4 | 0.20 | 0.05 |
| 5 | 0.25 | 0.15 |
| 6 | 0.45 | 0.25 |
| 7 | 0.45 | 0.35 |
| 8 | 0.50 | 0.10 |
| 9 | 0.45 | 0.15 |
| 10 | 0.25 | 0.00 |
| 11 | 0.35 | 0.10 |
| 12 | 0.30 | 0.10 |
| 13 | 0.15 | 0.00 |
| 14 | 0.05 | 0.00 |

White Blood Cell Counts

The vaccination group by day interaction was statistically significant for WBC counts ($P<0.05$, Table 1). Statistically significant group effects were seen on Days 2 and 3 post-challenge. Horses in the vaccinated group had higher WBC counts than those in the control group, indicating the vaccine prevented the horses from suffering the leucopenia caused by infection with EHV 1 ($P<0.05$).

TABLE 17

| Mean WBC counts (N = 20 horses per group) | | | |
|---|---|---|---|
| Days post-challenge | Control | Vaccinated | P-value[1] |
| 1 | 14.0413 | 14.4887 | 0.6081 |
| 2 | 10.7963 | 14.1287 | **0.0001** |
| 3 | 11.1263 | 14.0687 | **0.0008** |
| 4 | 11.5013 | 13.1037 | 0.0667 |
| 5 | 10.7413 | 11.1987 | 0.6001 |
| 6 | 9.1063 | 9.4187 | 0.7203 |
| 7 | 10.1563 | 9.9037 | 0.7721 |
| 8 | 10.7813 | 10.6037 | 0.8386 |
| 9 | 11.1813 | 12.0737 | 0.3065 |
| 10 | 11.9713 | 12.4187 | 0.6081 |
| 11 | 12.6713 | 13.2137 | 0.5341 |
| 12 | 13.2913 | 13.5637 | 0.7549 |
| 13 | 14.7063 | 14.1737 | 0.5415 |
| 14 | 15.8463 | 14.4587 | 0.1121 |

[1]P-values from the ANOVA

Serological Studies

Titers were log transformed prior to the statistical analysis. The vaccination group by day interaction was statistically significant for SN titers ($P<0.05$). Statistically significant group effects were seen on Days 35 (the day of challenge) and 7 and 14 days post-challenge (study days 42 and 49). Horses in the vaccinated group had higher titers than those in the control group ($P<0.05$).

TABLE 18

| Geometric mean - serum neutralization titers (N = 20 horses per group) | | | |
|---|---|---|---|
| Study day | Control | Vaccinated | P-value[1] |
| 0 | 3.987 | 3.384 | 0.4005 |
| 21 | 3.190 | 2.624 | 0.3168 |
| 35 (day of challenge) | 3.480 | 6.863 | **0.0006** |
| 42 | 3.519 | 19.252 | **<0.0001** |
| 49 | 33.153 | 187.417 | **<0.0001** |

[1]P-values from the ANOVA. Serum neutralization titers were log (natural) transformed prior to the statistical analysis.

Results and Discussion

Respiratory disease caused by equine herpesvirus type 1 is usually an epidemic disease of naïve weanling and yearling horses that occurs in the first year of life, usually in the fall and winter months. Signs of acute infection include fever up to 106° F., viremia and leucopenia and/or neutropenia. Nasal discharge is usually evident during febrile periods of this first exposure. Natural infection by EHV-1 does not result in permanent immunity of the respiratory tract. Indeed, horses may be re-infected naturally every 3 to 6 months throughout life. After the first experience with this virus, re-infection results in production of virus, but usually without clinical signs of disease, resulting in carrier animals that act as natural reservoirs of the virus.

The equine herpesvirus-1 multi-component vaccine described in this report has been shown to be efficacious in reducing the respiratory manifestations, clinical symptoms and virus shedding from nasal exudate of horses challenged with a virulent heterologous strain of Equine Herpesvirus type 1. Reduction in shedding of virus from the respiratory route is important epidemiologically due to this being the natural route of exposure to naive animals as well as for re-infection of herd mates from those experiencing a natural infection. It was also a safe vaccine with no adverse reactions, either systemic or at the site of vaccine administration, observed following vaccine use in the study horses.

In this study, vaccination group by day interaction showed statistical significance for the primary outcome variables nasal discharge scores and conjunctivitis. Statistically significant group effects were seen in the vaccinate group for nasal discharge on Days 4, 5 and on Days 7-11 post-challenge. Group effects for conjunctivitis were also statistically significant on Days 5 and 6 and 9-14 with lower scores in the vaccinate group ($P<0.05$). This is significant epidemiologically because the EHV-1 virus is delicate and does not survive in the environment readily. Close contact is important for transmission of disease through nasal secretions containing virulent EHV-1 virus (Campbell and Studdert, 1983).

Importantly, another primary outcome variable in this study, virus shedding in nasal exudates, showed a main effect of vaccination as statistically significant ($P<0.05$). Horses in the vaccinated group also had statistically fewer days of virus shedding than those in the control group ($P<0.05$).

Serum neutralization titers were statistically significant after vaccination and throughout the challenge period in vaccinates versus control horses ($P<0.05$). Humoral immunity and mucosal antibodies may be important in determining whether an EHV-1 infection becomes a productive or limited infection event (Kidd, Smith, Hannant, et. al, 1994).

Example 6

This example illustrates the efficacy and 6 month duration of immunity of an immunogenic composition of the present invention when challenged with West Nile Virus.

Materials and Methods

The WNV viral antigen used in the vaccine evaluated in this study was produced on E vero cells as described in Example 1. A total of 15 horses were randomly divided into groups, one being a control group of 5 horses. The vaccinated group of 10 horses received 2 doses of vaccine at 21-day intervals cells. On completion of satisfactory residual live virus testing the inactivated viral fluids were then used to formulate a vaccine which also contained inactivated Venezuelan Equine Encephalomyelitis, TC-83 strain (ATCC Accession No. PTA-9411), Eastern Equine Encephalomyelitis, NJO strain (ATCC Accession No. PTA-9412), and Western Equine Encephalomyelitis, Fleming strain (ATCC Accession No. PTA-9410) viruses, inactivated influenza A/equine-2/Kentucky/95 (ATCC Accession No. PTA-9523), influenza A/equine-2/NewMarket/2/93 (ATCC Accession No. PTA-9524) and influenza A/equine-2/Ohio/03 (ATCC Accession No. PTA-9522) viruses, inactivated West Nile Virus (ATCC Accession No. 9409) and tetanus toxoid. Vaccine was formulated to minimum specifications for all antigens included in the product.

The final formulated vaccine contains the following ingredients per 1 mL dose:

| | |
|---|---|
| EHV-1 | $10^{7.0\text{-}9.0}$ $TCID_{50}$/mL |
| Influenza A2/Ohio/03 | $10^{6.7\text{-}9.5}$ $TCID_{50}$/mL |
| Influenza A2/KY/95 | $10^{6.7\text{-}9.5}$ $TCID_{50}$/mL |
| Influenza A2/NewMarket/2/93 | $10^{6.7\text{-}9.5}$ $TCID_{50}$/mL |
| Tetanus Toxoid | 5-10 CPU |
| Eastern Equine Encephalomyelitis | $10^{6.7\text{-}9.2}$ $TCID_{50}$/mL |
| Western Equine Encephalomyelitis | $10^{6.7\text{-}9.2}$ L PFU/mL |
| Venezuelan Equine Encephalomyelitis | $10^{6.7\text{-}9.2}$ $TCID_{50}$/mL |
| West Nile Virus | $10^{7.0\text{-}9.0}$ $TCID_{50}$/mL |
| Adjuvant (preferably mineral oil) | 100-200 μl |
| Glycerol | 100-200 μl |
| EDTA 240 mM solution | 10-20 μl |
| Diluent - DMEM containing | q.s. |
| Gentamicin (30 μg/mL of diluent volume) | |
| Formaldehyde (0.1-0.2% of diluent volume) | |

Fifteen horses were used in this study. Horses were randomly assigned to either vaccinate or control groups and then vaccinated. Ten horses served as vaccinates and five horses were mock-vaccinated control horses.

The vaccine was administered intramuscularly in a 1 mL dose volume to each of the horses in the vaccinate group. Each control received a 1 mL dose of adjuvanted DMEM containing excipients used in the 9-way vaccine (gentamycin and formaldehyde) but no antigens.

All groups were challenged approximately 6 months following vaccination with intrathecal inoculation of 1 ml PBS containing approximately $10^5$ pfu of a heterologous strain of WNV (NY99, 4132, crow isolate). The challenge was conducted under ketamine-xylazine anesthesia.

Horses were monitored for a maximum of 14 days.

Results and Discussion

Viremia after challenge was considered the primary outcome variable in this study. The horses that had been vaccinated were 90% protected from viremia after challenge in this study. In comparison, all of the 5 control horses demonstrated viremia for 3-5 days post-challenge.

In addition, serum neutralization titers of vaccinated horses were significantly higher than those of control horses after vaccination. All the vaccinated horses developed measurable serum neutralization titers following vaccination, whereas none of the controls displayed any titer to WNV. This study demonstrated that 2 doses of the experimental combination vaccine reliably and effectively stimulated protective serological serum neutralization titers.

Since viremia is a prerequisite before virus can cross the blood-brain barrier to cause WNV encephalitis, viremia is well justified as the primary parameter for evaluation of protection in an experimental study of this type.

The results demonstrated that an immunogenic reaction is induced in the animals that were administered the vaccine, and that the vaccine is effective at providing protection for at least 6 months following vaccination. The effectiveness of the vaccine was evidenced in this example by reduction in WNV viremia and by stimulation of high serum neutralization titers to WNV. Because this vaccine is comprised of unique constituents including a long lasting non-metabolizable adjuvant, is formulated in a low 1 mL dose volume to provide a high degree of safety as a highly immunogenic low passage whole inactivated virus WNV isolate of recent origin and high epidemiological prevalence (a North American Dominant WNV strain), and a WNV isolated from the tissues of an infected horse, it provides more comprehensive safety and long lasting effectiveness of at least 6 months duration than other vaccines currently available. Additionally, it has the effect of providing a safe vaccine when administered to animals, and in particular to horses.

Example 7

This example illustrates the efficacy of one embodiment of the immunogenic composition of the present invention including encephalomyelitis antigens with tetanus toxoid antigen.

Materials and Methods

Host animal and laboratory animal immunization/serology were evaluated to demonstrate efficacy of encephalomyelitis antigens and the tetanus toxoid antigen fraction in an Encephalomyelitis-Rhinopneumonitis-Influenza-West Nile Virus Vaccine, including Eastern, Western, and Venezuelan Encephalomyelitis, Killed Virus, and Tetanus Toxoid. The efficacy and lack of interference on equine encephalitis virus vaccines and tetanus toxoid fractions can be unequivocally demonstrated by laboratory animal potency testing of the combination vaccine. Demonstration of serological response following vaccination of horses is also indicative of vaccine-toxoid efficacy. Hence, both lab animal potency and host animal serology were used in this study to confirm the efficacy of the experimental vaccine. The vaccine was also evaluated for safety in animals including horses.

Horses 4-5 months of age, from non-vaccinated mares, were vaccinated with an efficacy serial of WNV combination vaccine containing inactivated Venezuelan Equine Encephalomyelitis Virus, TC-83 strain (ATCC Accession No. PTA-9411) Eastern Equine Encephalomyelitis Virus, NJO strain (ATCC Accession No. PTA-9412) Western Equine Encephalomyelitis Virus, Fleming strain (ATCC Accession No. PTA-9410) West Nile Virus (WNV), Horse Origin 2005 (ATCC Accession No. PTA-9409) Equine Herpesvirus Type 1 (ATCC Accession No. PTA-9525) (EHV-1), Influenza A/equine-2/Ohio/03 (ATCC Accession No. PTA-9522), Influenza A/equine-2/Kentucky/95 (ATCC Accession No. PTA-9523), Influenza A/equine-2/NewMarket/2/93 (ATCC Accession No. PTA-9524) and Tetanus Toxoid. Horses were vaccinated on Day 0 and Day 21 of the study. Blood samples were collected at Day 0, Day 21 and Day 35. Day 0 and Day 35 serological results are reported herein.

In addition, the same WNV combination vaccine used to vaccinate horses was tested for potency in guinea pigs. Data presented in this report collectively and definitively establish the efficacy of each antigen tested (EEE, VEE, WEE, tetanus) in this study and also confirm the safety of a WNV combination vaccine.

Bulk lots of EEE, WEE, and VEE viruses and tetanus toxoid were produced. Following growth, viral fluids were filtered, formalin inactivated, and concentrated. The inactivated viral fluids were tested for residual live virus after inactivation.

Inactivated viral and toxoid fluids described above were used to formulate a vaccine that also contained inactivated Equine Herpesvirus Type 1, inactivated influenza A/equine-2/Kentucky/95, influenza A/equine-2/NewMarket/2/93 and influenza A/equine-2/Ohio/03 viruses.

The vaccine was formulated to specifications for all antigens included in the product.

The final formulated vaccine contained the following ingredients per 1 mL dose:

| | |
|---|---|
| EHV-1 | $10^{7.0-9.0}$ $TCID_{50}$/mL |
| Influenza A2/Ohio/03 | $10^{6.7-9.5}$ $TCID_{50}$/mL |
| Influenza A2/KY/95 | $10^{6.7-9.5}$ $TCID_{50}$/mL |
| Influenza A2/NewMarket/2/93 | $10^{6.7-9.5}$ $TCID_{50}$/mL |
| Tetanus Toxoid | 5-10 CPU |
| Eastern Equine Encephalomyelitis | $10^{6.7-9.2}$ $TCID_{50}$/mL |
| Western Equine Encephalomyelitis | $10^{6.7-9.2}$ PFU/mL |
| Venezuelan Equine Encephalomyelitis | $10^{6.7-9.2}$ $TCID_{50}$/mL |
| West Nile Virus | $10^{7.0-9.0}$ $TCID_{50}$/mL |
| Adjuvant (preferably mineral oil) | 100-200 µl |
| Glycerol | 100-200 µl |
| EDTA 240 mM solution | 10-20 µl |
| Diluent - DMEM containing | q.s. |
| Gentamicin (30 µg/mL of diluent volume) | |
| Formaldehyde (0.1-0.2% of diluent volume) | |

Forty horses, four to 5 months of age, were used in this study. Horses remained with their dams on pasture throughout the vaccination period and were weaned from their dams when the 2-week post-booster sera were collected. Horses were assigned to either one of the two treatment groups randomly as they were vaccinated intramuscularly (IM) with a 1.0 ml dose. The primary immunization was followed three weeks later by a 1.0 ml IM booster vaccination. Twenty horses received vaccine. Twenty horses received placebo.

Guinea pigs were also vaccinated with the same combination WNV vaccine.

Horses were vaccinated and serum samples collected using the following schedule:

TABLE 19

| Vaccination and Serum Sampling Schedule | |
|---|---|
| Day of Test | Activity |
| 0 | Collect pre-vaccination blood and give primary vaccination |
| 21 | Collect blood and give booster vaccination |
| 35 | Collect blood for final serology |

Guinea pigs were vaccinated and serum collected using the schedule outlined by 9 CFR, 113.207(b) and 113.114(c.).

Sera from horses in this study were tested following general guidelines. The assay was modified to determine titers by testing at 1:2 and 1:10 dilutions for Day 0 samples and at 1:10 and 1:40 dilutions for the 2-week post-booster serum samples. Sera were tested for EEE, WEE and VEE antibody and were tested for Tetanus toxoid antibody.

Results and Discussion

Horse Serological Evaluation for EEE, WEE and VEE

At Day 0 of the Study, not all foals were sero-negative to encephalomyelitis viruses. Five of the vaccinated foals had significant (>1:10) residual maternal antibody to EEE virus. In addition, two of the vaccinated foals had residual maternal antibody (>1:10) to WEE virus. Despite existing and potentially interfering passively acquired, maternal antibody at the time of administration of the first dose of the WNV combination vaccine, titers for all three fractions increased substantially (>4 fold in 80% of horses tested for EEE, >4 fold in 90% of horses tested for WEE and >4 fold in 100% of horses tested for VEE) following vaccination, yet remained negative or low for the non-vaccinated foals. Individual foal data are presented below.

EEE, WEE and VEE Equine Serological Titers

TABLE 20

| Plaque Reduction Neutralization Titration | | | | | | | |
|---|---|---|---|---|---|---|---|
| Horse ID | Test Article | Day 0 EEE | Day 35 EEE | Day 0 WEE | Day 35 WEE | Day 0 VEE | Day 35 VEE |
| 1 | V | >10 | >40 | 2 | >40 | <2 | >40 |
| 2 | V | <2 | >40 | <2 | 10 | <2 | 40 |
| 3 | V | <2 | >40 | <2 | <10 | <2 | >40 |
| 4 | V | <2 | >40 | <2 | 10 | <2 | >40 |
| 5 | V | >10 | >40 | >10 | >40 | <2 | >40 |
| 6 | V | >10 | >40 | <2 | >40 | NS | 10 |
| 7 | V | <2 | >40 | <2 | >40 | <2 | >40 |
| 8 | V | >10 | >40 | 2 | >40 | <2 | >40 |
| 9 | V | <2 | >40 | <2 | >40 | <2 | >40 |
| 10 | V | <2 | >40 | <2 | >40 | <2 | 10 |
| 11 | V | <2 | >40 | <2 | >40 | <2 | >40 |
| 12 | V | <2 | >40 | <2 | >40 | <2 | 40 |
| 13 | V | <2 | >40 | <2 | >40 | <2 | >40 |
| 14 | V | <2 | >40 | <2 | 10 | <2 | >40 |
| 15 | V | >10 | >40 | >10 | >40 | 2 | >40 |
| 16 | V | 2 | >40 | <2 | 10 | <2 | >40 |
| 17 | V | <2 | >40 | <2 | 10 | <2 | >40 |
| 18 | V | <2 | >40 | <2 | >40 | <2 | 40 |
| 19 | V | <2 | 10 | <2 | >40 | <2 | >40 |
| 20 | V | 2 | >40 | <2 | >40 | <2 | 10 |
| 21 | C | <2 | <10 | <2 | <10 | <2 | 10 |
| 22 | C | <2 | <10 | <2 | <10 | <2 | <10 |
| 23 | C | <2 | <10 | <2 | 10 | <2 | <10 |
| 24 | C | <2 | <10 | NS | <10 | <2 | <10 |
| 25 | C | <2 | <10 | <2 | <10 | <2 | <10 |
| 26 | C | <2 | <10 | <2 | 10 | <2 | <10 |
| 27 | C | <2 | <10 | <2 | <10 | <2 | <10 |
| 28 | C | 2 | <10 | <2 | <10 | <2 | 10 |
| 29 | C | 2 | <10 | <2 | 10 | <2 | <10 |
| 30 | C | <2 | <10 | <2 | <10 | <2 | <10 |
| 31 | C | <2 | <10 | <2 | <10 | <2 | <10 |
| 32 | C | <2 | <10 | <2 | <10 | <2 | <10 |
| 33 | C | >10 | >40 | <2 | 10 | <2 | <10 |
| 34 | C | <2 | <10 | <2 | <10 | <2 | <10 |
| 35 | C | >10 | 10 | 2 | <10 | <2 | 10 |
| 36 | C | 2 | <10 | <2 | <10 | <2 | <10 |
| 37 | C | <2 | <10 | <2 | <10 | <2 | <10 |
| 38 | C | <2 | <10 | 2 | <10 | <2 | <10 |
| 39 | C | <2 | 10 | <2 | <10 | <2 | <10 |
| 40 | C | <2 | >40 | <2 | <10 | <2 | <10 |

Guinea Pig Serological Evaluation for EEE, WEE, VEE and Tetanus Toxoid

Nine of ten guinea pigs vaccinated with the combination vaccine seroconverted satisfactorily at (≥1:40) to EEE virus. Ten of ten guinea pigs had satisfactory titers for VEE virus (≥1:4) and ten of ten guinea pigs seroconverted satisfactorily to WEE virus (≥1:40). Also a serum pool from 10 vaccinated guinea pigs was tested for tetanus antibody and was shown to be satisfactory with a value of 4.3 anti-toxin units/ml (AU/ml).

Guinea pig potency tests were completed and found to be satisfactory for all four antigens including tetanus toxoid, EEE, VEE, and WEE.

The vaccine was also administered to horses (20 vaccinates and 20 controls) via primary immunization followed by booster immunization 3 weeks later. Fourteen days post-booster vaccination, horses were bled and serum collected for all serological testing. Equine response to encephalomyelitis antigens was tested utilizing 2 dilutions (1:2 and 1:10 for Day 0 samples and 1:10 and 1:40 for Day 35 samples) in 24-well plates to determine antibody titers.

The satisfactory guinea pig potency testing conclusively establishes the efficacy of 4 antigens (VEE, EEE, WEE and tetanus toxoid) in the West Nile Virus combination vaccine as a 9-antigen-containing vaccine-toxoid. Furthermore, satisfactory potency results are substantiated and confirmed by host animal horse serology data in which vaccinated horses demonstrated a substantial rise in titer to each encephalitis virus fraction following vaccination. Additionally, the absence of observation of any adverse reactions in any of the vaccinated horses or guinea pigs confirms the safety of the WNV combination vaccine in animals.

Example 8

This example illustrates that a vaccine or immunogenic composition in accordance with the present invention has a duration of immunity of at least one year.

Materials and Methods

Host animal vaccination and challenge at least 1 year post-booster vaccination was used to confirm duration of immunity for the West Nile Virus antigen fraction in an Encephalomyelitis-Rhinopneumonitis-Influenza-West Nile Virus Vaccine, Eastern, Western & Venezuelan, Killed Virus, Tetanus Toxoid prepared from a North American Dominant isolate of WNV designated North American Equine E159 (NAEE159).

TABLE 21

The final formulated vaccine contains the following ingredients per 1 mL dose:

| Ingredients | 1 mL Dose | |
|---|---|---|
| Eastern Equine Encephalomyelitis | $10^{7.5-9.2}$ | $TCID_{50}$/mL |
| Western Equine Encephalomyelitis | $10^{8.2-9.2}$ | PFU/mL |
| Venezuelan Equine Encephalomyelitis | $10^{7.7-9.2}$ | $TCID_{50}$/mL |
| West Nile Virus (North American Dominant prepared from NAEE159) | $10^{8.0-9.2}$ | $TCID_{50}$/mL |
| EHV-1 | $10^{7.0-9.0}$ | $TCID_{50}$/mL |
| Equine Influenza A2/Ohio/2003 | $10^{7.3-9.5}$ | $TCID_{50}$/mL |
| Equine Influenza A2/Kentucky/95 | $10^{7.3-9.5}$ | $TCID_{50}$/mL |
| Equine Influenza A2/NewMarket/2/93 | $10^{7.3-9.5}$ | $TCID_{50}$/mL |
| Tetanus Toxoid | 5-10 | CPU |
| Non-metabolizable Oil Adjuvant | 100-200 | μL |
| Diluent - DMEM containing | | q.s. |
| Gentamicin | 30 | μg/mL of diluent volume |
| Formaldehyde | 0.1% | of diluent volume |

Thirty horses (20 vaccinates and 10 controls), 4-5 months of age were used in this study. Horses were randomly assigned to one of two treatments and vaccinated intramuscularly (IM) with a 1.0 mL dose of the assigned vaccine or control product. The primary immunization was followed three weeks later by a 1.0 mL IM booster vaccination.

Horses were vaccinated once and then again about 30 days later. Horses were randomly assigned to either vaccine or control groups. Twenty horses received the vaccine group receiving VEWT/WNV/EHV-1/Influenza vaccine. Ten horses received adjuvanted DMEM containing excipients used in the vaccine (Gentamicin and formaldehyde) but no antigens. The non-metabolizable oil adjuvant used for all administrations was preferably mineral oil.

Challenge inoculation of the virulent heterologous WNV NY99 strain virus was performed 380 days post-booster vaccination. The second cohort of horses were challenged 408 days post-booster inoculation in a similar manner.

Serum samples for serological evaluation were collected from the vaccinated and control horses prior to initial vaccination, at 21 days post first dose vaccination (day of booster vaccination), monthly post-booster, on the day of challenge, and at 7 and 14 days post-challenge. Body temperature and serum samples were obtained from each horse on the day of challenge, twice daily on Days 1 through 6 post-challenge, and daily on Days 7-10 and Day 14 post-challenge. Clinical data was also recorded during those same time periods for the 15-day observation period.

The heterologous challenge virus, designated WNV NY99, was originally isolated from the brain of an infected crow (CDC, Ft. Collins, Colo.). On the day of challenge, the stock virus was thawed on ice and virus was diluted to the desired concentration in phosphate-buffered saline immediately prior to inoculation of horses.

Rectal temperatures were recorded for each of the vaccinated and control horses on the day before challenge, day of challenge and twice daily on days 1-14, then daily on Days 14-21 post challenge by means of a calibrated, electronic thermometer (GSA Electronics) probe. The daily rectal temperatures were recorded in degrees Fahrenheit (° F.).

Venous blood from each of the vaccinated and control horses was collected on the Day of Challenge, twice daily on Days 1-6, and daily on Days 7-10 and Day 14 days post-challenge by Vacutainer into an SST tube. After centrifugation, serum was aliquoted and frozen immediately.

Vero Cells were grown in 6-well plates to confluency. To perform the plaque assay, serial 10-fold dilutions of serum were prepared in 96-well plates in BA-1 medium (MEM salts containing 1% BSA, 250 mg/L sodium bicarbonate, 500 gentamicin and 2.5 μg amphotericin B/mL in 50 mM Tris, pH 7.6). Serum dilutions (0.1 mL) were inoculated into each well of the 6-well plate and incubated for 45-60 minutes with rocking every 15 minutes. After the incubation period, 2 mL of overlay (2× medium containing MEM without phenol red prepared at twice the normal concentration and supplemented with 4% FBS, 200 IU penicillin G/mL and 100 μg streptomycin/mL—warmed to 45° C.) was added to each well. Plates were incubated at 37° C.

Two days after inoculation, 2 mL of a second overlay containing 2× agarose prepared by mixing equal volumes of 2× medium and 2× agarose was added to each well. Plates were examined and plaque numbers recorded in each well on days 3, 4 and 5 following inoculation. The virus titer per mL of original material is calculated as the number of plaques in a well (or average of multiple wells inoculated with the same dilution) times the dilution for the well being counted multiplied by 10.

A standard microtiter serum neutralization test was employed in this study. All sera were tested in sterile flat bottom 96 well microtiter plates using five wells per dilution and an 8 well dilution series for each of the 5 test wells. Each of the 5 test wells contained 25 μL of serum dilution mixed with 25 μL of the indicator virus and 150 μL of a freshly planted Vero cell suspension containing approximately $4\times10^4$ cells. The test indicator virus used was WNV NY99. Serum neutralizing antibody titers are expressed as Reed-Muench $ID_{50}$ titers.

For performance of the test, two-fold dilutions of each test serum were made in a sterile flat bottom microtiter plate using five replicate wells per test serum and an 8 well dilution series. Dilutions were made with an adjustable volume single or multi-channel pipetting instrument using sterile microtiter tips. The volume of serum added to each of 5 wells of the first row was 50 μL. All other wells contained 25 μL of DMEM (no FBS). Following serial dilution down the plate, 25 μL was discarded from the last row. 25 μL of a pre-determined dilution of the indicator virus was added to each test well. Plates were then mixed and incubated for one hour at 37° C. in 5% $CO_2$. On conclusion of the incubation period, 150 μL of a suspension containing 4×104 Vero cells were added to each test and cell control well. The plates were incubated at 37° C. in a $CO_2$ incubator for 5-7 days, at which time plates were microscopically examined for CPE typical of WNV.

Histopathology was evaluated by a Board Certified Veterinary Pathologist. The scoring system used to describe defects in the pons or medulla was as follows:

Score:

0=no significant lesions in section 0.5=rare, small, multifocal glial nodules scattered throughout the parenchyma 1=mild, nonsuppurative encephalitis. This is characterized by mild multifocal perivascular cuffs with lymphocytes and plasma cells and a rare neutrophil and scattered multifocal glial nodules composed of glial cells with a few mononuclear inflammatory cells. Occasionally within this grade, there may be minimal perivascular cuffing and more moderate scattered glial nodules.

2=moderate nonsuppurative encephalitis characterized by moderate lymphoplasmacytic perivascular cuffs around many vessels and multifocal accumulations of glial nodules scattered throughout the parenchyma 3=severe nonsuppurative encephalitis characterized by severe and thick lymphoplasmacytic perivascular cuffing with multiple scattered glial nodules throughout the parenchyma

Results and Discussion

There were no adverse reactions to vaccine administration at either dosing time point. All 4 to 5 month old foals receiving the experimental vaccine were free of either systemic or injection site adverse reactions in the study. This confirms the excellent safety of the vaccine of the present invention against WNV containing North American Dominant WNV antigen prepared from isolate NAEE159.

Horse Challenge with Heterologous West Nile Virus

Viremia

Each of the 10 control horses (100%) were viremic for at least 1 day post-challenge, while only 2 of 20 horses (10%) in the WNV vaccine group were viremic.

Clinical Signs

Seven of the 10 horses (70%) in the control group developed signs of encephalomyelitis consistent with West Nile Virus infection. Each of these animals was viremic for at least one day during the challenge period. In the WNV vaccine group, 1 of the 20 horses (5%) developed signs consistent with West Nile Virus infection. Notably clinical signs progressed to death or euthanasia in 70% of the controls and only 5% of the vaccinates. All control mortalities were viremic, confirming fatal encephalitis due to WNV, whereas only one of two vaccinated animals that died was viremic during the challenge period.

Serum Neutralization Titers

All vaccinated horses responded favorably to the WNV vaccine by developing protective levels of serum neutralizing (SN) antibody following vaccination. Over one year following vaccination, 17 of 20 (85%) of vaccinated horses maintained protective SN titers. By contrast, none of the control horses developed rising SN titers prior to virulent WNV challenge. Also, all vaccinated horses displayed an anamnestic rise in SN titers following virulent WNV challenge

Histopathology

Severity scores were provided for both the medulla and pons. Also with regard to this efficacy parameter, WNV vaccine containing North American Dominant WNV antigen prepared from isolate NAEE159 proved highly effective. Among the control horses, 50% displayed severe lesions of WNV encephalitis whereas only 10% of vaccinates were similarly affected.

Discussion and Conclusions

The WNV vaccine was prepared from a viral isolate (North American Equine E159) obtained from a horse in 2005 during the North American pandemic when a specific dominant WNV genotype emerged. This genotype is characterized by a specific valine to alanine amino acid change at the $159^{th}$ amino acid in the envelope (E) protein of the virus (when compared to the publicly available sequence for the WNV-NY99 isolate having the ATCC Accession No. AF196835), which has made all such isolates more robust and prolific, thereby displacing other WNV isolates, and making this genotype dominant among disease-causing WNV isolates in North America. Because it was prepared from the dominant genotype, the vaccine used in this study is indicative of the unique safety and efficacy achievable with vaccine prepared from all such North American Dominant isolates with this E protein profile and resulting prolificacy. Notably, all previously tested WNV vaccines have been prepared from a less prolific isolate of differing genotype and E protein amino acid sequence, namely WNV NY99. Based on this difference in nucleic acid sequence, E protein amino acid sequence, viral prolificacy, and unique ability to cause a pandemic, the North American Dominant isolates are displacing or have displaced NY99 from the environment. The unique genotype and phenotype (prolificacy), and, most importantly, the overwhelming environmental presence of North American Dominant WNV isolates and the absence of WNV NY99 is compelling evidence for the superiority of the North American Dominant West Nile Virus vaccine. Such superiority is confirmed by the safety and efficacy of the vaccine as demonstrated in this challenge study using vaccine prepared from North American Dominant isolate North American Equine E159 (NAEE159) (ATCC Accession No PTA-9409).

In this study, 4 to 5 month old horses were safely and effectively vaccinated with a multi-component VEWT/WNV/EHV-1/Equine Influenza vaccine batched at an appropriate antigen amount with the WNV component being North American Dominant WNV antigen prepared from isolate NAEE159c(ATCC Accession No. PTA-9409).

Study horses were intrathecally challenged at least 380 days post-booster vaccination with $10^5$ PFU of a virulent heterologous West Nile Virus strain. Horses were evaluated for 14 days post-challenge for clinical signs (including temperature and mortality), viremia, serum neutralization titers, and histopathology scores from sections of the pons and medulla taken after euthanasia and necropsy.

Viremia after challenge and serum neutralization titers were key outcome variables in this study that were highly indicative of vaccine efficacy. Horses that had been vaccinated more than one year earlier with VEWT/WNV/EHV-1/Influenza Lot 916 were 90% protected from viremia after challenge in this study. In comparison, 100% of control horses demonstrated viremia post-challenge. Additionally, serum neutralization titers of vaccinated horses were significantly higher than those of control horses at 14 days post-challenge, and displayed an anamnestic response typical of an effective vaccine following heterologous, virulent WNV challenge.

In addition the vaccine containing North American Dominant WNV antigen prepared from isolate NAEE159 reduced clinical signs and mortality resulting from encephalomyelitis following heterologous challenge with virulent WNV. Vaccine efficacy at least one year following vaccination was also confirmed by reduction in lesions typical of WNV infection.

This study demonstrated for the first time that 2 doses of the experimental combination vaccine prepared at appropriate doses of antigen including North American Dominant WNV antigen prepared from isolate NAEE159 administered to foals 4 to 5 months of age safely, reliably and effectively stimulated protective serological serum neutralization titers that resulted in duration of immunity of at least one year with protection from viremia, clinical signs, mortality, and encephalitic lesions after virulent heterologous challenge with West Nile Virus.

Example 9

In this study, a combination vaccine was prepared using a North American Dominant isolate of WNV, North American Equine E159(NAEE159) (ATCC Accession No. PTA-9409). The 14-day post second-vaccination sera samples from the guinea pigs vaccinated with this Encephalomyelitis-Rhinopneumonitis-Influenza-West Nile Virus Vaccine, Eastern, Western & Venezuelan, Killed Virus, Tetanus Toxoid were collected and tested for West Nile Virus plaque reduction neutralization (PRN). The sera from the vaccinated guinea pigs were tested for neutralizing antibody to both a North American Dominant isolate of WNV and to WNV isolate NY99. Notably, the vaccine displayed superior activity in stimulating neutralizing antibodies to North American Dominant WNV, as opposed to NY99 WNV. These data support the conclusion of the superior efficacy of WNV vaccines prepared from North American Dominant WNV isolates as contrasted with earlier less effective vaccines prepared from or based on the NY99 WNV isolate.

Furthermore, a vaccine prepared from an additional North American Dominant isolate of WNV, North American Donkey E159 (NADE159) will similarly demonstrate, as described above, the superior efficacy of such vaccines over the former NY99 based vaccines. Hence, data from multiple North American Dominant isolates cultivated from different host species, originating from unique North American locations, and obtained at different times in North America will confirm the unexpected but superior efficacy of North American Dominant isolates of WNV for vaccine preparation.

The data from the plaque reduction neutralization assay also established that a vaccine prepared from a North American Dominant isolate of WNV that stimulates a titer of 1:12 or higher in vaccinated guinea pigs that provides 50% viral plaque reduction in at least 90% of vaccinated guinea pigs, correlates to vaccine protection against WNV challenge in the horse and provides for a duration of immunity of at least one year. West Nile Virus vaccination/challenge data in the horse at an antigen inclusion level of $10^{7.6-9.0}$ $TCID_{50}$ or higher per dose correlated with these guinea pig PRN titer results and confirmed the WNV immunizing dose that provides 1 year or longer duration of immunity in the horse. The corresponding dose in guinea pigs also stimulates serum neutralizing antibodies to a titer of at least 1:12 against North American Dominant WNV in guinea pigs.

Data presented in this report collectively demonstrate the unexpected efficacy of vaccines prepared from North American Dominant isolates of WNV, define the correlation between vaccine efficacy in the horse and guinea pig serum levels of neutralizing antibody, confirm that a 1:12 titer or higher in guinea pigs identifies an effective equine vaccine providing at least one year duration of immunity, and quite notably, demonstrate the superior efficacy of vaccines prepared from North American Dominant WNV as contrasted with NY99 WNV.

Materials and Methods

In order to demonstrate efficacy of the West Nile Virus antigen, prepared using a North American Dominant isolate of WNV, North American Equine E159(NAEE159) (ATCC Accession No. PTA-9409), in an Encephalomyelitis-Rhinopneumonitis-Influenza-West Nile Virus Vaccine, Eastern, Western & Venezuelan, Killed Virus, Tetanus Toxoid and to establish an effective dose measurable in horses or guinea pigs, host animal vaccination/challenge studies were performed in conjunction with guinea pig vaccination/serology studies. In this study, 14-day post second-vaccination sera samples from guinea pigs vaccinated with Encephalomyelitis-Rhinopneumonitis-Influenza-West Nile Virus Vaccine, Eastern, Western & Venezuelan, Killed Virus, Tetanus Toxoid were collected and tested. Additionally, a plaque reduction neutralization assay was developed to measure the titer correlated to protection against challenge in the host animal. This titer was determined to be 1:12 or higher in the guinea pig.

Vaccine Formulations

Experimental Serials (Protective Dose Vaccine)

Experimental Serials were formulated to confirm protective antigen specifications for all antigens in the vaccine.

TABLE 22

| The final formulated vaccines contained the following ingredients per 1 mL dose: | |
|---|---|
| Ingredients | 1 mL Dose |
| Eastern Equine Encephalomyelitis | $10^{7.5-9.2}$ $TCID_{50/mL}$ |
| Western Equine Encephalomyelitis | $10^{8.2-9.2}$ PFU/mL |
| Venezuelan Equine Encephalomyelitis | $10^{7.7-9.2}$ $TCID_{50}$/mL |
| West Nile Virus (North American Dominant prepared from NAEE159) | $10^{7.3-9.2}$ $TCID_{50}$/mL |
| EHV-1 | $10^{7.0-9.0}$ $TCID_{50}$/mL |
| Equine Influenza A2/Ohio/2003 | $10^{7.3-9.5}$ $TCID_{50}$/mL |
| Equine Influenza A2/Kentucky/95 | $10^{7.3-9.5}$ $TCID_{50}$/mL |
| Equine Influenza A2/NewMarket/2/93 | $10^{7.3-9.5}$ $TCID_{50}$/mL |
| Tetanus Toxoid | 5-10 CPU |
| Non-metabolizable Oil Adjuvant | 100-200 μL |
| Diluent - DMEM containing | q.s. |
| Gentamicin | 30 μg/mL of diluent volume |
| Formaldehyde | 0.1% of diluent volume |

Experimental serial 916 was formulated for host animal vaccination studies. Experimental serial 916 is a multi-component vaccine containing VEWT-WNV-EHV-1 and 3 strains of equine influenza type A2 virus. Experimental serial 916 is batched at $10^{7.6-9.2}$ $TCID_{50}$/mL of West Nile Virus antigen North American Equine E159(NAEE159). It is a 1 mL dose vaccine in the horse.

This vaccine was also tested in guinea pigs at the time of host animal vaccinations to confirm the WNV efficacy and laboratory animal potency. Four replicate guinea pig sera dilution experiments were performed for experimental serial 916 to validate a guinea pig assay criterion for this one-year duration of immunity (DOI) vaccine.

Experimental Serial 507 (Comparative Efficacy Serial)

Data from Experimental Serial 507 is included in this report to demonstrate that serials formulated with a North American Dominant isolate of WNV antigen show superior efficacy, measured as guinea pig titers, of the relevant North American Dominant isolates of WNV as compared to the earlier NY99 isolate.

Guinea Pig Serological Evaluation

Sera were tested for WNV antibody as follows:

1) West Nile Virus Indicator Strain: North American Equine E159(NAEE159) (ATCC Accession No. PTA-9409) & North American Donkey E159 (NADE159)
2) Growth medium for Vero Cells is DMEM+5% FBS, 2 mM L-glutamine and 30 μg/mL gentamycin
3) Diluent for Test Serum is DMEM plus 30 μg/mL gentamycin
4) Diluent for indicator virus working solution is DMEM+10% normal guinea pig serum (specific to WNV assay)
5) Guinea pig test sera is diluted 1:12
7) Use 4 mL overlay instead of 3 mL (specific to WNV assay)
8) Titers are calculated using 50% plaque reduction
9) Nine of ten vaccinated guinea pigs must have an antibody titer of ≥1:12 to demonstrate efficacy, and negative guinea pigs must be <1:4 (same criteria as VEE assay in SAM).

Results and Discussion

Serological Evaluation for West Nile Virus

TABLE 23

Number of Plaques/Sera Dilution
Experimental Serial 916 Replicate I West Nile Guinea Pig Plaque Reduction Neutralization Results Using North American Equine E159 (NAEE159) as Indicator Virus
The study was initiated and the guinea pigs were bled 25 days later.

| | 916 (I) | | | | | | | | |
|---|---|---|---|---|---|---|---|---|---|
| | 2 | 3 | 4 | 6 | 8 | 12 | 16 | 32 | 64 |
| GP1 | 0 | 2 | 2 | 4 | 5.5 | 2.5 | 17 | 14 | 11 |
| GP2 | 6.5 | 9.5 | 11 | 14 | 9 | 11.5 | 13 | 20 | 22.5 |
| GP3 | 7 | 5 | 6 | 9.5 | 10 | 9.5 | 11 | 10 | 16.5 |
| GP4 | 7 | 5 | 4 | 4 | 1 | 6 | 15.5 | 9.5 | 12.5 |
| GP5 | 6 | 4.5 | 9 | 7 | 17.5 | 13.5 | 12 | 16 | 17 |
| GP6 | 1 | 1 | 2.5 | 7.5 | 3 | 8 | 19.5 | 19.5 | 20.5 |
| GP7 | 9.5 | 8 | 8 | 15.5 | 17.5 | 21.5 | 36 | 17.5 | 20.5 |
| GP8 | 5 | 3.5 | 7.5 | 7.5 | 14.5 | 11 | 26.5 | 26.5 | 27.5 |
| GP9 | 0 | 2 | 7 | 6 | 7 | 12 | 9 | 10.5 | 11.5 |
| GP10 | 4.5 | 4.5 | 5.5 | 11 | 22 | 8.5 | 23 | 29 | 30.5 |
| # Passed | 10/10 | 10/10 | 10/10 | 10/10 | 10/10 | 10/10 | 10/10 | 10/10 | 10/10 |
| Neg. Control 1 | 68.5 | 64.5 | 72.5 | 93.5 | 68 | 82 | 89.5 | 78.5 | 71 |
| Neg. Control 2 | 72 | 61 | 87 | 69.5 | 70.5 | 85.5 | 77.5 | 69.5 | 88 |

Virus Control Values: 99, 70, 68, 88, 77, 64
Virus Control Average Plaques: 79
Virus Control 50% Reduction: 39.5

TABLE 24

Experimental Serial 916 Replicate II West Nile Guinea Pig Plaque Reduction Neutralization Results Using North American Equine E159 (NAEE159) as Indicator Virus
Guinea Pigs were bled 35 days after the initiation of the study
Number of Plaques/Sera Dilution

| | 916 (II) | | | | | | | | |
|---|---|---|---|---|---|---|---|---|---|
| | 2 | 3 | 4 | 6 | 8 | 12 | 16 | 32 | 64 |
| GP1 | 1 | 3 | 6 | 6 | 14.5 | 6.5 | 13.5 | 18 | 17.5 |
| GP2 | 1.5 | 3.5 | 6.5 | 6.5 | 8.5 | 9.5 | 10.5 | 12.5 | 19 |
| GP3 | 12 | 5.5 | 22 | 21 | 41.5 | 34 | 41 | 41 | 43.5 |
| GP4 | 4 | 8.5 | 17.5 | 16.5 | 21 | 36.5 | 28 | 41.5 | 42.5 |
| GP5 | 3.5 | 4.5 | 9.5 | 15 | 26.5 | 25.5 | 13.5 | 23 | 40 |
| GP6 | 1 | 3 | 7 | 13.5 | 17.5 | 14 | 24.5 | 26 | 23 |
| GP7 | 8 | 5.5 | 14.5 | 11.5 | 21.5 | 15.5 | 34 | 26.5 | 28 |
| GP8 | 1 | 1.5 | 2.5 | 3.5 | 4 | 11 | 9 | 20 | 17.5 |
| GP9 | 13.5 | 18 | 25.5 | 29.5 | 29.5 | 35.5 | 28 | 37.5 | 43 |
| GP10 | 9 | 8 | 10.5 | 21.5 | 21 | 20.5 | 27 | 31.5 | 27.5 |
| # Passed | 10/10 | 10/10 | 10/10 | 10/10 | 9/10 | 10/10 | 9/10 | 8/10 | 6/10 |
| Neg. Control 1 | 69.5 | 67 | 71.5 | 69.5 | 72.5 | 73 | 83 | 68 | 78 |
| Neg. Control 2 | 68 | 70.5 | 69 | 72.5 | 82.5 | 66 | 75 | 76 | 74 |

Virus Control Values: 99, 70, 68, 88, 77, 64
Virus Control Average Plaques: 79
Virus Control 50% Reduction: 39.5

TABLE 25

Experimental Serial 916 Replicate III West Nile Guinea Pig Plaque Reduction Neutralization
Results Using North American Equine E159 (NAEE159) as Indicator Virus
Guinea Pigs were bled 35 days after initiation
Number of Plaques/Sera Dilution

| | 916 (III) | | | | | | | | |
|---|---|---|---|---|---|---|---|---|---|
| | 2 | 3 | 4 | 6 | 8 | 12 | 16 | 32 | 64 |
| GP1 | 0.5 | 1.5 | 0 | 0 | 0 | 1 | 4 | 6 | 3.5 |
| GP2 | 0 | 0 | 1 | 0.5 | 0 | 0 | 0 | 0 | 0 |
| GP3 | 7.5 | 9 | 9 | 16 | 17 | 13.5 | 12 | 18.5 | 23 |
| GP4 | 2.5 | 0 | 0 | 3 | 2 | 2 | 3.5 | 1 | 2.5 |
| GP5 | 13.5 | 15.5 | 18 | 18 | 19.5 | 24 | 16.5 | 21.5 | 33.5 |
| GP6 | 6.5 | 15.5 | 31.5 | 10 | 29.5 | 26.5 | 28.5 | 31.5 | 32 |
| GP7 | 14.5 | 12 | 17.5 | 20.5 | 19.5 | 29.5 | 21.5 | 16 | 22.5 |
| GP8 | 21 | 24.5 | 36 | 28 | 34.5 | 30.5 | 27.5 | 29 | 26 |
| GP9 | 0.5 | 0.5 | 3 | 4 | 6.5 | 5 | 10 | 9.5 | 18 |
| GP10 | 2.5 | 7.5 | 11 | 8 | 12.5 | 9 | 20 | 10.5 | 17 |
| # Passed | 10/10 | 10/10 | 8/10 | 10/10 | 9/10 | 10/10 | 10/10 | 9/10 | 8/10 |
| Neg. Control 1 | 73 | 61.5 | 79.5 | 53.5 | 58.5 | 78 | 57 | 70 | 63 |
| Neg. Control 2 | 55 | 54.5 | 64 | 52.5 | 58 | 68.5 | 66 | 67.5 | 79 |

Virus Control Values: 51, 58, 61, 66, 78

Virus Control Average Plaques: 62

Virus Control 50% Reduction: 31

TABLE 26

Experimental Serial 916 Replicate IV West Nile Guinea Pig Plaque Reduction Neutralization
Results Using North American Equine E159 (NAEE159) as Indicator Virus Guinea Pigs were bled 30 days after the initiation of the study
Number of Plaques/Sera Dilution

| | 916 (IV) | | | | | | | | |
|---|---|---|---|---|---|---|---|---|---|
| | 2 | 3 | 4 | 6 | 8 | 12 | 16 | 32 | 64 |
| GP1 | 11.5 | 7 | 5.5 | 20.5 | 12 | 17.5 | 22.5 | 20 | 25 |
| GP2 | 31 | 21.5 | 20.5 | 36.5 | 32 | 30 | 27 | 15 | 28.5 |
| GP3 | 16 | 20.5 | 18 | 23.5 | 21.5 | 16 | 35.5 | 16.5 | 15 |
| GP4 | 1 | 2 | 6.5 | 7 | 11 | 15 | 19 | 14 | 18.5 |
| GP5 | 4 | 1 | 9.5 | 12 | 20 | 17 | 24.5 | 19.5 | 23.5 |
| GP6 | 0 | 0 | 0 | 1.5 | 2.5 | 2.5 | 0.5 | 3 | 3 |
| GP7 | 5.5 | 6.5 | 5.5 | 10 | 7 | 13 | 5.5 | 9.5 | 13 |
| GP8 | 1 | 4.5 | 0.5 | 3 | 7.5 | 4.5 | 13.5 | 17.5 | 11.5 |
| # Passed | 8/8 | 8/8 | 8/8 | 7/8 | 8/8 | 8/8 | 7/8 | 8/8 | 8/8 |
| Neg. Control 1 | 48 | 39 | 46.5 | 39 | 48 | 54 | 39.5 | 54 | 67.5 |
| Neg. Control 2 | 40.5 | 53 | 44 | 44.5 | 54 | 48.5 | 59.5 | 61.5 | 45.5 |

Virus Control Values: 93, 53, 56, 92, 67, 44

Virus Control Average Plaques: 67.5

Virus Control 50% Reduction: 33.8

EXPERIMENTAL SERIAL 507 (Demonstrating Superior Efficacy of North American Equine E159(NAEE159) Vaccines, and that other North American Dominant Vaccines, such as North American Donkey E159(NADE159 will provide superior efficacy to NY99 vaccines)

Guinea Pig Serological Evaluation for West Nile Virus

TABLE 27

Experimental Serial 507 West Nile Guinea Pig Plaque Reduction Neutralization Results using WNV NY1999 Isolate as Indicator Virus
Number of Plaques/Sera Dilution

| Guinea Pig Number | 4 | 8 | 16 | 32 | 64 |
|---|---|---|---|---|---|
| GP1 | ≥10 | ≥15 | ≥15 | ≥14.5 | ≥10.5 |
| GP2 | 4.5 | 5 | 7.5 | 9.5 | 13 |
| GP3 | 1 | 3.5 | 3.5 | 6 | 6.5 |
| GP4 | 8 | 11.5 | ≥13.5 | ≥14.5 | ≥14.5 |
| GP5 | 6 | 7.5 | 7.5 | 8.5 | 9 |
| GP6 | 8.5 | 9.5 | 9.5 | 12 | 14 |
| GP7 | 7 | 8.5 | 9 | ≥10.5 | ≥14.5 |
| GP8 | 5 | 10.5 | 10.5 | 14 | 14 |
| GP9 | 5.5 | 7 | 7.5 | 10 | 10 |
| GP10 | 5.5 | 6.5 | 8.5 | ≥12.5 | 14 |
| # Passed | 9/10 | 6/10 | 5/10 | 2/10 | 1/10 |
| Neg. Control 1 | ≥13.5 | ≥13.5 | ≥13 | ≥13 | ≥14.5 |
| Neg. Control 2 | ≥15.5 | ≥14.5 | ≥16 | ≥17 | ≥16.5 |

Virus Control Values: ≥24, ≥15, ≥14, ≥16, ≥18, ≥20

Virus Control Average Plaques: ≥17.8

Virus Control 50% Reduction: ≥8.9

TABLE 28

Experimental Serial 507 West Nile Guinea Pig Plaque Reduction Neutralization
Results Using North American Equine E159 (NAEE159) as Indicator Virus Number of Plaques/Sera Dilution

| | Guinea Pig Number | | | | | |
|---|---|---|---|---|---|---|
| | 2 | 4 | 8 | 16 | 32 | 64 |
| GP1 | 17 | 14 | 18.5 | 14.5 | 19.5 | 26 |
| GP2 | 2.5 | 3.5 | 2 | 6 | 17 | 15 |
| GP3 | 5.5 | 10 | 4.5 | 9 | 5 | 11.5 |
| GP4 | 11.5 | 10 | 15 | 15.5 | 19 | 19.5 |
| GP5 | 13 | 23 | 23.5 | 19.5 | 32.5 | 13 |
| GP6 | 5.5 | 8.5 | 12 | 11 | 13 | 14 |
| GP7 | 8.5 | 12 | 14 | 15 | 16 | 12 |
| GP8 | 14.5 | 14 | 18 | 19.5 | 25.5 | 27.5 |
| GP9 | 1.5 | 3 | 3 | 8.5 | 15.5 | 7 |
| GP10 | 12.5 | 12 | 7 | 18.5 | 14 | 13 |
| # Passed | 9/10 | 9/10 | 7/10 | 7/10 | 5/10 | 7/10 |
| Neg. Control 1 | 24.5 | 21 | 22 | 23.5 | 22 | 25 |
| Neg. Control 2 | 24 | 33 | 29 | 29 | 24.5 | 34.5 |

Virus Control Values: 40, 38, 34, 35, 28, 23

Virus Control Average: 33

Virus Control 50% Reduction: 16.5

Discussion and Conclusions

Guinea pigs were vaccinated and sera tested for West Nile Virus antibody. This assay established that a titer of 1:12 in vaccinated guinea pigs correlates to protection in a horse vaccination/challenge study that provides at least one year duration of immunity for WNV vaccine prepared using a North American Dominant isolate of WNV, such as North American Equine E159(NAEE159).

Concurrently with guinea pig vaccinations, WNV vaccine prepared using a North American Dominant isolate of WNV, North American Equine E159(NAEE159), was also administered to horses (20 vaccinates and 10 controls) via primary immunization followed by booster immunization 3 weeks later. More than one year post-booster vaccination, horses were subjected to virulent West Nile Virus challenge, and were protected when compared to non-vaccinated controls. Vaccinated horses were protected from viremia, clinical signs, mortality, and encephalitic lesions after virulent heterologous challenge with West Nile Virus.

In addition the data substantiate the superior efficacy of WNV vaccines prepared using North American Dominant WNV, as opposed to previously developed vaccines derived from WNV NY99. The sera from the vaccinated guinea pigs were tested for neutralizing antibody to both a North American Dominant isolate of WNV and to WNV isolate NY99. Titers to the isolate frequently occurring in North America, namely North American Dominant (NAEE159), were consistently higher in vaccinated guinea pigs as compared to titers to the isolate that is no longer reported to be present in nor causing disease in North America, WNV NY99. Hence, the vaccine displayed superior activity in stimulating neutralizing antibodies to North American Dominant WNV, as opposed to NY99 WNV. These data support the conclusion of the superior efficacy of WNV vaccines prepared from North American Dominant WNV isolates as contrasted with earlier less effective vaccines prepared from or based on the NY99 WNV isolate.

Example 10

This Example illustrates the genetic differences between North American WNV strains and North American Dominant WNV strains, as used in the present invention.

Materials and Methods

Relevant areas of the genome of WNV NY99 and the North American Dominant WNV isolates suitable for preparation of a novel, superior vaccine were sequenced and compared to confirm the key genetic differences. Examples of North American Dominant isolates used in vaccine preparation include North American Equine E159(NAEE159) (ATCC Accession No. PTA-9409) and North American Donkey E159(NADE159).

Results and Conclusions

The critical Envelope (E) protein and Non-Structural 5 (NS5) protein was sequenced in these WNV isolates using standard laboratory techniques to determine genetic differences in nucleotide sequence as contrasted with WNV NY99. Notably, the North American Dominant isolates, of which specific examples are North American Equine E159 (NAEE159) and North American Donkey E159(NADE159), displayed the changes which characterize North American Dominant WNV isolates and distinguish them from NY99 WNV, namely, the U to C mutation and C to U mutation at positions 1442 and 2466, respectively, of the nucleotide sequence encoding the E protein and the C to U mutation at position 9352 in the sequence encoding the NS5 protein. FIGS. 10-17 show the sequence alignments of various regions of isolates. The alignments in the E region are relative to publically available reference sequences for a NY 99 isolate (deposited in GenBank as AY590210) and a North American Dominant isolate (WN 02 isolate) deposited in GenBank as AY590223. The alignments in the NS5 region are also relative to publically available reference sequences for a NY 99 isolate (deposited in GenBank as AY369442) and a North American Dominant isolate (WN 02 isolate) deposited in GenBank as AY369440). As shown by these alignments, North American Dominant WNV isolates have the same sequence changes relative to the NY 99 isolate as those defined in the definition for a North American Dominant WNV isolate. These sequences are provided herein as SEQ ID NOS. 1-22, the full length genome of a WN99 isolate is provided as SEQ ID NO. 23, and the protein encoded by the full length genome of SEQ ID NO. 23 is provided as SEQ ID NO. 24.

What is claimed is:

1. An immunogenic composition comprising one or more strains of North American Dominant killed or inactivated West Nile Virus or any antigen thereof.

2. The immunogenic composition according to claim 1, wherein said immunogenic composition comprises at least one antigen or one additional strain of Equine Herpes Virus.

3. The immunogenic composition according to claim 1, wherein said immunogenic composition comprises at least one antigen or one additional strain of Equine Influenza Virus.

4. The immunogenic composition according to claim 1, wherein said West Nile Virus is one of the strains selected from the group consisting of Horse Origin 2005, deposited with the ATCC under accession number PTA-9409; NY2002Nassau; NY2002Clinton; NY2002Queens; GA20021; GA20022; TX20021; TX20022; IN2002; NY2003Albany; NY2003Suffolk; NY2003Chatauqua; CO20031; CO20032; TX2003; TX2003Harris4; TX2003Harris6; TX2003Harris7; TX2003Harris10; AZ2004; TX2004Harris4; and combination thereof.

5. The immunogenic composition according to claim 1, wherein any of the strains are present in an amount from about $10^{2.0}$ $TCID_{50}$/mL-$10^{10.0}$ $TCID_{50}$/mL per dose.

6. The immunogenic composition according to claim 1, wherein said immunogenic composition further comprises suitable excipients or pharmaceutical carrier.

7. The immunogenic composition according to claim 6, wherein said suitable excipients or pharmaceutical carrier is/are selected from the group consisting of a diluent, adjuvant, antimicrobial agent, inactivating agent, and combinations thereof.

8. The immunogenic composition according to claim 7, wherein said adjuvant is selected from the group consisting of, a polymer of acrylic or methacrylic acid, non-metabolized oil, and combinations thereof.

9. The immunogenic composition according to claim 1, wherein one dose of said immunogenic composition is formulated in 0.5 ml to 2.5 ml.

10. The immunogenic composition according to claim 1, wherein said immunogenic composition provides duration of immunity of at least 12 months after the administration of one dose.

11. The immunogenic composition according to claim 1, wherein said immunogenic composition is safe for use in foals or horses 4 months of age or older.

12. A method for reducing the incidence or lessening the severity of clinical symptoms associated with or caused by West Nile Virus in an animal or a herd of animals comprising the step of administering the immunogenic composition according to claim 1 to an animal in need thereof.

13. The method according to claim 12, wherein said immunogenic composition is administered in one or more doses.

14. The immunogenic composition according to claim 1, wherein said immunogenic composition further comprises at least one antigen of one or more additional strains selected from the group consisting of Eastern Equine Encephalomyelitis Virus, Western Equine Encephalomyelitis Virus and Venezuelan Equine Encephalomyelitis Virus, Tetanus Toxoid, and combinations thereof.

15. The immunogenic composition according to claim 14, wherein said Western Equine Encephalomyelitis Virus is the strain deposited with the ATCC under accession number PTA-9410.

16. The immunogenic composition according to claim 14, wherein said Venezuelan Equine Encephalomyelitis Virus is the strain deposited with the ATCC under accession number PTA-9411.

17. The immunogenic composition according to claim 14, wherein said Eastern Equine Encephalomyelitis Virus is the strain deposited with the ATCC under accession number PTA-9412.

18. The immunogenic composition according to claim 14, wherein said Equine Herpes Virus is selected from the group consisting of the strains deposited with the ATCC under accession Nos. PTA-9525 or PTA-9526, and combinations thereof.

19. The immunogenic composition according to claim 14, wherein said Equine Influenza Virus is selected from the group consisting of Influenza/Equine-2/Ohio/03, Influenza/Equine-2/KY/95, Influenza/Equine-2/New Market/2/93, and combinations thereof.

20. The immunogenic composition according to claim 14, wherein said Equine Influenza Virus is selected from the group consisting of the strains deposited with the ATCC under accession Nos. PTA-9522, PTA-9523 or PTA-9524 and combinations thereof.

21. A method for reducing the incidence or lessening the severity of clinical symptoms associated with or caused by one or more of the pathogens selected from the group consisting of West Nile Virus, Eastern Equine Encephalomyelitis Virus, Western Equine Encephalomyelitis Virus, Venezuelan Equine Encephalomyelitis Virus and *Clostridium tetani* in an animal or a herd of animals comprising the step of administering the immunogenic composition according to claim 14 to an animal in need thereof.

* * * * *

SEQUENCE LISTING

```
<160> NUMBER OF SEQ ID NOS: 40

<210> SEQ ID NO 1
<211> LENGTH: 608
<212> TYPE: DNA
<213> ORGANISM: West Nile virus

<400> SEQUENCE: 1

cgggggaat gtcacacttg catttacaac atgatgggaa agagagagaa aaaacccgga      60

gaattcggaa aggccaaggg aagcagagcc atttggttca tgtggctcgg agctcgcttt    120

ctggagttcg aggctctggg ttttctcaat gaagaccact ggcttggaag aaagaactca    180

ggaggaggtg tcgagggctt gggcctccaa aaactgggtt acatcctgcg tgaagttggc    240

acccggcctg ggggcaagat ctatgctgat gacacagctg gctgggacac ccgcatcacg    300

agagctgact tggaaaatga agctaaggtg cttgagctgc ttgatgggga acatcggcgt    360

cttgccaggg ccatcattga gctcacctat cgtcacaaag ttgtgaaagt gatgcgcccg    420

gctgctgatg gaagaaccgt catggatgtt atctccagag aagatcagag ggggagtgga    480

caagttgtca cctacgccct aaacactttc accaacctgg ccgtccagct ggtgaggatg    540

atggaagggg aaggagtgat tggcccagat gatgtggaga aactcacaaa agggaaagga    600

cccaaagt                                                             608

<210> SEQ ID NO 2
```

<211> LENGTH: 608
<212> TYPE: DNA
<213> ORGANISM: West Nile virus

<400> SEQUENCE: 2
cggggggaat gtcacacttg catttacaac atgatgggaa agagagagaa aaaacccgga 60
gagttcggaa aggccaaggg aagcagagcc atttggttca tgtggctcgg agctcgcttt 120
ctggagttcg aggctctggg ttttctcaat gaagaccact ggcttggaag aaagaactca 180
ggaggaggtg tcgagggctt gggcctccaa aaactgggtt acatcctgcg tgaagttggc 240
acccggcctg gggcaagat ctatgctgat gacacagctg gctgggacac ccgcatcacg 300
agtgctgact tggaaaatga agctaaggtg cttgagttgc ttgatgggga acatcggcgt 360
cttgccaggg ccatcattga gctcacctat cgtcacaaag ttgtgaaagt gatgcgcccg 420
gctgctgatg gaagaaccgt catggatgtt atctccagag aagatcagag gggagtgga 480 caagttgtca cctacgccct aaacactttc accaacctgg ccgtccagct ggtgaggatg 540
atggaagggg aaggagtgat tggcccagat gatgtggaga aactcacaaa agggaaagga 600
cccaaagt 608

<210> SEQ ID NO 3
<211> LENGTH: 909
<212> TYPE: DNA
<213> ORGANISM: West Nile virus
<220> FEATURE:
<221> NAME/KEY: modified_base
<222> LOCATION: (57)..(57)
<223> OTHER INFORMATION: a, c, g or t

<400> SEQUENCE: 3
gcaatgcagc tttgggtgcc atgtttgaag agcagaatca atggaggagc gccaganaag 60
cagttgaaga tccaaaattt tgggagatgg tggatgagga gcgcgaggca catctgcggg 120
gggaatgtca cacttgcatt tacaacatga tgggaaagag agagaaaaaa cccggagagt 180
tcggaaaggc taagggaagc agagccattt ggttcatgtg gctcggagct cgctttctgg 240
agttcgaggc tctgggtttt ctcaatgaag accactggct tggaagaaag aactcaggag 300
gaggtgtcga gggcttgggc ctccaaaaac tgggttacat cctgcgtgaa gttggcaccc 360
gacctggggg caagatctat gctgatgaca cagccggctg ggacacccgc atcacgagag 420
ctgacttgga aaatgaagct aaggtgcttg agttgcttga tggggaacat cggcgtcttg 480
ccagggccat cattgagctc acctatcgtc acaaagttgt gaaagtgatg cgcccggctg 540
ctgatggaag aaccgtcatg gatgttatct ccagagaaga tcagaggggg agtggacaag 600
ttgtcaccta cgccctaaac actttcacca acctggccgt ccagctggtg aggatgatgg 660
aaggggaagg agtgattggc ccagatgatg tggagaaact cacaaaaggg aaaggaccca 720
aagtcaggac ctggctgttt gagaatgggg aagaaagact cagccgcatg gctgtcagtg 780
gagatgactg tgtggtaaag cccctggacg atcgctttgc cacctcgctc cacttcctca 840
atgctatgtc aaaggttcgc aaagacatcc aagagtggaa accgtcaact ggatggtatg 900
attggcagc 909

<210> SEQ ID NO 4
<211> LENGTH: 975
<212> TYPE: DNA
<213> ORGANISM: West Nile virus
<220> FEATURE:
<221> NAME/KEY: modified_base
<222> LOCATION: (3)..(3)
<223> OTHER INFORMATION: a, c, g or t
<220> FEATURE:
<221> NAME/KEY: modified_base
<222> LOCATION: (12)..(12)
<223> OTHER INFORMATION: a, c, g or t
<220> FEATURE:
<221> NAME/KEY: modified_base
<222> LOCATION: (813)..(813)
<223> OTHER INFORMATION: a, c, g or t
<220> FEATURE:
<221> NAME/KEY: modified_base
<222> LOCATION: (881)..(882)
<223> OTHER INFORMATION: a, c, g or t

<400> SEQUENCE: 4
tcncggattc cncgcacgag atgtattggg tgagtcgagc ttcaggcaat gtggtacatt 60
cagtgaatat gaccagccag gtgctcctag gaagaatgga aaaaaggacc tggaagggac 120
cccaatacga ggaagatgta aacttgggaa gtggaaccag ggcggtggga aaacccctgc 180
tcaactcaga caccagtaaa atcaagaaca ggattgaacg actcaggcgt gagtacagtt 240
cgacgtggca ccacgatgag aaccacccat atagaacctg gaactatcac ggcagttatg 300
atgtgaagcc cacaggctcc gccagttcgc tggttaatgg agtggtcagg ctcctctcaa 360
aaccatggga caccatcacg aatgttacca ccatggccat gactgacact actcccttcg 420
ggcagcagcg agtgttcaaa gagaaggtgg acacgaaagc tcctgaaccg ccagaaggag 480
tgaagtacgt gctcaacgag accaccaact ggttgtgggc gtttttggcc agagaaaaac 540
gtcccagaat gtgctctcga gaggaattca taagaaaggt caacagcaat gcagctttgg 600
gtgccatgtt tgaagagcag aatcaatgga ggagcgccag agaagcagtt gaagatccaa 660
aattttggga gatggtggat gaggagcgcg aggcacatct gcggggggaa tgtcacactt 720
gcatttacaa catgatggga aagagagaga aaaaacccgg agagttcgga aaggctaagg 780
gaagcagagc catttggttc atgtggctcg ganctcgctt tctggagttc gaggctctgg 840
gttttctcaa tgaagaccac tggcttggaa gaaagaactc nngaggaggt gtcgagggct 900
tgggcctcca aaaactgggt tacatcctgc gtgaagttgg cacccgacct gggggcaaga 960
tctatgctga tgaca 975

<210> SEQ ID NO 5
<211> LENGTH: 957
<212> TYPE: DNA
<213> ORGANISM: West Nile virus
<220> FEATURE:
<221> NAME/KEY: modified_base
<222> LOCATION: (8)..(8)
<223> OTHER INFORMATION: a, c, g or t
<220> FEATURE:
<221> NAME/KEY: modified_base
<222> LOCATION: (31)..(31)
<223> OTHER INFORMATION: a, c, g or t
<220> FEATURE:
<221> NAME/KEY: modified_base
<222> LOCATION: (51)..(51)
<223> OTHER INFORMATION: a, c, g or t
<220> FEATURE:
<221> NAME/KEY: modified_base
<222> LOCATION: (83)..(83)
<223> OTHER INFORMATION: a, c, g or t
<220> FEATURE:
<221> NAME/KEY: modified_base
<222> LOCATION: (130)..(130)
<223> OTHER INFORMATION: a, c, g or t

<400> SEQUENCE: 5

-continued aatggagngg tcaggctcct ctcaaaaccc ntgggacacc atcacgaatg ntaccaccat 60
ggccatgact gacactactc ccnttcgggc agcagcgagt gttcaaagag aaggtggaca 120
cgaaagctcn tgaaccgcca gaaggagtga agtacgtgct caacgagacc accaactggt 180
tgtgggcgtt tttggccaga gaaaaacgtc ccagaatgtg ctctcgagag gaattcataa 240
gaaaggtcaa cagcaatgca gctttgggtg ccatgtttga agagcagaat caatggagga 300
gcgccagaga agcagttgaa gatccaaaat tttgggagat ggtggatgag gagcgcgagg 360
cacatctgcg gggggaatgt cacacttgca tttacaacat gatgggaaag agagagaaaa 420
aacccggaga gttcggaaag gctaagggaa gcagagccat ttggttcatg tggctcggag 480
ctcgctttct ggagttcgag gctctgggtt ttctcaatga agaccactgg cttggaagaa 540
agaactcagg aggaggtgtc gagggcttgg gcctccaaaa actgggttac atcctgcgtg 600
aagttggcac ccgacctggg ggcaagatct atgctgatga cacagccggc tgggacaccc 660
gcatcacgag agctgacttg gaaaatgaag ctaaggtgct tgagttgctt gatggggaac 720
atcggcgtct tgccagggcc atcattgagc tcacctatcg tcacaaagtt gtgaaagtga 780
tgcgcccggc tgctgatgga agaaccgtca tggatgttat ctccagagaa gatcagaggg 840
ggagtggaca agttgtcacc tacgccctaa acactttcac caacctggcc gtccagctgg 900
tgaggatgat ggaaggggaa ggagtgattg gcccagatga tgtggagaaa ctcacaa 957

<210> SEQ ID NO 6
<211> LENGTH: 961
<212> TYPE: DNA
<213> ORGANISM: West Nile virus
<220> FEATURE:
<221> NAME/KEY: modified_base
<222> LOCATION: (30)..(30)
<223> OTHER INFORMATION: a, c, g or t
<220> FEATURE:
<221> NAME/KEY: modified_base
<222> LOCATION: (41)..(41)
<223> OTHER INFORMATION: a, c, g or t
<220> FEATURE:
<221> NAME/KEY: modified_base
<222> LOCATION: (62)..(63)
<223> OTHER INFORMATION: a, c, g or t
<220> FEATURE:
<221> NAME/KEY: modified_base
<222> LOCATION: (107)..(107)
<223> OTHER INFORMATION: a, c, g or t

<400> SEQUENCE: 6
gggaccccaa tacgaggaag atgtaaactn gggaagtgga nccagggcgg tgggaaaacc 60
cnngctcaac tcagacacca gtaaaatcaa gaacaggatt gaacgantca ggcgtgagta 120
cagttcgacg tggcaccacg atgagaacca cccatataga acctggaact atcacggcag 180
ttatgatgtg aagcccacag gctccgccag ttcgctggtt aatggagtgg tcaggctcct 240
ctcaaaacca tgggacacca tcacgaatgt taccaccatg gccatgactg acactactcc 300
cttcgggcag cagcgagtgt tcaaagagaa ggtggacacg aaagctcctg aaccgccaga 360
aggagtgaag tacgtgctca acgagaccac caactggttg tgggcgtttt tggccagaga 420
aaaacgtccc agaatgtgct ctcgagagga attcataaga aaggtcaaca gcaatgcagc 480
tttgggtgcc atgtttgaag agcagaatca atggaggagc gccagagaag cagttgaaga 540
tccaaaattt tgggagatgg tggatgagga gcgcgaggca catctgcggg gggaatgtca 600
cacttgcatt tacaacatga tgggaaagag agagaaaaaa cccggagagt tcggaaaggc 660
taagggaagc agagccattt ggttcatgtg gctcggagct cgctttctgg agttcgaggc 720

-continued tctgggtttt ctcaatgaag accactggct tggaagaaag aactcaggag gaggtgtcga 780
gggcttgggc ctccaaaaac tgggttacat cctgcgtgaa gttggcaccc gacctggggg 840
caagatctat gctgatgaca cagccggctg ggacacccgc atcacgagag ctgacttgga 900
aaatgaagct aaggtgcttg agttgcttga tggggaacat cggcgtcttg ccagggccat 960
c 961

<210> SEQ ID NO 7
<211> LENGTH: 1503
<212> TYPE: DNA
<213> ORGANISM: West Nile virus

<400> SEQUENCE: 7
ttcaactgcc ttggaatgag caacagagac ttcttggaag gagtgtctgg agcaacatgg 60
gtggatttgg ttctcgaagg cgacagctgc gtgactatca tgtctaagga caagcctacc 120
atcgatgtga agatgatgaa tatggaggcg gccaacctgg cagaggtccg cagttattgc 180
tatttggcta ccgtcagcga tctctccacc aaagctgcgt gcccgaccat gggagaagct 240
cacaatgaca aacgtgctga cccagctttt gtgtgcagac aaggagtggt ggacaggggc 300
tggggcaacg gctgcggact atttggcaaa ggaagcattg acacatgcgc caaatttgcc 360
tgctctacca aggcaatagg aagaaccatc ttgaaagaga atatcaagta cgaagtggcc 420
atttttgtcc atggaccaac tactgtggag tcgcacggaa actactccac acaggttgga 480
gccactcagg cagggagatt cagcatcact cctgcggcgc cttcacacac actaaagctt 540
ggagaatatg gagaggtgac agtggactgt gaaccacggt cagggattga caccaatgca 600
tactacgtga tgactgttgg aacaaagacg ttcttggtcc atcgtgagtg gttcatggac 660
ctcaacctcc cttggagcag tgctggaagt actgtgtgga ggaacagaga gacgttaatg 720
gagtttgagg aaccacacgc cacgaagcag tctgtgatag cattgggctc acaagaggga 780
gctctgcagc aagctttggc tggagccatt cctgtggaat tttcaagcaa cactgtcaag 840
ttgacgtcgg gtcatttgaa gtgtagagtg aagatggaaa aattgcagtt gaagggaaca 900
acctatggcg tctgttcaaa ggctttcaag tttcttggga ctcccgcaga cacaggtcac 960
ggcactgtgg tgttggaatt gcagtacact ggcacggatg gaccttgcaa agttcctatc 1020
tcgtcagtgg cttcattgaa cgacctaacg ccagtgggca gattggtcac tgtcaaccct 1080
tttgtttcag tggccacggc caacgctaag gtcctgattg aattggaacc accctttgga 1140
gactcataca tagtggtggg cagaggagaa caacagatca atcaccattg gcacaagtct 1200
ggaagcagca ttggcaaagc ctttacaacc accctcaaag gagcgcagag actagccgct 1260
ctaggagaca cagcttggga ctttggatca gttggagggg tgttcacctc agttgggaag 1320
gctgtccatc aagtgttcgg aggagcattc cgctcactgt tcggaggcat gtcctggata 1380
acgcaaggat tgctgggggc tctcctgttg tggatgggca tcaatgctcg tgataggtcc 1440
atagctctca cgtttctcgc agttggagga gttctgctct tcctctccgt gaacgtgcac 1500
gct 1503

<210> SEQ ID NO 8
<211> LENGTH: 1503
<212> TYPE: DNA
<213> ORGANISM: West Nile virus

<400> SEQUENCE: 8

```
ttcaactgcc ttggaatgag caacagagac ttcttggaag gagtgtctgg agcaacatgg      60

gtggatttgg ttctcgaagg cgacagctgc gtgactatca tgtctaagga caagcctacc     120

atcgatgtga agatgatgaa tatggaggcg gccaacctgg cagaggtccg cagttattgc     180

tatttggcta ccgtcagcga tctctccacc aaagctgcgt gcccgaccat gggagaagct     240

cacaatgaca aacgtgctga cccagctttt gtgtgcagac aaggagtggt ggacaggggc     300

tggggcaacg gctgcggact atttggcaaa ggaagcattg acacatgcgc caaatttgcc     360

tgctctacca aggcaatagg aagaaccatc ttgaaagaga atatcaagta cgaagtggcc     420

atttttgtcc atggaccaac tactgtggag tcgcacggaa actattccac acaggctgga     480

gccactcagg cagggagatt cagcatcact cctgcggcgc cttcatacac actaaagctt     540

ggagaatatg gagaggtgac agtggactgt gaaccacggt cagggattga caccaatgca     600

tactacgtga tgactgttgg aacaaagacg ttcttggtcc atcgtgagtg gttcatggac     660

ctcaacctcc cttggagcag tgctggaagt actgtgtgga ggaacagaga gacgttaatg     720

gagtttgagg aaccacacgc cacgaagcag tctgtgatag cattgggctc acaagaggga     780

gctctgcatc aagctttggc tggagccatt cctgtggaat tttcaagcaa cactgtcaag     840

ttgacgtcgg gtcatttgaa gtgtagagtg aagatggaaa aattgcagtt gaagggaaca     900

acctatggcg tctgttcaaa ggctttcaag tttcttggga ctcccgcaga cacaggtcac     960

ggcactgtgg tgttggaatt gcagtacact ggcacggatg gaccttgcaa agttcctatc    1020

tcgtcagtgg cttcattgaa cgacctaacg ccagtgggca gattggtcac tgtcaaccct    1080

tttgtttcag tggccacggc caacgctaag gtcctgattg aattggaacc accctttgga    1140

gactcataca tagtggtggg cagaggagaa caacagatca atcaccattg gcacaagtct    1200

ggaagtagca ttggcaaagc ctttacaacc accctcaaag gagcgcagag actagccgct    1260

ctaggagaca cagcttggga ctttggatca gttggagggg tgttcacctc agttgggaag    1320

gctgtccatc aagtgttcgg aggagcattc cgctcactgt tcggaggcat gtcctggata    1380

acgcaaggat tgctgggggc tctcctgttg tggatgggca tcaatgctcg tgataggtcc    1440

atagctctca cgtttctcgc agttggagga gttctgctct tcctctccgt gaacgtgcat    1500

gct                                                                  1503
```

```
<210> SEQ ID NO 9
<211> LENGTH: 1376
<212> TYPE: DNA
<213> ORGANISM: West Nile virus
<220> FEATURE:
<221> NAME/KEY: modified_base
<222> LOCATION: (1358)..(1358)
<223> OTHER INFORMATION: a, c, g or t

<400> SEQUENCE: 9
```

```
gatgtggaga gaatatggag gcggccaacc tggcagaggt ccgcagttat tgctatttgg      60

ctaccgtcag cgatctctcc accaaagctg cgtgcccgac catgggagaa gctcacaatg     120

acaaacgtgc tgacccagct tttgtgtgca gacaaggagt ggtggacagg ggctggggca     180

acggctgcgg actatttggc aaaggaagca ttgacacatg cgccaaattt gcctgctcta     240

ccaaggcaat aggaagaacc atcttgaaag agaatatcaa gtacgaagtg gccatttttg     300

tccatggacc aactactgtg gagtcgcacg gaaactactc cacacaggtt ggagccactc     360

aggcagggag attcagcatc actcctgcgg cgccttcata cacactaaag cttggagaat     420

atggagaggt gacagtggac tgtgaaccac ggtcagggat tgacaccaat gcatactatg     480
```

-continued

```
tgatgactgt tggaacaaag acgttcttgg tccatcgtga gtggttcatg gacctcaacc    540

tcccttggag cagtgctgga agtactgtgt ggaggaacag agagacgtta atggagtttg    600

aggaaccaca cgccacgaag cagtctgtga tagcattggg ctcacaagag ggagctctgc    660

atcaagcttt ggctggagcc attcctgtgg aattttcaag caacactgtc aagttgacgt    720

cgggtcattt gaagtgtaga gtgaagatgg aaaaattgca gttgaaggga acaacctatg    780

gcgtctgttc aaaggctttc aagtttcttg ggactcccgc agacacaggt cacggcactg    840

tggtgttgga attgcagtac actggcacgg atggaccttg caaagttcct atctcgtcag    900

tggcttcatt gaacgaccta acgccagtgg gcagattggt cactgtcaac ccttttgttt    960

cagtggccac ggccaacgct aaggtcctga ttgaattgga accacccttt ggagactcat   1020

acatagtggt gggcagagga gaacaacaga tcaatcacca ttggcacaag tctggaagca   1080

gcattggcaa agcctttaca accaccctca aaggagcgca gagactagcc gctctaggag   1140

acacagcttg ggactttgga tcagttggag ggtgttcac ctcagttggg aaggctgtcc   1200

atcaagtgtt cggaggagca ttccgctcac tgttcggagg catgtcctgg ataacgcaag   1260

gattgctggg ggctctcctg ttgtggatgg gcatcaatgc tcgtgatagg tccatagctc   1320

tcacgtttct cgcagttgga ggagttctgc tcttcctntc cgtgaacgtg cacgct       1376
```

<210> SEQ ID NO 10
<211> LENGTH: 1376
<212> TYPE: DNA
<213> ORGANISM: West Nile virus

<400> SEQUENCE: 10

```
gatgtggaga gaatatggag gcggccaacc tggcagaggt ccgcagttat tgctatttgg     60

ctaccgtcag cgatctctcc accaaagctg cgtgcccgac catgggagaa gctcacaatg    120

acaaacgtgc tgacccagct tttgtgtgca gacaaggagt ggtggacagg ggctggggca    180

acggctgcgg actatttggc aaaggaagca ttgacacatg cgccaaattt gcctgctcta    240

ccaaggcaat aggaagaacc atcttgaaag agaatatcaa gtacgaagtg gccatttttg    300

tccatggacc aactactgtg gagtcgcacg gaaactactc cacacaggct ggagccactc    360

aggcagggag attcagcatc actcctgcgg cgccttcata cacactaaag cttggagaat    420

atggagaggt gacagtggac tgtgaaccac ggtcagggat tgacaccaat gcatactacg    480

tgatgactgt tggaacaaag acgttcttgg tccatcgtga gtggttcatg gacctcaacc    540

tcccttggag cagtgctgga agtactgtgt ggaggaacag agagacgtta atggagtttg    600

aggaaccaca cgccacgaag cagtctgtga tagcattggg ctcacaagag ggagctctgc    660

atcaagcttt ggctggagcc attcctgtgg aattttcaag caacactgtc aagttgacgt    720

cgggtcattt gaagtgtaga gtgaagatgg aaaaattgca gttgaaggga acaacctatg    780

gcgtctgttc aaaggctttc aagtttcttg ggactcccgc agacacaggt cacggcactg    840

tggtgttgga attgcagtac actggcacgg atggaccttg caaagttcct atctcgtcag    900

tggcttcatt gaacgaccta acgccagtgg gcagattggt cactgtcaac ccttttgttt    960

cagtggccac ggccaacgct aaggtcctga ttgaattgga accacccttt ggagactcat   1020

acatagtggt gggcagagga gaacaacaga tcaatcacca ttggcacaag tctggaagca   1080

gcattggcaa agcctttaca accaccctca aaggagcgca gagactagcc gctctaggag   1140

acacagcttg ggactttgga tcagttggag ggtgttcac ctcagttggg aaggctgtcc   1200
```

-continued

```
atcaagtgtt cggaggagca ttccgctcac tgttcggagg catgtcctgg ataacgcaag   1260

gattgctggg ggctctcctg ttgtggatgg gcatcaatgc tcgtgatagg tccatagctc   1320

tcacgtttct cgcagttgga ggagttctgc tcttcctctc cgtgaacgtg catgct       1376


<210> SEQ ID NO 11
<211> LENGTH: 1376
<212> TYPE: DNA
<213> ORGANISM: West Nile virus

<400> SEQUENCE: 11

gatgtggaga gaatatggag gcggccaacc tggcagaggt ccgcagttat tgctatttgg     60

ctaccgtcag cgatctctcc accaaagctg cgtgcccgac catgggagaa gctcacaatg    120

acaaacgtgc tgacccagct tttgtgtgca gacaaggagt ggtggacagg ggctggggca    180

acggctgcgg actatttggc aaaggaagca ttgacacatg cgccaaattt gcctgctcta    240

ccaaggcaat aggaagaacc atcttgaaag agaatatcaa gtacgaagtg gccatttttg    300

tccatggacc aactactgtg gagtcgcacg gaaactactc cacacaggct ggagccactc    360

aggcagggag attcagcatc actcctgcgg cgccttcata cacactaaag cttggagaat    420

atggagaggt gacagtggac tgtgaaccac ggtcagggat tgacaccaat gcatactacg    480

tgatgactgt tggaacaaag acgttcttgg tccatcgtga gtggttcatg gacctcaacc    540

tcccttggag cagtgctgga agtactgtgt ggaggaacag agagacgtta atggagtttg    600

aggaaccaca cgccacgaag cagtctgtga tagcattggg ctcacaagag ggagctctgc    660

atcaagcttt ggctggagcc attcctgtgg aattttcaag caacactgtc aagttgacgt    720

cgggtcattt gaagtgtaga gtgaagatgg aaaaattgca gttgaaggga acaacctatg    780

gcgtctgttc aaaggctttc aagtttcttg ggactcccgc agacacaggt cacggcactg    840

tggtgttgga attgcagtac actggcacgg atggaccttg caaagttcct atctcgtcag    900

tggcttcatt gaacgatcta acgccagtgg gcagattggt cactgtcaac ccttttgttt    960

cagtggccac ggccaacgct aaggtcctga ttgaattgga accacccttt ggagactcat   1020

acatagtggt gggcagagga gaacaacaga tcaatcacca ttggcacaag tctggaagca   1080

gcattggcaa agcctttaca accaccctca aaggagcgca gagactagcc gctctaggag   1140

acacagcttg ggactttgga tcagttggag gggtgttcac ctcagttggg aaggctgtcc   1200

atcaagtgtt cggaggagca ttccgcacac tgttcggagg catgtcctgg ataacgcaag   1260

gattgctggg ggctctcctg ttgtggatgg gcatcaatgc tcgtgatagg tccatagctc   1320

tcacgtttct cgcagttgga ggagttctgc tcttcctctc cgtgaacgtg catgct       1376


<210> SEQ ID NO 12
<211> LENGTH: 608
<212> TYPE: DNA
<213> ORGANISM: West Nile virus

<400> SEQUENCE: 12

cggggggaat gtcacacttg catttacaac atgatgggaa agagagagaa aaaacccgga     60

gaattcggaa aggccaaggg aagcagagcc atttggttca tgtggctcgg agctcgcttt    120

ctggagttcg aggctctggg ttttctcaat gaagaccact ggcttggaag aaagaactca    180

ggaggaggtg tcgagggctt gggcctccaa aaactgggtt acatcctgcg tgaagttggc    240

acccggcctg gggcaagat ctatgctgat gacacagctg gctgggacac ccgcatcacg    300

agagctgact tggaaaatga agctaaggtg cttgagctgc ttgatgggga acatcggcgt    360
```

-continued cttgccaggg ccatcattga gctcacctat cgtcacaaag ttgtgaaagt gatgcgcccg 420
gctgctgatg gaagaaccgt catggatgtt atctccagag aagatcagag ggggagtgga 480
caagttgtca cctacgccct aaacactttc accaacctgg ccgtccagct ggtgaggatg 540
atggaagggg aaggagtgat tggcccagat gatgtggaga aactcacaaa agggaaagga 600
cccaaagt 608

<210> SEQ ID NO 13
<211> LENGTH: 608
<212> TYPE: DNA
<213> ORGANISM: West Nile virus

<400> SEQUENCE: 13
cggggggaat gtcacacttg catttacaac atgatgggaa agagagagaa aaaacccgga 60
gagttcggaa aggccaaggg aagcagagcc atttggttca tgtggctcgg agctcgcttt 120
ctggagttcg aggctctggg ttttctcaat gaagaccact ggcttggaag aaagaactca 180
ggaggaggtg tcgagggctt gggcctccaa aaactgggtt acatcctgcg tgaagttggc 240
acccggcctg gggcaagat ctatgctgat gacacagctg gctgggacac ccgcatcacg 300
agtgctgact tggaaaatga agctaaggtg cttgagttgc ttgatgggga acatcggcgt 360
cttgccaggg ccatcattga gctcacctat cgtcacaaag ttgtgaaagt gatgcgcccg 420
gctgctgatg gaagaaccgt catggatgtt atctccagag aagatcagag ggggagtgga 480
caagttgtca cctacgccct aaacactttc accaacctgg ccgtccagct ggtgaggatg 540
atggaagggg aaggagtgat tggcccagat gatgtggaga aactcacaaa agggaaagga 600
cccaaagt 608

<210> SEQ ID NO 14
<211> LENGTH: 981
<212> TYPE: DNA
<213> ORGANISM: West Nile virus

<400> SEQUENCE: 14
ggaactatcc ggagtatgat gtgaagctcg ctgtcaatga gtgtcaggct cttcaaaacc 60
tgggacccat ccgaaccgcc atgactgcac tactcccttc gggcagcagc gagtgttcaa 120
agagaaggtg gacacgaaag ctcgaaccgc cagaaggagt gaagtacgtg ctcaacgaga 180
ccaccaactg gttgtgggcg tttttggcca gagaaaaacg tcccagaatg tgctctcgag 240
agatagaaag gtcaacagca atgcagcttt gggtgccatg tttgaagagc agaatcaatg 300
gaggagcgcc agagaagcag ttgaagatcc aaaattttgg gagatggtgg atgaggagcg 360
cgaggcacat ctgcgggggg aatgtcacac ttgcatttac aacatgatgg gaaagagaga 420
gaaaaaaccc ggagagttcg gaaaggccaa gggaagcaga gccatttggt tcatgtggct 480
cggagctcgc tttctggagt tcgaggctct gggttttctc aatgaagatc actggcttgg 540
aagaaagaac tcaggaggag gtgtcgaggg cttgggcctc caaaaactgg gttacatcct 600
gcgtgaagtt ggcacccggc ctgggggcaa gatctatgct gatgacacag ctggctggga 660
cacccgcatc acgagagctg acttggaaaa tgaagctaag gtgcttgagc tgcttgatgg 720
ggaacatcgg cgtcttgcca gggccatcat tgagctcacc tatcgtcaca aagttgtgaa 780
agtgatgcgc ccggctgctg atggaagaac cgtcatggat gttatctcca gagaagatca 840
gagggggagt ggacaagttg tcacctacgc cctaaacact ttcaccaacc tggccgtcca 900

-continued gctggtgagg atgatggaag gggaaggagt gattggccca gatgatgtgg agaaactcac 960
aaaagggaaa ggacccaaag t 981

<210> SEQ ID NO 15
<211> LENGTH: 974
<212> TYPE: DNA
<213> ORGANISM: West Nile virus

<400> SEQUENCE: 15
ttcgctgtca atggagtgtc aggctcctct caaaaccatg ggacaccatc acgaatccac 60
catggccatg actgacacta ctcccttcgg gcagcagcga gtgttcaaag agaaggtgga 120
cacgaaagct gaaccgccag aaggagtgaa gtacgtgctc aacgagacca ccaactggtt 180
gtgggcgttt ttggccagag aaaaacgtcc cagaatgtgc tctcgagagg aattcataga 240
aaggtcaaca gcaatgcagc tttgggtgcc atgtttgaag agcagaatca atggaggagc 300
gccagagaag cagttgaaga tccaaaattt tgggagatgg tggatgagga gcgcgaggca 360
catctgcggg gggaatgtca cacttgcatt tacaacatga tgggaaagag agagaaaaaa 420
cccggagagt tcggaaaggc caagggaagc agagccattt ggttcatgtg gctcggagct 480
cgctttctgg agttcgaggc tctgggtttt ctcaatgaag accactggct tggaagaaag 540
aactcaggag gaggtgtcga gggcttgggc ctccaaaaac tgggttacat cctgcgtgaa 600
gttggcaccc ggcctggggg caagatctat gctgatgaca cagctggctg ggacacccgc 660
atcacgagag ctgacttgga aaatgaagct aaggtgcttg agttgcttga tggggaacat 720
cggcgtcttg ccagggccat cattgagctc acctatcgtc acaaagttgt gaaagtgatg 780
cgcccggctg ctgatggaag aaccgtcatg gatgttatct ccagagaaga tcagaggggg 840
agtggacaag ttgtcaccta cgccctaaac actttcacca acctggccgt ccagctggtg 900
aggatgatgg aaggggaagg agtgattggc ccagatgatg tggagaaact cacaaaaggg 960
aaaggaccca aagt 974

<210> SEQ ID NO 16
<211> LENGTH: 970
<212> TYPE: DNA
<213> ORGANISM: West Nile virus

<400> SEQUENCE: 16
aatggagggt caggctcctc tcaaaacctg ggacaccatc acgaatgtac caccatggcc 60
atgactgaca ctactccctt cgggcagcag cgagtgttca aagagaaggt ggacacgaaa 120
gctctgaacc gccagaagga gtgaagtacg tgctcaacga gaccaccaac tggttgtggg 180
cgtttttggc cagagaaaaa cgtcccagaa tgtgctctcg agaggaattc ataagaaagg 240
tcaacagcaa tgcagctttg ggtgccatgt ttgaagagca gaatcaatgg aggagcgcca 300
gagaagcagt tgaagatcca aaattttggg agatggtgga tgaggagcgc gaggcacatc 360
tgcgggggga atgtcacact tgcatttaca acatgatggg aaagagagag aaaaaacccg 420
gagagttcgg aaaggctaag ggaagcagag ccatttggtt catgtggctc ggagctcgct 480
ttctggagtt cgaggctctg ggttttctca atgaagacca ctggcttgga agaaagaact 540
caggaggagg tgtcgagggc ttgggcctcc aaaaactggg ttacatcctg cgtgaagttg 600
gcacccgacc tgggggcaag atctatgctg atgacacagc cggctgggac acccgcatca 660
cgagagctga cttggaaaat gaagctaagg tgcttgagtt gcttgatggg gaacatcggc 720
gtcttgccag ggccatcatt gagctcacct atcgtcacaa agttgtgaaa gtgatgcgcc 780
cggctgctga tggaagaacc gtcatggatg ttatctccag agaagatcag agggggagtg 840
gacaagttgt cacctacgcc ctaaacactt tcaccaacct ggccgtccag ctggtgagga 900
tgatggaagg ggaaggagtg attggcccag atgatgtgga gaaactcaca aaagggaaag 960
gacccaaagt 970

<210> SEQ ID NO 17
<211> LENGTH: 1503
<212> TYPE: DNA
<213> ORGANISM: West Nile virus

<400> SEQUENCE: 17
ttcaactgcc ttggaatgag caacagagac ttcttggaag gagtgtctgg agcaacatgg 60
gtggatttgg ttctcgaagg cgacagctgc gtgactatca tgtctaagga caagcctacc 120
atcgatgtga agatgatgaa tatggaggcg gccaacctgg cagaggtccg cagttattgc 180
tatttggcta ccgtcagcga tctctccacc aaagctgcgt gcccgaccat gggagaagct 240
cacaatgaca aacgtgctga cccagctttt gtgtgcagac aaggagtggt ggacaggggc 300
tggggcaacg gctgcggact atttggcaaa ggaagcattg acacatgcgc caaatttgcc 360
tgctctacca aggcaatagg aagaaccatc ttgaaagaga atatcaagta cgaagtggcc 420
atttttgtcc atggaccaac tactgtggag tcgcacggaa actactccac acaggttgga 480
gccactcagg cagggagatt cagcatcact cctgcggcgc cttcacacac actaaagctt 540
ggagaatatg gagaggtgac agtggactgt gaaccacggt cagggattga caccaatgca 600
tactacgtga tgactgttgg aacaaagacg ttcttggtcc atcgtgagtg gttcatggac 660
ctcaacctcc cttggagcag tgctggaagt actgtgtgga ggaacagaga gacgttaatg 720
gagtttgagg aaccacacgc cacgaagcag tctgtgatag cattgggctc acaagaggga 780
gctctgcagc aagctttggc tggagccatt cctgtggaat tttcaagcaa cactgtcaag 840
ttgacgtcgg gtcatttgaa gtgtagagtg aagatggaaa aattgcagtt gaagggaaca 900
acctatggcg tctgttcaaa ggctttcaag tttcttggga ctcccgcaga cacaggtcac 960
ggcactgtgg tgttggaatt gcagtacact ggcacggatg gaccttgcaa agttcctatc 1020
tcgtcagtgg cttcattgaa cgacctaacg ccagtgggca gattggtcac tgtcaaccct 1080
tttgtttcag tggccacggc caacgctaag gtcctgattg aattggaacc accctttgga 1140
gactcataca tagtggtggg cagaggagaa caacagatca atcaccattg gcacaagtct 1200
ggaagcagca ttggcaaagc ctttacaacc accctcaaag gagcgcagag actagccgct 1260
ctaggagaca cagcttggga ctttggatca gttggagggg tgttcacctc agttgggaag 1320
gctgtccatc aagtgttcgg aggagcattc cgctcactgt tcggaggcat gtcctggata 1380
acgcaaggat tgctgggggc tctcctgttg tggatgggca tcaatgctcg tgataggtcc 1440
atagctctca cgtttctcgc agttggagga gttctgctct tcctctccgt gaacgtgcac 1500
gct 1503

<210> SEQ ID NO 18
<211> LENGTH: 1503
<212> TYPE: DNA
<213> ORGANISM: West Nile virus

<400> SEQUENCE: 18
ttcaactgcc ttggaatgag caacagagac ttcttggaag gagtgtctgg agcaacatgg 60

-continued

```
gtggatttgg ttctcgaagg cgacagctgc gtgactatca tgtctaagga caagcctacc    120

atcgatgtga agatgatgaa tatggaggcg gccaacctgg cagaggtccg cagttattgc    180

tatttggcta ccgtcagcga tctctccacc aaagctgcgt gcccgaccat gggagaagct    240

cacaatgaca aacgtgctga cccagctttt gtgtgcagac aaggagtggt ggacaggggc    300

tggggcaacg gctgcggact atttggcaaa ggaagcattg acacatgcgc caaatttgcc    360

tgctctacca aggcaatagg aagaaccatc ttgaaagaga atatcaagta cgaagtggcc    420

atttttgtcc atggaccaac tactgtggag tcgcacggaa actattccac acaggctgga    480

gccactcagg cagggagatt cagcatcact cctgcggcgc cttcatacac actaaagctt    540

ggagaatatg gagaggtgac agtggactgt gaaccacggt cagggattga caccaatgca    600

tactacgtga tgactgttgg aacaaagacg ttcttggtcc atcgtgagtg gttcatggac    660

ctcaacctcc cttggagcag tgctggaagt actgtgtgga ggaacagaga gacgttaatg    720

gagtttgagg aaccacacgc cacgaagcag tctgtgatag cattgggctc acaagaggga    780

gctctgcatc aagctttggc tggagccatt cctgtggaat tttcaagcaa cactgtcaag    840

ttgacgtcgg gtcatttgaa gtgtagagtg aagatggaaa aattgcagtt gaagggaaca    900

acctatggcg tctgttcaaa ggctttcaag tttcttggga ctcccgcaga cacaggtcac    960

ggcactgtgg tgttggaatt gcagtacact ggcacggatg gaccttgcaa agttcctatc   1020

tcgtcagtgg cttcattgaa cgacctaacg ccagtgggca gattggtcac tgtcaaccct   1080

tttgtttcag tggccacggc caacgctaag gtcctgattg aattggaacc accctttgga   1140

gactcataca tagtggtggg cagaggagaa caacagatca atcaccattg gcacaagtct   1200

ggaagtagca ttggcaaagc ctttacaacc accctcaaag gagcgcagag actagccgct   1260

ctaggagaca cagcttggga ctttggatca gttggagggg tgttcacctc agttgggaag   1320

gctgtccatc aagtgttcgg aggagcattc cgctcactgt tcggaggcat gtcctggata   1380

acgcaaggat tgctgggggc tctcctgttg tggatgggca tcaatgctcg tgataggtcc   1440

atagctctca cgtttctcgc agttggagga gttctgctct tcctctccgt gaacgtgcat   1500

gct                                                                  1503
```

<210> SEQ ID NO 19
<211> LENGTH: 968
<212> TYPE: DNA
<213> ORGANISM: West Nile virus
<220> FEATURE:
<221> NAME/KEY: modified_base
<222> LOCATION: (7)..(7)
<223> OTHER INFORMATION: a, c, g or t
<220> FEATURE:
<221> NAME/KEY: modified_base
<222> LOCATION: (10)..(10)
<223> OTHER INFORMATION: a, c, g or t
<220> FEATURE:
<221> NAME/KEY: modified_base
<222> LOCATION: (13)..(13)
<223> OTHER INFORMATION: a, c, g or t
<220> FEATURE:
<221> NAME/KEY: modified_base
<222> LOCATION: (941)..(942)
<223> OTHER INFORMATION: a, c, g or t

<400> SEQUENCE: 19

```
gatgtgngan gangaatatg gaggcggcca acctggcaga ggtccgcagt tattgctatt     60

tggctaccgt cagcgatctc tccaccaaag ctgcgtgccc gaccatggga gaagctcaca    120

atgacaaacg tgctgaccca gcttttgtgt gcagacaagg agtggtggac aggggctggg    180
```

```
gcaacggctg cggactattt ggcaaaggaa gcattgacac atgcgccaaa tttgcctgct    240

ctaccaaggc aataggaaga accatcttga aagagaatat caagtacgaa gtggccattt    300

ttgtccatgg accaactact gtggagtcgc acggaaacta ctccacacag gctggagcca    360

ctcaggcagg gagattcagc atcactcctg cggcgccttc atacacacta aagcttggag    420

aatatggaga ggtgacagtg gactgtgaac cacggtcagg gattgacacc aatgcatact    480

acgtgatgac tgttggaaca aagacgttct tggtccatcg tgagtggttc atggacctca    540

acctcccttg gagcagtgct ggaagtactg tgtggaggaa cagagagacg ttaatggagt    600

ttgaggaacc acacgccacg aagcagtctg tgatagcatt gggctcacaa gagggagctc    660

tgcatcaagc tttggctgga gccattcctg tggaattttc aagcaacact gtcaagttga    720

cgtcgggtca tttgaagtgt agagtgaaga tggaaaaatt gcagttgaag ggaacaacct    780

atggcgtctg ttcaaaggct ttcaagtttc ttgggactcc cgcagacaca ggtcacggca    840

ctgtggtgtt ggaattgcag tacactggca cggatggacc ttgcaaagtt cctatctcgt    900

cagtggcttc attgaacgat ctaacgccag tgggcagatt nntcactgtc aacccttttg    960

tttcagtg                                                              968
```

<210> SEQ ID NO 20
<211> LENGTH: 979
<212> TYPE: DNA
<213> ORGANISM: West Nile virus
<220> FEATURE:
<221> NAME/KEY: modified_base
<222> LOCATION: (4)..(4)
<223> OTHER INFORMATION: a, c, g or t
<220> FEATURE:
<221> NAME/KEY: modified_base
<222> LOCATION: (6)..(6)
<223> OTHER INFORMATION: a, c, g or t
<220> FEATURE:
<221> NAME/KEY: modified_base
<222> LOCATION: (10)..(10)
<223> OTHER INFORMATION: a, c, g or t
<220> FEATURE:
<221> NAME/KEY: modified_base
<222> LOCATION: (974)..(974)
<223> OTHER INFORMATION: a, c, g or t

<400> SEQUENCE: 20

```
cttnanagan atcaagtacg aagtggccat ttttgtccat ggaccaacta ctgtggagtc     60

gcacggaaac tactccacac aggctggagc cactcaggca gggagattca gcatcactcc    120

tgcggcgcct tcatacacac taaagcttgg agaatatgga gaggtgacag tggactgtga    180

accacggtca gggattgaca ccaatgcata ctacgtgatg actgttggaa caaagacgtt    240

cttggtccat cgtgagtggt tcatggacct caacctccct tggagcagtg ctggaagtac    300

tgtgtggagg aacagagaga cgttaatgga gtttgaggaa ccacacgcca cgaagcagtc    360

tgtgatagca ttgggctcac aagagggagc tctgcatcaa gctttggctg gagccattcc    420

tgtggaattt tcaagcaaca ctgtcaagtt gacgtcgggt catttgaagt gtagagtgaa    480

gatggaaaaa ttgcagttga agggaacaac ctatggcgtc tgttcaaagg ctttcaagtt    540

tcttgggact cccgcagaca caggtcacgg cactgtggtg ttggaattgc agtacactgg    600

cacggatgga ccttgcaaag ttcctatctc gtcagtggct tcattgaacg atctaacgcc    660

agtgggcaga ttggtcactg tcaacccttt tgtttcagtg gccacggcca acgctaaggt    720

cctgattgaa ttggaaccac cctttggaga ctcatacata gtggtgggca gaggagaaca    780
```

-continued

```
acagatcaat caccattggc acaagtctgg aagcagcatt ggcaaagcct ttacaaccac    840

cctcaaagga gcgcagagac tagccgctct aggagacaca gcttgggact ttggatcagt    900

tggaggggtg ttcacctcag ttgggaaggc tgtccatcaa gtgttcggag gagcattccg    960

cacactgttc ggangcatg                                                 979


<210> SEQ ID NO 21
<211> LENGTH: 1004
<212> TYPE: DNA
<213> ORGANISM: West Nile virus
<220> FEATURE:
<221> NAME/KEY: modified_base
<222> LOCATION: (4)..(4)
<223> OTHER INFORMATION: a, c, g or t
<220> FEATURE:
<221> NAME/KEY: modified_base
<222> LOCATION: (12)..(12)
<223> OTHER INFORMATION: a, c, g or t
<220> FEATURE:
<221> NAME/KEY: modified_base
<222> LOCATION: (14)..(15)
<223> OTHER INFORMATION: a, c, g or t
<220> FEATURE:
<221> NAME/KEY: modified_base
<222> LOCATION: (17)..(17)
<223> OTHER INFORMATION: a, c, g or t
<220> FEATURE:
<221> NAME/KEY: modified_base
<222> LOCATION: (32)..(32)
<223> OTHER INFORMATION: a, c, g or t
<220> FEATURE:
<221> NAME/KEY: modified_base
<222> LOCATION: (35)..(35)
<223> OTHER INFORMATION: a, c, g or t

<400> SEQUENCE: 21

agantatgga gngnngncag tggactgtga anccncggtc agggattgac accaatgcat     60

actacgtgat gactgttgga acaaagacgt tcttggtcca tcgtgagtgg ttcatggacc    120

tcaacctccc ttggagcagt gctggaagta ctgtgtggag gaacagagag acgttaatgg    180

agtttgagga accacacgcc acgaagcagt ctgtgatagc attgggctca caagagggag    240

ctctgcatca agctttggct ggagccattc ctgtggaatt ttcaagcaac actgtcaagt    300

tgacgtcggg tcatttgaag tgtagagtga agatggaaaa attgcagttg aagggaacaa    360

cctatggcgt ctgttcaaag gctttcaagt ttcttgggac tcccgcagac acaggtcacg    420

gcactgtggt gttggaattg cagtacactg gcacggatgg accttgcaaa gttcctatct    480

cgtcagtggc ttcattgaac gatctaacgc cagtgggcag attggtcact gtcaaccctt    540

ttgtttcagt ggccacggcc aacgctaagg tcctgattga attggaacca ccctttggag    600

actcatacat agtggtgggc agaggagaac aacagatcaa tcaccattgg cacaagtctg    660

gaagcagcat tggcaaagcc tttacaacca ccctcaaagg agcgcagaga ctagccgctc    720

taggagacac agcttgggac tttggatcag ttggaggggt gttcacctca gttgggaagg    780

ctgtccatca agtgttcgga ggagcattcc gcacactgtt cggaggcatg tcctggataa    840

cgcaaggatt gctgggggct ctcctgttgt ggatgggcat caatgctcgt gataggtcca    900

tagctctcac gtttctcgca gttggaggag ttctgctctt cctctccgtg aacgtgcatg    960

ctgacactgg gtgtgccata gacatcagcc ggcaagagct gaga                    1004


<210> SEQ ID NO 22
<211> LENGTH: 1006
<212> TYPE: DNA
<213> ORGANISM: West Nile virus
```

<220> FEATURE:
<221> NAME/KEY: modified_base
<222> LOCATION: (28)..(28)
<223> OTHER INFORMATION: a, c, g or t
<220> FEATURE:
<221> NAME/KEY: modified_base
<222> LOCATION: (996)..(996)
<223> OTHER INFORMATION: a, c, g or t
<220> FEATURE:
<221> NAME/KEY: modified_base
<222> LOCATION: (1004)..(1004)
<223> OTHER INFORMATION: a, c, g or t

<400> SEQUENCE: 22
agcagtgctg gaagtactgt gtggaggnaa cagagagacg ttaatggagt ttgaggaacc 60
acacgccacg aagcagtctg tgatagcatt gggctcacaa gagggagctc tgcatcaagc 120
tttggctgga gccattcctg tggaattttc aagcaacact gtcaagttga cgtcgggtca 180
tttgaagtgt agagtgaaga tggaaaaatt gcagttgaag ggaacaacct atggcgtctg 240
ttcaaaggct ttcaagtttc ttgggactcc cgcagacaca ggtcacggca ctgtggtgtt 300
ggaattgcag tacactggca cggatggacc ttgcaaagtt cctatctcgt cagtggcttc 360
attgaacgat ctaacgccag tgggcagatt ggtcactgtc aacccttttg tttcagtggc 420
cacggccaac gctaaggtcc tgattgaatt ggaaccaccc tttggagact catacatagt 480
ggtgggcaga ggagaacaac agatcaatca ccattggcac aagtctggaa gcagcattgg 540
caaagccttt acaaccaccc tcaaaggagc gcagagacta gccgctctag gagacacagc 600
ttgggacttt ggatcagttg gaggggtgtt cacctcagtt gggaaggctg tccatcaagt 660
gttcggagga gcattccgca cactgttcgg aggcatgtcc tggataacgc aaggattgct 720
gggggctctc ctgttgtgga tgggcatcaa tgctcgtgat aggtccatag ctctcacgtt 780
tctcgcagtt ggaggagttc tgctcttcct ctccgtgaac gtgcatgctg acactgggtg 840
tgccatagac atcagccggc aagagctgag atgtggaagt ggagtgttca tacacaatga 900
tgtggaggct tggatggacc ggtacaagta ttaccctgaa acgccacaag gcctagccaa 960
gatcattcag aaagctcata aggaaggagt gtgcgntcta cganca 1006

<210> SEQ ID NO 23
<211> LENGTH: 11029
<212> TYPE: DNA
<213> ORGANISM: West Nile virus

<400> SEQUENCE: 23
agtagttcgc ctgtgtgagc tgacaaactt agtagtgttt gtgaggatta acaacaatta 60
acacagtgcg agctgtttct tagcacgaag atctcgatgt ctaagaaacc aggagggccc 120
ggcaagagcc gggctgtcaa tatgctaaaa cgcggaatgc cccgcgtgtt gtccttgatt 180
ggactgaaga gggctatgtt gagcctgatc gacggcaagg ggccaatacg atttgtgttg 240
gctctcttgg cgttcttcag gttcacagca attgctccga cccgagcagt gctggatcga 300
tggagaggtg tgaacaaaca aacagcgatg aaacaccttc tgagttttaa gaaggaacta 360
gggaccttga ccagtgctat caatcggcgg agctcaaaac aaaagaaaag aggaggaaag 420
accggaattg cagtcatgat tggcctgatc gccagcgtag gagcagttac cctctctaac 480
ttccaaggga aggtgatgat gacggtaaat gctactgacg tcacagatgt catcacgatt 540
ccaacagctg ctggaaagaa cctatgcatt gtcagagcaa tggatgtggg atacatgtgc 600
gatgatacta tcacttatga atgcccagta ctgtcggctg gtaatgatcc agaagacatc 660

-continued

```
gactgttggt gcacaaagtc agcagtctac gtcaggtatg gaagatgcac caagacacgc    720
cactcaagac gcagtcggag gtcactgaca gtgcagacac acggagaaag cactctagcg    780
aacaagaagg gggcttggat ggacagcacc aaggccacaa ggtatttggt aaaaacagaa    840
tcatggatct tgaggaaccc tggatatgcc ctggtggcag ccgtcattgg ttggatgctt    900
gggagcaaca ccatgcagag agttgtgttt gtcgtgctat tgcttttggt ggccccagct    960
tacagcttca actgccttgg aatgagcaac agagacttct tggaaggagt gtctggagca   1020
acatgggtgg atttggttct cgaaggcgac agctgcgtga ctatcatgtc taaggacaag   1080
cctaccatcg atgtgaagat gatgaatatg gaggcggcca acctggcaga ggtccgcagt   1140
tattgctatt tggctaccgt cagcgatctc tccaccaaag ctgcgtgccc gaccatggga   1200
gaagctcaca atgacaaacg tgctgaccca gcttttgtgt gcagacaagg agtggtggac   1260
aggggctggg gcaacggctg cggactattt ggcaaaggaa gcattgacac atgcgccaaa   1320
tttgcctgct ctaccaaggc aataggaaga accatcttga aagagaatat caagtacgaa   1380
gtggccattt ttgtccatgg accaactact gtggagtcgc acggaaacta ctccacacag   1440
gttggagcca ctcaggcagg gagactcagc atcactcctg cggcgccttc atacacacta   1500
aagcttggag aatatggaga ggtgacagtg gactgtgaac cacggtcagg gattgacacc   1560
aatgcatact acgtgatgac tgttggaaca aagacgttct tggtccatcg tgagtggttc   1620
atggacctca acctcccttg gagcagtgct ggaagtactg tgtggaggaa cagagagacg   1680
ttaatggagt ttgaggaacc acacgccacg aagcagtctg tgatagcatt gggctcacaa   1740
gagggagctc tgcatcaagc tttggctgga gccattcctg tggaattttc aagcaacact   1800
gtcaagttga cgtcgggtca tttgaagtgt agagtgaaga tggaaaaatt gcagttgaag   1860
ggaacaacct atggcgtctg ttcaaaggct ttcaagtttc ttgggactcc cgcagacaca   1920
ggtcacggca ctgtggtgtt ggaattgcag tacactggca cggatggacc ttgcaaagtt   1980
cctatctcgt cagtggcttc attgaacgac ctaacgccag tgggcagatt ggtcactgtc   2040
aacccttttg tttcagtggc cacggccaac gctaaggtcc tgattgaatt ggaaccaccc   2100
tttggagact catacatagt ggtgggcaga ggagaacaac agatcaatca ccattggcac   2160
aagtctggaa gcagcattgg caaagccttt acaaccaccc tcaaaggagc gcagagacta   2220
gccgctctag gagacacagc ttgggacttt ggatcagttg gaggggtgtt cacctcagtt   2280
gggaaggctg tccatcaagt gttcggagga gcattccgct cactgttcgg aggcatgtcc   2340
tggataacgc aaggattgct gggggctctc ctgttgtgga tgggcatcaa tgctcgtgat   2400
aggtccatag ctctcacgtt tctcgcagtt ggaggagttc tgctcttcct ctccgtgaac   2460
gtgcacgctg acactgggtg tgccatagac atcagccggc aagagctgag atgtggaagt   2520
ggagtgttca tacacaatga tgtggaggct tggatggacc ggtacaagta ttaccctgaa   2580
acgccacaag gcctagccaa gatcattcag aaagctcata aggaaggagt gtgcggtcta   2640
cgatcagttt ccagactgga gcatcaaatg tgggaagcag tgaaggacga gctgaacact   2700
cttttgaagg agaatggtgt ggaccttagt gtcgtggttg agaaacagga gggaatgtac   2760
aagtcagcac ctaaacgcct caccgccacc acggaaaaat tggaaattgg ctggaaggcc   2820
tggggaaaga gtattttatt tgcaccagaa ctcgccaaca acacctttgt ggttgatggt   2880
ccggagacca aggaatgtcc gactcagaat cgcgcttgga atagcttaga agtggaggat   2940
tttggatttg gtctcaccag cactcggatg ttcctgaagg tcagagagag caacacaact   3000
gaatgtgact cgaagatcat tggaacggct gtcaagaaca acttggcgat ccacagtgac   3060
```

```
ctgtcctatt ggattgaaag caggctcaat gatacgtgga agcttgaaag ggcagttctg   3120
ggtgaagtca aatcatgtac gtggcctgag acgcatacct tgtggggcga tggaatcctt   3180
gagagtgact tgataatacc agtcacactg gcgggaccac gaagcaatca caatcggaga   3240
cctgggtaca agacacaaaa ccagggccca tgggacgaag gccgggtaga gattgacttc   3300
gattactgcc caggaactac ggtcaccctg agtgagagct gcggacaccg tggacctgcc   3360
actcgcacca ccacagagag cggaaagttg ataacagatt ggtgctgcag gagctgcacc   3420
ttaccaccac tgcgctacca aactgacagc ggctgttggt atggtatgga gatcagacca   3480
cagagacatg atgaaaagac cctcgtgcag tcacaagtga atgcttataa tgctgatatg   3540
attgaccctt ttcagttggg ccttctggtc gtgttcttgg ccacccagga ggtccttcgc   3600
aagaggtgga cagccaagat cagcatgcca gctatactga ttgctctgct agtcctggtg   3660
tttgggggca ttacttacac tgatgtgtta cgctatgtca tcttggtggg ggcagctttc   3720
gcagaatcta attcgggagg agacgtggta cacttggcgc tcatggcgac cttcaagata   3780
caaccagtgt ttatggtggc atcgtttctc aaagcgagat ggaccaacca ggagaacatt   3840
ttgttgatgt tggcggctgt tttctttcaa atggcttatc acgatgcccg ccaaattctg   3900
ctctgggaga tccctgatgt gttgaattca ctggcggtag cttggatgat actgagagcc   3960
ataacattca caacgacatc aaacgtggtt gttccgctgc tagccctgct aacacccggg   4020
ctgagatgct tgaatctgga tgtgtacagg atactgctgt tgatggtcgg aataggcagc   4080
ttgatcaggg agaagaggag tgcagccgca aaaaagaaag gagcaagtct gctatgcttg   4140
gctctagcct caacaggact tttcaacccc atgatccttg ctgctggact gattgcatgt   4200
gatcccaacc gtaaacgcgg atggcccgca actgaagtga tgacagctgt cggcctaatg   4260
tttgccatcg tcggagggct ggcagagctt gacattgact ccatggccat tccaatgact   4320
atcgcggggc tcatgtttgc tgctttcgtg atttctggga aatcaacaga tatgtggatt   4380
gagagaacgg cggacatttc ctgggaaagt gatgcagaaa ttacaggctc gagcgaaaga   4440
gttgatgtgc ggcttgatga tgatggaaac ttccagctca tgaatgatcc aggagcacct   4500
tggaagatat ggatgctcag aatggtctgt ctcgcgatta gtgcgtacac cccctgggca   4560
atcttgccct cagtagttgg attttggata actctccaat acacaaagag aggaggcgtg   4620
ttgtgggaca ctccctcacc aaaggagtac aaaaaggggg acacgaccac cggcgtctac   4680
aggatcatga ctcgtgggct gctcggcagt tatcaagcag gagcgggcgt gatggttgaa   4740
ggtgttttcc acaccctttg gcatacaaca aaaggagccg ctttgatgag cggagagggc   4800
cgcctggacc catactgggg cagtgtcaag gaggatcgac tttgttacgg aggaccctgg   4860
aaattgcagc acaagtggaa cggccaggat gaggtgcaga tgattgtggt ggaacctggc   4920
aagaacgtta agaacgtcca gacgaaacca ggggtgttca aaacacctga aggagaaatc   4980
ggggccgtga ctttggactt ccccactgga acatcaggct caccaatagt ggacaaaaac   5040
ggtgatgtga ttgggcttta tggcaatgga gtcataatgc ccaacggctc atacataagc   5100
gcgatagtgc agggtgaaag gatggatgag ccaatcccag ccggattcga acctgagatg   5160
ctgaggaaaa aacagatcac tgtactggat ctccatcccg gcgccggtaa aacaaggagg   5220
attctgccac agatcatcaa agaggccata aacagaagac tgagaacagc cgtgctagcg   5280
ccaaccaggg ttgtggctgc tgagatggct gaagcactga gaggactgcc catccggtac   5340
cagacatccg cagtgcccag agaacataat ggaaatgaga ttgttgatgt catgtgtcat   5400
```

-continued

```
gctaccctca cccacaggct gatgtctcct cacagggtgc cgaactacaa cctgttcgtg   5460
atggatgagg ctcatttcac cgacccagct agcattgcag caagaggtta catttccaca   5520
aaggtcgagc taggggaggc ggcggcaata ttcatgacag ccaccccacc aggcacttca   5580
gatccattcc cagagtccaa ttcaccaatt tccgacttac agactgagat cccggatcga   5640
gcttggaact ctggatacga atggatcaca gaatacaccg ggaagacggt ttggtttgtg   5700
cctagtgtca agatggggaa tgagattgcc ctttgcctac aacgtgctgg aaagaaagta   5760
gtccaattga acagaaagtc gtacgagacg gagtacccaa aatgtaagaa cgatgattgg   5820
gactttgtta tcacaacaga catatctgaa atgggggcta acttcaaggc gagcagggtg   5880
attgacagcc ggaagagtgt gaaaccaacc atcataacag aaggagaagg gagagtgatc   5940
ctgggagaac catctgcagt gacagcagct agtgccgccc agagacgtgg acgtatcggt   6000
agaaatccgt cgcaagttgg tgatgagtac tgttatgggg ggcacacgaa tgaagacgac   6060
tcgaacttcg cccattggac tgaggcacga atcatgctgg acaacatcaa catgccaaac   6120
ggactgatcg ctcaattcta ccaaccagag cgtgagaagg tatataccat ggatggggaa   6180
taccggctca gaggagaaga gagaaaaaac tttctggaac tgttgaggac tgcagatctg   6240
ccagtttggc tggcttacaa ggttgcagcg gctggagtgt cataccacga ccggaggtgg   6300
tgctttgatg gtcctaggac aaacacaatt ttagaagaca acaacgaagt ggaagtcatc   6360
acgaagcttg gtgaaaggaa gattctgagg ccgcgctgga ttgatgccag ggtgtactcg   6420
gatcaccagg cactaaaggc gttcaaggac ttcgcctcgg gaaaacgttc tcagataggg   6480
ctcattgagg ttctgggaaa gatgcctgag cacttcatgg ggaagacatg ggaagcactt   6540
gacaccatgt acgttgtggc cactgcagag aaaggaggaa gagctcacag aatggccctg   6600
gaggaactgc cagatgctct tcagacaatt gccttgattg ccttattgag tgtgatgacc   6660
atgggagtat tcttcctcct catgcagcgg aagggcattg gaaagatagg tttgggaggc   6720
gctgtcttgg gagtcgcgac ctttttctgt tggatggctg aagttccagg aacgaagatc   6780
gccggaatgt tgctgctctc ccttctcttg atgattgtgc taattcctga gccagagaag   6840
caacgttcgc agacagacaa ccagctagcc gtgttcctga tttgtgtcat gacccttgtg   6900
agcgcagtgg cagccaacga gatgggttgg ctagataaga ccaagagtga cataagcagt   6960
ttgtttgggc aaagaattga ggtcaaggag aatttcagca tgggagagtt tcttctggac   7020
ttgaggccgg caacagcctg gtcactgtac gctgtgacaa cagcggtcct cactccactg   7080
ctaaagcatt tgatcacgtc agattacatc aacacctcat tgacctcaat aaacgttcag   7140
gcaagtgcac tattcacact cgcgcgaggc ttccccttcg tcgatgttgg agtgtcggct   7200
ctcctgctag cagccggatg ctggggacaa gtcaccctca ccgttacggt aacagcggca   7260
acactccttt tttgccacta tgcctacatg gttcccggtt ggcaagctga ggcaatgcgc   7320
tcagcccagc ggcggacagc ggccggaatc atgaagaacg ctgtagtgga tggcatcgtg   7380
gccacggacg tcccagaatt agagcgcacc acacccatca tgcagaagaa agttggacag   7440
atcatgctga tcttggtgtc tctagctgca gtagtagtga acccgtctgt gaagacagta   7500
cgagaagccg gaattttgat cacggccgca gcggtgacgc tttgggagaa tggagcaagc   7560
tctgtttgga acgcaacaac tgccatcgga ctctgccaca tcatgcgtgg gggttggttg   7620
tcatgtctat ccataacatg gacactcata aagaacatgg aaaaaccagg actaaaaaga   7680
ggtggggcaa aaggacgcac cttgggagag gtttggaaag aaagactcaa ccagatgaca   7740
aaagaagagt tcactaggta ccgcaaagag gccatcatcg aagtcgatcg ctcagcggca   7800
```

-continued

```
aaacacgcca ggaaagaagg caatgtcact ggagggcatc cagtctctag gggcacagca   7860
aaactgagat ggctggtcga acggaggttt ctcgaaccgg tcggaaaagt gattgacctt   7920
ggatgtggaa gaggcggttg gtgttactat atggcaaccc aaaaaagagt ccaagaagtc   7980
agagggtaca caaagggcgg tcccggacat gaagagcccc aactagtgca aagttatgga   8040
tggaacattg tcaccatgaa gagtggagtg gatgtgttct acagaccttc tgagtgttgt   8100
gacaccctcc tttgtgacat cggagagtcc tcgtcaagtg ctgaggttga agagcatagg   8160
acgattcggg tccttgaaat ggttgaggac tggctgcacc gagggccaag ggaattttgc   8220
gtgaaggtgc tctgtcccta catgccgaaa gtcatagaga agatggagct gctccaacgc   8280
cggtatgggg ggggactggt cagaaaccca ctctcacgga attccacgca cgagatgtat   8340
tgggtgagtc gagcttcagg caatgtggta cattcagtga atatgaccag ccaggtgctc   8400
ctaggaagaa tggaaaaaag gacctggaag ggaccccaat acgaggaaga tgtaaacttg   8460
ggaagtggaa ccagggcggt gggaaaaccc ctgctcaact cagacaccag taaaatcaag   8520
aacaggattg aacgactcag gcgtgagtac agttcgacgt ggcaccacga tgagaaccac   8580
ccatatagaa cctggaacta tcacggcagt tatgatgtga agcccacagg ctccgccagt   8640
tcgctggtca atggagtggt caggctcctc tcaaaaccat gggacaccat cacgaatgtt   8700
accaccatgg ccatgactga cactactccc ttcgggcagc agcgagtgtt caaagagaag   8760
gtggacacga aagctcctga accgccagaa ggagtgaagt acgtgctcaa cgagaccacc   8820
aactggttgt gggcgttttt ggccagagaa aaacgtccca gaatgtgctc tcgagaggaa   8880
ttcataagaa aggtcaacag caatgcagct ttgggtgcca tgtttgaaga gcagaatcaa   8940
tggaggagcg ccagagaagc agttgaagat ccaaaatttt gggagatggt ggatgaggag   9000
cgcgaggcac atctgcgggg ggaatgtcac acttgcattt acaacatgat gggaaagaga   9060
gagaaaaaac ccggagagtt cggaaaggcc aagggaagca gagccatttg gttcatgtgg   9120
ctcggagctc gctttctgga gttcgaggct ctgggttttc tcaatgaaga ccactggctt   9180
ggaagaaaga actcaggagg aggtgtcgag ggcttgggcc tccaaaaact gggttacatc   9240
ctgcgtgaag ttggcacccg gcctgggggc aagatctatg ctgatgacac agctggctgg   9300
gacacccgca tcacgagagc tgacttggaa aatgaagcta aggtgcttga gctgcttgat   9360
ggggaacatc ggcgtcttgc cagggccatc attgagctca cctatcgtca caaagttgtg   9420
aaagtgatgc gcccggctgc tgatggaaga accgtcatgg atgttatctc cagagaagat   9480
cagaggggga gtggacaagt tgtcacctac gccctaaaca ctttcaccaa cctggccgtc   9540
cagctggtga ggatgatgga aggggaagga gtgattggcc cagatgatgt ggagaaactc   9600
acaaaaggga aaggacccaa agtcaggacc tggctgtttg agaatgggga agaaagactc   9660
agccgcatgg ctgtcagtgg agatgactgt gtggtaaagc ccctggacga tcgctttgcc   9720
acctcgctcc acttcctcaa tgctatgtca aaggttcgca aagacatcca agagtggaaa   9780
ccgtcaactg gatggtatga ttggcagcag gttccatttt gctcaaacca tttcactgaa   9840
ttgatcatga aagatggaag aacactggtg gttccatgcc gaggacagga tgaattggta   9900
ggcagagctc gcatatctcc aggggccgga tggaacgtcc gcgacactgc ttgtctggct   9960
aagtcttatg cccagatgtg gctgcttctg tacttccaca gaagagacct gcggctcatg  10020
gccaacgcca tttgctccgc tgtccctgtg aattgggtcc ctaccggaag aaccacgtgg  10080
tccatccatg caggaggaga gtggatgaca acagaggaca tgttggaggt ctggaaccgt  10140
```

```
gtttggatag aggagaatga atggatggaa gacaaaaccc cagtggagaa atggagtgac  10200

gtcccatatt caggaaaacg agaggacatc tggtgtggca gcctgattgg cacaagagcc  10260

cgagccacgt gggcagaaaa catccaggtg gctatcaacc aagtcagagc aatcatcgga  10320

gatgagaagt atgtggacta catgagttca ctaaagagat atgaagacac aactttggtt  10380

gaggacacag tactgtagat atttaatcaa ttgtaaatag acaatataag tatgcataaa  10440

agtgtagttt tatagtagta tttagtggtg ttagtgtaaa tagttaagaa aattttgagg  10500

agaaagtcag gccgggaagt tcccgccacc ggaagttgag tagacggtgc tgcctgcgac  10560

tcaaccccag gaggactggg tgaacaaagc cgcgaagtga tccatgtaag ccctcagaac  10620

cgtctcggaa ggaggacccc acatgttgta acttcaaagc ccaatgtcag accacgctac  10680

ggcgtgctac tctgcggaga gtgcagtctg cgatagtgcc ccaggaggac tgggttaaca  10740

aaggcaaacc aacgccccac gcggccctag ccccggtaat ggtgttaacc agggcgaaag  10800

gactagaggt tagaggagac cccgcggttt aaagtgcacg gcccagcctg gctgaagctg  10860

taggtcaggg gaaggactag aggttagtgg agaccccgtg ccacaaaaca ccacaacaaa  10920

acagcatatt gacacctggg atagactagg agatcttctg ctctgcacaa ccagccacac  10980

ggcacagtgc gccgacaatg gtggctggtg gtgcgagaac acaggatct             11029
```

<210> SEQ ID NO 24
<211> LENGTH: 3433
<212> TYPE: PRT
<213> ORGANISM: West Nile virus

<400> SEQUENCE: 24

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Ala Ser Val Gly Ala Val Thr Leu Ser Asn
        115                 120                 125

Phe Gln Gly Lys Val Met Met Thr Val Asn Ala Thr Asp Val Thr Asp
    130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
            180                 185                 190

Thr Lys Ser Ala Val Tyr Val Arg Tyr Gly Arg Cys Thr Lys Thr Arg
        195                 200                 205

His Ser Arg Arg Ser Arg Arg Ser Leu Thr Val Gln Thr His Gly Glu
    210                 215                 220
```

```
Ser Thr Leu Ala Asn Lys Lys Gly Ala Trp Met Asp Ser Thr Lys Ala
225                 230                 235                 240

Thr Arg Tyr Leu Val Lys Thr Glu Ser Trp Ile Leu Arg Asn Pro Gly
                245                 250                 255

Tyr Ala Leu Val Ala Ala Val Ile Gly Trp Met Leu Gly Ser Asn Thr
            260                 265                 270

Met Gln Arg Val Val Phe Val Val Leu Leu Leu Leu Val Ala Pro Ala
        275                 280                 285

Tyr Ser Phe Asn Cys Leu Gly Met Ser Asn Arg Asp Phe Leu Glu Gly
    290                 295                 300

Val Ser Gly Ala Thr Trp Val Asp Leu Val Leu Glu Gly Asp Ser Cys
305                 310                 315                 320

Val Thr Ile Met Ser Lys Asp Lys Pro Thr Ile Asp Val Lys Met Met
                325                 330                 335

Asn Met Glu Ala Ala Asn Leu Ala Glu Val Arg Ser Tyr Cys Tyr Leu
            340                 345                 350

Ala Thr Val Ser Asp Leu Ser Thr Lys Ala Ala Cys Pro Thr Met Gly
        355                 360                 365

Glu Ala His Asn Asp Lys Arg Ala Asp Pro Ala Phe Val Cys Arg Gln
    370                 375                 380

Gly Val Val Asp Arg Gly Trp Gly Asn Gly Cys Gly Leu Phe Gly Lys
385                 390                 395                 400

Gly Ser Ile Asp Thr Cys Ala Lys Phe Ala Cys Ser Thr Lys Ala Ile
                405                 410                 415

Gly Arg Thr Ile Leu Lys Glu Asn Ile Lys Tyr Glu Val Ala Ile Phe
            420                 425                 430

Val His Gly Pro Thr Thr Val Glu Ser His Gly Asn Tyr Ser Thr Gln
        435                 440                 445

Val Gly Ala Thr Gln Ala Gly Arg Leu Ser Ile Thr Pro Ala Ala Pro
    450                 455                 460

Ser Tyr Thr Leu Lys Leu Gly Glu Tyr Gly Glu Val Thr Val Asp Cys
465                 470                 475                 480

Glu Pro Arg Ser Gly Ile Asp Thr Asn Ala Tyr Tyr Val Met Thr Val
                485                 490                 495

Gly Thr Lys Thr Phe Leu Val His Arg Glu Trp Phe Met Asp Leu Asn
            500                 505                 510

Leu Pro Trp Ser Ser Ala Gly Ser Thr Val Trp Arg Asn Arg Glu Thr
        515                 520                 525

Leu Met Glu Phe Glu Glu Pro His Ala Thr Lys Gln Ser Val Ile Ala
    530                 535                 540

Leu Gly Ser Gln Glu Gly Ala Leu His Gln Ala Leu Ala Gly Ala Ile
545                 550                 555                 560

Pro Val Glu Phe Ser Ser Asn Thr Val Lys Leu Thr Ser Gly His Leu
                565                 570                 575

Lys Cys Arg Val Lys Met Glu Lys Leu Gln Leu Lys Gly Thr Thr Tyr
            580                 585                 590

Gly Val Cys Ser Lys Ala Phe Lys Phe Leu Gly Thr Pro Ala Asp Thr
        595                 600                 605

Gly His Gly Thr Val Val Leu Glu Leu Gln Tyr Thr Gly Thr Asp Gly
    610                 615                 620

Pro Cys Lys Val Pro Ile Ser Ser Val Ala Ser Leu Asn Asp Leu Thr
625                 630                 635                 640
```

-continued

```
Pro Val Gly Arg Leu Val Thr Val Asn Pro Phe Val Ser Val Ala Thr
                645                 650                 655

Ala Asn Ala Lys Val Leu Ile Glu Leu Glu Pro Pro Phe Gly Asp Ser
            660                 665                 670

Tyr Ile Val Val Gly Arg Gly Glu Gln Gln Ile Asn His His Trp His
        675                 680                 685

Lys Ser Gly Ser Ser Ile Gly Lys Ala Phe Thr Thr Thr Leu Lys Gly
    690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
                725                 730                 735

Gly Gly Ala Phe Arg Ser Leu Phe Gly Gly Met Ser Trp Ile Thr Gln
            740                 745                 750

Gly Leu Leu Gly Ala Leu Leu Leu Trp Met Gly Ile Asn Ala Arg Asp
        755                 760                 765

Arg Ser Ile Ala Leu Thr Phe Leu Ala Val Gly Gly Val Leu Leu Phe
    770                 775                 780

Leu Ser Val Asn Val His Ala Asp Thr Gly Cys Ala Ile Asp Ile Ser
785                 790                 795                 800

Arg Gln Glu Leu Arg Cys Gly Ser Gly Val Phe Ile His Asn Asp Val
                805                 810                 815

Glu Ala Trp Met Asp Arg Tyr Lys Tyr Tyr Pro Glu Thr Pro Gln Gly
            820                 825                 830

Leu Ala Lys Ile Ile Gln Lys Ala His Lys Glu Gly Val Cys Gly Leu
        835                 840                 845

Arg Ser Val Ser Arg Leu Glu His Gln Met Trp Glu Ala Val Lys Asp
    850                 855                 860

Glu Leu Asn Thr Leu Leu Lys Glu Asn Gly Val Asp Leu Ser Val Val
865                 870                 875                 880

Val Glu Lys Gln Glu Gly Met Tyr Lys Ser Ala Pro Lys Arg Leu Thr
                885                 890                 895

Ala Thr Thr Glu Lys Leu Glu Ile Gly Trp Lys Ala Trp Gly Lys Ser
            900                 905                 910

Ile Leu Phe Ala Pro Glu Leu Ala Asn Asn Thr Phe Val Val Asp Gly
        915                 920                 925

Pro Glu Thr Lys Glu Cys Pro Thr Gln Asn Arg Ala Trp Asn Ser Leu
    930                 935                 940

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
                965                 970                 975

Thr Ala Val Lys Asn Asn Leu Ala Ile His Ser Asp Leu Ser Tyr Trp
            980                 985                 990

Ile Glu Ser Arg Leu Asn Asp Thr  Trp Lys Leu Glu Arg  Ala Val Leu
        995                 1000                1005

Gly Glu  Val Lys Ser Cys Thr  Trp Pro Glu Thr His  Thr Leu Trp
    1010                 1015                 1020

Gly Asp  Gly Ile Leu Glu Ser  Asp Leu Ile Ile Pro  Val Thr Leu
    1025                 1030                 1035

Ala Gly  Pro Arg Ser Asn His  Asn Arg Arg Pro Gly  Tyr Lys Thr
    1040                 1045                 1050

Gln Asn  Gln Gly Pro Trp Asp  Glu Gly Arg Val Glu  Ile Asp Phe
```

```
    1055                1060                1065

Asp Tyr  Cys Pro Gly Thr Thr  Val Thr Leu Ser Glu  Ser Cys Gly
    1070                1075                1080

His Arg  Gly Pro Ala Thr Arg  Thr Thr Thr Glu Ser  Gly Lys Leu
    1085                1090                1095

Ile Thr  Asp Trp Cys Cys Arg  Ser Cys Thr Leu Pro  Pro Leu Arg
    1100                1105                1110

Tyr Gln  Thr Asp Ser Gly Cys  Trp Tyr Gly Met Glu  Ile Arg Pro
    1115                1120                1125

Gln Arg  His Asp Glu Lys Thr  Leu Val Gln Ser Gln  Val Asn Ala
    1130                1135                1140

Tyr Asn  Ala Asp Met Ile Asp  Pro Phe Gln Leu Gly  Leu Leu Val
    1145                1150                1155

Val Phe  Leu Ala Thr Gln Glu  Val Leu Arg Lys Arg  Trp Thr Ala
    1160                1165                1170

Lys Ile  Ser Met Pro Ala Ile  Leu Ile Ala Leu Leu  Val Leu Val
    1175                1180                1185

Phe Gly  Gly Ile Thr Tyr Thr  Asp Val Leu Arg Tyr  Val Ile Leu
    1190                1195                1200

Val Gly  Ala Ala Phe Ala Glu  Ser Asn Ser Gly Gly  Asp Val Val
    1205                1210                1215

His Leu  Ala Leu Met Ala Thr  Phe Lys Ile Gln Pro  Val Phe Met
    1220                1225                1230

Val Ala  Ser Phe Leu Lys Ala  Arg Trp Thr Asn Gln  Glu Asn Ile
    1235                1240                1245

Leu Leu  Met Leu Ala Ala Val  Phe Phe Gln Met Ala  Tyr His Asp
    1250                1255                1260

Ala Arg  Gln Ile Leu Leu Trp  Glu Ile Pro Asp Val  Leu Asn Ser
    1265                1270                1275

Leu Ala  Val Ala Trp Met Ile  Leu Arg Ala Ile Thr  Phe Thr Thr
    1280                1285                1290

Thr Ser  Asn Val Val Val Pro  Leu Leu Ala Leu Leu  Thr Pro Gly
    1295                1300                1305

Leu Arg  Cys Leu Asn Leu Asp  Val Tyr Arg Ile Leu  Leu Leu Met
    1310                1315                1320

Val Gly  Ile Gly Ser Leu Ile  Arg Glu Lys Arg Ser  Ala Ala Ala
    1325                1330                1335

Lys Lys  Lys Gly Ala Ser Leu  Leu Cys Leu Ala Leu  Ala Ser Thr
    1340                1345                1350

Gly Leu  Phe Asn Pro Met Ile  Leu Ala Ala Gly Leu  Ile Ala Cys
    1355                1360                1365

Asp Pro  Asn Arg Lys Arg Gly  Trp Pro Ala Thr Glu  Val Met Thr
    1370                1375                1380

Ala Val  Gly Leu Met Phe Ala  Ile Val Gly Gly Leu  Ala Glu Leu
    1385                1390                1395

Asp Ile  Asp Ser Met Ala Ile  Pro Met Thr Ile Ala  Gly Leu Met
    1400                1405                1410

Phe Ala  Ala Phe Val Ile Ser  Gly Lys Ser Thr Asp  Met Trp Ile
    1415                1420                1425

Glu Arg  Thr Ala Asp Ile Ser  Trp Glu Ser Asp Ala  Glu Ile Thr
    1430                1435                1440

Gly Ser  Ser Glu Arg Val Asp  Val Arg Leu Asp Asp  Asp Gly Asn
    1445                1450                1455
```

```
Phe Gln  Leu Met Asn Asp Pro  Gly Ala Pro Trp Lys  Ile Trp Met
    1460                 1465                 1470

Leu Arg  Met Val Cys Leu Ala  Ile Ser Ala Tyr Thr  Pro Trp Ala
    1475                 1480                 1485

Ile Leu  Pro Ser Val Val Gly  Phe Trp Ile Thr Leu  Gln Tyr Thr
    1490                 1495                 1500

Lys Arg  Gly Gly Val Leu Trp  Asp Thr Pro Ser Pro  Lys Glu Tyr
    1505                 1510                 1515

Lys Lys  Gly Asp Thr Thr Thr  Gly Val Tyr Arg Ile  Met Thr Arg
    1520                 1525                 1530

Gly Leu  Leu Gly Ser Tyr Gln  Ala Gly Ala Gly Val  Met Val Glu
    1535                 1540                 1545

Gly Val  Phe His Thr Leu Trp  His Thr Thr Lys Gly  Ala Ala Leu
    1550                 1555                 1560

Met Ser  Gly Glu Gly Arg Leu  Asp Pro Tyr Trp Gly  Ser Val Lys
    1565                 1570                 1575

Glu Asp  Arg Leu Cys Tyr Gly  Gly Pro Trp Lys Leu  Gln His Lys
    1580                 1585                 1590

Trp Asn  Gly Gln Asp Glu Val  Gln Met Ile Val Val  Glu Pro Gly
    1595                 1600                 1605

Lys Asn  Val Lys Asn Val Gln  Thr Lys Pro Gly Val  Phe Lys Thr
    1610                 1615                 1620

Pro Glu  Gly Glu Ile Gly Ala  Val Thr Leu Asp Phe  Pro Thr Gly
    1625                 1630                 1635

Thr Ser  Gly Ser Pro Ile Val  Asp Lys Asn Gly Asp  Val Ile Gly
    1640                 1645                 1650

Leu Tyr  Gly Asn Gly Val Ile  Met Pro Asn Gly Ser  Tyr Ile Ser
    1655                 1660                 1665

Ala Ile  Val Gln Gly Glu Arg  Met Asp Glu Pro Ile  Pro Ala Gly
    1670                 1675                 1680

Phe Glu  Pro Glu Met Leu Arg  Lys Lys Gln Ile Thr  Val Leu Asp
    1685                 1690                 1695

Leu His  Pro Gly Ala Gly Lys  Thr Arg Arg Ile Leu  Pro Gln Ile
    1700                 1705                 1710

Ile Lys  Glu Ala Ile Asn Arg  Arg Leu Arg Thr Ala  Val Leu Ala
    1715                 1720                 1725

Pro Thr  Arg Val Val Ala Ala  Glu Met Ala Glu Ala  Leu Arg Gly
    1730                 1735                 1740

Leu Pro  Ile Arg Tyr Gln Thr  Ser Ala Val Pro Arg  Glu His Asn
    1745                 1750                 1755

Gly Asn  Glu Ile Val Asp Val  Met Cys His Ala Thr  Leu Thr His
    1760                 1765                 1770

Arg Leu  Met Ser Pro His Arg  Val Pro Asn Tyr Asn  Leu Phe Val
    1775                 1780                 1785

Met Asp  Glu Ala His Phe Thr  Asp Pro Ala Ser Ile  Ala Ala Arg
    1790                 1795                 1800

Gly Tyr  Ile Ser Thr Lys Val  Glu Leu Gly Glu Ala  Ala Ala Ile
    1805                 1810                 1815

Phe Met  Thr Ala Thr Pro Pro  Gly Thr Ser Asp Pro  Phe Pro Glu
    1820                 1825                 1830

Ser Asn  Ser Pro Ile Ser Asp  Leu Gln Thr Glu Ile  Pro Asp Arg
    1835                 1840                 1845
```

```
Ala Trp  Asn Ser Gly Tyr Glu  Trp Ile Thr Glu Tyr  Thr Gly Lys
    1850                 1855                 1860

Thr Val  Trp Phe Val Pro Ser  Val Lys Met Gly Asn  Glu Ile Ala
    1865                 1870                 1875

Leu Cys  Leu Gln Arg Ala Gly  Lys Lys Val Val Gln  Leu Asn Arg
    1880                 1885                 1890

Lys Ser  Tyr Glu Thr Glu Tyr  Pro Lys Cys Lys Asn  Asp Asp Trp
    1895                 1900                 1905

Asp Phe  Val Ile Thr Thr Asp  Ile Ser Glu Met Gly  Ala Asn Phe
    1910                 1915                 1920

Lys Ala  Ser Arg Val Ile Asp  Ser Arg Lys Ser Val  Lys Pro Thr
    1925                 1930                 1935

Ile Ile  Thr Glu Gly Glu Gly  Arg Val Ile Leu Gly  Glu Pro Ser
    1940                 1945                 1950

Ala Val  Thr Ala Ala Ser Ala  Ala Gln Arg Arg Gly  Arg Ile Gly
    1955                 1960                 1965

Arg Asn  Pro Ser Gln Val Gly  Asp Glu Tyr Cys Tyr  Gly Gly His
    1970                 1975                 1980

Thr Asn  Glu Asp Asp Ser Asn  Phe Ala His Trp Thr  Glu Ala Arg
    1985                 1990                 1995

Ile Met  Leu Asp Asn Ile Asn  Met Pro Asn Gly Leu  Ile Ala Gln
    2000                 2005                 2010

Phe Tyr  Gln Pro Glu Arg Glu  Lys Val Tyr Thr Met  Asp Gly Glu
    2015                 2020                 2025

Tyr Arg  Leu Arg Gly Glu Glu  Arg Lys Asn Phe Leu  Glu Leu Leu
    2030                 2035                 2040

Arg Thr  Ala Asp Leu Pro Val  Trp Leu Ala Tyr Lys  Val Ala Ala
    2045                 2050                 2055

Ala Gly  Val Ser Tyr His Asp  Arg Arg Trp Cys Phe  Asp Gly Pro
    2060                 2065                 2070

Arg Thr  Asn Thr Ile Leu Glu  Asp Asn Asn Glu Val  Glu Val Ile
    2075                 2080                 2085

Thr Lys  Leu Gly Glu Arg Lys  Ile Leu Arg Pro Arg  Trp Ile Asp
    2090                 2095                 2100

Ala Arg  Val Tyr Ser Asp His  Gln Ala Leu Lys Ala  Phe Lys Asp
    2105                 2110                 2115

Phe Ala  Ser Gly Lys Arg Ser  Gln Ile Gly Leu Ile  Glu Val Leu
    2120                 2125                 2130

Gly Lys  Met Pro Glu His Phe  Met Gly Lys Thr Trp  Glu Ala Leu
    2135                 2140                 2145

Asp Thr  Met Tyr Val Val Ala  Thr Ala Glu Lys Gly  Gly Arg Ala
    2150                 2155                 2160

His Arg  Met Ala Leu Glu Glu  Leu Pro Asp Ala Leu  Gln Thr Ile
    2165                 2170                 2175

Ala Leu  Ile Ala Leu Leu Ser  Val Met Thr Met Gly  Val Phe Phe
    2180                 2185                 2190

Leu Leu  Met Gln Arg Lys Gly  Ile Gly Lys Ile Gly  Leu Gly Gly
    2195                 2200                 2205

Ala Val  Leu Gly Val Ala Thr  Phe Phe Cys Trp Met  Ala Glu Val
    2210                 2215                 2220

Pro Gly  Thr Lys Ile Ala Gly  Met Leu Leu Leu Ser  Leu Leu Leu
    2225                 2230                 2235

Met Ile  Val Leu Ile Pro Glu  Pro Glu Lys Gln Arg  Ser Gln Thr
```

```
    2240                2245                2250

Asp Asn  Gln Leu Ala Val Phe  Leu Ile Cys Val Met  Thr Leu Val
    2255                2260                2265

Ser Ala  Val Ala Ala Asn Glu  Met Gly Trp Leu Asp  Lys Thr Lys
    2270                2275                2280

Ser Asp  Ile Ser Ser Leu Phe  Gly Gln Arg Ile Glu  Val Lys Glu
    2285                2290                2295

Asn Phe  Ser Met Gly Glu Phe  Leu Leu Asp Leu Arg  Pro Ala Thr
    2300                2305                2310

Ala Trp  Ser Leu Tyr Ala Val  Thr Thr Ala Val Leu  Thr Pro Leu
    2315                2320                2325

Leu Lys  His Leu Ile Thr Ser  Asp Tyr Ile Asn Thr  Ser Leu Thr
    2330                2335                2340

Ser Ile  Asn Val Gln Ala Ser  Ala Leu Phe Thr Leu  Ala Arg Gly
    2345                2350                2355

Phe Pro  Phe Val Asp Val Gly  Val Ser Ala Leu Leu  Leu Ala Ala
    2360                2365                2370

Gly Cys  Trp Gly Gln Val Thr  Leu Thr Val Thr Val  Thr Ala Ala
    2375                2380                2385

Thr Leu  Leu Phe Cys His Tyr  Ala Tyr Met Val Pro  Gly Trp Gln
    2390                2395                2400

Ala Glu  Ala Met Arg Ser Ala  Gln Arg Arg Thr Ala  Ala Gly Ile
    2405                2410                2415

Met Lys  Asn Ala Val Val Asp  Gly Ile Val Ala Thr  Asp Val Pro
    2420                2425                2430

Glu Leu  Glu Arg Thr Thr Pro  Ile Met Gln Lys Lys  Val Gly Gln
    2435                2440                2445

Ile Met  Leu Ile Leu Val Ser  Leu Ala Ala Val Val  Val Asn Pro
    2450                2455                2460

Ser Val  Lys Thr Val Arg Glu  Ala Gly Ile Leu Ile  Thr Ala Ala
    2465                2470                2475

Ala Val  Thr Leu Trp Glu Asn  Gly Ala Ser Ser Val  Trp Asn Ala
    2480                2485                2490

Thr Thr  Ala Ile Gly Leu Cys  His Ile Met Arg Gly  Gly Trp Leu
    2495                2500                2505

Ser Cys  Leu Ser Ile Thr Trp  Thr Leu Ile Lys Asn  Met Glu Lys
    2510                2515                2520

Pro Gly  Leu Lys Arg Gly Gly  Ala Lys Gly Arg Thr  Leu Gly Glu
    2525                2530                2535

Val Trp  Lys Glu Arg Leu Asn  Gln Met Thr Lys Glu  Glu Phe Thr
    2540                2545                2550

Arg Tyr  Arg Lys Glu Ala Ile  Ile Glu Val Asp Arg  Ser Ala Ala
    2555                2560                2565

Lys His  Ala Arg Lys Glu Gly  Asn Val Thr Gly Gly  His Pro Val
    2570                2575                2580

Ser Arg  Gly Thr Ala Lys Leu  Arg Trp Leu Val Glu  Arg Arg Phe
    2585                2590                2595

Leu Glu  Pro Val Gly Lys Val  Ile Asp Leu Gly Cys  Gly Arg Gly
    2600                2605                2610

Gly Trp  Cys Tyr Tyr Met Ala  Thr Gln Lys Arg Val  Gln Glu Val
    2615                2620                2625

Arg Gly  Tyr Thr Lys Gly Gly  Pro Gly His Glu Glu  Pro Gln Leu
    2630                2635                2640
```

```
Val Gln Ser Tyr Gly Trp Asn Ile Val Thr Met Lys Ser Gly Val
    2645                2650                2655

Asp Val Phe Tyr Arg Pro Ser Glu Cys Cys Asp Thr Leu Leu Cys
    2660                2665                2670

Asp Ile Gly Glu Ser Ser Ser Ser Ala Glu Val Glu Glu His Arg
    2675                2680                2685

Thr Ile Arg Val Leu Glu Met Val Glu Asp Trp Leu His Arg Gly
    2690                2695                2700

Pro Arg Glu Phe Cys Val Lys Val Leu Cys Pro Tyr Met Pro Lys
    2705                2710                2715

Val Ile Glu Lys Met Glu Leu Leu Gln Arg Arg Tyr Gly Gly Gly
    2720                2725                2730

Leu Val Arg Asn Pro Leu Ser Arg Asn Ser Thr His Glu Met Tyr
    2735                2740                2745

Trp Val Ser Arg Ala Ser Gly Asn Val Val His Ser Val Asn Met
    2750                2755                2760

Thr Ser Gln Val Leu Leu Gly Arg Met Glu Lys Arg Thr Trp Lys
    2765                2770                2775

Gly Pro Gln Tyr Glu Glu Asp Val Asn Leu Gly Ser Gly Thr Arg
    2780                2785                2790

Ala Val Gly Lys Pro Leu Leu Asn Ser Asp Thr Ser Lys Ile Lys
    2795                2800                2805

Asn Arg Ile Glu Arg Leu Arg Arg Glu Tyr Ser Ser Thr Trp His
    2810                2815                2820

His Asp Glu Asn His Pro Tyr Arg Thr Trp Asn Tyr His Gly Ser
    2825                2830                2835

Tyr Asp Val Lys Pro Thr Gly Ser Ala Ser Ser Leu Val Asn Gly
    2840                2845                2850

Val Val Arg Leu Leu Ser Lys Pro Trp Asp Thr Ile Thr Asn Val
    2855                2860                2865

Thr Thr Met Ala Met Thr Asp Thr Thr Pro Phe Gly Gln Gln Arg
    2870                2875                2880

Val Phe Lys Glu Lys Val Asp Thr Lys Ala Pro Glu Pro Pro Glu
    2885                2890                2895

Gly Val Lys Tyr Val Leu Asn Glu Thr Thr Asn Trp Leu Trp Ala
    2900                2905                2910

Phe Leu Ala Arg Glu Lys Arg Pro Arg Met Cys Ser Arg Glu Glu
    2915                2920                2925

Phe Ile Arg Lys Val Asn Ser Asn Ala Ala Leu Gly Ala Met Phe
    2930                2935                2940

Glu Glu Gln Asn Gln Trp Arg Ser Ala Arg Glu Ala Val Glu Asp
    2945                2950                2955

Pro Lys Phe Trp Glu Met Val Asp Glu Glu Arg Glu Ala His Leu
    2960                2965                2970

Arg Gly Glu Cys His Thr Cys Ile Tyr Asn Met Met Gly Lys Arg
    2975                2980                2985

Glu Lys Lys Pro Gly Glu Phe Gly Lys Ala Lys Gly Ser Arg Ala
    2990                2995                3000

Ile Trp Phe Met Trp Leu Gly Ala Arg Phe Leu Glu Phe Glu Ala
    3005                3010                3015

Leu Gly Phe Leu Asn Glu Asp His Trp Leu Gly Arg Lys Asn Ser
    3020                3025                3030
```

```
Gly Gly  Gly Val Glu Gly Leu  Gly Leu Gln Lys Leu  Gly Tyr Ile
    3035                 3040                 3045

Leu Arg  Glu Val Gly Thr Arg  Pro Gly Gly Lys Ile  Tyr Ala Asp
    3050                 3055                 3060

Asp Thr  Ala Gly Trp Asp Thr  Arg Ile Thr Arg Ala  Asp Leu Glu
    3065                 3070                 3075

Asn Glu  Ala Lys Val Leu Glu  Leu Leu Asp Gly Glu  His Arg Arg
    3080                 3085                 3090

Leu Ala  Arg Ala Ile Ile Glu  Leu Thr Tyr Arg His  Lys Val Val
    3095                 3100                 3105

Lys Val  Met Arg Pro Ala Ala  Asp Gly Arg Thr Val  Met Asp Val
    3110                 3115                 3120

Ile Ser  Arg Glu Asp Gln Arg  Gly Ser Gly Gln Val  Val Thr Tyr
    3125                 3130                 3135

Ala Leu  Asn Thr Phe Thr Asn  Leu Ala Val Gln Leu  Val Arg Met
    3140                 3145                 3150

Met Glu  Gly Glu Gly Val Ile  Gly Pro Asp Asp Val  Glu Lys Leu
    3155                 3160                 3165

Thr Lys  Gly Lys Gly Pro Lys  Val Arg Thr Trp Leu  Phe Glu Asn
    3170                 3175                 3180

Gly Glu  Glu Arg Leu Ser Arg  Met Ala Val Ser Gly  Asp Asp Cys
    3185                 3190                 3195

Val Val  Lys Pro Leu Asp Asp  Arg Phe Ala Thr Ser  Leu His Phe
    3200                 3205                 3210

Leu Asn  Ala Met Ser Lys Val  Arg Lys Asp Ile Gln  Glu Trp Lys
    3215                 3220                 3225

Pro Ser  Thr Gly Trp Tyr Asp  Trp Gln Gln Val Pro  Phe Cys Ser
    3230                 3235                 3240

Asn His  Phe Thr Glu Leu Ile  Met Lys Asp Gly Arg  Thr Leu Val
    3245                 3250                 3255

Val Pro  Cys Arg Gly Gln Asp  Glu Leu Val Gly Arg  Ala Arg Ile
    3260                 3265                 3270

Ser Pro  Gly Ala Gly Trp Asn  Val Arg Asp Thr Ala  Cys Leu Ala
    3275                 3280                 3285

Lys Ser  Tyr Ala Gln Met Trp  Leu Leu Leu Tyr Phe  His Arg Arg
    3290                 3295                 3300

Asp Leu  Arg Leu Met Ala Asn  Ala Ile Cys Ser Ala  Val Pro Val
    3305                 3310                 3315

Asn Trp  Val Pro Thr Gly Arg  Thr Thr Trp Ser Ile  His Ala Gly
    3320                 3325                 3330

Gly Glu  Trp Met Thr Thr Glu  Asp Met Leu Glu Val  Trp Asn Arg
    3335                 3340                 3345

Val Trp  Ile Glu Glu Asn Glu  Trp Met Glu Asp Lys  Thr Pro Val
    3350                 3355                 3360

Glu Lys  Trp Ser Asp Val Pro  Tyr Ser Gly Lys Arg  Glu Asp Ile
    3365                 3370                 3375

Trp Cys  Gly Ser Leu Ile Gly  Thr Arg Ala Arg Ala  Thr Trp Ala
    3380                 3385                 3390

Glu Asn  Ile Gln Val Ala Ile  Asn Gln Val Arg Ala  Ile Ile Gly
    3395                 3400                 3405

Asp Glu  Lys Tyr Val Asp Tyr  Met Ser Ser Leu Lys  Arg Tyr Glu
    3410                 3415                 3420

Asp Thr  Thr Leu Val Glu Asp  Thr Val Leu
```

-continued 3425 3430

<210> SEQ ID NO 25
<211> LENGTH: 945
<212> TYPE: DNA
<213> ORGANISM: West Nile virus
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (726)..(726)
<223> OTHER INFORMATION: a, c, t, g, unknown or other
<220> FEATURE:
<221> NAME/KEY: modified_base
<222> LOCATION: (831)..(833)
<223> OTHER INFORMATION: a, c, t, g, unknown or other
<220> FEATURE:
<221> NAME/KEY: modified_base
<222> LOCATION: (838)..(838)
<223> OTHER INFORMATION: a, c, t, g, unknown or other
<220> FEATURE:
<221> NAME/KEY: modified_base
<222> LOCATION: (854)..(854)
<223> OTHER INFORMATION: a, c, t, g, unknown or other
<220> FEATURE:
<221> NAME/KEY: modified_base
<222> LOCATION: (893)..(893)
<223> OTHER INFORMATION: a, c, t, g, unknown or other
<220> FEATURE:
<221> NAME/KEY: modified_base
<222> LOCATION: (907)..(907)
<223> OTHER INFORMATION: a, c, t, g, unknown or other
<220> FEATURE:
<221> NAME/KEY: modified_base
<222> LOCATION: (917)..(917)
<223> OTHER INFORMATION: a, c, t, g, unknown or other
<220> FEATURE:
<221> NAME/KEY: modified_base
<222> LOCATION: (922)..(922)
<223> OTHER INFORMATION: a, c, t, g, unknown or other
<220> FEATURE:
<221> NAME/KEY: modified_base
<222> LOCATION: (928)..(929)
<223> OTHER INFORMATION: a, c, t, g, unknown or other
<220> FEATURE:
<221> NAME/KEY: modified_base
<222> LOCATION: (931)..(931)
<223> OTHER INFORMATION: a, c, t, g, unknown or other
<220> FEATURE:
<221> NAME/KEY: modified_base
<222> LOCATION: (937)..(937)
<223> OTHER INFORMATION: a, c, t, g, unknown or other
<220> FEATURE:
<221> NAME/KEY: modified_base
<222> LOCATION: (941)..(943)
<223> OTHER INFORMATION: a, c, t, g, unknown or other
<220> FEATURE:
<221> NAME/KEY: modified_base
<222> LOCATION: (945)..(945)
<223> OTHER INFORMATION: a, c, t, g, unknown or other

<400> SEQUENCE: 25
cgatgtgnga ngangaatat ggaggcggcc aacctggcag aggtccgcag ttattgctat 60
ttggctaccg tcagcgatct ctccaccaaa gctgcgtgcc cgaccatggg agaagctcac 120
aatgacaaac gtgctgaccc agcttttgtg tgcagacaag gagtggtgga caggggctgg 180
ggcaacggct gcggactatt tggcaaagga agcattgaca catgcgccaa atttgcctgc 240
tctaccaagg caataggaag aaccatcttg aaagagaata tcaagtacga agtggccatt 300
tttgtccatg gaccaactac tgtggagtcg cacggaaact actccacaca ggttggagcc 360
actcaggcag ggagattcag catcactcct gcggcgcctt catacacact aaagcttgga 420
gaatatggag aggtgacagt ggactgtgaa ccacggtcag ggattgacac caatgcatac 480
tatgtgatga ctgttggaac aaagacgttc ttggtccatc gtgagtggtt catggacctc 540
aacctccctt ggagcagtgc tggaagtact gtgtggagga acagagagac gttaatggag 600
tttgaggaac cacacgccac gaagcagtct gtgatagcat tgggctcaca agagggagct 660
ctgcatcaag ctttggctgg agccattcct gtggaatttt caagcaacac tgtcaagttg 720
acgtcnggtc atttgaagtg tagagtgaag atggaaaaat tgcagttgaa gggaacaacc 780
tatggcgtct gttcaaaggc tttcaagttt cttgggactc ccgcagacac nnntcacngc 840
actgtggtgt tggnattgca gtacactggg cacggatgga ccttgcaaag ttnctatctc 900
gtcagtngct tcattgnacg anctaacnnc ngtgggnaga nnngn 945

<210> SEQ ID NO 26
<211> LENGTH: 855
<212> TYPE: DNA
<213> ORGANISM: West Nile virus
<220> FEATURE:
<221> NAME/KEY: modified_base
<222> LOCATION: (649)..(649)
<223> OTHER INFORMATION: a, c, t, g, unknown or other
<220> FEATURE:
<221> NAME/KEY: modified_base
<222> LOCATION: (704)..(704)
<223> OTHER INFORMATION: a, c, t, g, unknown or other
<220> FEATURE:
<221> NAME/KEY: modified_base
<222> LOCATION: (761)..(761)
<223> OTHER INFORMATION: a, c, t, g, unknown or other
<220> FEATURE:
<221> NAME/KEY: modified_base
<222> LOCATION: (791)..(791)
<223> OTHER INFORMATION: a, c, t, g, unknown or other
<220> FEATURE:
<221> NAME/KEY: modified_base
<222> LOCATION: (823)..(823)
<223> OTHER INFORMATION: a, c, t, g, unknown or other
<220> FEATURE:
<221> NAME/KEY: modified_base
<222> LOCATION: (839)..(839)
<223> OTHER INFORMATION: a, c, t, g, unknown or other
<220> FEATURE:
<221> NAME/KEY: modified_base
<222> LOCATION: (844)..(844)
<223> OTHER INFORMATION: a, c, t, g, unknown or other
<220> FEATURE:
<221> NAME/KEY: modified_base
<222> LOCATION: (846)..(846)
<223> OTHER INFORMATION: a, c, t, g, unknown or other

<400> SEQUENCE: 26
caagtacgaa gtggccattt ttgtccatgg accaactact gtggagtcgc acggaaacta 60
ctccacacag gttggagcca ctcaggcagg gagattcagc atcactcctg cggcgccttc 120
atacacacta aagcttggag aatatggaga ggtgacagtg gactgtgaac cacggtcagg 180
gattgacacc aatgcatact atgtgatgac tgttggaaca aagacgttct tggtccatcg 240
tgagtggttc atggacctca acctcccttg gagcagtgct ggaagtactg tgtggaggaa 300
cagagagacg ttaatggagt ttgaggaacc acacgccacg aagcagtctg tgatagcatt 360

-continued

```
gggctcacaa gagggagctc tgcatcaagc tttggctgga gccattcctg tggaattttc    420

aagcaacact gtcaagttga cgtcgggtca tttgaagtgt agagtgaaga tggaaaaatt    480

gcagttgaag ggaacaacct atggcgtctg ttcaaaggct ttcaagtttc ttgggactcc    540

cgcagacaca ggtcacggca ctgtggtgtt ggaattgcag tacactggca cggatggacc    600

ttgcaaagtt cctatctcgt cagtggcttc attgaacgac ctaacgccng tgggcagatt    660

ggtcactgtc aacccttttg tttcagtggc cacggccaac gctnaggtcc tgattgaatt    720

ggaaccaccc tttggagact catacatagt ggtgggcaga ngagaacaac agatcaatca    780

ccattggcac nagtctggaa gcagcattgg caaagccttt acnaccaccc tcaaaggan c    840

gcananacta gccgc                                                     855
```

<210> SEQ ID NO 27
<211> LENGTH: 940
<212> TYPE: DNA
<213> ORGANISM: West Nile virus
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (30)..(32)
<223> OTHER INFORMATION: a, c, t, g, unknown or other
<220> FEATURE:
<221> NAME/KEY: modified_base
<222> LOCATION: (45)..(46)
<223> OTHER INFORMATION: a, c, t, g, unknown or other
<220> FEATURE:
<221> NAME/KEY: modified_base
<222> LOCATION: (130)..(130)
<223> OTHER INFORMATION: a, c, t, g, unknown or other

<400> SEQUENCE: 27

```
tntgatgact gtnggaacaa agacgttctn nntccatcgt gagtnnttca tggacctcaa     60

cctcccttgg agcagtgctg gaagtactgt gtggaggaac agagagacgt taatggagtt    120

tgaggaaccn cacgccacga agcagtctgt gatagcattg ggctcacaag agggagctct    180

gcatcaagct ttggctggag ccattcctgt ggaattttca agcaacactg tcaagttgac    240

gtcgggtcat ttgaagtgta gagtgaagat ggaaaaattg cagttgaagg gaacaaccta    300

tggcgtctgt tcaaaggctt tcaagtttct tgggactccc gcagacacag gtcacggcac    360

tgtggtgttg gaattgcagt acactggcac ggatggacct tgcaaagttc ctatctcgtc    420

agtggcttca ttgaacgacc taacgccagt gggcagattg gtcactgtca acccttttgt    480

ttcagtggcc acggccaacg ctaaggtcct gattgaattg gaaccaccct ttggagactc    540

atacatagtg gtgggcagag gagaacaaca gatcaatcac cattggcaca agtctggaag    600

cagcattggc aaagccttta caaccaccct caaaggagcg cagagactag ccgctctagg    660

agacacagct tgggactttg gatcagttgg aggggtgttc acctcagttg ggaaggctgt    720

ccatcaagtg ttcggaggag cattccgctc actgttcgga ggcatgtcct ggataacgca    780

aggattgctg gggctctcc tgttgtggat gggcatcaat gctcgtgata ggtccatagc    840

tctcacgttt ctcgcagttg gaggagttct gctcttcctt tccgtgaacg tgcacgctga    900

cactgggtgt gccatagaca tcagccggca agagctgaga                          940
```

<210> SEQ ID NO 28
<211> LENGTH: 1005
<212> TYPE: DNA
<213> ORGANISM: West Nile virus
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (59)..(59)
<223> OTHER INFORMATION: a, c, t, g, unknown or other
<220> FEATURE:
<221> NAME/KEY: modified_base
<222> LOCATION: (997)..(997)
<223> OTHER INFORMATION: a, c, t, g, unknown or other

<400> SEQUENCE: 28

```
nagcagtgct ggnangtact gtgtggagga acagagagac gttaatggag tttgagganc      60
cacacgccac gaagcagtct gtgatagcat tgggctcaca agagggagct ctgcatcaag     120
ctttggctgg agccattcct gtggaatttt caagcaacac tgtcaagttg acgtcgggtc     180
atttgaagtg tagagtgaag atggaaaaat tgcagttgaa gggaacaacc tatggcgtct     240
gttcaaaggc tttcaagttt cttgggactc ccgcagacac aggtcacggc actgtggtgt     300
tggaattgca gtacactggc acggatggac cttgcaaagt tcctatctcg tcagtggctt     360
cattgaacga cctaacgcca gtgggcagat tggtcactgt caaccctttt gtttcagtgg     420
ccacggccaa cgctaaggtc ctgattgaat tggaaccacc ctttggagac tcatacatag     480
tggtgggcag aggagaacaa cagatcaatc accattggca caagtctgga agcagcattg     540
gcaaagcctt tacaaccacc ctcaaaggag cgcagagact agccgctcta ggagacacag     600
cttgggactt tggatcagtt ggaggggtgt tcacctcagt tgggaaggct gtccatcaag     660
tgttcggagg agcattccgc tcactgttcg gaggcatgtc ctggataacg caaggattgc     720
tgggggctct cctgttgtgg atgggcatca atgctcgtga taggtccata gctctcacgt     780
ttctcgcagt tggaggagtt ctgctcttcc tttccgtgaa cgtgcacgct gacactgggt     840
gtgccataga catcagccgg caagagctga gatgtggaag tggagtgttc atacacaatg     900
atgtggaggc ttggatggac cggtacaagt attaccctga aacgccacaa ggcctagcca     960
agatcattca gaaagctcat aaggaaggag tgtgcgntct acgat                    1005
```

<210> SEQ ID NO 29
<211> LENGTH: 944
<212> TYPE: DNA
<213> ORGANISM: West Nile virus
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:

<221> NAME/KEY: modified_base
<222> LOCATION: (886)..(886)
<223> OTHER INFORMATION: a, c, t, g, unknown or other
<220> FEATURE:
<221> NAME/KEY: modified_base
<222> LOCATION: (892)..(892)
<223> OTHER INFORMATION: a, c, t, g, unknown or other
<220> FEATURE:
<221> NAME/KEY: modified_base
<222> LOCATION: (921)..(921)
<223> OTHER INFORMATION: a, c, t, g, unknown or other
<220> FEATURE:
<221> NAME/KEY: modified_base
<222> LOCATION: (934)..(935)
<223> OTHER INFORMATION: a, c, t, g, unknown or other
<220> FEATURE:
<221> NAME/KEY: modified_base
<222> LOCATION: (939)..(939)
<223> OTHER INFORMATION: a, c, t, g, unknown or other
<220> FEATURE:
<221> NAME/KEY: modified_base
<222> LOCATION: (943)..(943)
<223> OTHER INFORMATION: a, c, t, g, unknown or other

<400> SEQUENCE: 29
cgatgtgnga ngangaatat ggaggcggcc aacctggcag aggtccgcag ttattgctat 60
ttggctaccg tcagcgatct ctccaccaaa gctgcgtgcc cgaccatggg agaagctcac 120
aatgacaaac gtgctgaccc agcttttgtg tgcagacaag gagtggtgga caggggctgg 180
ggcaacggct gcggactatt tggcaaagga agcattgaca catgcgccaa atttgcctgc 240
tctaccaagg caataggaag aaccatcttg aaagagaata tcaagtacga agtggccatt 300
tttgtccatg gaccaactac tgtggagtcg cacggaaact actccacaca ggctggagcc 360
actcaggcag ggagattcag catcactcct gcggcgcctt catacacact aaagcttgga 420
gaatatggag aggtgacagt ggactgtgaa ccacggtcag ggattgacac caatgcatac 480
tacgtgatga ctgttggaac aaagacgttc ttggtccatc gtgagtggtt catggacctc 540
aacctccctt ggagcagtgc tggaagtact gtgtggagga acagagagac gttaatggag 600
tttgaggaac cacacgccac gaagcagtct gtgatagcat tgggctcaca agagggagct 660
ctgcatcaag ctttggctgg agccattcct gtggaatttt caagcaacac tgtcaagttg 720
acgtcgggtc atttgaagtg tagagtgaag atggaaaaat tgcagttgaa gggaacaacc 780
tatggcgtct gttcaaaggc tttcaagttt cttgggactc ccgcagacac aggtcacggc 840
actgtggtgt tggaattgca gtacactggc acggatggac cttgcnaagt tnctatctcg 900
tcagtggctt cattgaacga nctaacgcca gtgnnagant ggnc 944

<210> SEQ ID NO 30
<211> LENGTH: 997
<212> TYPE: DNA
<213> ORGANISM: West Nile virus
<220> FEATURE:
<221> NAME/KEY: modified_base
<222> LOCATION: (839)..(839)
<223> OTHER INFORMATION: a, c, t, g, unknown or other
<220> FEATURE:
<221> NAME/KEY: modified_base
<222> LOCATION: (863)..(863)
<223> OTHER INFORMATION: a, c, t, g, unknown or other
<220> FEATURE:
<221> NAME/KEY: modified_base
<222> LOCATION: (873)..(873)
<223> OTHER INFORMATION: a, c, t, g, unknown or other
<220> FEATURE:
<221> NAME/KEY: modified_base
<222> LOCATION: (916)..(916)
<223> OTHER INFORMATION: a, c, t, g, unknown or other
<220> FEATURE:
<221> NAME/KEY: modified_base
<222> LOCATION: (919)..(919)
<223> OTHER INFORMATION: a, c, t, g, unknown or other
<220> FEATURE:
<221> NAME/KEY: modified_base
<222> LOCATION: (933)..(933)
<223> OTHER INFORMATION: a, c, t, g, unknown or other
<220> FEATURE:
<221> NAME/KEY: modified_base
<222> LOCATION: (947)..(947)
<223> OTHER INFORMATION: a, c, t, g, unknown or other
<220> FEATURE:
<221> NAME/KEY: modified_base
<222> LOCATION: (958)..(958)
<223> OTHER INFORMATION: a, c, t, g, unknown or other
<220> FEATURE:
<221> NAME/KEY: modified_base
<222> LOCATION: (971)..(971)
<223> OTHER INFORMATION: a, c, t, g, unknown or other
<220> FEATURE:
<221> NAME/KEY: modified_base
<222> LOCATION: (973)..(973)
<223> OTHER INFORMATION: a, c, t, g, unknown or other
<220> FEATURE:
<221> NAME/KEY: modified_base
<222> LOCATION: (976)..(978)
<223> OTHER INFORMATION: a, c, t, g, unknown or other
<220> FEATURE:
<221> NAME/KEY: modified_base
<222> LOCATION: (987)..(987)
<223> OTHER INFORMATION: a, c, t, g, unknown or other
<220> FEATURE:
<221> NAME/KEY: modified_base
<222> LOCATION: (989)..(989)
<223> OTHER INFORMATION: a, c, t, g, unknown or other
<220> FEATURE:
<221> NAME/KEY: modified_base
<222> LOCATION: (991)..(991)
<223> OTHER INFORMATION: a, c, t, g, unknown or other

<400> SEQUENCE: 30
caagtacgaa gtggccattt ttgtccatgg accaactact gtggagtcgc acggaaacta 60
ctccacacag gctggagcca ctcaggcagg gagattcagc atcactcctg cggcgccttc 120
atacacacta aagcttggag aatatggaga ggtgacagtg gactgtgaac cacggtcagg 180
gattgacacc aatgcatact acgtgatgac tgttggaaca aagacgttct tggtccatcg 240
tgagtggttc atggacctca acctcccttg gagcagtgct ggaagtactg tgtggaggaa 300
cagagagacg ttaatggagt ttgaggaacc acacgccacg aagcagtctg tgatagcatt 360
gggctcacaa gagggagctc tgcatcaagc tttggctgga gccattcctg tggaattttc 420
aagcaacact gtcaagttga cgtcgggtca tttgaagtgt agagtgaaga tggaaaaatt 480
gcagttgaag ggaacaacct atggcgtctg ttcaaaggct ttcaagtttc ttgggactcc 540
cgcagacaca ggtcacggca ctgtggtgtt ggaattgcag tacactggca cggatggacc 600
ttgcaaagtt cctatctcgt cagtggcttc attgaacgac ctaacgccag tgggcagatt 660
ggtcactgtc aacccttttg tttcagtggc cacggccaac gctaaggtcc tgattgaatt 720
ggaaccaccc tttggagact catacatagt ggtgggcaga ggagaacaac agatcaatca 780
ccattggcac aagtctggaa gcagcattgg caaagccttt acaaccaccc tcaaaggant 840
gcagagacta gccgctctag ganacacagc ttnggacttt ggatcagttg gaggggtgtt 900
cacctcagtt gggaanggnt gtccatcaag tgntcggagg agcattnccg ctcactgntc 960
ggaggcatgt ncnggnnnac gcaaggntng ntgggg 997

<210> SEQ ID NO 31

<211> LENGTH: 941
<212> TYPE: DNA
<213> ORGANISM: West Nile virus
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (21)..(22)
<223> OTHER INFORMATION: a, c, t, g, unknown or other
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (30)..(35)
<223> OTHER INFORMATION: a, c, t, g, unknown or other
<220> FEATURE:
<221> NAME/KEY: modified_base
<222> LOCATION: (47)..(49)
<223> OTHER INFORMATION: a, c, t, g, unknown or other
<220> FEATURE:
<221> NAME/KEY: modified_base
<222> LOCATION: (56)..(56)
<223> OTHER INFORMATION: a, c, t, g, unknown or other
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (65)..(65)
<223> OTHER INFORMATION: a, c, t, g, unknown or other
<220> FEATURE:
<221> NAME/KEY: modified_base
<222> LOCATION: (68)..(69)
<223> OTHER INFORMATION: a, c, t, g, unknown or other
<220> FEATURE:
<221> NAME/KEY: modified_base
<222> LOCATION: (91)..(91)
<223> OTHER INFORMATION: a, c, t, g, unknown or other
<220> FEATURE:
<221> NAME/KEY: modified_base
<222> LOCATION: (126)..(126)
<223> OTHER INFORMATION: a, c, t, g, unknown or other
<220> FEATURE:
<221> NAME/KEY: modified_base
<222> LOCATION: (131)..(131)
<223> OTHER INFORMATION: a, c, t, g, unknown or other
<220> FEATURE:
<221> NAME/KEY: modified_base
<222> LOCATION: (133)..(133)
<223> OTHER INFORMATION: a, c, t, g, unknown or other
<220> FEATURE:
<221> NAME/KEY: modified_base
<222> LOCATION: (180)..(180)
<223> OTHER INFORMATION: a, c, t, g, unknown or other
<220> FEATURE:
<221> NAME/KEY: modified_base
<222> LOCATION: (197)..(197)
<223> OTHER INFORMATION: a, c, t, g, unknown or other
<220> FEATURE:
<221> NAME/KEY: modified_base
<222> LOCATION: (238)..(238)
<223> OTHER INFORMATION: a, c, t, g, unknown or other
<220> FEATURE:
<221> NAME/KEY: modified_base
<222> LOCATION: (247)..(247)
<223> OTHER INFORMATION: a, c, t, g, unknown or other
<220> FEATURE:
<221> NAME/KEY: modified_base
<222> LOCATION: (299)..(299)
<223> OTHER INFORMATION: a, c, t, g, unknown or other

<400> SEQUENCE: 31
atgcnnacta cgtgatgact nnganaagan nnnnntccat cgtgagnnnc atgganctca 60

```
ncctnccnng gagcagtgct ggaagtactg ngtggaggaa cagagagacg ttaatggagt    120

ttgagnaacc ncncgccacg aagcagtctg tgatagcatt gggctcacaa gagggagctn    180

tgcatcaagc tttggcngga gccattcctg tggaattttc aagcaacact gtcaagtnga    240

cgtcggntca tttgaagtgt agagtgaaga tggaaaaatt gcagttgaag ggaacaacnt    300

atggcgtctg ttcaaaggct ttcaagtttc ttgggactcc cgcagacaca ggtcacggca    360

ctgtggtgtt ggaattgcag tacactggca cggatggacc ttgcaaagtt cctatctcgt    420

cagtggcttc attgaacgac ctaacgccag tgggcagatt ggtcactgtc aacccttttg    480

tttcagtggc cacggccaac gctaaggtcc tgattgaatt ggaaccaccc tttggagact    540

catacatagt ggtgggcaga ggagaacaac agatcaatca ccattggcac aagtctggaa    600

gcagcattgg caaagccttt acaaccaccc tcaaaggagc gcagagacta gccgctctag    660

gagacacagc ttgggacttt ggatcagttg gaggggtgtt cacctcagtt gggaaggctg    720

tccatcaagt gttcggagga gcattccgct cactgttcgg aggcatgtcc tggataacgc    780

aaggattgct gggggctctc ctgttgtgga tgggcatcaa tgctcgtgat aggtccatag    840

ctctcacgtt tctcgcagtt ggaggagttc tgctcttcct ctccgtgaac gtgcatgctg    900

acactgggtg tgccatagac atcagccggc aagagctgag a                        941
```

<210> SEQ ID NO 32
<211> LENGTH: 931
<212> TYPE: DNA
<213> ORGANISM: West Nile virus
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: modified_base
<222> LOCATION: (62)..(62)

<223> OTHER INFORMATION: a, c, t, g, unknown or other
<220> FEATURE:
<221> NAME/KEY: modified_base
<222> LOCATION: (154)..(154)
<223> OTHER INFORMATION: a, c, t, g, unknown or other
<220> FEATURE:
<221> NAME/KEY: modified_base
<222> LOCATION: (225)..(225)
<223> OTHER INFORMATION: a, c, t, g, unknown or other

<400> SEQUENCE: 32
cagtnngtga tancntnggc tcananaggn agntntgcat caagctttgg cnggagccat 60
tnctgtggaa ttttcaagca acactgtcaa gttgacgtcg ggtcatttga agtgtagagt 120
gaagatggaa aaattgcagt tgaagggaac aacntatggc gtctgttcaa aggctttcaa 180
gtttcttggg actcccgcag acacaggtca cggcactgtg gtgtnggaat tgcagtacac 240
tggcacggat ggaccttgca aagttcctat ctcgtcagtg gcttcattga acgacctaac 300
gccagtgggc agattggtca ctgtcaaccc ttttgtttca gtggccacgg ccaacgctaa 360
ggtcctgatt gaattggaac caccctttgg agactcatac atagtggtgg gcagaggaga 420
acaacagatc aatcaccatt ggcacaagtc tggaagcagc attggcaaag cctttacaac 480
caccctcaaa ggagcgcaga gactagccgc tctaggagac acagcttggg actttggatc 540
agttggaggg gtgttcacct cagttgggaa ggctgtccat caagtgttcg gaggagcatt 600
ccgctcactg ttcggaggca tgtcctggat aacgcaagga ttgctggggg ctctcctgtt 660
gtggatgggc atcaatgctc gtgataggtc catagctctc acgtttctcg cagttggagg 720
agttctgctc ttcctctccg tgaacgtgca tgctgacact gggtgtgcca tagacatcag 780
ccggcaagag ctgagatgtg gaagtggagt gttcatacac aatgatgtgg aggcttggat 840
ggaccggtac aagtattacc ctgaaacgcc acaaggccta gccaagatca ttcagaaagc 900
tcataaggaa ggagtgtgcg gtctacgatc a 931

<210> SEQ ID NO 33
<211> LENGTH: 967
<212> TYPE: DNA
<213> ORGANISM: West Nile virus
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (673)..(673)
<223> OTHER INFORMATION: a, c, t, g, unknown or other
<220> FEATURE:
<221> NAME/KEY: modified_base
<222> LOCATION: (859)..(861)
<223> OTHER INFORMATION: a, c, t, g, unknown or other
<220> FEATURE:
<221> NAME/KEY: modified_base
<222> LOCATION: (915)..(915)
<223> OTHER INFORMATION: a, c, t, g, unknown or other
<220> FEATURE:
<221> NAME/KEY: modified_base
<222> LOCATION: (940)..(941)
<223> OTHER INFORMATION: a, c, t, g, unknown or other
<220> FEATURE:
<221> NAME/KEY: modified_base
<222> LOCATION: (959)..(959)
<223> OTHER INFORMATION: a, c, t, g, unknown or other
<220> FEATURE:
<221> NAME/KEY: modified_base
<222> LOCATION: (961)..(961)
<223> OTHER INFORMATION: a, c, t, g, unknown or other

<400> SEQUENCE: 33

```
cacagcaatg cagctttggg tgccntgttt gaagagcaga atcaatggag gagcgccaga      60

gaagcagttg aagatccaaa attttgggag atggtggatg aggagcgcga ggcacatctg     120

cggggggaat gtcacacttg catttacaac atgatgggaa agagagagaa aaaacccgga     180

gagttcggaa aggccaaggg aagcagagcc atttggttca tgtggctcgg agctcgcttt     240

ctggagttcg aggctctggg ttttctcaat gaagaccact ggcttggaag aaagaactca     300

ggaggaggtg tcgagggctt gggcctccaa aaactgggtt acatcctgcg tgaagttggc     360

acccggcctg gggcaagat ctatgctgat gacacagctg gctgggacac ccgcatcacg     420

agagctgact tggaaaatga agctaaggtg cttgagttgc ttgatgggga acatcggcgt     480

cttgccaggg ccatcattga gctcacctat cgtcacaaag ttgtgaaagt gatgcgcccg     540

gctgctgatg gaagaaccgt catggatgtt atctccagag aagatcagag gggagtgga     600

caagttgtca cctacgccct aaacactttc accaacctgg ccgtccagct ggtgaggatg     660

atggaagggg aanggagtga ttggcccaga tgatgtggag aaactcacaa aagggaaagg     720

acccaaagtc aggacctggc tgtttgagaa tggggaagaa agactcagcc gcatggctgt     780

cagtggagat gactgtgtgg taaagcccct ggacgatcgc tttgccacct cgctccactt     840

cctcaatgct atgtcaaann ntcgcaaaga catccaagag tggaaaccgt caactggatg     900

gtatgattgg cagcnggttc cattttgctc aaaccatttn nctgaattga tcatgaaana     960

nggaaga                                                               967
```

<210> SEQ ID NO 34
<211> LENGTH: 955
<212> TYPE: DNA
<213> ORGANISM: West Nile virus
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (815)..(815)
<223> OTHER INFORMATION: a, c, t, g, unknown or other
<220> FEATURE:
<221> NAME/KEY: modified_base
<222> LOCATION: (874)..(876)
<223> OTHER INFORMATION: a, c, t, g, unknown or other
<220> FEATURE:
<221> NAME/KEY: modified_base
<222> LOCATION: (882)..(886)
<223> OTHER INFORMATION: a, c, t, g, unknown or other
<220> FEATURE:
<221> NAME/KEY: modified_base
<222> LOCATION: (903)..(905)
<223> OTHER INFORMATION: a, c, t, g, unknown or other
<220> FEATURE:
<221> NAME/KEY: modified_base
<222> LOCATION: (928)..(928)
<223> OTHER INFORMATION: a, c, t, g, unknown or other
<220> FEATURE:
<221> NAME/KEY: modified_base
<222> LOCATION: (938)..(938)
<223> OTHER INFORMATION: a, c, t, g, unknown or other
<220> FEATURE:
<221> NAME/KEY: modified_base
<222> LOCATION: (945)..(945)
<223> OTHER INFORMATION: a, c, t, g, unknown or other
<220> FEATURE:
<221> NAME/KEY: modified_base
<222> LOCATION: (947)..(947)

<223> OTHER INFORMATION: a, c, t, g, unknown or other

<400> SEQUENCE: 34
tctcncggat tccncgcacg agatgtattg ggtgagtcga gcttcaggca atgtggtaca 60
ttcagtgaat atgaccagcc aggtgctcct aggaagaatg gaaaaaagga cctggaaggg 120
accccaatac gaggaagatg taaacttggg aagtggaacc agggcggtgg gaaaacccct 180
gctcaactca gacaccagta aaatcaagaa caggattgaa cgactcaggc gtgagtacag 240
ttcgacgtgg caccacgatg agaaccaccc atatagaacc tggaactatc acggcagtta 300
tgatgtgaag cccacaggct ccgccagttc gctggtcaat ggagtggtca ggctcctctc 360
aaaaccatgg gacaccatca cgaatgttac caccatggcc atgactgaca ctactccctt 420
cgggcagcag cgagtgttca aagagaaggt ggacacgaaa gctcctgaac cgccagaagg 480
agtgaagtac gtgctcaacg agaccaccaa ctggttgtgg gcgtttttgg ccagagaaaa 540
acgtcccaga atgtgctctc gagaggaatt cataagaaag gtcaacagca atgcagcttt 600
gggtgccatg tttgaagagc agaatcaatg gaggagcgcc agagaagcag ttgaagatcc 660
aaaattttgg gagatggtgg atgaggagcg cgaggcacat ctgcgggggg aatgtcacac 720
ttgcatttac aacatgatgg gaaagagaga gaaaaaaccc ggagagttcg gaaaggccaa 780
gggaagcaga gccatttggt tcatgtggct cgganctcgc tttctggagt tcgaggctct 840
gggttttctc aatgaagacc actggcttgg aagnnnaact cnnnnngagg tgtcgagggc 900
ttnnnctcca aaaactgggt tacatccngc gtgaagtngc acccngnctg ggggc 955

<210> SEQ ID NO 35
<211> LENGTH: 971
<212> TYPE: DNA
<213> ORGANISM: West Nile virus
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (59)..(61)
<223> OTHER INFORMATION: a, c, t, g, unknown or other
<220> FEATURE:
<221> NAME/KEY: modified_base
<222> LOCATION: (91)..(91)
<223> OTHER INFORMATION: a, c, t, g, unknown or other
<220> FEATURE:
<221> NAME/KEY: modified_base
<222> LOCATION: (137)..(139)
<223> OTHER INFORMATION: a, c, t, g, unknown or other
<220> FEATURE:
<221> NAME/KEY: modified_base
<222> LOCATION: (247)..(247)
<223> OTHER INFORMATION: a, c, t, g, unknown or other

<400> SEQUENCE: 35
ttcgctngtc aatggagtng tcaggctcct ctcaaaacca tgggacacca tcacgaatnn 60
nccaccatgg ccatgactga cactactccc nttcgggcag cagcgagtgt tcaaagagaa 120
ggtggacacg aaagctnnng aaccgccaga aggagtgaag tacgtgctca acgagaccac 180
caactggttg tgggcgtttt tggccagaga aaaacgtccc agaatgtgct ctcgagagga 240
attcatnaga aaggtcaaca gcaatgcagc tttgggtgcc atgtttgaag agcagaatca 300
atggaggagc gccagagaag cagttgaaga tccaaaattt tgggagatgg tggatgagga 360
gcgcgaggca catctgcggg gggaatgtca cacttgcatt tacaacatga tgggaaagag 420
agagaaaaaa cccggagagt tcggaaaggc caagggaagc agagccattt ggttcatgtg 480
gctcggagct cgctttctgg agttcgaggc tctgggtttt ctcaatgaag accactggct 540
tggaagaaag aactcaggag gaggtgtcga gggcttgggc ctccaaaaac tgggttacat 600
cctgcgtgaa gttggcaccc ggcctggggg caagatctat gctgatgaca cagctggctg 660
ggacacccgc atcacgagag ctgacttgga aaatgaagct aaggtgcttg agttgcttga 720
tggggaacat cggcgtcttg ccagggccat cattgagctc acctatcgtc acaaagttgt 780
gaaagtgatg cgcccggctg ctgatggaag aaccgtcatg gatgttatct ccagagaaga 840
tcagaggggg agtggacaag ttgtcaccta cgccctaaac actttcacca acctggccgt 900
ccagctggtg aggatgatgg aaggggaagg agtgattggc ccagatgatg tggagaaact 960
cacaaaaggg a 971

<210> SEQ ID NO 36
<211> LENGTH: 971
<212> TYPE: DNA
<213> ORGANISM: West Nile virus
<220> FEATURE:
<221> NAME/KEY: modified_base
<222> LOCATION: (14)..(15)
<223> OTHER INFORMATION: a, c, t, g, unknown or other
<220> FEATURE:
<221> NAME/KEY: modified_base
<222> LOCATION: (36)..(37)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (58)..(59)
<223> OTHER INFORMATION: a, c, t, g, unknown or other
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (73)..(73)
<223> OTHER INFORMATION: a, c, t, g, unknown or other
<220> FEATURE:
<221> NAME/KEY: modified_base
<222> LOCATION: (89)..(89)
<223> OTHER INFORMATION: a, c, t, g, unknown or other
<220> FEATURE:
<221> NAME/KEY: modified_base
<222> LOCATION: (103)..(103)
<223> OTHER INFORMATION: a, c, t, g, unknown or other
<220> FEATURE:
<221> NAME/KEY: modified_base
<222> LOCATION: (157)..(157)
<223> OTHER INFORMATION: a, c, t, g, unknown or other
<220> FEATURE:
<221> NAME/KEY: modified_base
<222> LOCATION: (159)..(160)
<223> OTHER INFORMATION: a, c, t, g, unknown or other
<220> FEATURE:
<221> NAME/KEY: modified_base
<222> LOCATION: (970)..(970)
<223> OTHER INFORMATION: a, c, t, g, unknown or other

<400> SEQUENCE: 36

```
gggaccccaa tacnngaaga tgtaaacttg ggaagnnanc nngggcggtg ggaaaccnng     60

ntcaactcag acnccagtaa aatcaaganc aggattgaac gantcaggcg tgagtacagt    120

tcgacgtggc accacgatga gaaccaccca tatagancnn ggaactatca cggcagttat    180

gatgtgaagc ccacaggctc cgccagttcg ctggtcaatg gagtggtcag gctcctctca    240

aaaccatggg acaccatcac gaatgttacc accatggcca tgactgacac tactcccttc    300

gggcagcagc gagtgttcaa agagaaggtg gacacgaaag ctcctgaacc gccagaagga    360

gtgaagtacg tgctcaacga gaccaccaac tggttgtggg cgtttttggc cagagaaaaa    420

cgtcccagaa tgtgctctcg agaggaattc ataagaaagg tcaacagcaa tgcagctttg    480

ggtgccatgt ttgaagagca gaatcaatgg aggagcgcca gagaagcagt tgaagatcca    540

aaattttggg agatggtgga tgaggagcgc gaggcacatc tgcgggggga atgtcacact    600

tgcatttaca acatgatggg aaagagagag aaaaaacccg gagagttcgg aaaggccaag    660

ggaagcagag ccatttggtt catgtggctc ggagctcgct ttctggagtt cgaggctctg    720

ggttttctca atgaagacca ctggcttgga agaaagaact caggaggagg tgtcgagggc    780

ttgggcctcc aaaaactggg ttacatcctg cgtgaagttg gcacccggcc tgggggcaag    840

atctatgctg atgacacagc tggctgggac acccgcatca cgagagctga cttggaaaat    900

gaagctaagg tgcttgagtt gcttgatggg gaacatcggc gtcttgccag ggccatcatt    960

gagctcaccn a                                                         971
```

```
<210> SEQ ID NO 37
<211> LENGTH: 945
<212> TYPE: DNA
<213> ORGANISM: West Nile virus
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (618)..(618)
<223> OTHER INFORMATION: a, c, t, g, unknown or other
<220> FEATURE:
<221> NAME/KEY: modified_base
<222> LOCATION: (673)..(673)
<223> OTHER INFORMATION: a, c, t, g, unknown or other
<220> FEATURE:
<221> NAME/KEY: modified_base
<222> LOCATION: (859)..(859)
<223> OTHER INFORMATION: a, c, t, g, unknown or other
<220> FEATURE:
<221> NAME/KEY: modified_base
<222> LOCATION: (884)..(884)
<223> OTHER INFORMATION: a, c, t, g, unknown or other
<220> FEATURE:
<221> NAME/KEY: modified_base
<222> LOCATION: (915)..(917)
<223> OTHER INFORMATION: a, c, t, g, unknown or other

<400> SEQUENCE: 37

cacagcaatg cagctttggg tgccntgttt gaagagcaga atcaatggag gagcgccaga     60

gaagcagttg aagatccaaa attttgggag atggtggatg aggagcgcga ggcacatctg    120

cgggggggaat gtcacacttg catttacaac atgatgggaa agagagagaa aaaacccgga    180

gagttcggaa aggccaaggg aagcagagcc atttggttca tgtggctcgg agctcgcttt    240

ctggagttcg aggctctggg ttttctcaat gaagatcact ggcttggaag aaagaactca    300

ggaggaggtg tcgagggctt gggcctccaa aaactgggtt acatcctgcg tgaagttggc    360

acccggcctg gggcaagat ctatgctgat gacacagctg gctgggacac ccgcatcacg    420
```

```
agagctgact tggaaaatga agctaaggtg cttgagctgc ttgatgggga acatcggcgt    480

cttgccaggg ccatcattga gctcacctat cgtcacaaag ttgtgaaagt gatgcgcccg    540

gctgctgatg gaagaaccgt catggatgtt atctccagag aagatcagag gggagtgga     600

caagttgtca cctacgcnct aaacactttc accaacctgg ccgtccagct ggtgaggatg    660

atggaagggg aanggagtga ttggcccaga tgatgtggag aaactcacaa aagggaaagg    720

acccaaagtc aggacctggc tgtttgagaa tggggaagaa agactcagcc gcatggctgt    780

cagtggagat gactgtgtgg taaagcccct ggacgatcgc tttgccacct cgctccactt    840

cctcaatgct atgtcaaang ttcgcaaaga catccaagag tggnaaccgt caactggatg    900

gtatgattgg cagcnnntcc attttgctca aaccatttca ctgaa                    945
```

<210> SEQ ID NO 38
<211> LENGTH: 1027
<212> TYPE: DNA
<213> ORGANISM: West Nile virus
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (841)..(841)
<223> OTHER INFORMATION: a, c, t, g, unknown or other
<220> FEATURE:
<221> NAME/KEY: modified_base
<222> LOCATION: (883)..(885)
<223> OTHER INFORMATION: a, c, t, g, unknown or other
<220> FEATURE:
<221> NAME/KEY: modified_base
<222> LOCATION: (887)..(887)
<223> OTHER INFORMATION: a, c, t, g, unknown or other
<220> FEATURE:
<221> NAME/KEY: modified_base
<222> LOCATION: (948)..(948)
<223> OTHER INFORMATION: a, c, t, g, unknown or other
<220> FEATURE:
<221> NAME/KEY: modified_base
<222> LOCATION: (950)..(950)
<223> OTHER INFORMATION: a, c, t, g, unknown or other
<220> FEATURE:
<221> NAME/KEY: modified_base
<222> LOCATION: (978)..(978)
<223> OTHER INFORMATION: a, c, t, g, unknown or other
<220> FEATURE:
<221> NAME/KEY: modified_base
<222> LOCATION: (985)..(986)
<223> OTHER INFORMATION: a, c, t, g, unknown or other
<220> FEATURE:
<221> NAME/KEY: modified_base
<222> LOCATION: (991)..(992)
<223> OTHER INFORMATION: a, c, t, g, unknown or other
<220> FEATURE:
<221> NAME/KEY: modified_base
<222> LOCATION: (997)..(997)
<223> OTHER INFORMATION: a, c, t, g, unknown or other
<220> FEATURE:
<221> NAME/KEY: modified_base
<222> LOCATION: (1007)..(1007)
<223> OTHER INFORMATION: a, c, t, g, unknown or other
<220> FEATURE:
<221> NAME/KEY: modified_base
<222> LOCATION: (1013)..(1013)
<223> OTHER INFORMATION: a, c, t, g, unknown or other
<220> FEATURE:
<221> NAME/KEY: modified_base
<222> LOCATION: (1016)..(1018)

<223> OTHER INFORMATION: a, c, t, g, unknown or other
<220> FEATURE:
<221> NAME/KEY: modified_base
<222> LOCATION: (1024)..(1024)
<223> OTHER INFORMATION: a, c, t, g, unknown or other

<400> SEQUENCE: 38
tctcncggat tccncgcacg agatgtattg ggtgagtcga gcttcaggca atgtggtaca 60
ttcagtgaat atgaccagcc aggtgctcct aggaagaatg gaaaaaagga cctggaaggg 120
accccaatac gaggaagatg taaacttggg aagtggaacc agggcggtgg gaaaacccct 180
gctcaactca gacaccagta aaatcaagaa caggattgaa cgactcaggc gtgagtacag 240
ttcgacgtgg caccacgatg agaaccaccc atatagaacc tggaactatc acggcagtta 300
tgatgtgaag cccacaggct ccgccagttc gctggtcaat ggagtggtca ggctcctctc 360
aaaaccatgg gacaccatga cgaatgttac caccatggcc atgactgaca ctactccctt 420
cgggcagcag cgagtgttca aagagaaggt ggacacgaaa gctcctgaac cgccagaagg 480
agtgaagtac gtgctcaacg agaccaccaa ctggttgtgg gcgtttttgg ccagagaaaa 540
acgtcccaga atgtgctctc gagaggaatt cataagaaag gtcaacagca atgcagcttt 600
gggtgccatg tttgaagagc agaatcaatg gaggagcgcc agagaagcag ttgaagatcc 660
aaaattttgg gagatggtgg atgaggagcg cgaggcacat ctgcgggggg aatgtcacac 720
ttgcatttac aacatgatgg gaaagagaga gaaaaaaccc ggagagttcg gaaaggccaa 780
gggaagcaga gccatttggt tcatgtggct cggagctcgc tttctggagt tcgaggctct 840
nggttttctc aatgaagatc actggcttgg aagaaagaac tcnnnangag gtgtcgaggg 900
cttgggcctc caaaaactgg gttacatcct gcgtgaagtt ggcacccngn cctgggggca 960
agatctatgc tgatgacnca gctgnntggg nnacccncat cacgagngct ganttnnnaa 1020 atgnagc 1027

<210> SEQ ID NO 39
<211> LENGTH: 1019
<212> TYPE: DNA
<213> ORGANISM: West Nile virus
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (29)..(31)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (39)..(42)
<223> OTHER INFORMATION: a, c, t, g, unknown or other
<220> FEATURE:
<221> NAME/KEY: modified_base
<222> LOCATION: (44)..(47)
<223> OTHER INFORMATION: a, c, t, g, unknown or other
<220> FEATURE:
<221> NAME/KEY: modified_base
<222> LOCATION: (54)..(54)
<223> OTHER INFORMATION: a, c, t, g, unknown or other
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other
<220> FEATURE:
<221> NAME/KEY: modified_base
<222> LOCATION: (75)..(75)
<223> OTHER INFORMATION: a, c, t, g, unknown or other
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: modified_base
<222> LOCATION: (94)..(94)
<223> OTHER INFORMATION: a, c, t, g, unknown or other
<220> FEATURE:
<221> NAME/KEY: modified_base
<222> LOCATION: (100)..(100)
<223> OTHER INFORMATION: a, c, t, g, unknown or other
<220> FEATURE:
<221> NAME/KEY: modified_base
<222> LOCATION: (105)..(108)
<223> OTHER INFORMATION: a, c, t, g, unknown or other
<220> FEATURE:
<221> NAME/KEY: modified_base
<222> LOCATION: (116)..(116)
<223> OTHER INFORMATION: a, c, t, g, unknown or other
<220> FEATURE:
<221> NAME/KEY: modified_base
<222> LOCATION: (118)..(118)
<223> OTHER INFORMATION: a, c, t, g, unknown or other
<220> FEATURE:
<221> NAME/KEY: modified_base
<222> LOCATION: (128)..(128)
<223> OTHER INFORMATION: a, c, t, g, unknown or other
<220> FEATURE:
<221> NAME/KEY: modified_base
<222> LOCATION: (139)..(139)
<223> OTHER INFORMATION: a, c, t, g, unknown or other
<220> FEATURE:
<221> NAME/KEY: modified_base
<222> LOCATION: (186)..(187)
<223> OTHER INFORMATION: a, c, t, g, unknown or other
<220> FEATURE:
<221> NAME/KEY: modified_base
<222> LOCATION: (295)..(295)
<223> OTHER INFORMATION: a, c, t, g, unknown or other
<220> FEATURE:
<221> NAME/KEY: modified_base
<222> LOCATION: (920)..(920)
<223> OTHER INFORMATION: a, c, t, g, unknown or other
<220> FEATURE:
<221> NAME/KEY: modified_base
<222> LOCATION: (922)..(922)
<223> OTHER INFORMATION: a, c, t, g, unknown or other

<400> SEQUENCE: 39
ggaactatcn cggnagtnat gatgtgaann nacnggntnn nncnnnntcg ctgntcaatg 60
nagtgntcag gctcntntca aaacccntgg gacnccatcn cgaannnncc accatngncc 120
atgactgnca ctactcccnt tcgggcagca gcgagtgttc aaagagaagg tggacacgaa 180

```
agctcnngaa ccgccagaag gagtgaagta cgtgctcaac gagaccacca actggttgtg    240

ggcgtttttg gccagagaaa aacgtcccag aatgtgctct cgagaggaat tcatnagaaa    300

ggtcaacagc aatgcagctt tgggtgccat gtttgaagag cagaatcaat ggaggagcgc    360

cagagaagca gttgaagatc caaaattttg ggagatggtg gatgaggagc gcgaggcaca    420

tctgcggggg gaatgtcaca cttgcattta caacatgatg ggaaagagag agaaaaaacc    480

cggagagttc ggaaaggcca agggaagcag agccatttgg ttcatgtggc tcggagctcg    540

ctttctggag ttcgaggctc tgggttttct caatgaagat cactggcttg gaagaaagaa    600

ctcaggagga ggtgtcgagg gcttgggcct ccaaaaactg ggttacatcc tgcgtgaagt    660

tggcacccgg cctgggggca agatctatgc tgatgacaca gctggctggg acacccgcat    720

cacgagagct gacttggaaa atgaagctaa ggtgcttgag ctgcttgatg gggaacatcg    780

gcgtcttgcc agggccatca ttgagctcac ctatcgtcac aaagttgtga aagtgatgcg    840

cccggctgct gatggaagaa ccgtcatgga tgttatctcc agagaagatc agagggggag    900

tggacaagtt gtcacctacn cnctaaacac tttcaccaac ctggccgtcc agctggtgag    960

gatgatggaa ggggaaggag tgattggccc agatgatgtg gagaaactca caaaaggga    1019
```

<210> SEQ ID NO 40
<211> LENGTH: 1015
<212> TYPE: DNA
<213> ORGANISM: West Nile virus
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (8)..(9)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (34)..(38)
<223> OTHER INFORMATION: a, c, t, g, unknown or other
<220> FEATURE:
<221> NAME/KEY: modified_base
<222> LOCATION: (41)..(41)
<223> OTHER INFORMATION: a, c, t, g, unknown or other
<220> FEATURE:
<221> NAME/KEY: modified_base
<222> LOCATION: (43)..(43)
<223> OTHER INFORMATION: a, c, t, g, unknown or other
<220> FEATURE:
<221> NAME/KEY: modified_base
<222> LOCATION: (52)..(53)
<223> OTHER INFORMATION: a, c, t, g, unknown or other
<220> FEATURE:
<221> NAME/KEY: modified_base -continued
<222> LOCATION: (73)..(73)
<223> OTHER INFORMATION: a, c, t, g, unknown or other
<220> FEATURE:
<221> NAME/KEY: modified_base
<222> LOCATION: (83)..(84)
<223> OTHER INFORMATION: a, c, t, g, unknown or other
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: modified_base
<222> LOCATION: (104)..(105)
<223> OTHER INFORMATION: a, c, t, g, unknown or other
<220> FEATURE:
<221> NAME/KEY: modified_base
<222> LOCATION: (119)..(119)
<223> OTHER INFORMATION: a, c, t, g, unknown or other
<220> FEATURE:
<221> NAME/KEY: modified_base
<222> LOCATION: (244)..(244)
<223> OTHER INFORMATION: a, c, t, g, unknown or other
<220> FEATURE:
<221> NAME/KEY: modified_base
<222> LOCATION: (491)..(496)
<223> OTHER INFORMATION: a, c, t, g, unknown or other

<400> SEQUENCE: 40

```
tgncancnng ngctcnnngn ngaatgnaaa aaannnnngg nangggaccc cnntacgagg      60

aagatgtaaa ctngggaagt ggnnccnggg cggtgggaaa accnngctca actcagacnc     120

cagtaaaatc aagaacagga ttgaacgact caggcgtgag tacagttcga cgtggcacca     180

cgatgagaac cacccatata gaacctggaa ctatcacggc agttatgatg tgaagcccac     240

aggntccgcc agttcgctgg tcaatggagt ggtcaggctc ctctcaaaac catgggacac     300

catcacgaat gttaccacca tggccatgac tgacactact cccttcgggc agcagcgagt     360

gttcaaagag aaggtggaca cgaaagctcc tgaaccgcca gaaggagtga agtacgtgct     420

caacgagacc accaactggt tgtgggcgtt tttggccaga gaaaaacgtc ccagaatgtg     480

ctctcgagag nnnnnnataa gaaaggtcaa cagcaatgca gctttgggtg ccatgtttga     540

agagcagaat caatggagga gcgccagaga agcagttgaa gatccaaaat tttgggagat     600

ggtggatgag gagcgcgagg cacatctgcg gggggaatgt cacacttgca tttacaacat     660

gatgggaaag agagagaaaa aacccggaga gttcggaaag gccaagggaa gcagagccat     720

ttggttcatg tggctcggag ctcgctttct ggagttcgag gctctgggtt ttctcaatga     780

agatcactgg cttggaagaa agaactcagg aggaggtgtc gagggcttgg gcctccaaaa     840

actgggttac atcctgcgtg aagttggcac ccggcctggg ggcaagatct atgctgatga     900

cacagctggc tgggacaccc gcatcacgag agctgacttg gaaaatgaag ctaaggtgct     960

tgagctgctt gatggggaac atcggcgtct tgccagggcc atcattgagc tcacc         1015
```